(12) United States Patent
Alderson et al.

(10) Patent No.: US 7,524,501 B2
(45) Date of Patent: Apr. 28, 2009

(54) METHODS OF TREATING AN INJURY TO, OR DISORDER OF, THE EYE INVOLVING PHOTORECEPTOR PROLIFERATION BY ADMINISTERING VEGF2 ANTIBODIES

(75) Inventors: Ralph Alderson, Gaithersburg, MD (US); Robert Melder, Boyds, MD (US); Viktor Roschke, Rockville, MD (US); Steven M. Ruben, Brookeville, MD (US); Craig A. Rosen, Laytonsville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 213 days.

(21) Appl. No.: 11/078,507

(22) Filed: Mar. 14, 2005

(65) Prior Publication Data

US 2005/0181979 A1 Aug. 18, 2005

Related U.S. Application Data

(62) Division of application No. 09/499,468, filed on Feb. 7, 2000, now Pat. No. 7,223,724.

(60) Provisional application No. 60/119,179, filed on Feb. 8, 1999, provisional application No. 60/119,926, filed on Feb. 12, 1999, provisional application No. 60/137,796, filed on Jun. 3, 1999, provisional application No. 60/171,505, filed on Dec. 22, 1999.

(51) Int. Cl.
*A61K 39/395* (2006.01)
*A61K 39/00* (2006.01)

(52) U.S. Cl. .............. 424/145.1; 424/141.1; 424/142.1

(58) Field of Classification Search .................. None
See application file for complete search history.

(56) References Cited

U.S. PATENT DOCUMENTS

| | | | |
|---|---|---|---|
| 5,073,492 A | 12/1991 | Chen et al. | |
| 5,194,596 A | 3/1993 | Tischer et al. | |
| 5,219,739 A | 6/1993 | Tischer et al. | |
| 5,234,908 A | 8/1993 | Szabo et al. | |
| 5,240,848 A | 8/1993 | Keck et al. | |
| 5,283,354 A | 2/1994 | Lemischka | |
| 5,326,695 A | 7/1994 | Andersson et al. | |
| 5,607,918 A | 3/1997 | Eriksson et al. | |
| 5,633,147 A | 5/1997 | Meissner et al. | |
| 5,652,225 A | 7/1997 | Isner | |
| 5,661,133 A | 8/1997 | Leiden et al. | |
| 5,693,622 A | 12/1997 | Wolff et al. | |
| 5,776,755 A | 7/1998 | Alitalo et al. | |
| 5,792,453 A | 8/1998 | Hammond et al. | |
| 5,840,693 A | 11/1998 | Eriksson et al. | |
| 5,861,301 A | 1/1999 | Terman et al. | |
| 5,932,540 A | 8/1999 | Hu et al. | |
| 5,935,820 A | 8/1999 | Hu et al. | |
| 6,040,157 A | 3/2000 | Hu et al. | |
| 6,121,246 A | 9/2000 | Isner | |
| 6,130,071 A | 10/2000 | Alitalo et al. | |
| 6,221,839 B1 | 4/2001 | Alitalo et al. | |
| 6,245,530 B1 | 6/2001 | Alitalo et al. | |
| 6,297,238 B1 | 10/2001 | Doyle et al. | |
| 6,361,946 B1 | 3/2002 | Alitalo et al. | |
| 6,403,088 B1 | 6/2002 | Alitalo et al. | |
| 6,451,764 B1 | 9/2002 | Lee et al. | |
| 6,515,105 B1 | 2/2003 | Alitalo et al. | |
| 6,608,182 B1 | 8/2003 | Rosen et al. | |
| 6,645,933 B1 * | 11/2003 | Alitalo et al. .................. 514/2 |
| 6,660,744 B1 | 12/2003 | Hirst et al. | |
| 6,713,474 B2 | 3/2004 | Hirst et al. | |
| 6,734,285 B2 | 5/2004 | Hu et al. | |
| 7,109,308 B1 | 9/2006 | Rosen et al. | |
| 7,115,392 B2 | 10/2006 | Rosen et al. | |
| 7,153,827 B1 | 12/2006 | Hu et al. | |
| 7,153,942 B2 | 12/2006 | Hu et al. | |
| 7,186,688 B1 | 3/2007 | Hu et al. | |
| 7,208,582 B2 | 4/2007 | Rosen et al. | |
| 7,223,724 B1 * | 5/2007 | Alderson et al. ................ 514/2 |
| 7,227,005 B1 * | 6/2007 | Hu et al. ..................... 530/399 |
| 7,273,751 B2 | 9/2007 | Coleman | |
| 7,402,312 B2 | 7/2008 | Rosen et al. | |
| 7,439,333 B2 | 10/2008 | Hu et al. | |
| 2002/0019350 A1 | 2/2002 | Levine et al. | |
| 2002/0086004 A1 | 7/2002 | Adnot et al. | |
| 2002/0111362 A1 | 8/2002 | Rubinfeld | |
| 2002/0156081 A1 | 10/2002 | Hirst et al. | |
| 2003/0125523 A1 | 7/2003 | Alitalo et al. | |
| 2003/0153752 A1 | 8/2003 | Hirst et al. | |
| 2003/0187001 A1 | 10/2003 | Calderwood et al. | |
| 2003/0211988 A1 | 11/2003 | Epstein | |
| 2003/0215921 A1 | 11/2003 | Coleman | |
| 2004/0002140 A1 | 1/2004 | Gilbert et al. | |
| 2004/0214286 A1 | 10/2004 | Hu et al. | |
| 2004/0248781 A1 | 12/2004 | Kerbel | |
| 2005/0059117 A1 | 3/2005 | Rosen et al. | |
| 2005/0118180 A1 | 6/2005 | Rubinfeld | |
| 2005/0176103 A1 | 8/2005 | Hu et al. | |
| 2005/0192429 A1 | 9/2005 | Rosen et al. | |
| 2005/0232921 A1 | 10/2005 | Rosen et al. | |
| 2005/0287143 A1 | 12/2005 | Rosen et al. | |
| 2006/0014252 A1 | 1/2006 | Lyman | |
| 2006/0025331 A1 | 2/2006 | Hu et al. | |
| 2006/0057117 A1 | 3/2006 | Coleman | |

FOREIGN PATENT DOCUMENTS

AU 710696 9/1999

(Continued)

OTHER PUBLICATIONS

U.S. Appl. No. 11/730,696, inventors Rosen et al., filed Apr. 3, 2007.

(Continued)

*Primary Examiner*—Robert Landsman
(74) *Attorney, Agent, or Firm*—Sterne, Kessler, Goldstein & Fox, P.L.L.C.

(57) ABSTRACT

The present invention is directed to VEGF-2 polynucleotides and polypeptides and methods of using such polynucleotides and polypeptides. In particular, provided are methods of treating retinal disorders with VEGF-2 polynucleotides and polypeptides.

11 Claims, 38 Drawing Sheets

FOREIGN PATENT DOCUMENTS

| EP | 0 186 084 A2 | 7/1986 |
|---|---|---|
| EP | 0 399 816 A1 | 11/1990 |
| EP | 0 476983 | 3/1992 |
| EP | 0 506477 | 9/1992 |
| JP | 64-38100 A | 2/1989 |
| JP | 2-117698 A | 5/1990 |
| WO | WO-91/02058 | 2/1991 |
| WO | WO-92/14748 | 9/1992 |
| WO | WO 94/11506 A1 | 5/1994 |
| WO | WO-95/19985 | 7/1995 |
| WO | WO-95/24414 | 9/1995 |
| WO | WO-95/24473 | 12/1995 |
| WO | WO-96/05856 | 2/1996 |
| WO | WO-96/39515 | 12/1996 |
| WO | WO-97/00271 | 1/1997 |
| WO | WO-97/05250 | 2/1997 |
| WO | WO-97/08320 | 3/1997 |
| WO | WO-97/09427 | 3/1997 |
| WO | WO-97/17442 | 5/1997 |
| WO | WO-97/19694 | 6/1997 |
| WO | WO-98/06844 | 2/1998 |
| WO | WO-98/07832 | 2/1998 |
| WO | WO-98/24811 | 6/1998 |
| WO | WO-98/33917 | 6/1998 |
| WO | WO-98/39035 | 9/1998 |
| WO | WO-98/49300 | 11/1998 |
| WO | WO-98/55619 | 12/1998 |
| WO | WO-98/56936 | 12/1998 |
| WO | WO-99/02545 | 1/1999 |
| WO | WO-99/08522 | 2/1999 |
| WO | WO-99/20749 | 4/1999 |
| WO | WO-99/21590 | 5/1999 |
| WO | WO-99/46364 | 9/1999 |
| WO | WO 99/49882 A2 | 10/1999 |
| WO | WO 00/21560 A1 | 4/2000 |
| WO | WO 00/24412 A2 | 5/2000 |
| WO | WO 00/45835 A1 | 8/2000 |
| WO | WO 00/58511 A1 | 10/2000 |
| WO | WO 00/61186 A1 | 10/2000 |
| WO | WO 00/62798 A2 | 10/2000 |
| WO | WO-00/73430 A3 | 12/2000 |
| WO | WO-00/75163 | 12/2000 |
| WO | WO-01/57226 A1 | 8/2001 |
| WO | WO-01/58956 A3 | 8/2001 |
| WO | WO 02/11769 A1 | 2/2002 |
| WO | WO 02/083704 A1 | 10/2002 |
| WO | WO 02/083849 A2 | 10/2002 |
| WO | WO 02/083850 A2 | 10/2002 |
| WO | WO 03/097660 A1 | 11/2003 |
| ZA | 9-403464 | 1/1996 |

OTHER PUBLICATIONS

Danis, R.P., et al., "Anti-angiogenic therapy of proliferative diabetic retinopathy," *Exp. Opin. Pharma.* 2:395-407, Ashley Publications Ltd. (Mar. 2001).

Enholm, B., et al., "Vascular Endothelial Growth Factor-C: A Growth Factor for Lymphatic and Blood Vascular Endothelial Cells," *Trends Cardiovasc. Med.* 8:292-297, Elsevier Science Inc. (Oct. 1998).

Ferrara, N., "Vascular Endothelial Growth Factor and the Regulation of angiogenesis," *Recent Prog. Hormone Res.* 55:15-36, The Endocrine Society (Mar. 2000).

Halin, C. and Neri, D., "Antibody-Based Targeting of Angiogenesis," *Crit. Rev. Ther. Drug Carrier Syst.* 18:299-339, Begell House, Inc. (Aug. 2001).

Longo, R., et al., "anti-angiogenic therapy: Rationale, challenges and clinical studies," *Angiogenesis* 5:237-256, Kluwer Academic Publishers (Dec. 2002).

Walsh, D.A., "Angiogenesis and arthritis," *Rheumatology* 38:103-112, British Society for Rheumatology (Feb. 1999).

NCBI Entrez, Accession No. AF010302, Mandriota, S.J. and Pepper, M.S. (first available and last updated 1997).

Anderson, W.F., "Human gene therapy," *Nature* 392:25-30, Macmillan Magazines Ltd. (Apr. 1998).

Borg, J.-P., et al., "Biochemical characterization of two isoforms of FLT4, a VEGF receptor-related tyrosine kinase," *Oncogene* 10:973-984, Stockton Press (Mar. 1995).

Capogrossi, M.C., "Gene Therapy of Coronary Artery Disease," Project No. Z01 AG00811-01, Abstract (Jan. 1994).

Capogrossi, M.C., "Gene Therapy of Coronary Artery Disease," Project No. Z01 AG00811-02, Abstract (Jan. 1995).

Choi, I.H., et al., "Angiogenesis and Mineralization During Distraction Osteogenesis," *J. Korean Med. Sci.* 17:435-447, The Korean Academy of Medical Sciences (Aug. 2002).

Declaration of Dr. Kari Alitalo, In re of: U.S. Appl. No. 08/585,895, Alitalo et al., filed Jan. 12, 1996, submitted Nov. 26, 1997.

Dias, S., et al., "Vascular endothelial growth factor (VEGF)-C signaling through FLT-4 (VEGFR-3) mediates leukemic cell proliferation, survival, and resistance to chemotherapy," *Blood* 99:2179-2184, The American Society of Hematology (Mar. 2002).

English language abstract of JP 64-38100 A, cited as document FP2 on Form PTO/SB/08A, Derwent Accession No. 1989-088700/198912.

English language abstract of JP 2-117698 A, cited as document FP3 on Form PTO/SB/08A, Derwent Accession No. 1990-181364/199024.

Fan, T.-P., et al., "Controlling the vasculature: angiogenesis, anti-angiogenesis and vascular targeting of gene therapy," *Trends Pharmaco. Sci.* 16:57-66, Elsevier Science Ltd. (Feb. 1995).

Isner, J.M., et al., "Arterial Gene Therapy for Therapeutic Angiogenesis in Patients With Peripheral Artery Disease," *Circulation* 91:2687-2692, American Heart Association, Inc. (Jun. 1995).

Isner, J.M. and Feldman, L.J., "Gene therapy for arterial disease," *Lancet* 344:1653-1654, The Lancet Ltd. (Dec. 1994).

Isner, J.M., et al., "Physiologic Assessment of Angiogenesis by Arterial Gene Therapy with Vascular Endothelial Growth Factor," *J. Cell. Biochem. (Suppl. 21A)*:378, Abstract C6-215, Wiley-Liss (Mar.-Apr. 1995).

Isner, J.M., "Therapeutic Angiogenesis in Vascular Medicine," Project No. R01 HL53354-01, Abstract (Mar. 1995).

Kubo, H., et al., "Blockade of vascular endothelial growth factor receptor-3 signaling inhibits fibroblasts growth factor-2-induced lymphangiogenesis in mouse cornea," *Proc. Natl. Acad. Sci.* 99:8868-8873, The National Academy of Sciences (Jun. 2002).

Kuzuya, M. and Kinsella, J.L., "Induction of Endothelial Cell differentiation in Vitro by Fibroblast-Derived Soluble Factors," *Exp. Cell Res.* 215:310-318, Academic Press, Inc. (Dec. 1994).

Maher, P.A., "Stimulation of Endothelial Cell Proliferation by Vanadate Is Specific for Microvascular Endothelial Cells," *J. Cell. Physiol.* 151:549-554, Wiley-Liss, Inc. (1992).

Mesri, E.A., et al., "Expression of Vascular Endothelial Growth Factor From a Defective Herpes Simplex Virus Type 1 Amplicon Vector Induces Angiogenesis in Mice," *Circulation Res.* 76:161-167, American Heart Association, Inc. (Feb. 1995).

Mülhauser, J., et al., "In Vivo Gene Transfer into Porcine Cardiac Cells with a Replication-Deficient Recombinant Adenovirus Vector," *Circulation* 88:I-475, Abstract No. 2558, American Heart Association (Oct. 1993).

Mülhauser, J., et al., "VEGF$_{165}$ Expressed by a Replication-Deficient Recombinant Adenovirus Vector Induces Angiogenesis In Vivo," *Circulation Res.* 77:1077-1086, American Heart Association, Inc. (Dec. 1995).

Oikawa, T., et al., "Three Isoforms of Platelet-Derived Growth Factors All Have the Capacity to Induce Angiogenesis In Vivo," *Biol. Pharm. Bull.* 17:1686-1688, Pharmaceutical Society of Japan (Dec. 1994).

Pajusola, K., et al., "Signalling properties of FLT4, a proteolytically processed receptor tyrosine kinase related to two VEGF receptors," *Oncogene* 9:3545-3555, Stockton Press Ltd. (Dec. 1994).

Pepper, M.S., et al., "In Vitro Angiogenic and Proteolytic Properties of Bovine Lymphatic Endothelial Cells," *Exp. Cell Res.* 210:298-305, Academic Press, Inc. (Feb. 1994).

Plate, K.H., "From angiogenesis to lymphangiogenesis," *Nat. Med.* 7:151-152, Nature America, Inc. (Feb. 2001).

Spranger, J. and Pfeiffer, A.F.H., "New concepts in pathogenesis and treatment of diabetic retinopathy," *Exp. Clin. Endocrinol. Diabetes 109(Suppl. 2)*:S438-S450, J.A. Barth Verlag (2001).

Symes, J.F. and Sniderman, A.D., "Angiogenesis: potential therapy for ischaemic disease," *Curr. Opin. Lipidol.* 5:305-312, Current Science Ltd. (Aug. 1994).

Takeshita, S., et al., "In Vivo Evidence of Enhanced Angiogenesis Following Direct Arterial Gene Transfer of the Plasmid Encoding Vascular Endothelial Growth Factor," *Circulation* 88:I-476, Abstract No. 2565, American Heart Association (Oct. 1993).

Takeshita, S., et al., "Therapeutic Angiogenesis. A Single Intraarterial Bolus of Vascular Endothelial Growth Factor Augments Revascularization in a Rabbit Ischemic Hind Limb Model," *J. Clin. Invest.* 93:662-670, The American Society for Clinical Investigation, Inc. (Feb. 1994).

Walsh, D.A. and Pearson, C.I., "Angiogenesis in the pathogenesis of inflammatory joint and lung diseases," *Arthritis Res.* 3:147-153, BioMed Central Ltd. (Feb. 2001).

Williams, R.S., "Southwestern Internal Medicine Conference: Prospects for Gene Therapy of Ischemic Heart Disease," *Am. J. Med. Sci.* 306:129-136, Lippincott Williams & Wilkins (Aug. 1993).

Witzenbichler, B., et al., "Vascular Endothelial Growth Factor-C (VEGF-C/VEGF-2) Promotes Angiogenesis in the Setting of Tissue Ischemia," *Am. J. Pathol.* 153:381-394, American Society for Investigative Pathology, Inc. (Aug. 1998).

Yeung, P.K.F., "VEGF-2," *Curr. Opin. Invest. Drugs* 2:796-800, PharmaPress Ltd.(Jun. 2001).

Maynard, J. and Georgiou, G., "Antibody Engineering," *Annu. Rev. Biomed. Eng.* 2:339-376, Annual Reviews (Aug. 2000).

Morea, V., et al., "Antibody Modeling: Implications for Engineering and Design," *Methods* 20:267-279, Academic Press (Mar. 2000).

Letter from John J. Chicca II, Ph.D., Molecular Diagnostic Services, Inc. regarding a third progress report for a project entitled "Cloning and Expression of VEGF-2 gene and the efficacy of VEGF-2 protein utilizing the 3-D collagen angiogenesis assay and proliferation," dated Feb. 16, 2006.

Letter from John J. Chicca II, Ph.D., Molecular Diagnostic Services, Inc. regarding a fourth progress report for a project entitled "Cloning and expression of VEGF-2 gene and the efficacy of VEGF-2 protein utilizing the 3-D collagen angiogenesis assay and proliferation," dated Mar. 14, 2006.

Achen et al., "Vascular endothelial growth factor D (VEGF-D) is a ligand for the tyrosine kinases VEGF receptor-2 (Flk1) and VEGF receptor 3 (Flt4)," *Proc. Natl. Acad. Sci. (USA)*, 95(2):548-553 (1998).

Alderson et al. (1999) Vascular endothelial cell growth factor (VEGF)-2 enhances the development of rat photoreceptor cells in vitro. Keystone Symposia, Ocular Cell and Molecular Biology, 202. (Abstract provided).

Altshuler et al., "Taurine promotes the differentiation of a vertebrate retinal cell type in vitro," *Development*, 119:1317-1328 (1993).

Andersson et al., "Assignment of interchain disulfide bonds in platelet-derived growth factor (PDGF) and evidence for agonist activity of monomeric PDGF," *J. Biol. Chem.*, 267(16):11260-11266 (1992).

Andersson W.F., "Human gene therapy," *Science*, 256:808-813 (1992).

Aprelikova et al., "FLT4, a novel class III receptor tyrosine kinase in chromosome 5q33-qter," *Cancer Research*, 52:746-748 (1992).

Bell et al., "Human epidermal growth factor precursor: cDNA sequence, expression in vitro and gene organization," *Nucl. Acids Res.* 14(21):8427-8446 (1986).

Bellomo et al., "Mice Lacking the Vascular Endothelial Growth Factor-B Gene (Vegfb) Have Smaller Hearts, Dysfunctional Coronary Vasculature, and Impaired Recovery From Cardiac Ischemia," *Circ. Research* 89(2):e29-e35 (2000).

Berse et al., "Vascular permeability factor (vascular endothelial growth factor) gene is expressed differentially in normal tissues, macrophages, and tumors," *Mol. Biol. Cell.* 3:211-220 (1992).

Betsholtz et al., "cDNA sequence and chromosomal localization of human platelet-derived growth factor A-chain and its expression in tumor cell lines," *Nature* 320:695-699 (1986).

Bocker-Meffert et al., "Erythropoietin and VEGF Promote Neural Outgrowth from Retinal Explants in Postnatal Rats," *Invest. Ophthalmol. Vis. Sci.*, 43(6):2021-2026 (2002).

Breier et al., "Expression of vascular endothelial growth factor during embryonic angiogenesis and endothelial cell differentiation," *Development* 114:521-532 (1992).

Claffey et al., "Vascular endothelial growth factor," *J. Biol. Chem.* 267(23):16317-16322 (1992).

Cockerill et al., "Angiogenesis: Models and Modulators" *Intl. Rev. Cytology* 159:113-160 (1995).

Corson et al., "Fibrillin binds calcium and is coded by cDNAs that reveal a multidomain structure and alternatively spliced exons at the 5' end," *Genomics* 17:476-484 (1993).

Dignam et al., "Balbiani ring 3 in *chironomus tentans* encodes a 185-kDa secretory protein which is synthesized throughout the fourth larval instar," *Gene* 88:133-140 (1990).

Eichmann et al., "Avian VEGF-C: cloning, embryonic expression pattern and stimulation of the differentiation of VEGFR2-expressing endothelial cell precursors," *Development* 125(4):743-752 (1998).

Ferrara et al., "Molecular and biological properties of the vascular endothelial growth factor family of proteins," *Endocrine Rev.* 13(I):18-32 (1992).

Ferrara et al., "The vascular endothelial growth factor family of polypeptides," *J. Cellular Biochemistry* 47:211-218 (1991).

Finnerty et al., "Molecular cloning of murine FLT and FLT4," *Oncogene* 8(11):2293-2298 (1993).

Friedman, T., "A brief history of gene therapy," *Nat. Genetics* 2:93-98 (1992).

Gail M. Seigel, "The golden age of retinal cell culture," *Molec. Vis.* 5:4 (1999).

Gamble et al., "Regulation of In Vitro Capillary Tube Formation by Anti-Integrin Antibodies," *J. Cell. Bio.* 121(4):931-943 (1993).

George et al., "Current Methods in Sequence Comparison and Analysis," Macromolecular Seq. and Syn. Selected Meth—Application (Alan R. Liss), pp. 127-149 (1988).

Gerhardinger et al., "Expression of Vascular Endothelial Growth Factor in the Human Retina and in Nonproliferative Diabetic Retinopathy," *Am. J. Pathol.*, 152(6):1453-1462 (Jun. 6, 1998).

Goldspiel et al., "Human Gene Therapy," *Clinical Pharmacy* 12:488-505 (1993).

Grimmond et al., "Cloning and Characterization of a Novel Human Gene Related to Vascular Endothelial Growth Factor," *Genome Research* 6:124-131 (1996).

Guzman et al. "Efficient gene transfer into myocardium by direct injection of adenovirus vectors," *Circ. Res.* 73:1202-1207 (1993).

Hannink et al., "Deletions in the C-Terminal Coding Region of the v-sis Gene: Dimerization Is Required for Transformation" *Mol. And Cellular Biol.* 1304-1314 (1986).

Hirai et al., "Expression of Vascular Endothelial Growth Factors (VEGF-A/VEGF-1 and VEGF-C/VEGF-2) in Postmenopausal Uterine Endometrial Carcinoma," *Gynecol. Oncol.* 80:181-188 (2001).

Heldin et al., "Structure of platelet-derived growth factor: implications for functional properties," *Growth Factors* 8:245-252 (1993).

Hockel et al., "Therapeutic angiogenesis," *Arch. Surg.* 128:423-429 (1993).

Hu et al., "A novel regulatory function of proteolytically cleaved VEGF-2 for vascular endothelial smooth muscle cells," *FASEB J.*, 11:498-504 (1997).

Hyde et al., "Correction of the ion transport defect in cystic fibrosis transgenic mice by gene therapy," *Nature* 362:250-255 (1993).

Joukov et al., "A novel vascular endothelial growth factor, VEGF-C, is a ligand for the Flt4 (VEGFR-3) and KDR (VEGFR-2) receptor tyrosine kinases," *EMBO J.* 15(2):290-298 (1996).

Joukov et al., "Proteolytic processing regulates receptor specificity and activity of VEGF-C," *EMBO J.* 16(13):3898-3911 (1997).

Kaipainen et al., "The related FLT4, FLT1 and KDR receptor tyrosine kinases show distinct expression patterns in human fetal endothelial cells," *J. Exp. Med.* 178:2077-2088 (1993).

Kay et al., "In Vivo Gene Therapy of Hemophilia B: Sustained Partial Correction in Factor IX-Deficient Dogs," *Science* 262:117-119 (1993).

Keck et al., "Vascular permeability factor, an endothelial cell mitogen related to PDGF," *Science* 246:1309 (1989).

Kelley et al., "Regulation of a Proliferation and Photoreceptor Differentiation in Fetal Human Retinal Cell Cultures," *Invest. Ophthalmol. Vis. Sci.* 36(7):1280-1289 (1995).

Kingsley, D., "The TGF-b superfamily: new members, new receptors, and new genetic tests of function in different organisms," *Genes & Development* 8:133-146 (1994).

Kolodka et al., "Hepatic Gene Therapy: Efficient Retroviral-Mediated Gene Transfer into Rat Hepatocytes in Vivo," *Somatic Cell and Molecular Genetics* 19(5):491-497 (1993).

Kukk et al., "VEGF-C receptor binding and pattern of expression with VEGFR-3 suggests a role in lymphatic vascular development," *Development* 122:3829-37 (1996).

Lee et al., "Vascular endothelial growth factor-related protein: a ligand and specific activator of the tyrosine kinase receptor Flt4," *Proc. Natl. Acad. Sci. (USA )*, 93:1988-1992 (1996).

Leung et al., "Vascular endothelial growth factor is a secreted angiogenic mitogen," *Science* 246:1306-1309 (1989).

Litwin et al., "Role of Cytokines in Endothelial Cell Functions," *Human Cytokines* pp. 101-129 (1995).

Maglione et al., "Isolation of a human placenta cDNA coding for a protein related to the vascular permeability factor," *Proc. Natl. Acad. Sci. (USA)*, 88:9267-9271 (1991).

Maglione et al., "Two alternative mRNAs coding for the angiogenic factor, placenta growth factor (PlGF), are transcribed from a single gene of chromosome 14," *Oncogene* 8:925-931 (1993).

Massague, J., "The transforming growth factor-beta family," *Annu. Rev. Cell Biol.* 6:597-641 (1990).

Matthews et al., "A receptor tyrosine kinase cDNA isolated from a population of enriched primitive hematopoietic cells and exhibiting close genetic linkage to c-kit," *Proc. Natl. Acad. Sci. (USA)*, 88:9026-9030 (1991).

Millauer et al., "Glioblastoma growth inhibited in vivo by a dominant-negative Flk-1 mutant," *Nature* 367:576-579 (1994).

Millauer et al., "High affinity VEGF binding and developmental expression suggest FLK-1 as a major regulator of vasculogenesis and angiogenesis," *Cell* 72:835-846 (1993).

Ngo et al., The Protein Folding Problem and Teritary Structure Prediction, Kenneth Merz, Jr. and Scott LeGrand, eds., Birkhauser, Boston, pp. 492-495 (1994).

Oltvai et al., "Bcl-2 heterodimerizes in vivo with a conserved homolog, bax, that accelerates programmed cell death," *Cell* 74:609-619 (1993).

Pajusola et al., "FLT4 receptor tyrosine kinase contains seven immunoglobulin-like loops and is expressed in multiple human tissues and cell lines," *Cancer Research* 52:5738-5743 (1992).

Pajusola et al., "Two human FLT4 receptor tyrosine kinase isoforms with distinct carboxy terminal tails are produced by alternative processing of primary transcripts," *Oncogene* 8:2931-2937 (1993).

Paulsson et al., "The balbani ring 3 gene in *Chironomus tentans* has a diverged repetitive structure split by many introns," *J. Mol. Biol.* 211:331-349 (1990).

Rudikoff et al., "Single amino acid substitution altering antigen-binding specificity," *Proc. Natl. Acad. Sci. USA*, 79(6):1979-1983 (Mar. 1982).

Schratzberger et al., "Reversal of experimental diabetic neuropathy by VEGF gene transfer," *J. Clin. Invest.* 107(9):1083-1092 (May 2001).

Schulz-key et al., "Ciliary Neurotrophic Factor as a Transient Negative Regulator of Rod Development in Rat Retina," *Invest. Ophthalmol. Vis. Sci.* 43(9):3099-3108 (2002).

Shibuya et al., "Nucleotide sequence and expression of a novel human receptor-type tyrosine kinase gene (*flt*) closely related to the *fms* family," *Oncogene* 519-524 (1990).

Silins et al., "Analysis of the Promoter Region of the Human VEGF-Related Factor Gene," *Biochem. Biophys. Res. Comm.* 230:413-418 (1997).

Stacker et al., "The Vascular Endothelial Growth Factor Family: Signalling for Vascular Development," *Growth Factors*, vol. 17, pp. 1-11 (1999).

Stewart et al., "Insulin delivery by somatic cell gene therapy," *J. of Mol. Endocrinology* 11:335-341 (1993).

Tanaka et al., "DNA sequence encoding the amino-terminal region of the human c-*src* protein: implications of sequence divergence among *src*-type kinase oncogenes," *Mol. Cell Biol.* 7(5):1978-1983 (1987).

Terman et al., "Identification of a new endothelial cell growth factor receptor tyrosine kinase," *Oncogene* 6:1677-1683 (1991).

Terman et al., "Identification of the kdr tyrosine as a receptor for vascular endothelial cell growth factor," *Biochem. Biophys. Res. Commun.* 187(3):1579-1586 (1992).

Tischer et al., "Vascular endothelial growth factor: A new member of the platelet-derived growth factor gene family," *Biochem. & Biophys. Res. Comms.* 165(3):1198-1206 (1989).

Tischer et al., "The Human Gene for Vascular Endothelial Growth Factor," *J. Biol.Chem.* 266(18):11947-11954 (1991).

Townson et al., "Characterization of the Murine VEGF-Related Factor Gene," *Biochem. & Biophys. Res. Comms.* 220:922-928 (1996).

Tsujimoto et al., "Analysis of the structure, transcripts, and protein products of *bcl-2*, the gene involved in human follicular lymphoma," *Proc. Natl. Acad. Sci. (USA)*, 83:5214-5218 (1986).

Vale et al., "Percutaneous Electromechanical Mapping Demonstrates Efficacy of pVGI.1 (VEGF2) in an Animal Model of Chronic Myocardial Ischemia," *Circulation* (Supplement), 100(18):I.22 (Nov. 2, 1999).

Vale et al., "Randomized, Single-Blind, Placebo-Controlled Pilot Study of Catheter-Based Myocardial Gene Transfer for Therapeutic Angiogenesis Using Left Ventricular Electromechanical Mapping in Patients with Chronic Myocardial Ischemia," *Circulation*, 103:17:2138-2143 (May 1, 2001).

Walsh et al., "Gene Therapy for Human Hemoglobinopathies," *P.S. E.B.M.* 204:289-300 (1993).

Williams, R.S. "Southwestern internal medicine conference: prospects for gene therapy of ischemic heart disease," *Am. J. Med. Sci.* 306(2):129-136 (1993).

Yang et al., "Flk-1, a Receptor for Vascular Endothelial Growth Factor (VEGF), Is Expressed by Retinal Progenitor Cells," *J. Neuroscience*, 16(19):6089-6099 (Oct. 1, 1996).

Yourey et al., "Vascular Endothelial Cell Growth Factors Promote the In Vitro Development of Rat Photoreceptor Cells," *Molecul. Biol. Cell*, 10(Suppl.):39a (Nov. 1999) and 39th Ann. Mtg. Am. Soc. Cell Biol., Wash, DC, (Dec. 11-15, 1999) (abstract (227) only).

Yourey, et al., "Vascular Endothelial Cell Growth Factors Promote the In Vitro Development of Rat Photoreceptor Cells" *J. Neuroscience*, 20:6781-6788 (2000).

GenBank Accession No. X68203, Aprelikova et al., "H.sapiens mRNA for FLT4, class III receptor tyrosine kinase," Nov. 30, 1993.

GenBank Accession No. M95200, Claffey et al., "Mouse vascular endothelial growth factor mRNA, complete cds," Apr. 27, 1993.

GenBank Accession No. M24160, Dignam et al., "C.tentans 185-kd secretory protein (sp185) mRNA, partial cds, clone pCt185," Apr. 26, 1993.

GenBank Accession No. M24276, Dignam et al., "C.tentans 140-kd secretory protein (sp140) mRNA, partial cds, clone pCt140.1," Apr. 26, 1993.

GenBank Accession No. M24277, Dignam et al., "C.tentans 140-kd secretory protein (sp140) mRNA, partial cds, clone pCt140.2," Apr. 26, 1993.

GenBank Accession No. D88689, Finnerty et al., "Mus musculus mRNA for flt-1, complete cds," Apr. 14, 2000.

GenBank Accession No. L07296, Finnerty et al., "Mus musculus receptor tyrosine kinase (FLT4) mRNA, complete cds," Aug. 9, 1993.

GenBank Accession No. X54936, Maglione et al., "H.sapiens mRNA for placenta growth factor (PlGF)," Nov. 12, 1991.

GenBank Accession No. S57152, Maglione et al., "Homo sapiens placenta growth factor 2 (PlGF-2) gene, partial cds," Mar. 5, 2001.

GenBank Accession No. X59397, Matthews et al., "Mouse Flk-1 mRNA for a tyrosine kinase receptor," Nov. 6, 1991.

GenBank Accession No. X52263, Paulsson et al., "C.tentans balbiani ring 3 (BR3) gene," Dec. 18, 1992.

GenBank Accession No. M63971, Tischer et al., "Human vascular endothelial growth factor gene, exon 1," Aug. 1993.

GenBank Accession No. M63972, Tischer et al., "Human vascular endothelial growth factor gene, exon 2," Aug. 3, 1993.

GenBank Accession No. M63973, Tischer et al., "Human vascular endothelial growth factor gene, exon 3," Aug. 3, 1993.

GenBank Accession No. M63974, Tischer et al., "Human vascular endothelial growth factor gene, exon 4," Aug. 3, 1993.
GenBank Accession No. M63975, Tischer et al., "Human vascular endothelial growth factor gene, exon 5," Aug. 3, 1993.
GenBank Accession No. M63976, Tischer et al., "Human vascular endothelial growth factor gene, exon 6," Aug. 3, 1993.
GenBank Accession No. M63977, Tischer et al., "Human vascular endothelial growth factor gene, exon 7," Aug. 3, 1993.
GenBank Accession No. M63978, Tischer et al., "Human vascular endothelial growth factor gene, exon 8," Aug. 3, 1993.
GenBank Accession No. M27281, Keck et al., "Human vascular permeability factor mRNA, complete cds," Aug. 3, 1993.
GenBank Accession No. X04571, Bell et al., "Human mRNA for kidney epidermal growth factor (EGF) precursor," Mar. 21, 1995.
GenBank Accession No. X63556, Corson et al., "H. sapiens mRNA for fibrillin," Feb. 17, 1997.
GenBank Accession No. L19896, Corson et al., "Human fibrillin (FBN1) gene, 5'end including alternative exons A, B, and C, an exon M," Nov. 8, 1994.
GenBank Accession No. L04947, Terman et al., "Homo sapiens (clones BT3.081.8, BT3.129.5 and BT4.169," Jan. 6, 1995.
GenBank Accession No. M16237, Tanaka et al., "Human c-src-1 proto-oncogene, exon 2," Jan. 13, 1995.
GenBank Accession No. M16243, Tanaka et al., "Human c-src-1 proto-oncogene, exon 3," Jan. 13, 1995.
GenBank Accession No. M16244, Tanaka et al., Human c-src-1 proto-oncogene, exon 4, Jan. 13, 1995.
GenBank Accession No. M16245, Tanaka et al., "Human c-src-1 proto-oncogene, exon 5," Jan. 13, 1995.
GenBank Accession No. K03212, Anderson et al., "Human c-src-1 proto-oncogene, exon 6" Jan. 13, 1995.
GenBank Accession No. K03213, Anderson et al., "Human c-src-1 proto-oncogene, exon 7," Jan. 13, 1995.
GenBank Accession No. K03214, Anderson et al., "Human c-src-1 proto-oncogene, exon 8", Jan. 13, 1995.
GenBank Accession No. K03215, Anderson et al., "Human c-src-1 proto-oncogene, exon 9," Jan. 13, 1995.
GenBank Accession No. K03216, Tanaka et al., Human c-src-1 proto-oncogene, exon 10, Jan. 13, 1995.
GenBank Accession No. K03217, Tanaka et al., "Human c-src-1 proto-oncogene, exon 11," Jan. 13, 1995.
GenBank Accession No. K03218, Tanaka et al., "Human c-src-1 proto-oncogene, exon 12," Jan. 13, 1995.
GenBank Accession No. M13994, Tsujimoto et al., "Human B-cell leukemia/lymphoma 2 (bcl-2) proto-oncogene mRNA encoding bcl-2-alpha protein, complete cds," Oct. 31, 1994.
GenBank Accession No. M13995, Tsujimoto et al., "Human B-cell leukemia/lymphoma 2 (bcl-2) proto-oncogene mRNA encoding bcl-3-beta protein, complete cds," Oct. 31, 1994.
GenBank Accession No. L22473, Oltvai et al., "Human Bax alpha mRNA, complete cds, "Dec. 15, 1993.
GenBank Accession No. L22474, Oltvai et al., "Human Bax beta mRNA, complete cds," Dec. 13, 1993.
GenBank Accession No. AJ000185, Achen et al., "Homo Sapiens mRNA for vascular endothelial growth factor-D," Feb. 11, 1998.
GenBank Accession No. S08167, Paulsson et al., "Balbiani ring 3 protein—midge (*Chironomus tentans*)," 1990.
International Search Report, Application No. PCT/US99/05021.
International Search Report, Application No. PCT/US94/05291.
International Search Report, Application No. PCT/US01/24658.
International Search Report, Application No. PCT/US02/26246, mailed May 21, 2003.
Statutory Declaration of Kari Alitalo, executed on Aug. 14, 2002, and accompanying Exhibits KA-1 and KA-2.
Statutory Declaration of Peter Adrian Walton Rogers, executed on Aug. 9, 2002.
Statutory Declaration of Francis John Ballard, executed on Jul. 16, 2002.
Statutory Declaration of Kari Alitalo, executed on Jul. 16, 2002, and accompanying Exhibit 1.
Statutory Declaration of Susan Power, executed on Mar. 22, 2002, and accompanying Appendices I to IV.

Statutory Declaration of Nicholas Kim Hayward, executed on Mar. 26, 2002.
Statutory Declaration of Stuart A. Aaronson, executed on Mar. 22, 2002, and accompanying Appendices I to III.
Statutory Declaration of Gary Baxter Cox, executed on Mar. 22, 2002, and accompanying Exhibit GBC24 (Statutory Declaration of Peter Adrian Walters, execution on Oct. 26, 2001).
Statutory Declaration of Frances John Ballard, executed on Dec. 12, 2001, and accompanying Exhibit 1.
Statutory Declaration of Kari Alitalo, executed on Sep. 24, 2001, and accompanying Exhibits 1 and 2.
Statutory Declaration of Peter Adrian Walton Rogers, executed on Nov. 12, 2001, and accompanying Exhibits PAWR1 to PAWR14.
Statutory Declaration of John Stanley Mattick, executed on Dec. 12, 2000, and accompanying Exhibits JSM1 to JSM4.
Statutory Declaration of Nicholas Kim Hayward, executed on Dec. 8, 2000, and accompanying Exhibits NKH 1 and 2.
Statutory Declaration of Jennifer Ruth Gamble, executed on Dec. 12, 2000, and accompany Exhibits JRG 1 to 3.
Statutory Declaration of Tom Rapoport, executed on Dec. 13, 2000, and accompanying Exhibits TP 1 and 2.
Statutory Declaration of Stuart A. Aaronson, executed on Dec. 14, 2000, and accompanying CV.
Statutory Declaration of Susan Power, executed on Dec. 13, 2000, and accompanying Appendices 1 to 2 and Figure 1.
Statutory Declaration of Gary Baxter Cox, executed on Dec. 13, 2000, and accompanying Exhibits GBC 1 to 23.
Statutory Declaration of Peter Adrian Walton Rogers, executed on Feb. 16, 2000, and accompanying Exhibit 1.
Statutory Declaration of Frances John Ballard, executed on Feb. 16, 2000, and accompanying Exhibit 1.
Statutory Declaration of Kari Alitalo, executed on Feb. 15, 2000, and accompany Exhibits 1 to 3.
European Supplementary Search Report, Application No. EP 01 96 3814, mailed Jul. 14, 2004.
Supplementary Partial European Search Report, Application No. EP 02 72 6730, mailed Aug. 4, 2004.
Supplementary Partial European Search Report, Application No. EP 02 72 1715, mailed Jan. 10, 2005.
Supplementary Partial European Search Report, Application No. EP 02 72 1715, mailed Oct. 22, 2004.
EBI Accession No. AAW27553, Knappik et al., "Human Ab heavy chain variable region VH3 consensus" (Jan. 23, 1998).
Supplementary European Search Report, Application No. EP 02 72 6730, mailed Oct. 25, 2004.
Supplementary European Search Report, Application No. EP 00 90 5992, mailed Nov. 8, 2004.
Joosten et al., "The production of antibody fragments and antibody fusion proteins by yeasts and filamentous fungi," *Microbial Cell Factories* 2:1 (Jan. 30, 2003).
Skerra et al., "Assembly of a functional immunoglobulin Fv fragment in *Escherichia coli*,"*Science* 240(4855):1038-1041 (May 20, 1988).
Better et al., "*Escherichia coli* secretion of an active chimeric antibody fragment," *Science* 240(4855):1041-1043 (May 20, 1988).
Verma et al., "Gene therapy—promises, problems and prospects," Nature 389:239-242 (1997).
Houck, et al., "The vascular endothelial growth factor family: identification of a fourth molecular species and characterization of alternative splicing of RNA." Molecular Endocrinology. 5(12):1806-14 (1991).
Colwell, et al., "Method for generating a high frequency of hybridomas producing monoclonal IgA antibodies." Methods Enzymol. 121:42-51 (1986).
Schlaeppi, et al., "Characterization of a new potent, in vivo neutralizing monoclonal antibody to human vascular endothelial growth factor." J Cancer Res. Clin. Oncol. 125:336-342 (1999).
Van der Flier, et al., "Antibody neutralization of vascular endothelial growth factor (VEGF) fails to attenuate vascular permeability and brain edema in experimental pneumococcal meningitis." J Neuroimmunology 160:170-177 (2005).
Winkler, et al., "Changing the antigen binding specificity by single point mutations of an Anti-p24 (HIV-1) antibody." J Immunology 165:4505-4514 (2000).

U.S. Appl. No. 11/980,495, inventors Rosen et al., filed Oct. 31, 2007.

U.S. Non-Provisional Patent Application No. *To be determined*, inventors Rosen et al., filed Apr. 1, 2008.

U.S. Appl. No. 12/258,109, inventors Rosen et al., filed Oct. 24, 2008 (Not Published).

U.S. Appl. No. 12/258,140, inventors Anderson et al., filed Oct. 24, 2008 (Not Published).

Extended European Search Report for European Application No. 08153873.8, mailed Oct. 13, 2008, European Patent Office, Berlin, Germany.

Tobe, T., et al., "Evolution of Neovascularization in Mice with Overexpression of Vascular Endothelial Growth Factor in Photoreceptors," *Invest. Opthalmol. Vis. Sci.* 39:180-188, Association for Research in Vision and Ophthalmology (Jan. 1998).

Vinores, S.A., et al., "Cellular mechanisms of blood-retinal barrier dysfunction in macular edema," *Documenta Opthalmologica* 97: 217-228 (Jan. 1999).

\* cited by examiner

```
      GTCCTTCCACCATGCACTCGCTGGGCTTCTTCTCTGTGGCCTGTTCTCTGCTGCCGCTG
  1   ----+----|----+----|----+----|----+----|----+----|----+----|   60
      CAGGAAGGTGGTACGTGAGCGACCCGAAGAAGAGACACCGGACAAGAGACGAGGGCGAC
                M  H  S  L  G  F  F  S  V  A  C  S  L  L  A  A  A  -

CGCTGCTCCCGGGTCCTCGGAGGCGCCCGACGCGCTCCGGCGGCGCGAAGCTCAGGCCTGAGC
 61   ----+----|----+----|----+----|----+----|----+----|----+----|  120
      GCGACGAGGGCCCAGGAGCGCTCCGCGGGCCGCCGCGCTTCGAGTCCGGACTCG
            L  L  P  G  P  R  E  A  P  A  A  A  A  F  E  S  G  L  D  -

ACCTCTCGGACGGGAGCCCGACGCGGAGCCCAGGCTTATGCAAGCAAAGATCTGG
121   ----+----|----+----|----+----|----+----|----+----|----+----|  180
      TGGAGAGCCTGCGCCTCGGGCTGCGCCGGTTCGTTTCTAGACC
            L  S  D  A  E  P  D  A  G  E  A  T  A  Y  A  S  K  D  L  E  -

AGGAGCAGTTACGGTTCTGTGTCCAGTGTAGATGAACTCATGACTGTACTCTACCCAGAAT
181   ----+----|----+----|----+----|----+----|----+----|----+----|  240
      TCCTCGTCAATGCCAAGACACAGTTCACATCTACTTGACTACTGAGATGGTCTTA
            E  Q  L  R  S  V  S  S  V  D  E  L  M  T  V  L  Y  P  E  Y  -

ATTGGAAAAATGTACAAGTGTCAGCTAAGGAAAGGAGGCTGGCAACATAACAGAGAACAGG
241   ----+----|----+----|----+----|----+----|----+----|----+----|  300
      TAACCTTTTACATGTTCACAGTCGATTCCTTCCTCCGACCGTTGTATTGTCTCTTGTCC
            W  K  M  Y  K  C  Q  L  R  K  G  G  W  Q  H  N  R  E  Q  A  -

CCAACCTCAACTCAAGGACAGAAGAGACTATAAAAATTGCTGCAGCACATTATAATACAG
```

FIG.1A

```
301 ----------+---------+---------+---------+---------+---------+ 360
    GGTTGGAGTTGAGTTCCTGTCTTCTGATATTTTAAACGACGTCGTGTAATATTATGTC
     N  L  N  S  R  T  E  E  T  I  K  F  A  A  A  H  Y  N  T  E  -

AGATCTTGAAAAGTATATTGATAATGAGTGGAGAAAGACTCAATGCATGCCACGGGAGGTGT
361 ----------+---------+---------+---------+---------+---------+ 420
    TCTAGAACTTTTCATATAACTATTACTCACCTCTTTCTGAGTTACGTACGGTGCCCTCCACA
     I  L  K  S  I  D  N  E  W  R  K  T  Q  C  M  P  R  E  V  C  -

GTATAGATGTGGGAAGGAGTTTGGAGTCGCCGACAAACACCTTCTTTAAACCTCCATGTG
421 ----------+---------+---------+---------+---------+---------+ 480
    CATATCTACACCCCTTCCTCAAACCTCAGCGCTGTTGTGGAAGAAATTTGGAGGTACAC
     I  D  V  G  K  E  F  G  V  A  T  N  T  F  F  K  P  P  C  V  -

TGTCCGTCTACAGATGTGGGGCTTGCTGCAATAGTGAGGGGCTGCAGTGCATGAACACCA
481 ----------+---------+---------+---------+---------+---------+ 540
    ACAGGCAGATGTCTACACCCCCAACGACGTTATCACTCCCGACGTCACGTACTTGTGGT
     S  V  Y  R  C  G  G  C  C  N  S  E  G  L  Q  C  M  N  T  S  -

GCACGAGCTACCTCAGCAAGACGTTATTTGAAATTACAGTGCCTCTCTCTCAAGGCCCCA
541 ----------+---------+---------+---------+---------+---------+ 600
    CGTGCTCGATGGAGTCGTTCTGCAATAAACTTTAATGTCACGGAGAGAGAGTTCCGGGGT
     T  S  Y  L  S  K  T  L  F  E  I  T  V  P  L  S  Q  G  P  K  -

AACCAGTAACAATCAGTTTTGCCAATCACACTTCCTGCCGATGCATGTCTAAACTGGATG
601 ----------+---------+---------+---------+---------+---------+ 660
    TTGGTCATTGTTAGTCAAAACGGTTAGTGTGAAGGACGGCTACAGATTTGACCTAC
     P  V  T  I  S  F  A  N  H  T  S  C  R  C  M  S  K  L  D  V  -
```

```
           V  C  K  N  K  L  F  P  P  S  Q  C  G  A  N  R  E  F  D  E  N  -
      ACACATGCCAGTGTGTATGTAAAGAACCTGCCCCAGAAATCAACCCCTAAATCCTGGAA
1021  ------+---------+---------+---------+---------+---------+  1080
      TGTGTACGGTCACACATACATTTCTTGGACGGGGTCTTTAGTTGGGGATTTAGGACCTT
         T  Q  C  V  C  K  R  T  C  P  R  N  Q  P  L  N  P  G  K  -

AATGTGCCTGTGAATGTACAGAAAGTCCACAGAAATGCTTGTTAAAAGGAAAGAAGTTCC
1081  ------+---------+---------+---------+---------+---------+  1140
      TTACACGGACACTTACATGTCTTTCAGTGTCTTTACGAACAATTTTCCTTTCTTCAAGG
         C  A  C  E  C  T  E  S  P  Q  K  C  L  L  K  G  K  K  F  H  -

ACCACCAAACATGCAGCTGTTACAGACGGCCATGTACGAACCGCCAGAAGGCTTGTGAGC
1141  ------+---------+---------+---------+---------+---------+  1200
      TGGTGGTTTGTACGTCGACAATGTCTGCCGGTACATGCTTGGCGGTCTTCCGAACACTCG
         H  Q  T  C  S  C  Y  R  R  P  C  T  N  R  Q  K  A  C  E  P  -

CAGGATTTCATATAGTGAAGAAGTGTGTCGTTGTGTCCCTTCATATTGGCAAAGACCAC
1201  ------+---------+---------+---------+---------+---------+  1260
      GTCCTAAAGTATATCACTTCTTCACACAGCAACAGGAAGTATAACCGTTTCTGGTG
         G  F  S  Y  S  E  E  V  C  R  C  V  P  S  Y  W  Q  R  P  Q  -

AAATGAGCTAAGATTGTACTGTTTCCAGTTCATGATTTTCTATTATGAAAACTGTGT
```

FIG. 1D

```
1261 ---------+---------+---------+---------+---------+---------+ 1320
     TTTACTCGATTCTAACATGACAAAAGGTCAAGTAGCTAAAAGATAATACCTTTGACACA
                      M  S

TGCCACAGTAGAACTGTCTGTGAACAGAGAGACCCTGTGGGTCCATGCTAACAAAGACA
1321 ---------+---------+---------+---------+---------+---------+ 1380
     ACGGTGTCATCTTGACAGACACTTGTCTCTCTGGGACACCCAGGTACGATTGTTTCTGT

AAAGTCTGTCTTTCCTGAACCATGGATAACTTACAGAAATGGACTGGAGCTCATCTG
1381 ---------+---------+---------+---------+---------+---------+ 1440
     TTTCAGACAGAAAGGACTTGGTACACCTATTGAAATGTCTTACCTGACCTCGAGTAGAC

CAAAAGGCCTCTTGTAAAGACTGGTTTCTGCCAATGACCAAACAGCCAAGATTTCCTC
1441 ---------+---------+---------+---------+---------+---------+ 1500
     GTTTTCCGGAGAACATTCTGACCAAAGACGGTTACTGGTTGTCGGTTCTAAAAGGAG

TTGTGATTCTTAAAAGAATGACTATATAATTTATTCCACTAAAAATATTGTTTCTGC
1501 ---------+---------+---------+---------+---------+---------+ 1560
     AACACTAAAGAATTTCTTACTGATATATTAAATAAGGTGATTTTATAACAAAGACG

ATTCATTTTATAGCAACAACAATTGTAAAACTCACTGTGATCAATATTTTATATCAT
1561 ---------+---------+---------+---------+---------+---------+ 1620
     TAAGTAAAATATCGTTGTTGTTAACCATTTGAGTGACACTAGTTATAAAATATAGTA

GCAAAATATGTTTAAAATAAAAATGAAAATTGTATTTATAAAAAAAAAAAAAA
1621 ---------+---------+---------+---------+---------+---- 1674
     CGTTTTATACAAATTTATTTTACTTTAACATAAATATTTTTTTTTTTT
```

FIG.1E

```
  1  CGAGGCCACGGCTTATGCAAGCAAAGATCTGGAGGAGCAGTTACGGTCTCTGTGTCCAGTGT
     -------+---------+---------+---------+---------+---------+
                       M  T  V  L  Y  P  E  Y  W  K  M  Y  K  C  Q  L  R

61  AGATGAACTCATGACTGTACTCTACCCAGAATATTGGAAAATGTACAAGTGTCAGCTAAG
     -------+---------+---------+---------+---------+---------+
       K  G  G  W  Q  H  N  R  E  Q  A  N  L  N  S  R  T  E  E  T

121  GAAAGGAGGCTGGCAACATAACAGAGAACAGGCCAACCTCAACTCAAGGACACAGAAGAGAC
     -------+---------+---------+---------+---------+---------+
         I  K  F  A  A  A  H  Y  N  T  E  I  L  K  S  I  D  N  E  W

181  TATAAAATTTGCTGCAGCACATTATAATACAGAGATCTTGAAAAGTATTGATAATGAGTG
     -------+---------+---------+---------+---------+---------+
           R  K  T  Q  C  M  P  R  E  V  C  I  D  V  G  K  E  F  G  V

241  GAGAAAGACTCAATGCATGCCACGGGAGGTGTGTATAGATGTGGGAAGGAGTTTGGAGT
     -------+---------+---------+---------+---------+---------+
             A  T  N  T  F  F  K  P  P  C  V  S  V  Y  R  C  G  G  C

301  CGCGACAAACACCTTCTTTAAACCTCCATGTGTCCGTCTACAGATGTGGGGGTTGCTG
     -------+---------+---------+---------+---------+---------+

FIG. 2A
```

```
361  CAATAGTGAGGGGCTGCAGTGCATGAACACCAGCACGAGCTACCTCAGCAAGACGTTATT
     ------------+---------+---------+---------+---------+---------+
      N  S  E  G  L  Q  C  M  N  T  S  T  S  Y  L  S  K  T  L  F

421  TGAAATTACAGTGCCTCTCTCAAGGCCCCAAACCAGTAACAATCAGTTTGCCAATCA
     ------------+---------+---------+---------+---------+---------+
      E  I  T  V  P  L  S  Q  G  P  K  P  V  T  I  S  F  A  N  H

481  CACTTCCTGCCGATGCATGTCTAAACTGGATGTTTACAGACAAGTTCATTCCATTATTAG
     ------------+---------+---------+---------+---------+---------+
      T  S  C  R  C  M  S  K  L  D  V  Y  R  Q  V  H  S  I  I  R

541  ACGTTCCCTGCCAGCAACACTACCACAGTGTCAGGCAGGCGAACAAGACCTGCCCCACCAA
     ------------+---------+---------+---------+---------+---------+
      R  S  L  P  A  T  L  P  Q  C  Q  A  A  N  K  T  C  P  T  N

601  TTACATGTGGAATAATCACATCTGCAGATGCCTCAGGAAGATTTTATGTTTTCCTC
     ------------+---------+---------+---------+---------+---------+
      Y  M  W  N  N  H  I  C  R  C  L  A  Q  E  D  F  M  F  S  S

661  GGATGCTGGAGATGACTCAACAGATGGATTCCATGACATCTGTGGACCAAACAAGGAGCT
     ------------+---------+---------+---------+---------+---------+
      D  A  G  D  D  S  T  D  G  F  H  D  I  C  G  P  N  K  E  L
```

FIG. 2B

```
721  GGATGAAGAGACCTGTCTCAGTGTGTCTGCCAGAGCGGGCTTCGGCCTGCCAGCTGTGGACC
     ----+----|----+----|----+----|----+----|----+----|----+----|
      D  E  E  T  C  Q  C  V  C  R  A  G  L  R  P  A  S  C  G  P

781  CCACAAAGAACTAGACAGAAACTCATGCCAGTGTGTCTGTAAAACAAACTCTTCCCAG
     ----+----|----+----|----+----|----+----|----+----|----+----|
      H  K  E  L  D  R  N  S  C  Q  C  V  C  K  N  K  L  F  P  S

841  CCAATGTGGGGCCAACCCAGAATTTGATGAAAACACAGCCAGTGTGTATGTAAAAGAAC
     ----+----|----+----|----+----|----+----|----+----|----+----|
      Q  C  G  A  N  R  E  F  D  E  N  T  C  Q  C  V  C  K  R  T

901  CTGCCCCAGAAATCAACCCCTAAATCCTGGAAAATGTGCCTGTGAATGTACAGAAAGTCC
     ----+----|----+----|----+----|----+----|----+----|----+----|
      C  P  R  N  Q  P  L  N  P  G  K  C  A  C  E  C  T  E  S  P

961  ACAGAAATGCTTGTTAAAGGAAAGAAGTTCCACCACCAAACATGCAGCTGTTACAGAACG
     ----+----|----+----|----+----|----+----|----+----|----+----|
      Q  K  C  L  L  K  G  K  K  F  H  H  Q  T  C  S  C  Y  R  R

1021 GCCATGTACGAACCGCCAGAAGGCTTGTGAGCCAGGATTTTCATATAGTGAAGAAGTGTG
     ----+----|----+----|----+----|----+----|----+----|----+----|
      P  C  T  N  R  Q  K  A  C  E  P  G  F  S  Y  S  E  E  V  C
```

FIG. 2C

```
1081  TCGTTGTGTGTCCCTTCATATATTGGCAAAGACCACCACAAATGAGCTAAGATTGTACTGTTTCA
       R  C  V  P  S  Y  W  Q  R  P  Q  M  S

1141  GTTCATCGATTTTCTATTATGGAAAACTGTGTTGCCACAGTAGAACTGTCTGTGAACAGA

1201  GAGACCCTTGTGGGTCCATGCTAACAAAGACAAAGTCTGTCTTTCCTGAACCATGTGGA

1261  TAACTTTACAGAAATGGACTGGAGCTCATCTGCAAAAGGCCTCTTGTAAAGACTGGTTTT

1321  CTGCCAATGACCAAACAGCCAAGATTTTCCTCTGTGATTTCTTTAAAAGAATGACTATA

1381  TAATTTTATTCCACTAAAAAAATATGTTCTGCATTCATTTTTATAGCAACAACAATTGT

1441  AAAACTCACTGTGATCAATATTTTTATATCATGCAAAATATGTTTAAAATAAATGAAA

1501  TTGTATTTATAAAAAAAAAAAAAA
```

FIG. 2D

```
      1                                                                    50
Pdgfa  .MRTLACLLL LGCGYLAHVL AEEAEIPREV IERLARSQIH SIRDLQRLLE
Pdgfb  MNRCWA.LFL SLCCYLRLVS AEGDPIPEEL YEMLSDHSIR SFDDLQRLLH
Vegf   .....MNFLL SWVHWSLALL LY................ .LHHAKWSQA
Vegf2  .......MTV LYPEYWKMYK CQ................. .LRKGGWQHN 51                                                                   100
Pdgfa  IDSVGSEDSL DTSLRAHGVH ATKHVPEKRP LPIRRKRSI. ......EEAVP
Pdgfb  GDP.GEEDGA ELDLNMTRSH SGGELES... .LARGRRSLG SLTIAEPAMI
Vegf   APMAE..... ......GGGQ NHHEVVKFMD .VYQR..... ..........
Vegf2  REQANLNSRT EETIKFAAAH YNTEILKSID NEWRK..... ..........

101                                                                  150
Pdgfa  AVCKTRTVIY EIPRSQVDPT SANFLIWPPC VEVKRCTGCC NTSSVKCQPS
Pdgfb  AECKTRTEVF EISRRLIDRT NANFLVWPPC VEVQRCSGCC NNRNVQCRPT
Vegf   SYCHPIETLV DIFQEYPDEI .EYIFKPSC VPLMRCGGCC NDEGLECVPT
Vegf2  TQCMPREVCI DVGKEFGVAT ..NTFFKPPC VSVYRCGGCC NSEGLQCMNT 151                                                                  200
Pdgfa  RVHHRSVKVA KVEYVRKKPK LKEVQVRLEE HLECAC.... AT........
Pdgfb  QVQLRPVQVR KIEIVRKKPI FKKATVLED HLACKC.... ETVAAARPVT
Vegf   EESNITMQIM RIK.PH..QG QHIGEMSFLQ HNKCECRPKK DRARQEKKSV
Vegf2  STSYLSKTLF EIT.VPLSQG PKPVTISFAN HTSCRCMSKL DVYRQVHSII
```

FIG. 3A

```
        201                                                                  250
Pdgfa   .....TSLNPD YREEDTDVR. .......... .......... ..........
Pdgfb   RSPGGSQEQR AKTPQTRVTI RTVRVRRPPK GKHRKFKHTH DKTALKETLG
Vegf    RGK....... .GKGQKRKRK KSRYKSWSVY VGARCCLMPW SLPGPHP...
Vegf2   RRSLPATLPQ CQAANKTCPT NYMWNNHICR CLAQEDFMFS SDAGDDSTDG 251                                                                  300
Pdgfa   .......... .......... .......... .......... ..........
Pdgfb   A......... .......... .......... .......... ..........
Vegf    ...CGP.... .......CSE RRKHLFVQDP ...DR QTCKCSCKNT
Vegf2   FHDICGPNKE LDEETCQCVC RAGLRPASCG PHKEL     NSCQCVCKNK 301                                                                  350
Pdgfa   .......... .......... .......... .......... ..........
Pdgfb   .......... .......... .......... .......... ..........
Vegf    ...DSRCKARQ LELNERTCRC DKPRR..... .......... ..........
Vegf2   .EFDENTCQC. VCKRTCPRNQ PLNPGKCACE CTESPQKCLL ..........

351                                                                  398
Pdgfa   .......... .......... .......... .......... ..........
Pdgfb   .......... .......... .......... .......... ..........
Vegf    .......... .......... .......... .......... ..........
Vegf2   KGKKFHHQTC SCYRRPCTNR QKACEPGFSY SEEVCRCVPS YWQRPQMS
```

FIG. 3B

| PERCENTAGE (%) OF AMINO ACID IDENTITIES BETWEEN EACH PAIR OF GENES IS SHOWN IN THE FOLLWING TABLE | | | | |
|---|---|---|---|---|
| | PDGFα | PDGFβ | VEGF | VEGF2 |
| PDGFβ | 48.0 | | | |
| VEGF | 20.7 | 22.7 | | |
| VEGF2 | 23.5 | 22.4 | 30.0 | |

FIG. 4

Expression of VEGF2 mRNA in Human Breast Tumor Cells

Lane 1. normal breast tissue
Lane 2. breast tumor tissue
Lane 3-9. breast tumor cell lines.

Expression of VEGF2 mRNA in human adult tissues.

Lane 1: 14-C and rainbow M.W. marker
Lane 2: FGF control
Lane 3: VEGF2 (M13-reverse & forward primers)
Lane 4: VEGF2 (M13-reverse & VEGF-F4 primers)
Lane 5: VEGF2 (M13-reverse & VEGF-F5 primers)

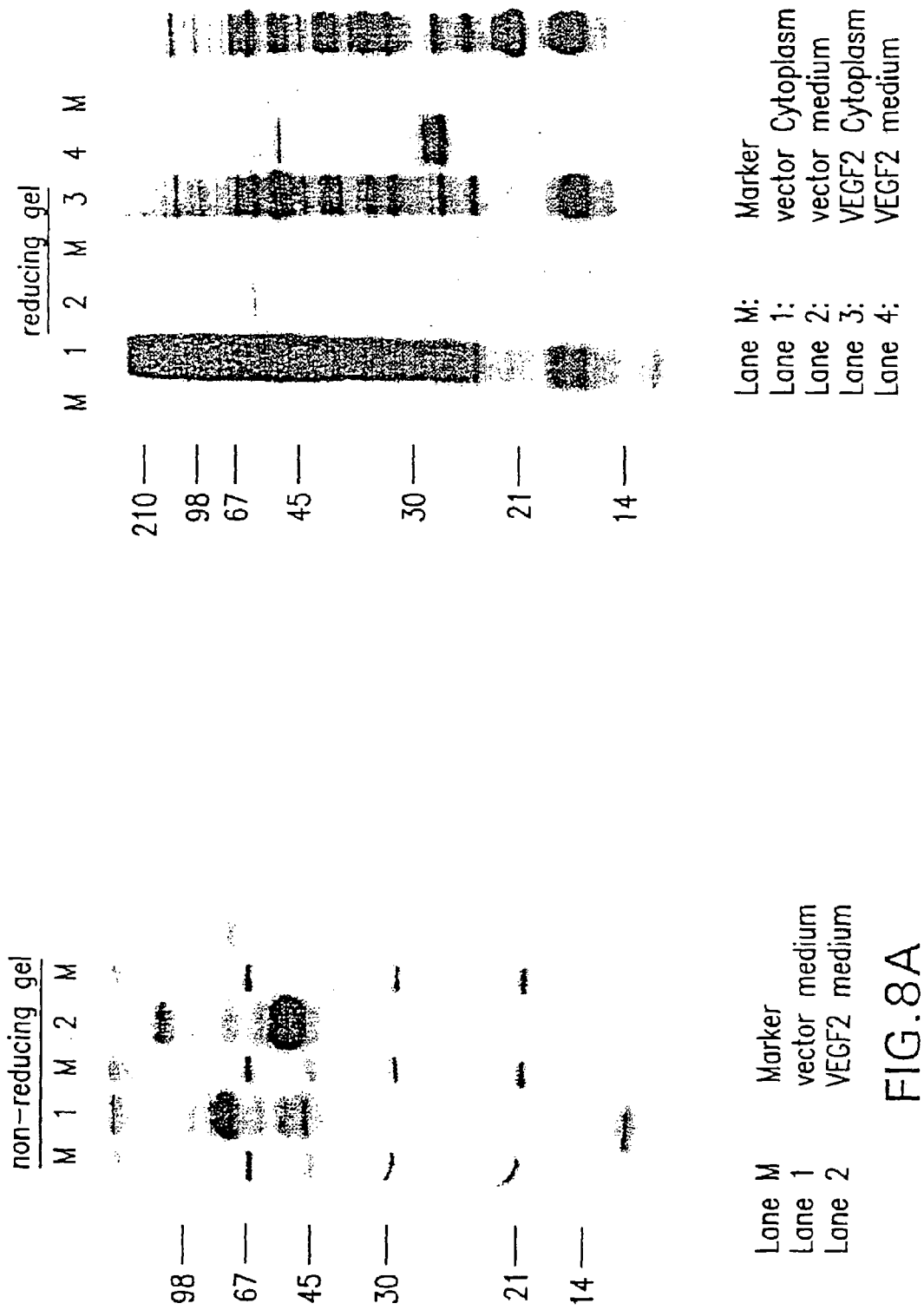

Lane 1: Molecular weight marker
Lane 2: Precipitates containing VEGF2.

```
  1 AAGCTTAAAAAAACTGCAAAAAATAGTT TTGACT(TGTGAGCGGATAAGAAT
                                        -35        OPERATOR 1

50 TAACCCAT GTACCCA(ATTGTGAGCGGATAACAAT)TTCACACATTAA
       -10              OPERATOR 2

94 A GAGGAG AAATTA CATATG
       S/D
```

FIG.13

MURINE VEGF-2 MAB STATUS

| | ISOTYPE | REL. AFFINITY ng/ml | SPECIFICITY | REACTIVITY | | PURIFIED mg |
|---|---|---|---|---|---|---|
| | | | | WESTERN | ELISA | |
| 12E2 | γ1 | <1 | C-1 | + | + | 27 |
| 13A2 | γ1 | <1 | C-1 | n.t | + | 27 |
| 15C2 | γ1 | <1 | C-1 | n.t | + | 10 |
| 13D6 | γ1 | 1 | N | + | + | 25 |
| 13E6 | γ1 | 1 | N | + | + | 38 |
| 19A3 | γ1 | 5 | N | + | + | 54 |
| 8G11 | γ1 | <1 | C-2 | + | + | 7 |
| 11A8 | γ1 | | C-3 | + | + | 9 |

FIG.25

METHODS OF TREATING AN INJURY TO, OR DISORDER OF, THE EYE INVOLVING PHOTORECEPTOR PROLIFERATION BY ADMINISTERING VEGF2 ANTIBODIES

CROSS-REFERENCE TO RELATED APPLICATIONS

This application is a divisional of U.S. application Ser. No. 09/499,468, filed Feb. 7, 2000, which issued as U.S. Pat. No. 7,223,724 on May 29, 2007 and which claims benefit of U.S. Provisional Application No. 60/119,179, filed on Feb. 8, 1999, U.S. Provisional Application No. 60/119,926, filed Feb. 12, 1999, U.S. Provisional Application No. 60/137,796, filed Jun. 3, 1999, and U.S. Provisional Application No. 60/171,505, filed Dec. 22, 1999. Each of the five aforementioned applications are hereby incorporated by reference in their entireties.

REFERENCE TO SEQUENCE LISTING ON COMPACT DISC

This application refers to a "Sequence Listing" listed below, which is provided as an electronic document on two identical compact discs (CD-R), labeled "Copy 1" and "Copy 2." These compact discs each contain the file "PF112U1D1 SeqList.txt" (created Feb. 25, 2005, byte size=52,861 bytes), which is hereby incorporated by reference in its entirety.

BACKGROUND OF THE INVENTION

1. Field of the Invention

The present invention relates to newly identified polynucleotides, polypeptides encoded by such polynucleotides, the use of such polynucleotides and polypeptides, as well as the production of such polynucleotides and polypeptides. The polypeptides of the present invention have been identified as members of the vascular endothelial growth factor family. More particularly, the polypeptides of the present invention are human vascular endothelial growth factor 2 (VEGF2). The invention also relates to inhibiting the action of such polypeptides. Additionally, the present invention relates to antibodies directed to the polypeptides of the present invention. The present invention also relates to the administration of vascular endothelial growth factor 2 (VEGF-2) polynucleotides and polypeptides to treat disorders of or injuries to photoreceptor cells.

2. Related Art

The formation of new blood vessels, or angiogenesis, is essential for embryonic development, subsequent growth, and tissue repair. Angiogenesis is also an essential part of certain pathological conditions, such as neoplasia (i.e., tumors and gliomas). Abnormal angiogenesis is associated with other diseases such as inflammation, rheumatoid arthritis, psoriasis, and diabetic retinopathy (Folkman, J. and Klagsbrun, M., *Science* 235:442-447(1987)).

Both acidic and basic fibroblast growth factor molecules are mitogens for endothelial cells and other cell types. Angiotropin and angiogenin can induce angiogenesis, although their functions are unclear (Folkman, J., *Cancer Medicine*, Lea and Febiger Press, pp. 153-170 (1993)). A highly selective mitogen for vascular endothelial cells is vascular endothelial growth factor or VEGF (Ferrara, N. et al., *Endocr. Rev.* 13:19-32 (1992)), which is also known as vascular permeability factor (VPF).

Vascular endothelial growth factor is a secreted angiogenic mitogen whose target cell specificity appears to be restricted to vascular endothelial cells. The murine VEGF gene has been characterized and its expression pattern in embryogenesis has been analyzed. A persistent expression of VEGF was observed in epithelial cells adjacent to fenestrated endothelium, e.g., in choroid plexus and kidney glomeruli. The data was consistent with a role of VEGF as a multifunctional regulator of endothelial cell growth and differentiation (Breier, G. et al., *Development* 114:521-532 (1992)).

VEGF shares sequence homology with human platelet-derived growth factors, PDGFa and PDGFb (Leung, D. W., et al., *Science* 246:1306-1309, (1989)). The extent of homology is about 21% and 23%, respectively. Eight cysteine residues contributing to disulfide-bond formation are strictly conserved in these proteins. Although they are similar, there are specific differences between VEGF and PDGF. While PDGF is a major growth factor for connective tissue, VEGF is highly specific for endothelial cells. Alternatively spliced mRNAs have been identified for both VEGF, PLGF, and PDGF and these different splicing products differ in biological activity and in receptor-binding specificity. VEGF and PDGF function as homo-dimers or hetero-dimers and bind to receptors which elicit intrinsic tyrosine kinase activity following receptor dimerization.

VEGF has four different forms of 121, 165, 189 and 206 amino acids due to alternative splicing. VEGF121 and VEGF165 are soluble and are capable of promoting angiogenesis, whereas VEGF189 and VEGF206 are bound to heparin containing proteoglycans in the cell surface. The temporal and spatial expression of VEGF has been correlated with physiological proliferation of the blood vessels (Gajdusek, C. M., and Carbon, S. J., *Cell Physiol.* 139:570-579 (1989); McNeil, P. L., et al., *J. Cell. Biol.* 109:811-822 (1989)). Its high affinity binding sites are localized only on endothelial cells in tissue sections (Jakeman, L. B., et al., *Clin. Invest.* 89:244-253 (1989)). The factor can be isolated from pituitary cells and several tumor cell lines, and has been implicated in some human gliomas (Plate, K. H., *Nature* 359:845-848 (1992)). Interestingly, expression of VEGF121 or VEGF165 confers on Chinese hamster ovary cells the ability to form tumors in nude mice (Ferrara, N. et al., *J. Clin. Invest.* 91:160-170 (1993)). The inhibition of VEGF function by anti-VEGF monoclonal antibodies was shown to inhibit tumor growth in immune-deficient mice (Kim, K. J., *Nature* 362:841-844 (1993)). Further, a dominant-negative mutant of the VEGF receptor has been shown to inhibit growth of glioblastomas in mice.

Vascular permeability factor (VPF) has also been found to be responsible for persistent microvascular hyperpermeability to plasma proteins even after the cessation of injury, which is a characteristic feature of normal wound healing. This suggests that VPF is an important factor in wound healing. Brown, L. F. et al., *J. Exp. Med.*176:1375-1379 (1992).

The expression of VEGF is high in vascularized tissues, (e.g., lung, heart, placenta and solid tumors) and correlates with angiogenesis both temporally and spatially. VEGF has also been shown to induce angiogenesis in vivo. Since angiogenesis is essential for the repair of normal tissues, especially vascular tissues, VEGF has been proposed for use in promoting vascular tissue repair (e.g., in atherosclerosis).

U.S. Pat. No. 5,073,492, issued Dec. 17, 1991 to Chen et al., discloses a method for synergistically enhancing endothelial cell growth in an appropriate environment which comprises adding to the environment, VEGF, effectors and serum-derived factor. Also, vascular endothelial cell growth factor C sub-unit DNA has been prepared by polymerase chain reaction techniques. The DNA encodes a protein that may exist as either a heterodimer or homodimer. The protein is a mammalian vascular endothelial cell mitogen and, as such, is useful for the promotion of vascular development and repair, as disclosed in European Patent Application No. 92302750.2, published Sep. 30, 1992.

The Retina. The differentiated retina is composed of seven cell types: sensory (rod and cone photoreceptors), glia (Muller cells), and two types of neurons, interneurons, (horizontal, bipolar, and amacrine), and projection neurons (ganglion cells). The development of the various cell types in the retina does not occur synchronously with the majority of the cones, and ganglion and horizontal cells developing before birth. In contrast, differentiation of a majority of the rods, the main cell type in the rat retina, occurs postnatally. Clonal analysis of the progeny of retinal precursor cells has demonstrated that these progenitor cells can produce various combinations of retinal cell types indicating that at least some of the progenitors are multipotential. Furthermore, findings from both in vivo and in vitro studies suggest that the final phenotype of the cell is largely lineage independent which suggest that the changing microenvironment within the retina has a role in determining the cellular potential of the progenitor cells as well as the differentiated phenotype of the progeny.

In vitro, retinal cell proliferation and differentiation is regulated by a variety of factors, for example, FGF-2, CNTF, LIF, TGF, retinoic acid, and BDNF, as well as by extracellular matrix and cell adhesion molecules, for example s-laminin. Yang and Cepko (*J. Neurosci.* 16(19):6089-6099 (1996)) and more recently Wen et al. (*J. Biol. Chem.* 273(4):2090-2097 (1998)) have identified and characterized the expression pattern of VEGFR-2/FLK-1, a member of the VEGF receptor family. VEGFR transcripts are first detected at E11.5 in association with the developing retinal vasculature and with the central region of the neural retina (Yang and Cepko, *J. Neurosci.* 16(19):6089-6099 (1996)). Although it is not known if the two events are related, this developmental period is also marked by the onset of ganglion cell development. By developmental day E15, VEGFR-2 expression extends to the periphery of the retina consistent with the outward gradient of retinal development. VEGFR-2 expression was largely localized to the ventricular zone during the perinatal period when neurogenesis is at its peak and a large number of post-mitotic neurons are being formed.

The PDGF/VEGF superfamily currently includes 7 members. The 5 members of the VEGF sub-family bind to 4 different VEGF tyrosine kinase receptors with distinct but overlapping specificities. VEGF, a 34-36 kDa homodimeric glycoprotein that is the prototypic family member, binds to VEGFR-1 and VEGFR-2. VEGF-B and VEGF-D bind only to VEGFR-1 or VEGFR-3, respectively. While VEGF-C, VEGF-2, has the highest affinity for VEGFR-3, it also binds with a lower affinity to VEGFR-2. Once activated the VEGF receptors tyrosine phosphorylate a number of proteins downstream in the signal transduction pathway including phosphatidylinositol 3-kinase, phospholipase C, GAP, and Nck.

The hereditary retinal degenerative diseases ("HRD diseases") are a group of inherited conditions in which progressive, bilateral degeneration of retinal structures leads to loss of retinal function; these diseases include, for example, age-related macular degeneration, a leading cause of visual impairment in the elderly; Leber's congenital amaurosis, which causes its victims to be born blind; and retinitis pigmentosa ("RP"). RP is the name given to those inherited retinopathies which are characterized by loss of retinal photoreceptors (rods and cones), with retinal electrical responses to light flashes (i.e. electroretinograms, or "ERGs") that are reduced in amplitude. As the disease progresses, patients show attenuated retinal arterioles, and frequently show "bone spicule" pigmentation of the retina and waxy pallor of the optic discs.

The incidence of RP in the United States is estimated to be about 1:3500 births. Familial cases of RP usually present in childhood with night blindness and loss of midperipheral visual field due to the loss of rods in the peripheral retina. As the condition progresses, contraction of the visual fields eventually leads to blindness. Signs on fundus examination in advanced stages include retinal vessel attenuation, intraretinal pigment in the peripheral fundus, and waxy pallor of the optic disc. Patients have abnormal light-evoked electrical responses from the retina (i.e., electroretinograms or ERGs), even in the early stages in the absence of visible abnormalities on fundus examination. Histopathologic studies have revealed widespread loss of photoreceptors in advanced stages. Therefore, there is a need in the art for methods of treating photoreceptor cell disorders and injuries.

SUMMARY OF THE INVENTION

The polypeptides of the present invention have been identified as a novel vascular endothelial growth factor based on amino acid sequence homology to human VEGF.

In accordance with one aspect of the present invention, there are provided novel mature polypeptides, as well as biologically active and diagnostically or therapeutically useful fragments, analogs, and derivatives thereof. The polypeptides of the present invention are of human origin.

In accordance with another aspect of the present invention, there are provided isolated nucleic acid molecules comprising polynucleotides encoding full length or truncated VEGF-2 polypeptides having the amino acid sequences shown in SEQ ID NOS:2 or 4, respectively, or the amino acid sequences encoded by the cDNA clones deposited in bacterial hosts as ATCC™ Deposit Number 97149 on May 12, 1995 or ATCC™ Deposit Number 75698 on Mar. 4, 1994.

The present invention also relates to biologically active and diagnostically or therapeutically useful fragments, analogs, and derivatives of VEGF-2.

In accordance with still another aspect of the present invention, there are provided processes for producing such polypeptides by recombinant techniques comprising culturing recombinant prokaryotic and/or eukaryotic host cells, containing a nucleic acid sequence encoding a polypeptide of the present invention, under conditions promoting expression of said proteins and subsequent recovery of said proteins.

In accordance with yet another aspect of the present invention, there are provided antibodies against such polypeptides and processes for producing such antibodies.

In accordance with another aspect of the present invention, there are provided nucleic acid probes comprising nucleic acid molecules of sufficient length to specifically hybridize to nucleic acid sequences of the present invention.

In accordance with another aspect of the present invention, there are provided methods of diagnosing diseases or a susceptibility to diseases related to mutations in nucleic acid sequences of the present invention and proteins encoded by such nucleic acid sequences.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

In accordance with yet a further aspect of the present invention, there are provided processes for utilizing such polypeptides, or polynucleotides encoding such polypeptides for therapeutic purposes, for example, to protect or stimulate growth of photoreceptor cells.

In accordance with yet another aspect of the present invention, there are provided antagonists to such polypeptides, which may be used, for example, to inhibit or prevent photoreceptor growth.

These and other aspects of the present invention should be apparent to those slilled in the art from the teachings herein.

BRIEF DESCRIPTION OF THE FIGURES

FIGS. 1A-1E show the full length nucleotide (SEQ ID NO:1) and the deduced amino acid (SEQ ID NO:2) sequence of VEGF-2. The polypeptide comprises approximately 419 amino acid residues of which approximately 23 represent the leader sequence. The standard one letter abbreviations for amino acids are used. Sequencing was performed using the Model 373 Automated DNA Sequencer (Applied Biosystems, Inc.). Sequencing accuracy is predicted to be greater than 97%.

FIGS. 2A-2D show the nucleotide (SEQ ID NO:3) and the deduced amino acid (SEQ ID NO:4) sequence of a truncated, biologically active form of VEGF-2. The polypeptide comprises approximately 350 amino acid residues of which approximately the first 24 amino acids represent the leader sequence.

FIGS. 3A-3B are an illustration of the amino acid sequence homology between PDGFa (SEQ ID NO:5), PDGFb (SEQ ID NO:6), VEGF (SEQ ID NO:7), and VEGF-2 (SEQ ID NO:4). The boxed areas indicate the conserved sequences and the location of the eight conserved cysteine residues.

FIG. 4 shows, in table-form, the percent homology between PDGFa, PDGFb, VEGF, and VEGF-2.

FIGS. 8A and 8B depict photographs of SDS-PAGE gels. VEGF-2 polypeptide was expressed in a baculovirus system consisting of Sf9 cells. Protein from the medium and cytoplasm of cells were analyzed by SDS-PAGE under non-reducing (FIG. 8A) and reducing (FIG. 8B) conditions.

FIG. 13 shows the nucleotide sequence of the regulatory elements of the pHE promoter (SEQ ID NO:10). The two lac operator sequences, the Shine-Delgarno sequence (S/D), and the terminal HindIII and NdeI restriction sites (italicized) are indicated.

FIG. 25 shows the status of the murine VEGF-2 monoclonal antibodies.

DETAILED DESCRIPTION OF THE PREFERRED EMBODIMENTS

Figure 1C:
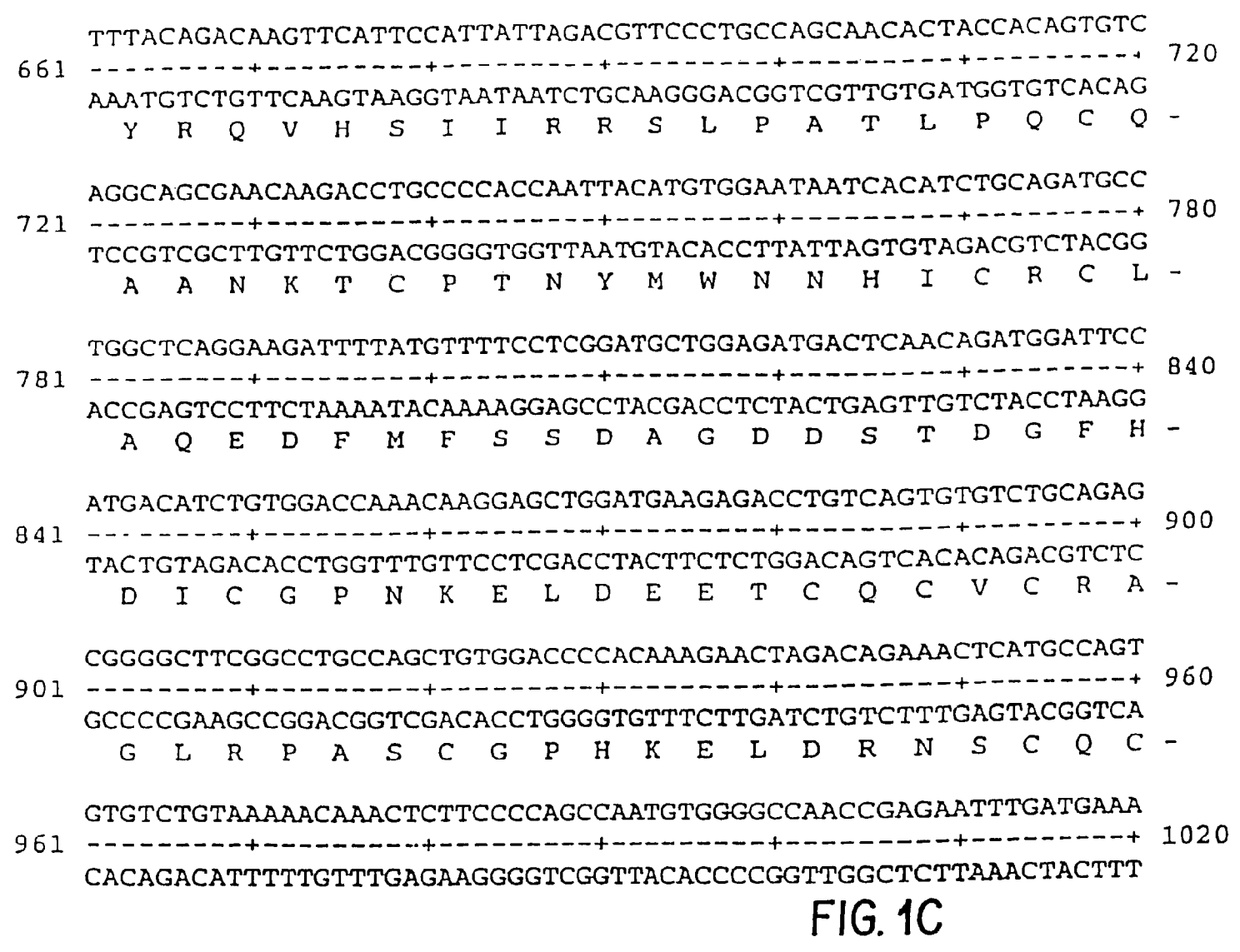
Figure 5:
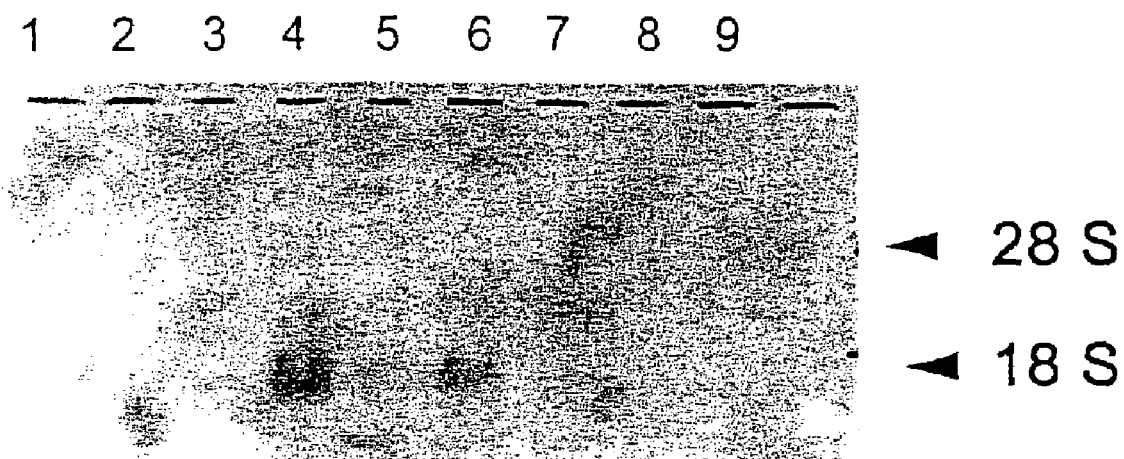
FIG. 5 shows the presence of VEGF-2 mRNA in human breast tumor cell lines.

In accordance with one aspect of the present invention, there are provided isolated nucleic acid molecules comprising a polynucleotide encoding a VEGF-2 polypeptide having the deduced amino acid sequence of FIG. 1 (SEQ ID NO:2), which was determined by sequencing a cloned cDNA. The nucleotide sequence shown in SEQ ID NO:1 was obtained by sequencing a cDNA clone, which was deposited on May 12, 1995 at the American Type Tissue Collection (ATCC™), 10801 University Boulevard, Manassas, Va. 20110-2209, and given ATCC™ Deposit No. 97149.

In accordance with another aspect of the present invention, there are provided isolated nucleic acid molecules comprising a polynucleotide encoding a truncated VEGF-2 polypeptide having the deduced amino acid sequence of FIG. 2 (SEQ ID) NO:4), which was determined by sequencing a cloned cDNA. The nucleotide sequence shown in SEQ ID NO:3 was obtained by sequencing a cDNA clone, which was deposited on Mar. 4, 1994 at the American Type Tissue Collection (ATCC™), 10801 University Boulevard, Manassas, Va. 20110-2209, and given ATCC™ Deposit Number 75698.

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

A polynucleotide encoding a polypeptide of the present invention may be obtained from early stage human embryo (week 8 to 9) osteoclastomas, adult heart or several breast cancer cell lines. The polynucleotide of this invention was discovered in a cDNA library derived from early stage human embryo week 9. It is structurally related to the VEGF/PDGF family. It contains an open reading frame encoding a protein of about 419 amino acid residues of which approximately the first 23 amino acid residues are the putative leader sequence such that the mature protein comprises 396 amino acids, and which protein exhibits the highest amino acid sequence homology to human vascular endothelial growth factor (30% identity), followed by PDGFa (24%) and PDGFb (22%). (See FIG. 4). It is particularly important that all eight cysteines are conserved within all four members of the family (see boxed areas of FIG. 3). In addition, the signature for the PDGF/VEGF family, PXCVXXXRCXGCCN, (SEQ ID NO:8) is conserved in VEGF-2 (see FIG. 3). The homology between VEGF-2, VEGF and the two PDGFs is at the protein sequence level. No nucleotide sequence homology can be detected, and therefore, it would be difficult to isolate the VEGF-2 through simple approaches such as low stringency hybridization.

The VEGF-2 polypeptide of the present invention is meant to include the full length polypeptide and polynucleotide sequence which encodes for any leader sequences and for active fragments of the full length polypeptide. Active fragments are meant to include any portions of the full length amino acid sequence which have less than the full 419 amino acids of the full length amino acid sequence as shown in SEQ ID NO:2, but still contain the eight cysteine residues shown conserved in FIG. 3 and that still have VEGF-2 activity.

There are at least two alternatively spliced VEGF-2 mRNA sequences present in normal tissues. The two bands in FIG. 7, lane 5 indicate the presence of the alternatively spliced mRNA encoding the VEGF-2 polypeptide of the present invention.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 or FIG. 2, or that of the deposited clones, or may be a different coding sequence which, as a result of the redundancy or degeneracy of the genetic code, encodes the same, mature polypeptide as the DNA of FIG. 1, FIG. 2, or the deposited cDNAs.

The polynucleotide which encodes for the mature polypeptide of FIG. 1 or FIG. 2 or for the mature polypeptides encoded by the deposited cDNAs may include: only the coding sequence for the mature polypeptide; the coding sequence for the mature polypeptide and additional coding sequences such as a leader or secretory sequence or a proprotein sequence; the coding sequence for the mature polypeptide (and optionally additional coding sequences) and non-coding sequences, such as introns or non-coding sequence 5' and/or 3' of the coding sequence for the mature polypeptide.

Thus, the term "polynucleotide encoding a polypeptide" encompasses a polynucleotide which includes only coding sequences for the polypeptide as well as a polynucleotide which includes additional coding and/or non-coding sequences.

The present invention further relates to variants of the hereinabove described polynucleotides which encode for fragments, analogs, and derivatives of the polypeptide having the deduced amino acid sequence of FIG. 1 or 2, or the polypeptide encoded by the cDNA of the deposited clones. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1 or 2 or the same mature polypeptide encoded by the cDNA of the deposited clones as well as variants of such polynucleotides which variants encode for a fragment, derivative, or analog of the polypeptides of FIGS. 1 or 2, or the polypeptide encoded by the cDNA of the deposited clones. Such nucleotide variants include deletion variants, substitution variants, and addition or insertion variants.

As hereinabove indicated, the polynucleotide may have a coding sequence which is a naturally occurring allelic variant of the coding sequence shown in FIG. 1 or 2, or of the coding sequence of the deposited clones. As known in the art, an allelic variant is an alternate form of a polynucleotide sequence which have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g COS-7 cells, is used. The HA tag corresponds to an epitope derived from the influenza hemagglutinin protein (Wilson, I., et al., *Cell* 37:767 (1984)).

Further embodiments of the invention include isolated nucleic acid molecules comprising a polynucleotide having a nucleotide sequence at least 95% identical, and more preferably at least 96%, 97%, 98% or 99% identical to (a) a nucleotide sequence encoding the polypeptide having the amino acid sequence in SEQ ID NO:2; (b) a nucleotide sequence encoding the polypeptide having the amino acid sequence in SEQ ID NO:2, but lacking the N-terminal methionine; (c) a nucleotide sequence encoding the polypeptide having the amino acid sequence at positions from about 1 to about 396 in SEQ ID NO:2; (d) a nucleotide sequence encoding the polypeptide having the amino acid sequence encoded by the cDNA clone contained in ATCC™ Deposit No.97149; (e) a nucleotide sequence encoding the mature VEGF-2 polypeptide having the amino acid sequence encoded by the cDNA clone contained in ATCC™ Deposit No.97149; or (f) a nucleotide sequence complementary to any of the nucleotide sequences in (a), (b), (c), (d), or (e).

Further embodiments of the invention include isolated nucleic acid molecules comprising a polynucleotide having a nucleotide sequence at least 95% identical, and more preferably at least 96%, 97%, 98% or 99% identical to (a) a nucleotide sequence encoding the polypeptide having the amino acid sequence in SEQ ID NO:4; (b) a nucleotide sequence encoding the polypeptide having the amino acid sequence in SEQ ID NO:4, but lacking the N-terminal methionine; (c) a nucleotide sequence encoding the polypeptide having the amino acid sequence at positions from about 1 to about 326 in SEQ ID NO:4; (d) a nucleotide sequence encoding the polypeptide having the amino acid sequence encoded by the cDNA clone contained in ATCC™ Deposit No.75698; (e) a nucleotide sequence encoding the mature VEGF-2 polypeptide having the amino acid sequence encoded by the cDNA clone contained in ATCC™ Deposit No.75698; or (f) a nucleotide sequence complementary to any of the nucleotide sequences in (a), (b), (c), (d), or (e).

By a polynucleotide having a nucleotide sequence at least, for example, 95% "identical" to a reference nucleotide sequence encoding a VEGF-2 polypeptide is intended that the nucleotide sequence of the polynucleotide is identical to the reference sequence except that the polynucleotide sequence may include up to five point mutations per each 100 nucleotides of the reference nucleotide sequence encoding the VEGF-2 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5N or 3N terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to, for instance, the nucleotide sequence shown in SEQ ID NOS:1 or 3, or to the nucleotides sequence of the deposited cDNA clone(s) can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The VEGF-2 variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred. VEGF-2 polynucleotide variants can be produced for a variety of reasons, e.g., to optimize codon expression for a particular host (change codons in the human mRNA to those preferred by a bacterial host such as *E. coli*).

For example, site directed changes at the amino acid level of VEGF-2 can be made by replacing a particular amino acid with a conservative amino acid. Preferred conservative mutations include: M1 replaced with A, G, I, L, S, T, or V; H2 replaced with K, or R; S3 replaced with A, G, I, L, T,M, or V; L4 replaced with A, G, L S, T, M, or V; G5 replaced with A, I, L, S, T, M, or V; F6 replaced with W, or Y; F7 replaced with W, or Y; S8 replaced with A, G, I, L, T, M, or V; V9 replaced with A, G, I, L, S, T, or M; A10 replaced with G, I, L, S, T, M, or V; S12 replaced with A, G, I, L, T, M, or V;L13 replaced with A, G, I, S, T, M, or V; L14 replaced with A, G, I, S, T, M, or V; A15 replaced with G, I, L, S, T, M, or V; A16 replaced with G, I, L, S,T, M, or V; A17 replaced with G, I, L, S, T, M, or V; L18 replaced with A, G, I, S, T, M, or V; L19 replaced with A, G, I, S, T, M, or V; G21 replaced with A, I, L, S, T, M, or V; R23 replaced with H, or K; E24 replaced with D; A25 replaced with G, I, L, S, T, M, or V; A27 replaced with G, I, L, S, T, M, or V; A28 replaced with G, I, L, S, T, M, or V; A29 replaced with G, I, L, S, T, M, or V; A30 replaced with G, I, L, S, T, M, or V; A31 replaced with G, I, L, S, T, M, or V; F32 replaced with W, or Y; E33 replaced with D; S34 replaced with A, G, I, L, T, M, or V; G35 replaced with A, I, L, S, T, M, or V; L36 replaced with A, G, I, S, T, M, or V; D37 replaced with E; L38 replaced with A, G, I, S, T, M, or V; S39 replaced with A, G, I, L, T, M, or V; D40 replaced with E; A41 replaced with G, I, L, S, T, M, or V; E42 replaced with D; D44 replaced with E; A45 replaced with G, I, L, S, T, M, or V; G46 replaced with A,I, L, S, T, M, or V; E47 replaced with D; A48 replaced with G, I, L, S, T, M, or V; T49 replaced with A, G, I, L, S, M, or V; A50 replaced with G, I, L, S,T, M, or V; Y51 replaced with F, or W; A52 replaced with G, I, L, S, T, M, or V; S53 replaced with A, G, I, L, T, M, or V; K54 replaced with H, or R; D55replaced with E; L56 replaced with A, G, I, S, T, M, or V; E57 replaced with D; E58 replaced with D; Q59 replaced with N; L60 replaced with A, G, I, S, T,M, or V; R61 replaced with H, or K; S62 replaced with A, G, I, L, T, M, or V; V63 replaced with A, G, I, L, S, T, or M; S64 replaced with A, G, I, L, T,M, or V; S65 replaced with A, G, I, L, T, M, or V; V66 replaced with A, G, I, L, S, T, or M; D67 replaced with E; E68 replaced with D; L69 replaced with A, G, I, S, T, M, or V; M70 replaced with A, G, I, L, S, T, or V; T71 replaced with A, G, I, L, S, M, or V; V72 replaced with A, G, I, L, S, T, or M; L73replaced with A, G, I, S, T, M, or V; Y74 replaced with F, or W; E76 replaced with D; Y77 replaced with F, or W; W78 replaced with F, or Y; K79 replaced wit H, or R; M80 replaced with A, G, I, L, S, T, or V; Y81 replaced with F, or W; K82 replaced with H, or R; Q84 replaced with N; L85 replaced with A,G, I, S, T, M, or V; R86 replaced with H, or K; K87 replaced with H, or R; G88 replaced with A, I, L, S, T, M, or V; G89 replaced with A, I, L, S, T, M, or V; W90 replaced with F, or Y; Q91 replaced with N; H92 replaced with K, or R; N93 replaced with Q; R94 replaced with H, or K; E95 replaced with D;Q96 replaced with N; A97 replaced with G, I, L, S, T, M, or V; N98 replaced with Q; L99 replaced with A, G, I, S, T, M, or V; N100 replaced with Q; S101 replaced with A, G, I, L, T, M, or V; R102 replaced with H, or K; T103 replaced with A, G, I, L, S, M, or V; E104 replaced with D; E105 replaced with D;T106 replaced with A, G, I, L, S, M, or V; I107 replaced with A, G, L, S, T, M, or V; K108 replaced with H, or R; F109 replaced with W, or Y; A110replaced with G, I, L, S, T, M, or V; A111 replaced with G, I, L, S, T, M, or V; A112 replaced with G, I, L, S, T, M, or V; H113 replaced with K, or R;Y114 replaced with F, or W; N115 replaced with Q; T116 replaced with A, G, I, L, S, M, or V; E117 replaced with D; I118 replaced with A, G, L, S, T, M, or V; L 19 replaced with A, G, I, S, T, M, or V; K120 replaced with H, or R; S121 replaced with A, G, I, L, T, M, or V; I122 replaced with A, G, L, S, T,M, or V; D123 replaced with E; N124 replaced with Q; E125 replaced with D; W126 replaced with F, or Y; R127 replaced with H, or K; K128 replaced with H, or R; T129 replaced with A, G, I, L, S, M, or V; Q130 replaced with N; M132 replaced with A, G, I, L, S, T, or V; R134 replaced with H, or K; E135replaced with D; V136 replaced with A, G, I, L, S, T, or M; I138 replaced with A, G, L, S, T, M, or V; D139 replaced with E; V140 replaced with A, G, I,L, S, T, or M; G141 replaced with A, I, L, S, T, M, or V; K142 replaced with H, or R; E143 replaced with D; F144 replaced with W, or Y; G145 replaced with A, I, L, S, T, M, or V; V146 replaced with A, G, I, L, S, T, or M; A147 replaced with G, I, L, S, T, M, or V; T148 replaced with A, G, I, L, S, M, or V; N149 replaced with Q; T150 replaced with A, G, I, L, S, M, or V; F151 replaced with W, or Y; F152 replaced with W, or Y; K153 replaced with H, or R;V157 replaced with A, G, I, L, S, T, or M; S158 replaced with A, G, I, L, T, M, or V;V159 replaced with A, G, I, L, S, T, or M;Y160 replaced with F, or W; R161 replaced with H, or K; G163 replaced with A, I, L, S, T, M, or V; G164 replaced with A, I, L, S, T, M, or V; N167 replaced with Q; S168replaced with A, G, I, L, T, M, or V; E169 replaced with D; G170 replaced with A, I, L, S, T, M, or V; L171 replaced with A, G, I, S, T, M, or V; Q172replaced with N; M174 replaced with A, G, I, L, S, T, or V; N175 replaced with Q; T176 replaced with A, G, I, L, S, M, or V; S177 replaced with A, G, I, L, T, M, or V; T178 replaced with A, G, I, L, S, M, or V; S179 replaced with A, G, I, L, T, M, or V; Y180 replaced with F, or W; L181 replaced with A,G, I, S, T, M, or V; S182 replaced with A, G, I, L, T, M, or V; K183 replaced with H, or R; T184 replaced with A, G, I, L, S, M, or V; L185 replaced with A, G, I, S, T, M, or V; F186 replaced with W, or Y; E187 replaced with D; I188 replaced with A, G, L, S, T, M, or V; T189 replaced with A, G, I, L, S, M, or V; V190 replaced with A, G, I, L, S, T, or M; L192 replaced with A, G, I, S, T, M, or V; S193 replaced with A, G, I, L, T, M, or V; Q194 replaced with N; G195 replaced with A, I, L, S, T, M, or V; K197 replaced with H, or R; V199 replaced with A, G, I, L, S, T, or M; T200 replaced with A, G, I, L, S, M, or V; I201 replaced with A, G, L, S, T, M, or V; S202 replaced with A, G, I, L, T, M, or V; F203 replaced with W, or Y; A204 replaced with G, I, L, S, T,M, or V; N205 replaced with Q; H206 replaced with K, or R; T207 replaced with A, G, I, L, S, M, or V; S208 replaced with A, G, I, L, T, M, or V; R210replaced with H, or K; M212 replaced with A, G, I, L, S, T, or V; S213 replaced with A, G, I, L, T, M, or V; K214 replaced with H, or R; L215 replaced with A, G, I, S, T, M, or V; D216 replaced with E; V217 replaced with A, G, I, L, S, T, or M; Y218 replaced with F, or W; R219 replaced with H, or K;Q220 replaced with N; V221 replaced with A, G, I, L, S, T, or M; H222 replaced with K, or R; S223 replaced with A, G, I, L, T, M, or V; I224 replaced with A, G, I, L, S, T, M, or V; I225 replaced with A, G, I, L, S, T, M, or V; R226 replaced wit H, or K; R227 replaced with H, or K, S228 replaced with A,G, I, L, T, M, or V; L229 replaced with A, G, I, S, T, M, or V;A231 replaced with G, I, L, S, T, M, or V; T232 replaced with A, G, I, L, S, M, or V; L233replaced with A, G, I, S, T, M, or V; Q235 replaced with N; Q237 replaced with N; A238 replaced with G, I, L, S, T, M, or V; A239 replaced with G, I, L,S, T, M, or V; N240 replaced with Q; K241 replaced with H, or R; T242 replaced with A, G, I, L, S, M, or V; T245 replaced with A, G, I, L, S, M, or V;N246 replaced with Q; Y247 replaced with F, or W; M248 replaced with A, G, I, L, S, T, or V; W249 replaced with F, or Y; N250 replaced with Q; N251 replaced with Q; H252 replaced with K, or R; I253 replaced with A, G, L, S, T, M, or V; R255 replaced with H, or K; L257 replaced with A, G, I, S, T, M, or V; A258 replaced with G, I, L, S, T, M, or V; Q259 replaced with N; E260 replaced with D; D261 replaced with E; F262 replaced with W, or Y; M263 replaced with A, G, I, L, S, T, or V; F264 replaced with W, or Y; S265 replaced with A, G, I, L, T, M, or V; S266 replaced with A, G, I, L, T, M, or V; D267 replaced with E; A268 replaced with G, I, L, S, T, M, or V; G269 replaced with A, I, L, S, T, M, or V; D270 replaced with E; D271 replaced with E; S272 replaced with A, G, I, L, T, M, or V; T273 replaced with A, G, I, L, S, M, or V; D274 replaced with E; G275 replaced with A, I, L, S, T, M, or V; F276 replaced with W, or Y; H277 replaced with K, or R; D278 replaced with E; I279 replaced with A, G, L, S, T, M, or V; G281 replaced with A, I, L, S, T, M, or V; N283 replaced with Q; K284 replaced with H, or R; E285 replaced with D; L286 replaced with A, G, I, S, T, M, or V; D287 replaced with E; E288 replaced with D; E289 replaced with D; T290 replaced with A, G, I, L, S, M, or V; Q292 replaced with N; V294 replaced with A, G, I, L, S, T, or M; R296 replaced with H, or K; A297 replaced with G, I, L, S, T, M, or V; G298 replaced with A, I, L, S, T, M, or V; L299 replaced with A, G, I, S, T, M, or V; R300 replaced with H, or K; A302 replaced with G, I, L, S, T, M, or V; S303 replaced with A, G, I, L, T, M, or V; G305 replaced with A, I, L, S, T, M, or V; H307 replaced with K, or R; K308 replaced with H, or R; E309 replaced with D; L310 replaced with A, G, I, S, T, M, or V; D311 replaced with E; R312 replaced with H, or K; N313 replaced with Q; S314 replaced with A, G, I, L, T, M, or V; Q316 replaced with N; V318 replaced with A, G, I, L, S, T, or M; K320 replaced with H, or R; N321 replaced with Q; K322 replaced with H, or R; L323 replaced with A, G, I, S, T, M, or V; F324 replaced with W, or Y; S326 replaced with A, G, I, L, T, M, or V; Q327 replaced with N; G329 replaced with A, I, L, S, T, M, or V; A330 replaced with G, I, L, S, T, M, or V; N331 replaced with Q; R332 replaced with H, or K; E333 replaced with D; F334 replaced with W, or Y; D335 replaced with E; E336 replaced with D; N337 replaced with Q; T338 replaced with A, G, I, L, S, M, or V; Q340 replaced with N; V342 replaced with A, G, I, L, S, T, or M; K344 replaced with H, or R; R345 replaced with H, or K; T346 replaced with A, G, I, L, S, M, or V; R349 replaced with H, or K; N350 replaced with Q; Q351 replaced with N; L353 replaced with A, G, I, S, T, M, or V; N354 replaced with Q; G356 replaced with A, I, L, S, T, M, or V; K357 replaced with H, or R; A359 replaced with G, I, L, S, T, M, or V; E361 replaced with D; T363 replaced with A, G, I, L, S, M, or V; E364 replaced with D; S365 replaced with A, G, I, L, T, M, or V; Q367 replaced with N; K368 replaced with H, or R; L370 replaced with A, G, I, S, T, M, or V; L371 replaced with A, G, I, S, T, M, or V; K372 replaced with H, or R; G373 replaced with A, I, L, S, T, M, or V; K374 replaced with H, or R; K375 replaced with H, or R; F376 replaced with W, or Y; H377 replaced with K, or R; H378 replaced with K, or R; Q379 replaced with N; T380 replaced with A, G, I, L, S, M, or V; S382 replaced with A, G, I, L, T, M, or V; Y384 replaced with F, or W; R385 replaced with H, or K; R386 replaced with H, or K; T389 replaced with A, G, I, L, S, M, or V; N390 replaced with Q; R391 replaced with H, or K; Q392 replaced with N; K393 replaced with H, or R; A394 replaced with G, I, L, S, T, M, or V; E396 replaced with D; G398 replaced with A, I, L, S, T, M, or V; F399 replaced with W, or Y; S400 replaced with A, G, I, L, T, M, or V; Y401 replaced with F, or W; S402 replaced with A, G, I, L, T, M, or V; E403 replaced with D; E404 replaced with D; V405 replaced with A, G, I, L, S, T, or M; R407 replaced with H, or K; V409 replaced with A, G, I, L, S, T, or M; S411 replaced with A, G, I, L, T, M, or V; Y412 replaced with F, or W; W413 replaced with F, or Y; Q414 replaced with N; R415 replaced with H, or K; Q417 replaced with N; M418 replaced with A, G, I, L, S, T, or V; and/or S419 replaced with A, G, I, L, T, M, or V of FIG. 1A-1E.

The resulting constructs can be routinely screened for activities or functions described throughout the specification and known in the art. Preferably, the resulting constructs have an increased and/or a decreased VEGF-2 activity or function, while the remaining VEGF-2 activities or functions are maintained. More preferably, the resulting constructs have more than one increased and/or decreased VEGF-2 activity or finction, while the remaining VEGF-2 activities or functions are maintained.

Besides conservative amino acid substitution, variants of VEGF-2 include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, VEGF-2 polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331-340 (1967); Robbins et al., Diabetes 36: 838-845 (1987); Cleland et al., Crit Rev. Therapeutic Drug Carrier Systems 10:307-377 (1993).)

For example, preferred non-conservative substitutions of VEGF-2 include: M1 replaced with D, E, H, K, R, N, Q, F, W, Y, P, or C; H2 replaced with D, E, A, G, I, L,S, T, M, V, N, Q, F, W, Y, P, or C; S3 replaced with D, E, H, K, R, N, Q, F, W, Y, P, or C; L4 replaced with D, E, H, K, R, N, Q, F, W, Y, P, or C; G5replaced with D, E, H, K, R, N, Q, F, W, Y, P, or C; F6 replaced with D, E, H, K, R, N, Q, A, G, I, L, S, T, M, V, P, or C; F7 replaced with D, E, H, K,R, N, Q, A, G, I, L, S, T, M, V, P, or C; S8 replaced with D, E, H, K, R, N, Q, F, W, Y, P, or C; V9 replaced with D, E, H, K, R, N, Q, F, W, Y, P, or C; A10 replaced with D, E, H, K, R, N, Q, F, W, Y, P, or C; C11replaced with D, E, H, K, R, A, G,I, L, S, T, M, V, N, Q, F, W, Y, or P; S12 replaced with D, E, H, K, R, N, Q, F, W, Y, P, or C; L13 replaced with D, E, H, K, R, N, Q, F, W, Y, P, or C; L14 replaced with D, E, H, K, R, N, Q, F, W, Y,P, or C; A15 replaced with D, E, H, K, R, N, Q, F, W, Y, P, or C; A16 replaced with D, E, H, K, R, N, Q, F, W, Y, P, or C;A17 replaced with D, E, H,K, R, N, Q, F, W, Y, P, or C; L18 replaced with D, E, H, K, R, N, Q, F, W, Y, P, or C; L19 replaced with D, E, H, K, R, N, Q, F, W, Y, P, or C; P20replaced with D, E, H, K, R, A, G, I, L, S, T, M, V, N, Q, F, W, Y, or C; G21 replaced with D, E, H, K, R, N, Q, F, W, Y, P, or C; P22 replaced with D,E, H, K, R, A, G, I, L, S, T, M, V, N, Q, F, W, Y, or C; R23 replaced with D, E, A, G, I, L, S, T, M, V, N, Q, F, W, Y, P, or C; E24 replaced with H,K, R, A, G, I, L, S, T, M, V, N, Q, F, W, Y, P, or C; A25 replaced with D, E, H, K, R, N, Q, F, W, Y, P, or C; P26 replaced with D, E, H, K, R, A, G,I, L, S, T, M, V, N, Q, F, W, Y, or C; A27 replaced with D, E, H, K, R, N, Q, F, W, Y, P, or C; A28 replaced with D, E, H, K, R, N, Q, F, W, Y, P, or C; A29 replaced with D, E, H, K, R, N, Q, F, W, Y, P, or C; A30 replaced with D, E, H, K, R, N, Q, F, W, Y, P, or C; A31 replaced with D, E, H, K, N, Q, F, W, Y, P, or C; F32 replaced with D, E, H, K, R, N, Q, A, G, I, L, S, T, M, V, P, or C; E33 replaced with H, K, R, A, G, I, L, S, T, M, V, N,Q, F, W, Y, P, or C; S34 replaced with D, E, H, K, R, N, Q, F, W, Y, P, or C; G35 replaced with D, E, H, K, R, N, Q, F, W, Y, P, or C; L36 replaced with D, E, H, K, R, N, Q, F, W, Y, P, or C; D37 replaced with H, K, R, A, G, I, L, S, T, M, V, N, Q, F, W, Y, P, or C; L38 replaced with D, E, H, K,R, N, Q, F, W, Y, P, or C; S39 replaced with D, E, H, K, R, N, Q, F, W, Y, P, or C; D40 replaced with H, K, R, A, G, I, L, S, T, M, V, N, Q, F, W, Y,P, or C; A41 replaced with D, E, H, K, R, N, Q, F, W, Y, P, or C; E42 replaced with H, K, R, A, G, I, L, S, T, M, V, N, Q, F, W, Y, P, or C; P43replaced with D, E, H, K, R, A, G, I, L, S, T, M, V, N, Q, F, W, Y, or C; D44 replaced with H, K, R, A, G, I, L, S, T, M, V, N, Q, F, W, Y, P, or C;A45 replaced with D, E, H, K, R, N, Q, F, W, Y, P, or C; G46 replaced with D, E, H, K, R, N, Q, F, W, Y, P, or C; E47 replaced with H, K, R, A, G, I, L, S, T, M, V, N, Q, F, W, Y, P, or C; A48 replaced with D, E, H, K, R, N, Q, F, W, Y, P, or C; T49 replaced with D, E, H, K, N, Q, F, W, Y, P, or C; A50 replaced with D, E, H, K, R, N, Q, F, W, Y, P, or C; Y51 replaced with D, E, H, K, R, N, Q, A, G, I, L, S, T, M, V, P, or C; A52 replaced with D, E, H,K, R, N, Q, F, W, Y, P, or C; S53 replaced with D, E, H, K, R, N, Q, F, W, Y, P, or C; K54 replaced with D, E, A, G, I, L, S, T, M, V,N, Q,F, W, Y, P, or C;D55replaced with H, K, R, A, G, I, L, S, T, M, V, N, Q, F, W, Y, P, or C; L56 replaced with D, E, H, K, R, N, Q, F, W, Y, P, or C;E57 replaced with H, K, R, A, G, I, L, S, T, M, V, N, Q, F, W, Y, P, or C; E58 replaced with H, K, R, A, G, I, L, S, T, M, V, N, Q, F, W, Y, P, or C;Q59 replaced with D, E, H, K, R, A, G, I, L, S, T, M, V, F, W, Y, P, or C; L60 replaced with D, E, H, K, R, N, Q, F, W, Y, P, or C; R61 replaced with D, E, A, G, I, L, S, T, M, V, N, Q, F, W, Y, P, or C; S62 replaced with D, E, H, K, R, N, Q, F, W, Y, P, or C; V63 replaced with D, E, H, K, R, N, Q,F, W, Y, P, or C; S64 replaced with D, E, H, K, R, N, Q, F, W, Y, P, or C; S65 replaced with D, E, H, K, R, N, Q, F, W, Y, P, or C; V66 replaced with D, E, H, K, R, N, Q, F, W, Y, P, or C; D67 replaced with H, K, R, A, G, I, L, S, T, M, V, N, Q, F, W, Y, P, or C; E68 replaced with H, K, R, A, G, I, L, S, T, M, V, N, Q, F, W, Y, P, or C; L69 replaced with D, E, H, K, R, N, Q, F, W, Y, P, or C; M70 replaced with D, E, H, K, N, Q, F, W, Y, P, or C; T71 replaced with D, E, H, K, R, N, Q, F, W, Y, P, or C; V72 replaced with D, E, H, K, R, N, Q, F, W, Y, P, or C; L73 replaced with D, E, H, K, R,N, Q, F, W, Y, P, or C; Y74 replaced with D, E, H, K, R, N, Q, A, G, I, L, S, T, M, V, P, or C; P75 replaced with D, E, H, K, R, A, G, I, L, S, T, M,V, N, Q, F, W, Y, or C; E76 replaced with H, K, R, A, G, I, L, S, T, M, V, N, Q, F, W, Y, P, or C; Y77 replaced with D, E, H, K, R, N, Q, A, G, I, L, S, T, M, V, P, or C; W78 replaced with D, E, H, K, R, N, Q, A, G, I, L, S, T, M, V, P, or C; K79 replaced with D, E, A, G, I, L, S, T, M, V, N, Q, F,W, Y, P, or C; M80 replaced with D, E, H, K, R, N, Q, F, W, Y, P, or C; Y81 replaced with D, E, H, K, R, N, Q, A, G, I, L, S, T, M, V, P, or C; K82replaced with D, E, A, G, I, L, S, T, M, V, N, Q, F, W, Y, P, or C; C83 replaced with D, E, H, K, R, A, G, I, L, S, T, M, V, N, Q, F, W, Y, or P; Q84replaced with D, E, H, K, R, A, G, I, L, S, T, M, V, F, W, Y, P, or C; L85 replaced with D, E, H, K, R, N, Q, F, W, Y, P, or C; R86 replaced with D, E, A, G, I, L, S, T, M, V, N, Q, F, W, Y, P, or C; K87 replaced with D, E, A, G, I, L, S, T, M, V, N, Q, F, W, Y, P, or C; G88 replaced with D, E, H, K, R, N, Q, F, W, Y, P, or C; G89 replaced with D, E, H, K, R, N, Q, F, W, Y, P, or C; W90 replaced with D, E, H, K, R, N, Q, A, G, I, L, S, T, M, V, P, or C; Q91 replaced with D, E, H, K, R, A, G, I, L, S, T, M, V, F, W, Y, P, or C; H92 replaced with D, E, A, G, I, L, S, T, M, V, N, Q, F, W, Y, P, or C;N93 replaced with D, E, H, K, R, A, G, I, L, S, T, M, V, F, W, Y, P, or C; R94 replaced with D, E, A, G, I, L, S, T, M, V, N, Q, F, W, Y, P, or C; E95replaced with H, K, R, A, G, I, L, S, T, M, V, N, Q, F, W, Y, P, or C; Q96 replaced with D, E, H, K, R, A, G, I, L, S, T, M, V, F, W, Y, P, or C; A97replaced with D, E, H, K, R, N, Q, F, W, Y, P, or C; N98 replaced with D, E, H, K, R, A, G, I, L, S, T, M, V, F, W, Y, P, or C; L99replaced with D, E, H, K, R, N, Q, F, W, Y, P, or C; N100 replaced with D, E, H, K, R, A, G, I, L, S, T, M, V, F, W, Y, P, or C; S101 replaced with D, E, H, K, R, N, Q, F, W, Y, P, or C; R102 replaced with D, E, A, G, I, L, S, T, M, V, N, Q, F, W, Y, P, or C; T103 replaced with D, E, H, K, R, N, Q, F, W, Y, P, or C;E104 replaced with H, K, R, A, G, I, L, S, T, M, V, N, Q, F, W, Y, P, or C; E105 replaced with H, K, R, A, G, I, L, S, T, M, V, N, Q, F, W, Y, P, or C; T106 replaced with D, E, H, K, R, N, Q, F, W, Y, P, or C; I107 replaced with D, E, H, K, R, N, Q, F, W, Y, P, or C; K108 replaced with D, E, A, G, I, L, S, T, M, V, N, Q, F, W, Y, P, or C; F109 replaced with D, E, H, K, R, N, Q, A, G, I, L, S, T, M, V, P, or C; A110 replaced with D, E, H, K, R, N, Q, F, W, Y, P, or C; A111 replaced with D, E, H, K, R, N, Q, F, W, Y, P, or C; A112 replaced with D, E, H, K, R, N, Q, F, W, Y, P, or C; H113replaced with D, E, A, G, I, L, S, T, M, V, N, Q, F, W, Y, P, or C; Y114 replaced with D, E, H, K, R, N, Q, A, G, I, L, S, T, M, V, P, or C; N115replaced with D, E, H, K, R, A, G, I, L, S, T, M, V, F, W, Y, P, or C;T116 replaced with D, E, H, K, R, N, Q, F, W, Y, P, or C; E117replaced with H, K, R, A, G, I, L, S, T, M, V, N, Q, F, W, Y, P, or C; I118 replaced with D, E, H, K, R, N, Q, F, W, Y, P, or C; L119 replaced with D, E, H, K, R, N, Q, F, W, Y, P, or C; K120 replaced with D, E, A, G, I, L, S, T, M, V, N, Q, F, W, Y, P, or C; S121 replaced with D, E, H, K, R, N, Q, F, W, Y, P, or C; I122 replaced with D, E, H, K, R, N, Q, F, W, Y, P, or C; D123 replaced with H, K, R, A, G, I, L, S, T, M, V, N, Q, F, W, Y, P, or C; N124 replaced with D, E, H, K, R, A, G, I, L, S, T, M, V, F, W, Y, P, or C; E125 replaced with H, K, R, A, G, I, L, S, T, M, V, N, Q, F, W, Y, P, or C; W126 replaced with D, E, H, K, R, N, Q, A, G, I, L, S, T, M, V, P, or C; R127 replaced with D, E, A, G, I, L, S, T, M, V, N, Q, F, W, Y, P, or C; K128 replaced with D, E, A, G, I, L, S, T, M, V, N, Q, F, W, Y, P, or C; T129 replaced with D, E, H, K, R, N, Q, F, W, Y, P, or C; Q130 replaced with D, E, H, K, R, A, G, I, L, S, T, M, V, F, W, Y, P, or C; C131 replaced with D, E, H, K, R, A, G, I, L, S, T, M, V, N, Q, F, W, Y, or P; M132 replaced with D, E, H, K, R, N, Q, F, W, Y, P, or C; P133 replaced with D, E, H, K, R, A, G, I, L, S, T, M, V, N, Q, F, W, Y, or C; R134 replaced with D, E, A, G, I, L, S, T, M, V, N, Q, F, W, Y, P, or C; E135 replaced with H, K, R, A, G, I, L, S, T, M, V, N, Q, F, W, Y, P, or C; V136 replaced with D, E, H, K, R, N, Q, F, W, Y, P, or C; C137 replaced with D, E, H, K, R, A, G, I, L, S, T, M, V, N, Q, F, W, Y, or P; I138 replaced with D, E, H, K, R, N, Q, F, W, Y, P, or C; D139 replaced with H, K, R, A, G, I, L, S, T, M, V, N, Q, F, W, Y, P, or C; V140 replaced with D, E, H, K, R, N, Q, F, W, Y, P, or C;G141 replaced with D, E, H, K, R, N, Q, F, W, Y, P, or C; K142 replaced with D, E, A, G, I, L, S, T, M, V, N, Q, F, W, Y, P, or C; E143 replaced with H, K, R, A, G, I, L, S, T, M, V, N, Q, F, W, Y, P, or C; F144 replaced with D, E, H, K, R, N, Q, A, G, I, L, S, T, M, V, P, or C; G145 replaced with D, E, H, K, R, N, Q, F, W, Y, P, or C; V146 replaced with D, E, H, K, R, N, Q, F, W, Y, P, or C; A147 replaced with D, E, H, K, R, N, Q, F, W, Y, P, or C; T148 replaced with D, E, H, K, R, N, Q, F, W, Y, P, or C; N149 replaced with D, E, H, K, R, A, G, I, L, S, T, M, V, F, W, Y, P, or C; T150 replaced with D, E, H, K, R, N, Q, F, W, Y, P, or C; F151 replaced with D, E, H, K, R, N, Q, A, G, I, L, S, T, M, V, P, or C; F152 replaced with D, E, H, K, P, N, Q, A, G, I, L, S, T, M, V, P, or C; K153 replaced with D, E, A, G, I, L, S, T, M, V, N, Q, F, W, Y, P, or C; P154 replaced with D, E, H, K, R, A, G, I, L, S, T, M, V, N, Q, F, W, Y, or C; P155 replaced with D, E, H, K, R, A, G, I, L, S, T, M, V, N, Q, F, W, Y, or C; C156 replaced with D, E, H, K, R, A, G, I, L, S, T, M, V, N, Q, F, W, Y, or P; V157 replaced with D, E, H, K, R, N, Q, F, W, Y, P, or C; S158 replaced with D, E, H, K, R, N, Q, F, W, Y, P, or C; V159 replaced with D, E, H, K, R, N, Q, F, W, Y, P, or C; Y160 replaced with D, E, H, K, R, N, Q, A, G, I, L, S, T, M, V, P, or C;R161 replaced with D, E, A, G, I, L, S, T, M, V, N, P, or C; C162 replaced with D, E, H, K, R, A, G, I, L, S, T, M, V, N, Q, F, W, Y, or P;G163 replaced with D, E, H, K, R, N, Q, F, W, Y, P, or C; G164 replaced with D, E, H, K, R, N, Q, F, W, Y, P, or C; C165 replaced with D, E, H, K, R, A, G, I, L, S, T, M, V, N, Q, F, W, Y, or P; C166 replaced with D, E, H, K, R, A, G, I, L, S, T, M, V, N, Q, F, W, Y, or P; N167 replaced with D, E,H, K, R, A, G, I, L, S, T, M, V, F, W, Y, P, or C; S168 replaced with D, E, H, K, R, N, Q, F, W, Y, P, or C; E169 replaced with H, K, R, A, G, I, L, S, T, M, V, N, Q, F, W, Y, P, or C; G170 replaced with D, E, H, K, R, N, Q, F, W, Y, P, or C;L171 replaced with D, E, H, K, R, N, Q, F, W, Y, P, or C;Q172 replaced with D, E, H, K, R, A, G, I, L, S, T, M, V, F, W, Y, P, or C; C173 replaced with D, E, H, K, R, A, G, I, L, S, T, M, V, N, Q, F, W, Y, or P; M174 replaced with D, E, H, K, R, N, Q, F, W, Y, P, or C; N175 replaced with D, E, H, K, R, A, G, I, L, S, T, M, V, F, W, Y, P, or C; T176 replaced with D, E, H, K, R, N, Q, F, W, Y, P, or C; S177 replaced with D, E, H, K, R, N, Q, F, W, Y, P, or C; T178 replaced with D, E, H, K, R, N, Q, F, W, Y, P, or C; S179 replaced with D, E, H, K, R, N, Q, F, W, Y, P, or C;Y180 replaced with D, E, H, K, R, N, Q, A, G, I, L, S, T, M, V, P, or C;L181 replaced with D, E, H, K, R, N, Q, F, W, Y, P, or C; S182 replaced with D, E, H, K, R, N, Q, F, W, Y, P, or C; K183 replaced with D, E, A, G, I, L, S, T, M, V, N, Q, F, W, Y, P, or C; T184 replaced with D, E, H, K, R, N, Q, F, W, Y, P, or C; L185 replaced with D, E, H, K, R, N, Q, F, W, Y, P, or C; F186 replaced with D, E, H, K, R, N, Q, A, G, I, L, S, T, M, V, P, or C; E187 replaced with H, K, R, A, G, I, L, S, T, M, V, N, Q, F, W, Y, P, or C; I188 replaced with D, E, H, K, R, N, Q, F, W, Y, P, or C; T189 replaced with D, E, H, K, R, N, Q, F, W, Y, P, or C; V190 replaced with D, E, H, K, R, N, Q, F, W, Y, P, or C; P191 replaced with D, E, H, K, R, A, G, I, L, S, T, M, V, N, Q, F, W, Y, or C; L192 replaced with D, E, H, K, R, N, Q, F, W, Y, P, or C; S193 replaced with D, E, H, K, R, N, Q, F, W, Y, P, or C; Q194 replaced with D, E, H, K, R, A, G, I, L, S, T, M, V, F, W, Y, P, or C;G195 replaced with D, E, H, K, R, N, Q, F, W, Y, P, or C; P196 replaced with D, E, H, K, R, A, G, I, L, S, T, M, V, N, Q, F, W, Y, or C; K197 replaced with D, E, A, G, I, L, S, T, M, V, N, Q, F, W, Y, P, or C; P198 replaced with D, E, H, K, R, A, G, I, L, S, T, M, V, N, Q, F, W, Y,or C; V199 replaced with D, E, H, K, R, N, Q, F, W, Y, P, or C; T200 replaced with D, E, H, K, R, N, Q, F, W, Y, P, or C; I201 replaced with D, E, H, K, R, N, Q, F, W, Y, P, or C; S202 replaced with D, E, H, K, R, N, Q, F, W, Y, P, or C; F203 replaced with D, E, H, K, R, N, Q, A, G, I, L, S, T, M, V, P, or C;A204 replaced with D, E, H, K, R, N, Q, F, W, Y, P, or C; N205 replaced with D, E, H, K, R, A, G, I, L, S, T, M, V, F, W, Y, P, or C; H206 replaced with D, E, A, G, I, L, S, T, M, V, N, Q, F, W, Y, P, or C; T207 replaced with D, E, H, K, R, N, Q, F, W, Y, P, or C; S208 replaced with D, E, H, K, R, N, Q, F, W, Y, P, or C; C209 replaced with D, E, H, K, R, A, G, I, L, S, T, M, V, N, Q, F, W, Y, or P; R210 replaced with D, E, A, G, I, L, S, T, M, V, N, Q, F, W, Y, P, or C; C211 replaced with D, E, H, K, R, A, G, I, L, S, T, M, V, N, Q, F, W, Y, or P; M212 replaced with D, E, H, K, R, N, Q, F, W, Y, P, or C; S213 replaced with D, E, H, K, R, N, Q, F, W, Y, P, or C; K214 replaced with D, E, A, G, I, L, S, T, M, V, N, Q, F, W, Y, P, or C; L215 replaced with D, E, H, K, R, N, Q, F, W, Y, P, or C; D216 replaced with H, K, R, A, G, I, L, S, T, M, V, N, Q, F, W, Y, P, or C; V217 replaced with D, E, H, K, R, N, Q, F, W, Y, P, or C; Y218 replaced with D, E, H, K, R, N, Q, A, G, I, L, S, T, M, V, P, or C; R219 replaced with D, E, A, G, I, L, S, T, M, V, N, Q, F, W, Y, P, or C; Q220 replaced with D, E, H, K, R, A, G, I, L, S, T, M, V, F, W, Y, P, or C; V221 replaced with D, E, H, K, R, N, Q, F, W, Y, P, or C; H222 replaced with D, E, A, G, I, L, S, T, M, V, N, Q, F, W, Y, P, or C; S223 replaced with D, E, H, K, R, N, Q, F, W, Y, P, or C; I224 replaced with D, E, H, K, R, N, Q, F, W, Y, P, or C; I225 replaced with D, E, H, K, R, N, Q, F, W, Y, P, or C; R226 replaced with D, E, A, G, I, L, S, T, M, V, N, Q, F, W, Y, P, or C; R227 replaced with D, E, A, G, I, L, S, T, M, V, N, Q, F, W, Y, P, or C; S228 replaced with D, E, H, K, R, N, Q, F, W, Y, P, or C; L229 replaced with D, E, H, K, R, N, Q, F, W, Y, P, or C; P230 replaced with D, E, H, K, R, A, G, I, L, S, T, M, V, N, Q, F, W, Y, or C; A231 replaced with D, E, H, K, R, N, Q, F, W, Y, P, or C; T232 replaced with D, E, H, K, R, N, Q, F, W, Y, P, or C; L233 replaced with D, E, H, K, R, N, Q, F, W, Y, P, or C; P234 replaced with D, E, H, K, R, A, G, I, L, S, T, M, V, N, Q, F, W, Y, or C; Q235 replaced with D, E, H, K, R, A, G, I, L, S, T, M, V, F, W, Y, P, or C; C236 replaced with D, E, H, K, R, A, G, I, L, S, T, M, V, N, Q, F, W, Y, or P; Q237 replaced with D, E, H, K, R, A, G, I, L, S, T, M, V, F, W, Y, P, or C; A238 replaced with D, E, H, K, R, N, Q, F, W, Y, P, or C; A239 replaced with D, E, H, K, R, N, Q, F, W, Y, P, or C; N240 replaced with D, E, H, K, R, A, G, I, L, S, T, M, V, F, W, Y, P, or C; K241 replaced with D, E, A, G, I, L, S, T, M, V, N, Q, F, W, Y, P, or C; T242 replaced with D, E, H, K, R, N, Q, F, W, Y, P, or C; C243 replaced with D, E, H, K, R, A, G, I, L, S, T, M, V, N, Q, F, W, Y, or P;P244replaced with D, E, H, K, R, A, G, I, L, S, T, M, V, N, Q, F, W, Y, or C; T245 replaced with D, E, H, K, R, N, Q, F, W, Y, P, or C; N246 replaced with D, E, H, K, R, A, G, I, L, S, T, M, V, F, W, Y, P, or C;Y247 replaced with D, E, H, K, R, N, Q, A, G, I, L, S, T, M, V, P, or C; M248 replaced with D, E, H, K, R, N, Q, F, W, Y, P, or C; W249 replaced with D, E, H, K, R, N, Q, A, G, I, L, S, T, M, V, P, or C; N250 replaced with D, E, H, K, R, A, G, I, L, S, T, M, V, F, W, Y, P, or C; N251 replaced with D, E, H, K, R, A, G, I, L, S, T, M, V, F, W, Y, P, or C; H252 replaced with D, E, A, G, I, L, S, T, M, V, N, Q, F, W, Y, P, or C; I253 replaced with D, E, H, K, R, N, Q, F, W, Y, P, or C; C254 replaced with D, E, H, K, R, A, G, I, L, S, T, M, V, N, Q, F, W, Y, or P; R255 replaced with D, E, A, G, I, L, S, T, M, V, N, Q, F, W, Y, P, or C; C256 replaced with D, E, H, K, R, A, G, I, L, S, T, M, V, N, Q, F, W, Y, or P; L257 replaced with D, E, H, K, R, N, Q, F, W, Y, P, or C; A258 replaced with D, E, H, K, R, N, Q, F, W, Y, P, or C; Q259replaced with D, E, H, K, R, A, G, I, L, S, T, M, V, F, W, Y, P, or C; E260 replaced with H, K, R, A, G, I, L, S, T, M, V, N, Q, F, W, Y, P, or C; D261replaced with H, K, R, A, G, I, L, S, T, M, V, N, Q, F, W, Y, P, or C; F262 replaced with D, E, H, K, R, N, Q, A, G, I, L, S, T, M, V, P, or C; M263replaced with D, E, H, K, R, N, Q, F, W, Y, P, or C; F264 replaced with D, E, H, K, R, N, Q, A, G, I, L, S, T, M, V, P, or C; S265 replaced with D, E, H, K, R, N, Q, F, W, Y, P, or C; S266 replaced with D, E, H, K, R, N, Q, F, W, Y, P, or C; D267 replaced with H, K, R, A, G, I, L, S, T, M, V, N, Q, F, W, Y, P, or C; A268 replaced with D, E, H, K, R, N, Q, F, W, Y, P, or C; G269 replaced with D, E, H, K, R, N, Q, F, W, Y, P, or C; D270 replaced with H, K, R, A, G, I, L, S, T, M, V, N, Q, F, W, Y, P, or C; D271 replaced with H, K, R, A, G, I, L, S, T, M, V, N, Q, F, W, Y, P, or C; S272replaced wih D, E, H, K, R, N, Q, F, W, Y, P, or C; T273 replaced with D, E, H, K, R, N, Q, F, W, Y, P, or C; D274 replaced with H, K, R, A, G, I, L, S, T, M, V, N, Q, F, W, Y, P, or C; G275 replaced with D, E, H, K, R, N, Q, F, W, Y, P, or C; F276 replaced with D, E, H, K, R, N, Q, A, G, I, L, S, T, M, V, P, or C; H277 replaced with D, E, A, G, I, L, S, T, M, V, N, Q, F, W, Y, P, or C; D278 replaced with H, K, R, A, G, I, L, S, T, M, V, N, Q, F, W, Y, P, or C; I279 replaced with D, E, H, K, R, N, Q, F, W, Y, P, or C; C280 replaced with D, E, H, K, R, A, G, I, L, S, T, M, V, N, Q, F, W, Y, or P;G281 replaced with D, E, H, K, R, N, Q, F, W, Y, P, or C; P282 replaced with D, E, H, K, R, A, G, I, L, S, T, M, V, N, Q, F, W, Y, or C; N283replaced with D, E, H, K, R, A, G, I, L, S, T, M, V, F, W, Y, P, or C; K284 replaced with D, E, A, G, I, L, S, T, M, V, N, Q, F, W, Y, P, or C; E285replaced with H, K, R, A, G, I, L, S, T, M, V, N, Q, F, W, Y, P, or C; L286 replaced with D, E, H, K, R, N, Q, F, W, Y, P, or C; D287 replaced with H, K, R, A, G, I, L, S, T, M, V, N, Q, F, W, Y, P, or C; E288 replaced with H, K, R, A, G, I, L, S, T, M, V, N, Q, F, W, Y, P, or C; E289 replaced with H, K, R, A, G, I, L, S, T, M, V, N, Q, F, W, Y, P, or C; T290 replaced with D, E, H, K, R, N, Q, F, W, Y, P, or C; C291 replaced with D, E, H, K, R, A, G, I, L, S, T, M, V, N, Q, F, W, Y, or P; Q292 replaced with D, E, H, K, R, A, G, I, L, S, T, M, V, F, W, Y, P, or C; C293 replaced with D, E, H, K, R, A, G, I, L, S, T, M, V, N, Q, F, W, Y, or P; V294 replaced with D, E, H, K, R, N, Q, F, W, Y, P, or C; C295 replaced with D, E, H, K, R, A, G, I, L, S, T, M, V, N, Q, F, W, Y, or P; R296 replaced with D, E, A, G, I, L, S, T, M, V, N, Q, F, W, Y, P, or C; A297 replaced with D, E, H, K, R, N, Q, F, W, Y, P, or C; G298 replaced with D, E, H, K, R, N, Q, F, W, Y, P, or C; L299 replaced with D, E, H, K, R, N, Q, F, W, Y, P, or C; R300 replaced with D, E, A, G, I, L, S, T, M, V, N, Q, F, W, Y, P, or C; P301 replaced with D, E, H, K, R, A, G, I, L, S, T, M, V, N, Q, F, W, Y, or C; A302 replaced with D, E, H, K, R, N, Q, F, W, Y, P, or C; S303 replaced with D, E, H, K, R, N, Q, F, W, Y, P, or C; C304 replaced with D, E, H, K, R, A, G, I, L, S, T, M, V, N, Q, F, W, Y, or P; G305 replaced with D, E, H, K, R, N, Q, F, W, Y, P, or C; P306 replaced with D, E, H, K, R, A, G, I, L, S, T, M, V, N, Q, F, W, Y, or C; H307 replaced with D, E, A, G, I, L, S, T, M, V, N, Q, F, W, Y, P, or C; K308 replaced with D, E, A, G, I, L, S, T, M, V, N, Q, F, W, Y, P, or C; E309 replaced with H, K, R, A, G, I, L, S, T, M, V, N, Q, F, W, Y, P, or C; L310 replaced with D, E, H, K, R, N, Q, F, W, Y, P, or C;D311 replaced with H, K, R, A, G, I, L, S, T, M, V, N, Q, F, W, Y, P, or C; R312 replaced with D, E, A, G, I, L, S, T, M, V, N, Q, F, W, Y, P, or C;N313 replaced with D, E, H, K, R, A, G, I, L, S, T, M, V, F, W, Y, P, or C; S314 replaced with D, E, H, K, R, N, Q, F, W, Y, P, or C; C315 replaced with D, E, H, K, R, A, G, I, L, S, T, M, V, N, Q, F, W, Y, or P; Q316 replaced with D, E, H, K, R, A, G, I, L, S, T, M, V, F, W, Y, P, or C; C317replaced with D, E, H, K, R, A, G, I, L, S, T, M, V, N, Q, F, W, Y, or P; V318 replaced with D, E, H, K, R, N, Q, F, W, Y, P, or C; C319 replaced with D, E, H, K, R, A, G, I, L, S, T, M, V, N, Q, F, W, Y, or P; 320 replaced with D, E, A, G, I, L, S, T, M, V, N, Q, F, W, Y, P, or C; N321 replaced with D, E, H, K, R, A, G, I, L, S, T, M, V, F, W, Y, P, or C; K322 replaced with D, E, A, G, I, L, S, T, M, V, N, Q, F, W, Y, P, or C; L323 replaced with D, E, H, K, R, N, Q, F, W, Y, P, or C; F324 replaced with D, E, H, K, R, N, Q, A, G, I, L, S, T, M, V, P, or C; P325 replaced with D, E, H, K, R, A, G, I, L, S, T, M, V, N, Q, F, W, Y, or C; S326 replaced with D, E, H, K, R, N, Q, F, W, Y, P, or C; Q327 replaced with D, E, H, K, R, A, G, I, L, S,T, M, V, F, W, Y, P, or C; C328 replaced with D, E, H, K, R, A, G, I, L, S, T, M, V, N, Q, F, W, Y, or P; G329 replaced with D, E, H, K, R, N, Q, F, W, Y, P, or C; A330 replaced with D, E, H, K, R, N, Q, F, W, Y, P, or C; N331 replaced with D, E, H, K, R, A, G, I, L, S, T, M, V, F, W, Y, P, or C;R332 replaced with D, E, A, G, I, L, S, T, M, V, N, Q, F, W, Y, P, or C; E333 replaced with H, K, R, A, G, I, L, S, T, M, V, N, Q, F, W, Y, P, or C;F334 replaced with D, E, H, K, R, N, Q, A, G, I, L, S, T, M, V, P, or C; D335 replaced with H, K, R, A, G, I, L, S, T, M, V, N, Q, F, W, Y, P, or C;E336 replaced with H, K, R, A, G, I, L, S, T, M, V, N, Q, F, W, Y, P, or C; N337 replaced with D, E, H, K, R, A, G, I, L, S, T, M, V, F, W, Y, P, or C; T338 replaced with D, E, H, K, R, N, Q, F, W, Y, P, or C; C339 replaced with D, E, H, K, R, A, G, I, L, S, T, M, V, N, Q, F, W, Y, or P; Q340replaced with D, E, H, K, R, A, G, I, L, S, T, M, V, F, W, Y, P, or C; C341 replaced with D, E, H, K, R, A, G, I, L, S, T, M, V, N, Q, F, W, Y, or P;V342 replaced with D, E, H, K, R, N, Q, F, W, Y, P, or C; C343 replaced with D, E, H, K, R, A, G, I, L, S, T, M, V, N, Q, F, W, Y, or P; K344replaced with D, E, A, G, I, L, S, T, M, V, N, Q, F, W, Y, P, or C; R345 replaced with D, E, A, G, I, L, S, T, M, V, N, Q, F, W, Y, P, or C;T346replaced with D, E, H, K, R, N, Q, F, W, Y, P, or C; C347 replaced with D, E, H, K, R, A, G, I, L, S, T, M, V, N, Q, F, W, Y, or P; P348 replaced with D, E, H, K, R, A, G, I, L, S, T, M, V, N, Q, F, W, Y, or C; R349 replaced with D, E, A, G, I, L, S, T, M, V, N, Q, F, W, Y, P, or C; N350 replaced with D, E, H, K, R, A, G, I, L, S, T, M, V, F, W, Y, P, or C; Q351 replaced with D, E, H, K, R, A, G, I, L, S, T, M, V, F, W, Y, P, or C; P352 replaced with D, E, H, K, R, A, G, I, L, S, T, M, V, N, Q, F, W, Y, or C; L353 replaced with D, E, H, K, R, N, Q, F, W, Y, P, or C; N354 replaced with D, E, H, K, R, A, G, I, L, S, T, M, V, F, W, Y, P, or C; P355 replaced with D, E, H, K, R, A, G, I, L, S, T, M, V, N, Q, F, W, Y, or C; G356 replaced with D, E, H, K, R, N, Q, F, W, Y, P, or C; K357 replaced with D, E, A, G, I, L, S, T, M, V, N, Q, F, W, Y, P, or C; C358 replaced with D, E, H, K, R, A, G, I, L, S, T, M, V, N, Q, F, W, Y, or P; A359 replaced with D, E, H, K, R, N, Q, F, W, Y, P, or C; C360 replaced with D, E, H, K, R, A, G, I, L, S, T, M, V, N, Q, F, W, Y, or P; E361 replaced with H, K, R, A, G, I, L, S, T, M, V, N, Q, F, W, Y, P, or C; C362 replaced with D, E, H, K, R, A, G, I, L, S, T, M, V, N, Q, F, W, Y, or P; T363 replaced with D, E, H, K, R, N, Q, F, W, Y, P, or C; E364 replaced with H, K, R, A, G, I, L, S, T, M, V, N, Q, F, W,Y, P, or C; S365 replaced with D, E, H, K, R, N, Q, F, W, Y, P, or C; P366 replaced with D, E, H, K, R, A, G, I, L, S, T, M, V, N, Q, F, W, Y, or C;Q367 replaced with D, E, H, K, R, A, G, I, L, S, T, M, V, F, W, Y, P, or C; K368 replaced with D, E, A, G, I, L, S, T, M, V, N, Q, F, W, Y, P, or C;C369 replaced with D, E, H, K, R, A, G, I, L, S, T, M, V, N, Q, F, W, Y, or P; L370 replaced with D, E, H, K, R, N, Q, F, W, Y, P, or C; L371 replaced with D, E, H, K, R, N, Q, F, W, Y, P, or C; K372 replaced with D, E, A, G, I, L, S, T, M, V, N, Q, F, W, Y, P, or C; G373 replaced with D, E, H, K, R, N, Q, F, W, Y, P, or C; K374 replaced with D, E, A, G, I, L, S, T, M, V, N, Q, F, W, Y, P, or C; K375 replaced with D, E, A, G, I, L, S, T, M, V, N, Q, F, W, Y, P, or C; F376 replaced with D, E, H, K, R, N, Q, A, G, I, L, S, T, M, V, P, or C; H377 replaced with D, E, A, G, I, L, S, T, M, V, N, Q, F, W,Y, P, or C; H378 replaced with D, E, A, G, I, L, S, T, M, V, N, Q, F, W, Y, P, or C; Q379 replaced with D, E, H, K, R, A, G, I, L, S, T, M, V, F, W, Y,P, or C; T380 replaced with D, E, H, K, R, N, Q, F, W, Y, P, or C; C381 replaced with D, E, H, K, R, A, G, I, L, S, T, M, V, N, Q, F, W, Y, or P; S382replaced with D, E, H, K, R, N, Q, F, W, Y, P, or C; C383 replaced with D, E, H, K, R, A, G, I, L, S, T, M, V, N, Q, F, W, Y, or P; Y384 replaced with D, E, H, K, R, N, Q, A, G, I, L, S, T, M, V, P, or C; R385 replaced with D, E, A, G, I, L, S, T, M, V, N, Q, F, W, Y, P, or C; R386 replaced with D, E, A, G, I, L, S, T, M, V, N, Q, F, W, Y, P, or C; P387 replaced with D, E, H, K, R, A, G, I, L, S, T, M, V, N, Q, F, W, Y, or C; C388 replaced with D, E, H, K, R, A, G, I, L, S, T, M, V, N, Q, F, W, Y, or P; T389 replaced with D, E, H, K, R, N, Q, F, W, Y, P, or C; N390 replaced with D, E, H, K, R, A, G, I, L, S, T, M, V, F, W, Y, P, or C; R391 replaced with D, E, A, G, I, L, S, T, M, V, N, Q, F, W, Y, P, or C; Q392 replaced with D, E, H, K, R, A, G, I, L, S, T, M, V, F, W, Y, P, or C; K393 replaced with D, E, A, G, I, L, S, T, M, V, N, Q, F, W, Y, P, or C; A394 replaced with D, E, H, K, R, N, Q, F, W, Y, P, or C; C395 replaced with D, E, H, K, R, A, G, I, L, S, T, M, V, N, Q, F, W, Y, or P; E396 replaced with H, K, R, A, G, I, L, S, T, M, V, N, Q, F, W, Y, P, or C; P397 replaced with D, E, H, K, R, A, G, I, L, S, T, M, V, N, Q, F, W, Y, or C; G398 replaced with D, E, H, K, R, N, Q, F, W, Y, P, or C; F399 replaced with D, E, H, K, R, N, Q, A, G, I, L, S, T, M, V, P, or C; S400 replaced with D, E, H, K, R, N, Q, F, W, Y, P, or C; Y401replaced with D, E, H, K, R, N, Q, A, G, I, L, S, T, M, V, P, or C; S402 replaced with D, E, H, K, R, N, Q, F, W, Y, P, or C; E403 replaced with H, K, R, A, G, I, L, S, T, M, V, N, Q, F, W, Y, P, or C; E404 replaced with H, K, R, A, G, I, L, S, T, M, V, N, Q, F, W, Y, P, or C; V405 replaced with D, E, H, K, R, N, Q, F, W, Y, P, or C; C406 replaced with D, E, H, K, R, A, G, I, L, S, T, M, V, N, Q, F, W, Y, or P; R407 replaced with D, E, A, G, I, L, S, T, M, V, N, Q, F, W, Y, P, or C; C408 replaced with D, E, H, K, R, A, G, I, L, S, T, M, V, N, Q, F, W, Y, or P; V409 replaced with D, E, H, K, R, N, Q, F, W, Y, P, or C; P410 replaced with D, E, H, K, R, A, G, I, L, S, T, M, V, N, Q, F, W, Y, or C; S411 replaced with D, E, H, K, R, N, Q, F, W, Y, P, or C; Y412 replaced with D, E, H, K, R, N, Q, A, G, I, L, S, T, M, V, P, or C; W413 replaced with D, E, H, K, R, N, Q, A, G, I, L, S, T, M, V, P, or C; Q414 replaced with D, E, H, K, R, A, G, I, L, S, T, M, V, F, W, Y, P, or C; R415 replaced with D, E, A, G, I, L, S, T, M, V, N, Q, F, W, Y, P, or C;P416 replaced with D, E, H, K, R, A, G, I, L, S, T, M, V, N, Q, F, W, Y, or C; Q417 replaced with D, E, H, K, R, A, G, I, L, S, T, M, V, F, W, Y, P, or C; M418 replaced with D, E, H, K, R, N, Q, F, W, Y, P, or C; and/or S419 replaced with D, E, H, K, R, N, Q, F, W, Y, P, or C of FIG. 1A-1E.

The resulting constructs can be routinely screened for activities or functions described throughout the specification and known in the art. Preferably, the resulting constructs have an increased and/or decreased VEGF-2 activity or function, while the remaining VEGF-2 activities or functions are maintained. More preferably, the resulting constructs have more than one increased and/or decreased VEGF-2 activity or function, while the remaining VEGF-2 activities or functions are maintained.

As described in detail below, the polypeptides of the present invention can be used to raise polyclonal and monoclonal antibodies, which are useful in diagnostic assays for detecting VEGF-2 protein expression or as agonists and antagonists capable of enhancing or inhibiting VEGF-2 protein function. Further, such polypeptides can be used in the yeast two-hybrid system to "capture" VEGF-2 protein binding proteins which are also candidate agonist and antagonist according to the present invention. The yeast two hybrid system is described in Fields and Song, *Nature* 340:245-246 (1989).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad Sci. USA* 81:3998-4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G, et al., (1983) *Science* 219:660-666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, soluble peptides, especially those containing proline residues, usually are effective. Sutcliffe et al., supra, at 661. For instance, 18 of 20 peptides designed according to these guidelines, containing 8-39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et at., supra, at 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson el al., *Cell* 37:767-778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30, 40, 50, 60, 70, 80, 90, 100, or 150 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

Non-limiting examples of antigenic polypeptides or peptides that can be used to generate VEGF-2-specific antibodies include the following: a polypeptide comprising amino acid residues from about leu-37 to about Glu45 in SEQ ID NO:2, from about Tyr-58 to about Gly-66 in SEQ ID NO:2, from about Gln-73 to about Glu-81 in SEQ ID NO:2, from about Asp-100 to about Cys-108 in SEQ ID NO:2, from about Gly-140 to about Leu-148 in SEQ ID NO:2, from about Pro-168 to about Val-176 in SEQ ID NO:2, from about His-183 to about Lys-191 in SEQ ID NO:2, from about Ile-201 to about Thr-209 in SEQ ID NO:2, from about Ala-216 to about Tyr-224 in SEQ ID NO:2, from about Asp-244 to about His-254 in SEQ ID NO:2, from about Gly-258 to about Glu-266 in SEQ ID NO:2, from about Cys-272 to about Ser-280 in SEQ ID NO:2, from about Pro-283 to about Ser-291 in SEQ ID NO:2, from about Cys-296 to about Gln-304 in SEQ ID NO:2, from about Ala-307 to about Cys-316 in SEQ ID NO:2, from about Val-319 to about Cys-335 in SEQ ID NO:2, from about Cys-339 to about Leu-347 in SEQ ID NO:2, from about Cys-360 to about Glu-373 in SEQ ID NO:2, from about Tyr-378 to about Val-386 in SEQ ID NO:2, and from about Ser-388 to about Ser-396 in SEQ ID NO:2. These polypeptide fragments have been determined to bear antigenic epitopes of the VEGF-2 protein by the analysis of the Jameson-Wolf antigenic index.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10-20 mg of 248 different 13 residue peptides representing single amino acid variants of a segment of the HA1 polypeptide which were prepared and characterized (by ELISA-type binding studies) in less than four weeks. Houghten, R, A. (1985) G *Proc. Natl. Acad Sci. USA* 82:5131-5135. This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500-1000 or more syntheses to be conducted simultaneously. Houghten et al., supra, at 5134.

Epitope-bearing peptides and polypeptides of the invention are used to induce antibodies according to methods well known in the art. See, for instance, Sutcliffe et al., supra; Wilson et al., supra; Chow, M. et al., *Proc. Natl. Acad Sci. USA* 82:910-914; and Bittle, F, J. et al., *J. Gen. Virol.* 66:2347-2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde.

Animals such as rabbits, rats and mice are immunized with either free or carrier-coupled peptides, for instance, by intraperitoneal and/or intradermal injection of emulsions containing about 100 mg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a Aminotope) which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$-$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

As one of skill in the art will appreciate, VEGF-2 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84-86 (1988)). In accordance with the present invention, novel variants of VEGF-2 are also described. These can be produced by deleting or substituting one or more amino acids of VEGF-2. Natural mutations are called allelic variations. Allelic variations can be silent (no change in the encoded polypeptide) or may have altered amino acid sequence.

In order to attempt to improve or alter the characteristics of native VEGF-2, protein engineering may be employed. Recombinant DNA technology known to those skilled in the art can be used to create novel polypeptides. Muteins and deletions can show, e.g., enhanced activity or increased stability. In addition, they could be purified in higher yield and show better solubility at least under certain purification and storage conditions. Set forth below are examples of mutations that can be constructed.

Amino Terminal and Carboxy Terminal Deletions

Figure 6:
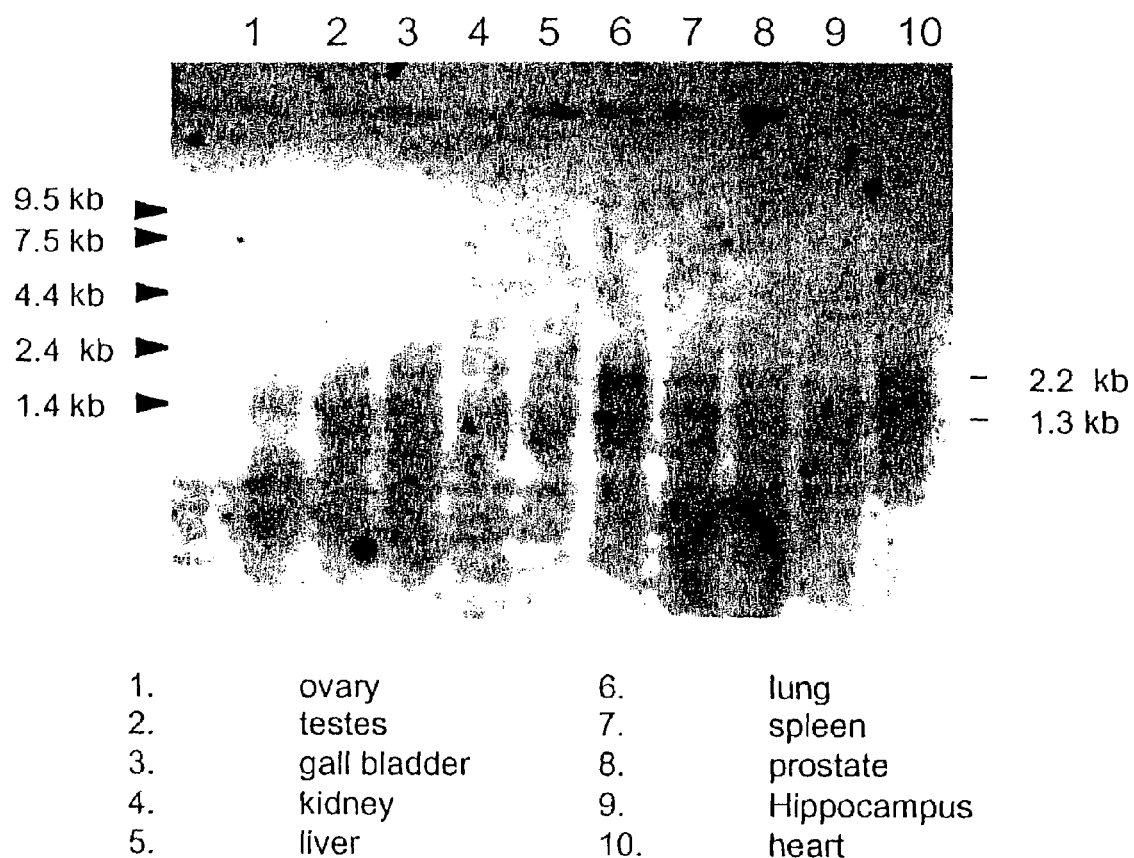
FIG. 6 depicts the results of a Northern blot analysis of VEGF-2 in human adult tissues.

Furthermore, VEGF-2 appears to be proteolytically cleaved upon expression resulting in polypeptide fragments of the following sizes when run on a SDS-PAGE gel (sizes are approximate) (See, FIG. 6-8, for example): 80, 59, 45, 43, 41, 40, 39, 38, 37, 36, 31, 29, 21, and 15 kDa. These polypeptide fragments are the result of proteolytic cleavage at both the N-terminal and C-terminal portions of the protein. These proteolytically generated fragments appears to have activity, particularly the 21 kDa fragment.

In addition, protein engineering may be employed in order to improve or alter one or more characteristics of native VEGF-2. The deletion of carboxy terminal amino acids can enhance the activity of proteins. One example is interferon gamma that shows up to ten times higher activity by deleting ten amino acid residues from the carboxy terminus of the protein (Dobeli et al., *J. of Biotechnology* 7:199-216 (1988)). Thus, one aspect of the invention is to provide polypeptide analogs of VEGF-2 and nucleotide sequences encoding such analogs that exhibit enhanced stability (e.g., when exposed to typical pH, thermal conditions or other storage conditions) relative to the native VEGF-2 polypeptide. Particularly, preferred VEGF-2 polypeptides are shown below (numbering starts with the first amino acid in the protein (Met) (FIG. 1 (SEQ ID NO:2)):

Ala (residue 25) to Ser (residue 419); Pro (26) to Ser (419); Ala (27) to Ser (419); Ala (28) to Ser (419); Ala (29) to Ser (419); Ala (30) to Ser (419); Ala (31) to Ser (419); Phe (32) to Ser (419); Glu (33) to Ser (419); Ser (34) to Ser (419); Gly (35) to Ser (419); Leu (36) to Ser (419); Asp (37) to Ser (419); Leu (38) to (Ser (419); Ser (39) to Ser (419); Asp (40) to Ser (419); Ala (41) to Ser (419); Glu (42) to Ser (419); Pro (43) to Ser (419); Asp (44) to Ser (419); Ala (45) to Ser (419); Gly (46) to Ser (419); Glu (47) to Ser (419); Ala (48) to Ser (419); Thr (49) to Ser (419); Ala (50) to Ser (419); Tyr (51) to Ser (419); Ser (53) to Ser (419); Asp (55) to Ser (419); Val (63) to Ser (419); Val (66) to Ser (419); Met(1), Glu (24), or Ala (25) to Met (418); Met (1), Glu (24), or Ala (25) to Gln (417); Met (1), Glu (24), or Ala (25) to Pro (416); Met(1), Glu (24), or Ala (25) to Arg (415); Met(1), Glu (24), or Ala (25) to Gln (414); Met(1), Glu (24), or Ala (25) to Trp (413); Met(1), Glu (24), or Ala (25) to Tyr (412); Met(1), Glu (24), or Ala (25) to Ser (411); Met(1), Glu (24), or Ala (25) to Pro (410); Met(1), Glu (24), or Ala (25) to Val (409); Met(1), Glu (24), or Ala (25) to Cys (408); Met(1), Glu (24), or Ala (25) to Arg (407); Met(1), Glu (24), or Ala (25) to Cys (406); Met(1), Glu (24), or Ala (25) to Val (405); Met(1), Glu (24), or Ala (25) to Glu (404); Met(1), Glu (24), or Ala (25) to Glu (403); Met(1), Glu (24), or Ala (25) to Ser (402); Met(1), Glu (24), or Ala (25) to Gly (398); Met(1), Glu (24), or Ala (25) to Pro (397); Met(1), Glu (24), or Ala (25) to Lys (393); Met(1), Glu (24), or Ala (25) to Met(263); Met(1), Glu (24), or Ala (25) to Asp(311); Met(1), Glu (24), or Ala (25) to Pro (366); Met(1) to Ser (419); Met(l) to Ser(228); Glu(47) to Ser(419); Ala(111) to Lys(214); Ala (112) to Lys(214); His(113) to Lys(214); Tyr(114) to Lys (214); Asn(115) to Lys(214); Thr(116) to Lys(214); Thr(103) to Leu(215); Glu(104) to Leu(215); Glu(105) to Leu(215); Thr(106) to Leu(215); Ile(107) to Leu(215); Lys(108) to Leu (215); Phe(109) to Leu(215); Ala(110) to Leu(215); Ala(111) to Leu(215); Ala(112) to Leu(215); His(113) to Leu(215); Tyr(114) to Leu(215); Asn(115) to Leu(215); Thr(116) to Leu(215); Thr(103) to Ser(228); Glu(104) to Ser(228); Glu (105) to Ser(228); Thr(106) to Ser(228); Ile(107) to Ser(228); Lys(108) to Ser(228); Phe(109) to Ser(228); Ala(110) to Ser (228); Ala(111) to Ser(228); Ala(112) to Ser(228); His(113) to Ser(228); Tyr(114) to Ser(228); Asn(115) to Ser(228); Thr(116) to Ser(228); Thr(103) to Leu(229); Glu(104) to Leu(229); Thr(103) to Arg(227); Glu(104) to Arg(227); Glu (105) to Arg (227); Thr(106) to Arg (227); Ile(107) to Arg (227); Lys(108) to Arg (227); Phe(109) to Arg (227); Ala (110) to Arg (227); Ala(111) to Arg (227); Ala(112) to Arg (227); His(113) to Arg (227); Tyr(114) to Arg (227); Asn(115) to Arg (227); Thr(116) to Arg (227); Thr(103) to Ser(213); Glu(104) to Ser(213); Glu(105) to Ser(213); Thr(106) to Ser (213); Ile(107) to Ser(213); Lys(108) to Ser(213); Phe(109) to Ser(213); Ala(110) to Ser(213); Ala(111) to Ser(213); Ala (112) to Ser(213); His(113) to); Tyr(114) to Ser(213); Asn (115) to Ser(213); Thr(116) to Ser(213); Thr(103) to Lys (214); Glu(104) to Lys(214); Glu(105) to Lys(214); Thr(106) to Lys(214); Ile(107) to Lys(214); Lys(108) to Lys(214); Phe (109) to Lys(214); Ala(110) to Lys(214); Glu(105) to Leu (229); Thr(106) to Leu(229); Ile(107) to Leu(229); Lys(108) to Leu(229); Phe(109) to Leu(229); Ala(110) to Leu(229); Ala(111) to Leu(229); Ala(112) to Leu(229); His(113) to Leu(229); Tyr(114) to Leu(229); Asn(115) to Leu(229); Thr (116) to Leu(229).

Preferred embodiments include the following deletion mutants: Thr(103)—Arg(227); Glu(104)—Arg(227); Ala (112)—Arg (227); Thr(103)—Ser(213); Glu(104)—Ser (213); Thr(103)—Leu(215); Glu(47)—Ser(419); Met(1), Glu (24), or Ala (25)—Met(263); Met(1), Glu (24), or Ala (25)—Asp(311); Met(1), Glu (24), or Ala (25)—Pro (366); Met(1)—Ser(419); and Met(1)—Ser(228) of (FIG. 1 (SEQ ID NO:2)).

Also included by the present invention are deletion mutants having amino acids deleted from both the NB terminus and the C-terminus. Such mutants include all combinations of the N-terminal deletion mutants and C-terminal deletion mutants described above. Those combinations can be made using recombinant techniques known to those skilled in the art.

Particularly, N-terminal deletions of the VEGF-2 polypeptide can be described by the general formula m-396, where m is an integer from −23 to 388, where m corresponds to the position of the amino acid residue identified in SEQ ID NO:2. Preferably, N-terminal deletions retain the conserved boxed area of FIG. 3 (PXCVXXXRCXGCCN)(SEQ ID NO: 8), and include polypeptides comprising the amino acid sequence of residues: A-2 to S-396; P-3 to S-396; A-4 to S-396; A-5 to S-396; A-6 to S-396; A-7 to S-396; A-8 to S-396; F-9 to S-396; E-10 to S-396; S-11 to S-396; G-12 to S-396; L-13 to S-396; D-14 to S-396; L-15 to S-396; S-16 to S-396; D-17 to S-396; A-18 to S-396; E-19 to S-396; P-20 to S-396; D-21 to S-396; A-22 to S-396; G-23 to S-396; E-24 to S-396; A-25 to S-396; T-26 to S-396; A-27 to S-396; Y-28 to S-396; A-29 to S-396; S-30 to S-396; K-31 to S-396; D-32 to S-396; L-33 to S-396; E-34 to S-396; E-35 to S-396; Q-36 to S-396; L-37 to S-396; R-38 to S-396; S-39 to S-396; V-40 to S-396; S-41 to S-396; S-42 to S-396; V-43 to S-396; D-44 to S-396; E-45 to S-396; L46 to S-396; M-47 to S-396; T-48 to S-396; V-49 to S-396; L-50 to S-396; Y-51 to S-396; P-52 to S-396; E-53 to S-396; Y-54 to S-396; W-55 to S-396; K-56 to S-396; M-57 to S-396; Y-58 to S-396; K-59 to S-396; C-60 to S-396; Q-61 to S-396; L-62 to S-396; R-63 to S-396; K-64 to S-396; G-65 to S-396; G-66 to S-396; W-67 to S-396; Q-68 to S-396; H-69 to S-396; N-70 to S-396; R-71 to S-396; E-72 to S-396; Q-73 to S-396; A-74 to S-396; N-75 to S-396; L-76 to S-396; N-77 to S-396; S-78 to S-396; R-79 to S-396; T-80 to S-396; E-81 to S-396; E-82 to S-396; T-83 to S-396; 1-84 to S-396; K-85 to S-396; F-86 to S-396; A-87 to S-396; A-88 to S-396; A-89 to S-396; H-90 to S-396; Y-91 to S-396; N-92 to S-396; T-93 to S-396; E-94 to S-396; I-95 to S-396; L-96 to S-396; K-97 to S-396; S-98 to S-396; I-99 to S-396; D-100 to S-396; N-101 to S-396; E-102 to S-396; W-103 to S-396; R-104 to S-396; K-105 to S-396; T-106to S-396; Q-107 to S-396; C-108 to S-396; M-109 to S-396; P-110 to S-396; R-111 to S-396; E-112 to S-396; V-113 to S-396; C-114 to S-396; I-115 to S-396; D-116 to S-396; V-117 to S-396; G-118 to S-396; K-119 to S-396; E-120 to S-396; F-121 to S-396; G-122 to S-396; V-123 to S-396; A-124 to S-396; T-125 to S-396; N-126 to S-396; T-127 to S-396; F-128 to S-396; F-129 to S-396; K-130 to S-396; P-131 to S-396 of SEQ ID NO:2. Also preferred are polynucleotides encoding these N-terminal deletion mutants.

Moreover, C-terminal deletions of the VEGF-2 polypeptide can also be described by the general formula -23-n, where n is an integer from −15 to 395 where n corresponds to the position of amino acid residue identified in SEQ ID NO:2. Preferably, C-terminal deletions retain the conserved boxed area of FIG. 3 (PXCVXXXRCXGCCN)(SEQ ID NO: 8), and include polypeptides comprising the amino acid sequence of residues: E-1 to M-395; E-1 to Q-394; E-1 to P-393; E-1 to R-392; E-1 to Q-391; E-1 to W-390; E-1 to Y-389; E-1 to S-388; E-1 to P-387; E-1 to V-386; E-1 to C-385; E-1 to R-384; E-1 to C-383; E-1 to V-382; E-1 to E-381; E-1 to E-380; E-1 to S-379; E-1 to Y-378; E-1 to S-377; E-1 to F-376; E-1 to G-375; E-1 to P-374; E-1 to E-373; E-1 to C-372; E-1 to A-371; E-1 to K-370; E-1 to Q-369; E-1 to R-368; E-1 to N-367; E-1 to T-366; E-1 to C-365; E-1 to P-364; E-1 to R-363; E-1 to R-362; E-1 to Y-361; E-1 to C-360; E-1 to S-359; E-1 to C-358; E-1 to T-357; E-1 to Q-356; E-1 to H-355; E-1 to H-354; E-1 to F-353; E-1 to K-352; E-1 to K-351; E-1 to G-350; E-1 to K-349; E-1 to L-348; E-1 to L-347; E-1 to C-346; E-1 to K-345; E-1 to Q-344; E-1 to P-343; E-1 to S-342; E-1 to E-341; E-1 to T-340; E-1 to C-339; E-1 to E-338; E-1 to C-337; E-1 to A-336; E-1 to C-335; E-1 to K-334; E-1 to G-333; E-1 to P-332; E-1 to N-331; E-1 to L-330; E-1 to P-329; E-1 to Q-328; E-1 to N-327; E-1 to R-326; E-1 to P-325; E-1 to C-324; E-1 to T-323; E-1 to R-322; E-1 to K-321; E-1 to C-320; E-1 to V-319; E-1 to C-318; E-1 to Q-317; E-1 to C-316; E-1 to T-315; E-1 to N-314; E-1 to E-313; E-1 to D-312; E-1 to F-311; E-1 to E-310; E-1 to R-309; E-1 to N-308; E-1 to A-307; E-1 to G-306; E-1 to C-305; E-1 to Q-304; E-1 to S-303; E-1 to P-302; E-1 to F-301; E-1 to L-300; E-1 to K-299; E-1 to N-298; E-1 to K-297; E-1 to C-296; E-1 to V-295; E-1 to C-294; E-1 to Q-293; E-1 to C-292; E-1 to S-291; E-1 to N-290; E-1 to R-289; E-1 to D-288; E-1 to L-287; E-1 to E-286; E-1 to K-285; E-1 to H-284; E-1 to P-283; E-1 to G-282; E-1 to C-281; E-1 to S-280; E-1 to A-279; E-1 to P-278; E-1 to R-277; E-1 to L-276; E-1 to G-275; E-1 to A-274; E-1 to R-273; E-1 to C-272; E-1 to V-271; E-1 to C-270; E-1 to Q-269; E-1 to C-268; E-1 to T-267; E-1 to E-266; E-1 to E-265; E-1 to D-264; E-1 to L-263; E-1 to E-262; E-1 to K-261; E-1 to N-260; E-1 to P-259; E-1 to G-258; E-1 to C-257; E-1 to I-256; E-1 to D-255; E-1 to H-254; E-1 to F-253; E-1 to G-252; E-1 to D-251; E-1 to T-250; E-1 to S-249; E-1 to D-248; E-1 to D-247; E-1 to G-246; E-1 to A-245; E-1 to D-244; E-1 to S-243; E-1 to S-242; E-1 to F-241; E-1 to M-240; E-1 to F-239; E-1 to D-238; E-1 to E-237; E-1 to Q-236; E-1 to A-235; E-1 to L-234; E-1 to C-233; E-1 to R-232; E-1 to C-231; E-1 to I-230; E-1 to H-229; E-1 to N-228; E-1 to N-227; E-1 to W-226; E-1 to M-225; E-1 to Y-224; E-1 to N-223; E-1 to T-222; E-1 to P-221; E-1 to C-220; E-1 to T-219; E-1 to K-218; E-1 to N-217; E-1 to A-216; E-1 to A-215; E-1 to Q-214; E-1 to C-213; E-1 to Q-212; E-1 to P-211; E-1 to L-210; E-1 to T-209; E-1 to A-208; E-1 to P-207; E-1 to L-206; E-1 to S-205; E-1 to R-204; E-1 to R-203; E-1 to I-202; E-1 to I-201; E-1 to S-200; E-1 to H-199; E-1 to V-198; E-1 to Q-197; E-1 to R-196; E-1 to Y-195; E-1 to V-194; E-1 to D-193; E-1 to L-192; E-1 to K-191; E-1 to S-190; E-1 to M-189; E-1 to C-188; E-1 to R-187; E-1 to C-186; E-1 to S-185; E-1 to T-184; E-1 to H-183; E-1 to N-182; E-1 to A-181; E-1 to F-180; E-1 to S-179; E-1 to I-178; E-1 to T-177; E-1 to V-176; E-1 to P-175; E-1 to K-174; E-1 to P-173; E-1 to G-172; E-1 to Q-171; E-1 to S-170; E-1 to L-169; E-1 to P-168; E-1 to V-167; E-1 to T-166; E-1 to I-165; E-1 to E-164; E-1 to F-163; E-1 to L-162; E-1 to T-161; E-1 to K-160; E-1 to S-159; E-1 to L-158; E-1 to Y-157; E-1 to S-156; E-1 to T-155; E-1 to S-154; E-1 to T-153; E-1 to N-152; E-1 to M-151; E-1 to C-150; E-1 to Q-149; E-1 to L-148; E-1 to G-147; E-1 to E-146; E-1 to S-145; E-1 to N-144; of SEQ ID NO:2. Also preferred are polynucleotides encoding these C-terminal deletion mutants. Preferably, any of the above listed N- or C-terminal deletions can be combined to produce a N- and C-terminal deleted VEGF-2 polypeptide, which retains the conserved box domain.

Moreover, the invention also provides polypeptides having one or more amino acids deleted from both the amino and the carboxyl termini, which may be described generally as having residues m-n of SEQ ID NO:2, where n and m are integers as described above.

Many polynucleotide sequences, such as EST sequences, are publicly available and accessible through sequence databases. Some of these sequences are related to SEQ ID NO:1 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1660 of SEQ ID NO:1, b is an integer of 15 to 1674, where both a and b correspond to the positions of nucleotide residues shown in SEQ ID NO:1, and where the b is greater than or equal to a +14.

Thus, in one aspect, N-terminal deletion mutants are provided by the present invention. Such mutants include those comprising the amino acid sequence shown in FIG. 1 (SEQ ID NO:2) except for a deletion of at least the first 24 N-terminal amino acid residues (i.e., a deletion of at least Met (1)—Glu (24)) but not more than the first 115 N-terminal amino acid residues of FIG. 1 (SEQ ID NO:2). Alternatively, first 24 N-terminal amino acid residues (i.e., a deletion of at least Met (1)—Glu (24)) but not more than the first 103 N-terminal amino acid residues of FIG. 1 (SEQ ID NO:2), etc., etc.

In another aspect, C-terminal deletion mutants are provided by the present invention. Such mutants include those comprising the amino acid sequence shown in FIG. 1 (SEQ ID NO:2) except for a deletion of at least the last C-terminal amino acid residue (Ser (419)) but not more than the last 220 C-terminal amino acid residues (i.e., a deletion of amino acid residues Val (199)—Ser (419)) of FIG. 1 (SEQ ID NO:2). Alternatively, the deletion will include at least the last C-terminal amino acid residue but not more than the last 216 C-terminal amino acid residues of FIG. 1 (SEQ ID NO:2). Alternatively, the deletion will include at least the last C-terminal amino acid residue but not more than the last 204 C-terminal amino acid residues of FIG. 1 (SEQ ID NO:2). Alternatively, the deletion will include at least the last C-terminal amino acid residues but not more than the last 192 C-terminal amino acid residues of FIG. 1 (SEQ ID NO:2).

Alternatively, the deletion will include at least the last C-terminal amino acid residues but not more than the last 156 C-terminal amino acid residues of FIG. 1 (SEQ ID NO:2). Alternatively, the deletion will include at least the last C-terminal amino acid residues but not more than the last 108 C-terminal amino acid residues of FIG. 1 (SEQ ID NO:2). Alternatively, the deletion will include at least the last C-terminal amino acid residues but not more than the last 52 C-terminal amino acid residues of FIG. 1 (SEQ ID NO:2).

In yet another aspect, also included by the present invention are deletion mutants having amino acids deleted from both the N-terminal and C-terminal residues. Such mutants include all combinations of the N-terminal deletion mutants and C-terminal deletion mutants described above.

The term "gene" means the segment of DNA involved in producing a polypeptide chain; it includes regions preceding and following the coding region (leader and trailer) as well as intervening sequences (introns) between individual coding segments (exons).

The present invention is further directed to fragments of the isolated nucleic acid molecules described herein. By a fragment of an isolated nucleic acid molecule having the nucleotide sequence of the deposited cDNA(s) or the nucleotide sequence shown in SEQ ID NO:1 or SEQ ID NO:3 is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments of 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1275, 1300, 1325, 1350, 1375, 1400, 1425, 1450, 1475, 1500, 1525, 1550, 1575, 1600, 1625, 1650 or 1674 nt in length are also useful according to the present invention as are fragments corresponding to most, if not all, of the nucleotide sequence of the deposited cDNA(s) or as shown in SEQ ID NO:1 or SEQ ID NO:3. By a fragment at least 20 nt in length, for example, is intended fragments which include 20 or more contiguous bases from the nucleotide sequence of the deposited cDNA(s) or the nucleotide sequence as shown in SEQ ID NOS:1 or 3.

Moreover, representative examples of VEGF-2 polynucleotide fragments include, for example, fragments having a sequence from about nucleotide number 1-50, 51-100, 101-150, 151-200, 201-250, 251-300, 301-350, 351-400, 401-450, 451-500, 501-550, 551-600, 651-700, 701-750, 751-800, 800-850, 851-900, 901-950, or 951 to the end of SEQ ID NO:1 or the cDNA contained in the deposited clone. In this context "about" includes the particularly recited ranges, larger or smaller by several (5, 4, 3, 2, or 1) nucleotides, at either terminus or at both termini. Preferably, these fragments encode a polypeptide which has biological activity.

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promoter regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

A VEGF-2 "polynucleotide" also includes those polynucleotides capable of hybridizing, under stringent hybridization conditions, to sequences contained in SEQ ID NO:1 or for instance, the cDNA clone(s) contained in ATCC™ Deposit Nos. 97149 or 75698, the complement thereof. "Stringent hybridization conditions" refers to an overnight incubation at 42° C. in absolution comprising 50% formamide, 5×SSC (750 mM NaCl, 75 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C.

Also contemplated are nucleic acid molecules that hybridize to the VEGF-2 polynucleotides at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M $NaH_2PO_4$; 0.02M EDTA, pH 7.4), 0.5% SDS, 30% formamide, 100 µg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone).

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in SEQ ID NO:1). Of course, a polynucleotide which hybridizes only to a poly A sequence (such as the 3N terminal poly(A) tract of the VEGF-2 cDNA shown in SEQ ID NOS:1 or 3), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

The present application is directed to nucleic acid molecules at least 95%, 96%, 97%, 98% or 99% identical to the nucleic acid sequence shown in SEQ ID NOS:1 or 3 or to the nucleic acid sequence of the deposited cDNA(s), irrespective of whether they encode a polypeptide having VEGF-2 activity. This is because even where a particular nucleic acid molecule does not encode a polypeptide having VEGF-2 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having VEGF-2 activity include, inter alia, (1) isolating the VEGF-2 gene or allelic variants thereof in a cDNA library; (2) in situ hybridization (e.g., "FISH") to metaphase chromosomal spreads to provide precise chromosomal location of the VEGF-2 gene, as described in Verma et al, *Human Chromosomes: A Manual of Basic Techniques*, Pergamon Press, New York (1988); and Northern Blot analysis for detecting VEGF-2 mRNA expression in specific tissues. Preferred, however, are nucleic acid molecules having sequences at least 95%, 96%, 97%, 98% or 99% identical to a nucleic acid sequence shown in SEQ ID NOS:1 or 3 or to a nucleic acid sequence of the deposited cDNA(s) which do, in fact, encode a polypeptide having VEGF-2 protein activity. By "a polypeptide having VEGF-2 activity" is intended polypeptides exhibiting VEGF-2 activity in a particular biological assay. For example, VEGF-2 protein activity can be measured using, for example, mitogenic assays and endothelial cell migration assays. See, e.g., Olofsson et al., *Proc. Natl. Acad. Sci. USA* 93:2576-2581 (1996) and Joukov et al., *EMBO J.* 5:290-298 (1996).

Of course, due to the degeneracy of the genetic code, one of ordinary skill in the art will immediately recognize that a large number of the nucleic acid molecules having a sequence at least 90%, 95%, 96%, 97%, 98%, or 99% identical to a nucleic acid sequence of the deposited cDNA(s) or the nucleic acid sequence shown in SEQ ID NO:1 or SEQ ID NO:3 will encode a polypeptide "having VEGF-2 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having VEGF-2 protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306-1310 (1990), wherein the authors indicate that proteins are surprisingly tolerant of amino acid substitutions.

Thus, the present invention is directed to polynucleotides having at least a 70% identity, preferably at least 90% and more preferably at least a 95%, 96%, 97%, or 98% identity to a polynucleotide which encodes the polypeptides of SEQ ID NOS:2 or 4, as well as fragments thereof, which fragments have at least 30 bases and preferably at least 50 bases and to polypeptides encoded by such polynucleotides.

"Identity" per se has an art-recognized meaning and can be calculated using published techniques. (See, e.g.: (Computational Molecular Biology, Lesk, A. M., ed., Oxford University Press, New York, (1988); Biocomputing: Informatics and Genome Projects, Smith, D. W,, ed., Academic Press, New York, (1993); Computer Analysis of Sequence Data, Part I, Griffin, A. M., and Griffi, H. G., eds., Humana Press, New Jersey, (1994); Sequence Analysis in Molecular Biology, von Heinje, G,, Academic Press, (1987); and Sequence Analysis Primer, Gribskov, M. and Devereux, J., eds., M Stockton Press, New York, (1991).) While there exists a number of methods to measure identity between two polynucleotide or polypeptide sequences, the term "identity" is well known to skilled artisans. (Carillo, H., and Lipton, D., *SIAM J. Applied Math.* 48:1073 (1988).) Methods commonly employed to determine identity or similarity between two sequences include, but are not limited to, those disclosed in "Guide to Huge Computers," Martin J. Bishop, ed., Academic Press, San Diego, (1994), and Carillo, H., and Lipton, D., *SIAM J. Applied Math.* 48:1073 (1988). Methods for aligning polynucleotides or polypeptides are codified in computer programs, including the GCG program package (Devereux, J., et al., *Nucleic Acids Research* 12(1):387 (1984)), BLASTP, BLASTN, FASTA (Atschul, S. F, et al., *J. Molec. Biol.* 215: 403 (1990), Bestfit program (Wisconsin Sequence Analysis Package, Version 8 for Unix, Genetics Computer Group, University Research Park, 575 Science Drive, Madison, Wis. 53711 (using the local homology algorithm of Smith and Waterman, *Advances in Applied Mathematics* 2:482-489 (1981)). By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the VEGF-2 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence SEQ ID NO:1, the ORF,(open reading frame), or any fragment specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* 6:237-245 (1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter. If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequences shown in SEQ ID NOs:2 or 4 or to the amino acid sequence encoded by deposited DNA clone can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* (1990) 6:237-245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore; the FASTDB alignment does not show a matching/alignment of the first 10 residues at the N-terminus. The 10 unpaired residues represent 10% of the sequence (number of residues at the N- and C- termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

VEGF-2 Polypeptides

The present invention further relates to polypeptides which have the deduced amino acid sequence of FIGS. 1 or 2, or which has the amino acid sequence encoded by the deposited cDNAs, as well as fragments, analogs, and derivatives of such polypeptides.

The terms "fragment," "derivative" and "analog" when referring to the polypeptide of FIGS. 1 or 2 or that encoded by the deposited cDNA, means a polypeptide which retains the conserved motif of VEGF proteins as shown in FIG. 3 and essentially the same biological function or activity.

In the present invention, a "polypeptide fragment" refers to a short amino acid sequence contained in SEQ ID NO:2 or encoded by the cDNA contained in the deposited clone. Protein fragments may be "free-standing," or comprised within a larger polypeptide of which the fragment forms a part or region, most preferably as a single continuous region. Representative examples of polypeptide fragments of the invention, include, for example, fragments from about amino acid number 1-20, 21-40, 41-60, 61-80, 81-100, 102-120, 121-140, 141-160, 161-180, 181-200, 201-220, 221-240, 241-260, 261-280, or 281 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes.

Preferred polypeptide fragments include the secreted VEGF-2 protein as well as the mature form. Further preferred polypeptide fragments include the secreted VEGF-2 protein or the mature form having a continuous series of deleted residues from the amino or the carboxy terminus, or both. For example, any number of amino acids, ranging from 1-60, can be deleted from the amino terminus of either the secreted VEGF-2 polypeptide or the mature form. Similarly, any number of amino acids, ranging from 1-30, can be deleted from the carboxy terminus of the secreted VEGF-2 protein or mature form. Furthermore, any combination of the above amino and carboxy terminus deletions are preferred. Similarly, polynucleotide fragments encoding these VEGF-2 polypeptide fragments are also preferred.

Also preferred are VEGF-2 polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:2 falling within conserved domains are specifically contemplated by the present invention. (See FIG. 2.) Moreover, polynucleotide fragments encoding these domains are also contemplated.

Other preferred fragments are biologically active VEGF-2 fragments. Biologically active fragments are those exhibiting activity similar, but not necessarily identical, to an activity of the VEGF-2 polypeptide. The biological activity of the fragments may include an improved desired activity, or a decreased undesirable activity.

The polypeptides of the present invention may be recombinant polypeptides, natural polypeptides, or synthetic polypeptides, preferably recombinant polypeptides.

It will be recognized in the art that some amino acid sequences of the VEGF-2 polypeptide can be varied without significant effect of the structure or function of the protein. If such differences in sequence are contemplated, it should be remembered that there will be critical areas on the protein which determine activity.

Thus, the invention further includes variations of the VEGF-2 polypeptide which show substantial VEGF-2 polypeptide activity or which include regions of VEGF-2 protein such as the protein portions discussed below. Such mutants include deletions, insertions, inversions, repeats, and type substitutions. As indicated above, guidance concerning which amino acid changes are likely to be phenotypically silent can be found in Bowie, J. U., et al., "Deciphering the Message in Protein Sequences: Tolerance to Amino Acid Substitutions," *Science* 247:1306-1310 (1990).

Thus, the fragments, derivatives, or analogs of the polypeptides of FIGS. 1 or 2, or that encoded by the deposited cDNAs may be: (1) one in which one or more of the amino acid residues are substituted with a conserved or non-conserved amino acid residue (preferably a conserved amino acid residue) and such substituted amino acid residue may or may not be one encoded by the genetic code; or (ii) one in which one or more of the amino acid residues includes a substituent group; or (iii) one in which the mature polypeptide is fused with another compound, such as a compound to increase the half-life of the polypeptide (for example, polyethylene glycol); or (iv) one in which the additional amino acids are fused to the mature polypeptide, such as a leader or secretory sequence or a sequence which is employed for purification of the mature polypeptide or a proprotein sequence; or (v) one in which comprises fewer amino acid residues shown in SEQ ID NOS: 2 or 4, and retains the conserved motif and yet still retains activity characteristics of the VEGF family of polypeptides. Such fragments, derivatives, and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the VEGF-2 protein. The prevention of aggregation is highly desirable. Aggregation of proteins not only results in a loss of activity but can also be problematic when preparing pharmaceutical formulations, because they can be immunogenic. (Pinckard et al., *Clin. Exp. Immunol.* 2:331-340 (1967); Robbins et al., *Diabetes* 36:838-845 (1987); Cleland et al. *Crit. Rev. Therapeutic Drug Carrier Systems* 10:307-377 (1993)).

The replacement of amino acids can also change the selectivity of binding to cell surface receptors. Ostade et al., *Nature* 361:266-268 (1993) describes certain mutations resulting in selective binding of TNF-a to only one of the two known types of TNF receptors. Thus, the VEGF-2 of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Tables 1 and 2).

TABLE 1

| Conservative Amino Acid Substitutions | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

TABLE 2

Preferred Amino Acid Substitutions

| Original Residue | Preferred Substitutions | Exemplary Substitutions |
| --- | --- | --- |
| Ala (A) | Val | Val; Leu; Ile |
| Arg (R) | Lys | Lys; Gln; Asn |
| Asn (N) | Gln | Gln; His; Lys; Arg |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Arg | Asn; Gln; Lys; Arg |
| Ile (I) | Leu | Leu; Val; Met; Ala; Phe; norleucine |
| Leu (L) | Ile | norleucine; Ile; Val; Met; Ala; Phe |
| Lys (K) | Arg | Arg; Gln; Asn |
| Met (M) | Leu | Leu; Phe; Ile |
| Phe (F) | Leu | Leu; Val; Ile; Ala |
| Pro (P) | Gly | Gly |
| Ser (S) | Thr | Thr |
| Thr (T) | Ser | Ser |
| Trp (W) | Tyr | Tyr |
| Tyr (Y) | Phe | Trp; Phe; Thr; Ser |
| Val (V) | Leu | Ile; Leu; Met; Phe; Ala; norleucine |

Of course, the number of amino acid substitutions a skilled artisan would make depends on many factors, including those described above. Generally speaking, the number of substitutions for any given VEGF-2 polypeptide will not be more than 50, 40, 30, 25, 20, 15, 10, 5 or 3.

Amino acids in the VEGF-2 protein of the present invention that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)).

The polypeptides and polynucleotides of the present invention are preferably provided in an isolated form, and preferably are purified to homogeneity.

The term "isolated" means that the material is removed from its original environment (e.g, the natural environment if it is naturally occurring). For example, a naturally-occuring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that such vector or composition is not part of its natural environment.

In specific embodiments, the polynucleotides of the invention are less than 300 kb, 200 kb, 100 kb, 50 kb, 15 kb, 10 kb, or 7.5 kb in length. In a further embodiment, polynucleotides of the invention comprise at least 15 contiguous nucleotides of VEGF-2 coding sequence, but do not comprise all or a portion of any VEGF-2 intron. In another embodiment, the nucleic acid comprising VEGF-2 coding sequence does not contain coding sequences of a genomic flanking gene (i.e., 5' or 3' to the VEGF-2 gene in the genome).

The polypeptides of the present invention include the polypeptides of SEQ ID NOS:2 and 4 (in particular the mature polypeptide) as well as polypeptides which have at least 70% similarity (preferably at least 70% identity) to the polypeptides of SEQ ID NOS:2 and 4, and more preferably at least 90% similarity (more preferably at least 95% identity) to the polypeptides of SEQ ID NOS:2 and 4, and still more preferably at least 95% similarity (still more preferably at least 90% identity) to the polypeptides of SEQ ID NOS:2 and 4 and also include portions of such polypeptides with such portion of the polypeptide generally containing at least 30 amino acids and more preferably at least 50 amino acids. As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The polypeptides of the present invention include the polypeptide encoded by the deposited cDNA including the leader, the mature polypeptide encoded by the deposited the cDNA minus the leader (i.e., the mature protein); a polypeptide comprising amino acids about −23 to about 396 in SEQ ID NO:2; a polypeptide comprising amino acids about −22 to about 396 in SEQ ID NO:2; a polypeptide comprising amino acids about 1 to about 396 in SEQ ID NO:2; as well as polypeptides which are at least 95% identical, and more preferably at least 96%, 97%, 98% or 99% identical to the polypeptides described above and also include portions of such polypeptides with at least 30 amino acids and more preferably at least 50 amino acids.

VEGF-2 Derivatives

The VEGF-2 wild type and analogs may be further modified to contain additional chemical moieties not normally part of the protein. Those derivatized moieties may improve the solubility, the biological half life or absorption of the protein. The moieties may also reduce or eliminate any desirable side effects of the proteins and the like. an overview for those moieties can be found in REMINGTON'S PHARMACEUTICAL SCIENCES, 18th ed., Mack Publishing Co., Easton, Pa. (1990).

The chemical moieties most suitable for derivatization include water soluble polymers. A water soluble polymer is desirable because the protein to which it is attached does not precipitate in an aqueous environment, such as a physiological environment. Preferably, the polymer will be pharmaceutically acceptable for the preparation of a therapeutic product or composition. One skilled in the art will be able to select the desired polymer based on such considerations as whether the polymer/protein conjugate will be used therapeutically, and if so, the desired dosage, circulation time, resistance to proteolysis, and other considerations. The effectiveness of the derivatization may be ascertained by administering the derivative, in the desired form (i.e., by osmotic pump, or, more preferably, by injection or infusion, or, further formulated for oral, pulmonary or other delivery routes), and determining its effectiveness.

Suitable water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water.

The polymer may be of any molecular weight, and may be branched or umbranched. For polyethylene glycol, the preferred molecular weight ranges from about 2 kDa to about 100 kDa for ease in handling and manufacturing (the term "about" indicating that in preparations of polyethylene glycol, some molecules will weigh more, some less, than the stated molecular weight). Other sizes may be used, depending on the desired therapeutic profile (e.g., the duration of sustained release desired, the effects, if any on biological activity, the ease in handling, the degree or lack of antigenicity and other known effects of polyethylene glycol on a therapeutic protein or variant).

The number of polymer molecules so attached may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proportion of polymer molecules to protein (or peptide) molecules will vary, as will their concentrations in the reaction mixture. In general, the optimum ratio (in terms of efficiency of reaction in that there is no excess unreacted protein or polymer) will be determined by factors such as the desired degree of derivatization (e.g., mono, di-, tri-, etc.), the molecular weight of the polymer selected, whether the polymer is branched or unbranched, and the reaction conditions.

The polyethylene glycol molecules (or other chemical moieties) should be attached to the protein with consideration of effects on functional or antigenic domains of the protein. There are a number of attachment methods available to those skilled in the art. See for example, EP 0 401 384, the disclosure of which is hereby incorporated by reference (coupling PEG to G-CSF), see also Malik et al., *Exp. Hematol* 20:1028-1035 (1992) (reporting pegylation of GM-CSF,using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residue. Those having a free carboxyl group may include aspartic acid residues, glutamic acid residues, and the C-terminal amino acid residue. Sulfhydryl groups may also be used as a reactive group for attaching the polyethylene glycol molecule(s). For therapeutic purposes, attachment at an amino group, such as attachment at the N-terminus or lysine group is preferred. Attachment at residues important for receptor binding should be avoided if receptor binding is desired.

One may specifically desire an N-terminal chemically modified protein. Using polyethylene glycol as an illustration of the present compositions, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one may selectively N-terminally pegylate the protein by performing the reaction at a pH which allows one to take advantage of the pKa differences between the epsilon-amino group of the lysine residues and that of the alpha-amino group of the N-terminal residue of the protein. By such selective derivatization, attachment of a water soluble polymer to a protein is controlled: the conjugation with the polymer takes place predominantly at the N-terminus of the protein and no significant modification of other reactive groups, such as the lysine side chain amino groups, occurs. Using reductive alkylation, the water soluble polymer may be of the type described above, and should have a single reactive aldehyde for coupling to the protein. Polyethylene glycol propionaldehyde, containing a single reactive aldehyde, may be used.

The present invention contemplates use of derivatives which are prokaryote-expressed VEGF-2, or variants thereof, linked to at least one polyethylene glycol molecule, as well as use of VEGF-2, or variants thereof, attached to one or more polyethylene glycol molecules via an acyl or alkyl linkage.

Pegylation may be carried out by any of the pegylation reactions known in the art. See, for example: Focus on Growth Factors, 3 (2): 4-10 (1992); EP 0 154 316, the disclosure of which is hereby incorporated by reference; EP 0 401 384; and the other publications cited herein that relate to pegylation. The pegylation may be carried out via an acylation reaction or an alkylation reaction with a reactive polyethylene glycol molecule (or an analogous reactive water-soluble polymer).

Pegylation by acylation generally involves reacting an active ester derivative of polyethylene glycol with the VEGF-2 protein or variant. Any known or subsequently discovered reactive PEG molecule may be used to carry out the pegylation of VEGF-2 protein or variant. A preferred activated PEG ester is PEG esterified to N-hydroxysuccinimide. As used herein, "acylation" is contemplated to include without limitation the following types of linkages between the therapeutic protein and a water soluble polymer such as PEG: amide, carbamate, urethane, and the like. See *Bioconjugate Chem.* 5:133-140 (1994). Reaction conditions may be selected from any of those known in the pegylation art or those subsequently developed, but should avoid conditions of temperature, solvent and pH that would inactivate the VEGF-2 or variant to be modified.

Pegylation by acylation will generally result in a poly-pegylated VEGF-2 protein or variant. Preferably, the connecting linkage will be an amide. Also preferably, the resulting product will be substantially only (e.g., >95%) mono-, di- or tri-pegylated. However, some species with higher degrees of peglylation may be formed in amounts depending on the specific reaction conditions used. If desired, more purified pegylated species may be separated from the mixture, particularly unreacted species, by standard purification techniques, including, among others, dialysis, salting-out, ultrafiltration, ion-exchange chromatography, gel filtration chromatography and electrophoresis.

Pegylation by alkylation generally involves reacting a terminal aldehyde derivative of PEG with the VEGF-2 protein or variant in the presence of a reducing agent. Pegylation by alkylation can also result in poly-pegylated VEGF-2 protein or variant. In addition, one can manipulate the reaction conditions to favor pegylation substantially only at the a-amino group of the N-terminus of the VEGF-2 protein or variant (i.e., a mono-pegylated protein). In either case of monopegylation or polypegylation, the PEG groups are preferably attached to the protein via a —CH2—NH— group. With particular reference to the —CH2— group, this type of linkage is referred to herein as an "alkyl" linkage.

Derivatization via reductive alkylation to produce a monopegylated product exploits differential reactivity of different types of primary amino groups (lysine versus the N-terminal) available for derivatization. The reaction is performed at a pH which allows one to take advantage of the pKa differences between the ε-amino groups of the lysine residues and that of the α-amino group of the N-terminal residue of the protein. By such selective derivatization, attachment of a water soluble polymer that contains a reactive group such as an aldehyde, to a protein is controlled: the conjugation with the polymer takes place predominantly at the N-terminus of the protein and no significant modification of other reactive groups, such as the lysine side chain amino groups, occurs. In one important aspect, the present invention contemplates use of a substantially homogeneous preparation of monopolymer/VEGF-2 protein (or variant) conjugate molecules (meaning VEGF-2 protein or variant to which a polymer molecule has been attached substantially only (i.e., >95%) in a single location). More specifically, if polyethylene glycol is used, the present invention also encompasses use of pegylated VEGF-2 protein or variant lacking possibly antigenic linking groups, and having the polyethylene glycol molecule directly coupled to the VEGF-2 protein or variant.

Thus, it is contemplated that VEGF-2 to be used in accordance with the present invention may include pegylated VEGF-2 protein or variants, wherein the PEG group(s) is (are) attached via acyl or alkyl groups. As discussed above, such products may be mono-pegylated or poly-pegylated (e.g., containing 2-6, and preferably 2-5, PEG groups). The PEG groups are generally attached to the protein at the α- or ϵ-amino groups of amino acids, but it is also contemplated that the PEG groups could be attached to any amino group attached to the protein, which is sufficiently reactive to become attached to a PEG group under suitable reaction conditions.

The polymer molecules used in both the acylation and alkylation approaches may be selected from among water soluble polymers as described above. The polymer selected should be modified to have a single reactive group, such as an active ester for acylation or an aldehyde for alkylation, preferably, so that the degree of polymerization may be controlled as provided for in the present methods. An exemplary reactive PEG aldehyde is polyethylene glycol propionaldehyde, which is water stable, or mono C1-C10 alkoxy or aryloxy derivatives thereof (see, U.S. Pat. No. 5,252,714). The polymer may be branched or unbranched. For the acylation reactions, the polymer(s) selected should have a single reactive ester group. For the present reductive alkylation, the polymer(s) selected should have a single reactive aldehyde group. Generally, the water soluble polymer will not be selected from naturally-occurring glycosyl residues since these are usually made more conveniently by mammalian recombinant expression systems. The polymer may be of any molecular weight, and may be branched or unbranched.

A particularly preferred water-soluble polymer for use herein is polyethylene glycol. As used herein, polyethylene glycol is meant to encompass any of the forms of PEG that have been used to derivatize other proteins, such as mono-(C1-C10) alkoxy- or aryloxy-polyethylene glycol.

In general, chemical derivatization may be performed under any suitable condition used to react a biologically active substance with an activated polymer molecule. Methods for preparing pegylated VEGF-2 protein or variant will generally comprise the steps of (a) reacting a VEGF-2 protein or variant with polyethylene glycol (such as a reactive ester or aldehyde derivative of PEG) under conditions whereby the protein becomes attached to one or more PEG groups, and (b) obtaining the reaction product(s). In general, the optimal reaction conditions for the acylation reactions will be determined case-by-case based on known parameters and the desired result. For example, the larger the ratio of PEG:protein, the greater the percentage of poly-pegylated product.

Reductive alkylation to produce a substantially homogeneous population of mono-polymer/VEGF-2 protein (or variant) conjugate molecule will generally comprise the steps of: (a) reacting a VEGF-2 protein or variant with a reactive PEG molecule under reductive alkylation conditions, at a pH suitable to permit selective modification of the a-amino group at the amino terminus of said VEGF-2 protein or variant; and (b) obtaining the reaction product(s).

For a substantially homogeneous population of monopolymer/VEGF-2 protein (or variant) conjugate molecules, the reductive alkylation reaction conditions are those which permit the selective attachment of the water soluble polymer moiety to the N-terminus of VEGF-2 protein or variant Such reaction conditions generally provide for pKa differences between the lysine amino groups and the α-amino group at the N-terminus (the pKa being the pH at which 50% of the amino groups are protonated and 50% are not). The pH also affects the ratio of polymer to protein to be used. In general, if the pH is lower, a larger excess of polymer to protein will be desired (i.e., the less reactive the N-terminal α-amino group, the more polymer needed to achieve optimal conditions). If the pH is higher, the polymer:protein ratio need not be as large (i.e., more reactive groups are available, so fewer polymer molecules are needed). For purposes of the present invention, the pH will generally fall within the range of 3-9, preferably 3-6.

Another important consideration is the molecular weight of the polymer. In general, the higher the molecular weight of the polymer, the fewer polymer molecules may be attached to the protein. Similarly, branching of the polymer should be taken into account when optimizing these parameters. Generally, the higher the molecular weight (or the more branches) the higher the polymer:protein ratio. In general, for the pegylation reactions contemplated herein, the preferred average molecular weight is about 2 kDa to about 100 kDa The preferred average molecular weight is about 5 kDa to about 50 kDa, particularly preferably about 12 kDa to about 25 kDa. The ratio of water-soluble polymer to VEGF-2 protein or variant will generally range from 1:1 to 100:1, preferably (for polypegylation) 1:1 to 20:1 and (for monopegylation) 1:1 to 5:1.

Using the conditions indicated above, reductive alkylation will provide for selective attachment of the polymer to any VEGF-2 protein or variant having an α-amino group at the amino terminus, and provide for a substantially homogenous preparation of monopolymer/VEGF-2 protein (or variant) conjugate. The term "monopolymer/VEGF-2 protein (or variant) conjugate" is used here to mean a composition comprised of a single polymer molecule attached to a molecule of VEGF-2 protein or VEGF-2 variant protein. The monopolymer/VEGF-2 protein (or variant) conjugate preferably will have a polymer molecule located at the N-terminus, but not on lysine amino side groups. The preparation will preferably be greater than 90% monopolymer/VEGF-2 protein (or variant)

conjugate, and more preferably greater than 95% monopolymer/VEGF-2 protein (or variant) conjugate, with the remainder of observable molecules being unreacted (i.e., protein lacking the polymer moiety).

For the present reductive alkylation, the reducing agent should be stable in aqueous solution and preferably be able to reduce only the Schiff base formed in the initial process of reductive alkylation. Preferred reducing agents may be selected from sodium borohydride, sodium cyanoborohydride, dimethylamine borane, trimethylamine borane and pyridine borane. A particularly preferred reducing agent is sodium cyanoborohydride. Other reaction parameters, such as solvent, reaction times, temperatures, etc., and means of purification of products, can be determined case-by-case based on the published information relating to derivatization of proteins with water soluble polymers (see the publications cited herein).

Epitopes and Antibodies

The present invention encompasses polypeptides comprising, or alternatively consisting of, an epitope of the polypeptide having an amino acid sequence of SEQ ID NOS:2 or 4, or an epitope of the polypeptide sequence encoded by a polynucleotide sequence contained in ATCC™ Deposit No: 97149 or 75698 or encoded by a polynucleotide that hybridizes to the complement of the sequence of SEQ ID NOS:1 or 3 or contained in ATCC™ Deposit No: 97149 or 75698 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NOS:1 or 3), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

Specific monoclonal antibodies have been raised against the VEGF-2 protein (SEQ ID NO:2). These monoclonal antibodies have been given the following designations: 12E2; 13A2; 15C2; 13D6; 13E6; 19A3; 8G11; 11A8, 15E10, 9B4, and 13G11. Monoclonal antibodies 15C2, 13D6, and 15E10 were deposited as a group on Jun. 8, 1999, and given ATCC™ Deposit Number PTA-198. Monoclonal antibody 13D6 was also deposited by itself on Jul. 29, 1999, and given ATCC™ Deposit Number PTA435. Monoclonal antibodies 13A2, 13E6, and 9B4 were deposited as a group on Jun. 8, 1999, and given ATCC™ Deposit Number PTA-199. Monoclonal antibodies 8G11, 12E2, and 13G11 were deposited as a group on Jun. 8, 1999, and given ATCC™ Deposit Number PTA-200. Monoclonal antibodies 11A8 and 19A3 were deposited as a group on Jun. 8, 1999, and given ATCC™ Deposit Number PTA-201. The antibodies deposited in a mixture can be isolated based on their characteristics, such as epitope map position, affinity, species as described in the Examples.

Figure 24:
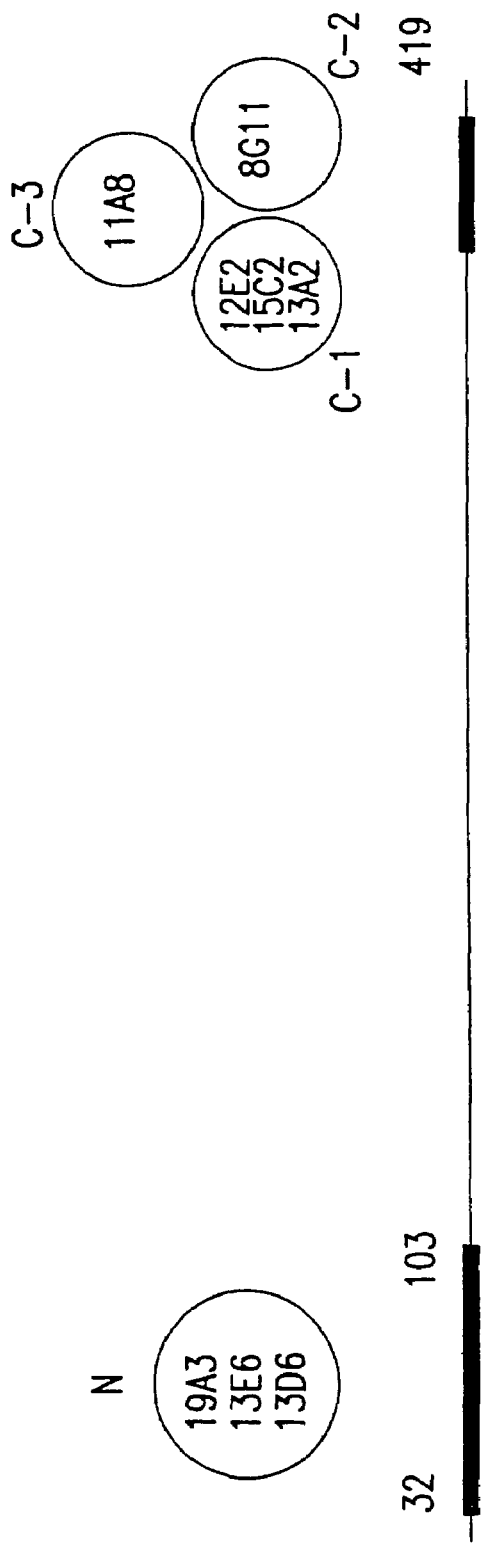
FIG. 24 shows the epitope map for murine anti VEGF-2 monoclonal antibodies.

The epitopes to which the above listed monoclonal antibodies have specificity have been mapped to the VEGF-2 protein (See FIG. 24). Furthermore, the status of each monoclonal-antibody, such as the relative affinity and ELISA and Western reactivity, have been disclosed for each of the monoclonal antibodies (See FIG. 25).

The term "epitopes," as used herein, refers to portions of a polypeptide having antigenic or immunogenic activity in an animal, preferably a mammal, and most preferably in a human. In a preferred embodiment the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998-4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131-5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767-778 (1984); Sutcliffe et al., Science 219:660-666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910-914; and Bittle et al., J. Gen. Virol. 66:2347-2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347-2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl- N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394, 827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811, 238; 5,830,721; 5,834,252; and 5,837,458, and Patten et al., Curr. Opinion Biotechnol. 8:724-33 (1997); Harayama, Trends Biotechnol. 16(2):76-82 (1998); Hansson, et al., J. Mol. Biol. 287:265-76 (1999); and Lorenzo and Blasco, Biotechniques 24(2):308-13 (1998) (each of these patents and publications are hereby incorporated by reference in its entirety). In one embodiment, alteration of polynucleotides corresponding to SEQ ID NO:1 or 3 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Antibodies

Further polypeptides of the invention relate to antibodies and T-cell antigen receptors (TCR) which immunospecifically bind a polypeptide, polypeptide fragment, or variant of SEQ ID NOS:2 or 4, and/or an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immmunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Preferred epitopes of the invention include: Leu-37 to about Glu-45 in SEQ ID NO:2, from about Tyr-58 to about Gly-66 in SEQ ID NO:2, from about Gln-73 to about Glu-81 in SEQ ID NO:2, from about Asp-100 to about Cys-108 in SEQ ID NO:2, from about Gly-140 to about Leu-148 in SEQ ID NO:2, from about Pro-168 to about Val-176 in SEQ ID NO:2, from about His-183 to about Lys-191 in SEQ ID NO:2, from about Ile-201 to about Thr-209 in SEQ ID NO:2, from about Ala-216 to about Tyr-224 in SEQ ID NO:2, from about Asp-244 to about His-254 in SEQ ID NO:2, from about Gly-258 to about Glu-266 in SEQ ID NO:2, from about Cys-272 to about Ser-280 in SEQ ID NO:2, from about Pro-283 to about Ser-291 in SEQ ID NO:2, from about Cys-296 to about Gln-304 in SEQ ID NO:2, from about Ala-307 to about Cys-316 in SEQ ID NO:2, from about Val-319 to about Cys-335 in SEQ ID NO:2, from about Cys-339 to about Leu-347 in SEQ ID NO:2, from about Cys-360 to about Glu-373 in SEQ ID NO:2, from about Tyr-378 to about Val-386 in SEQ ID NO:2, and from about Ser-388 to about Ser-396 in SEQ ID NO:2, as well as polynucleotides that encode these epitopes. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%/O, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55% and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16):3668-3678 (1998); Harrop et al., J. lmnunol. 161(4): 1786-1794 (1998); Zhu et al., Cancer Res. 58(15):3209-3214 (1998); Yoon et al., J. Immunol. 160(7):3170-3179 (1998); Prat et al., J. Cell. Sci. 111(Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167

(1998); Bartunek et al., Cytokine 8(1):14-20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC™. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et.al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698;

5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567; and 4,816,397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NOS:2 or 4.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties ), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242:1038-1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well-known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., T1 plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5 K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa califomica nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non- essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, tanscription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, 1993, TIB TECH 11(5):155-215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in vitro immunoassays and purification methods using methods known in the art. See e.g., Harbor et al., supra, and PCT publication WO 93/21232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452 (1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341(1992) (said references incorporated by reference in their entireties).

As discussed, supra, the polypeptides corresponding to a polypeptide, polypeptide fragment, or a variant of SEQ ID NOS:2 or 4 may be fused or conjugated to the above antibody portions to increase the in vivo half life of the polypeptides or for use in inumunoassays using methods known in the art. Further, the polypeptides corresponding to SEQ ID NOS:2 or 4 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker: et al., Nature 331:84-86 (1988). The polypeptides of the present invention fused or conjugated to an antibody having disulfide- linked dimeric structures (due to the IgG) may also be more efficient in binding and neutralizing other molecules, than the monomeric secreted protein or protein fragment alone. (Fountoulakis et al., J. Biochem. 270:3958-3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52-58 (1995); Johanson et al., J. Biol. Chem. 270:9459-9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexahistidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or frgments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis- dichlorodiamine platinum (11) (DDP) cisplatin), anthracyclines (e.g., daunorubicin (formerly daunomycin) and doxorubicin), antibiotics (e.g., dactinomycin (formerly actinomycin), bleomycin, mnithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., Int. Immunol., 6:1567-1574 (1994)), VEGI (See, International Publication No. WO 99/23105), a thrombotic agent or an anti- angiogenic agent, e.g., angiostatin or endostatin; or, biological response modifiers such as, for example, lymphokines, interleukin-1 ("IL-I"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R, Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al, Cell, 96:737-49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays For Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 40° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF, or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

In summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5\times10^{-2}$ M, $10^{-2}$ M, $5\times10^{-3}$ M, $10^{-4}$ M, $5\times10^{-4}$ M, $10^{-4}$ M, $5\times10^{-4}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{13}$ M, $10^{-13}$ M, $5\times10^{-4}$ M, $10^{-14}$ M, $5\times10^{-15}$ M, and $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, N.Y. (1993); and Kfiegler, Gene Transfer and Expression, A Laboratory Manual, Stockton Press, N.Y. (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid- carrying vectors, or indirect, in which case, cells are first transformed with the nucleic acids in vitro, then transplanted into the patient These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; W093/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contains nucleic acid sequences encoding an antibody of the invention are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient More detail about retroviral vectors can be found in Boesen et al., Biotherapy 6:291-302 (1994), which describes the use of a retroviral vector to deliver the mdrl gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

Adenoviruses are other viral vectors that can be used in gene therapy. Adenoviruses are especially attractive vehicles for delivering genes to respiratory epithelia Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). In a preferred embodiment, adenovirus vectors are used.

Adeno-associated virus (AAV) has also been proposed for use in gene therapy (Walsh et al., Proc. Soc. Exp. Biol. Med. 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993); Cohen et al., Meth. Enzymol. 217:618-644 (1993); Cline, Pharmac. Ther. 29:69-92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973-985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Demonstration of Therapeutic or Prophylactic Activity

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to detemniine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321: 574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228: 190 (1985); During et al., Ann. Neurol. 25:351 (1989); Howard et al., J.Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patients circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976-985 (1985); Jalkanen, et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($125I$, $121I$), carbon ($14C$), sulfur ($35S$), tritium ($3H$), indium ($112In$), and technetium ($99Tc$); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodiesand Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment the molecule is labeled with a positron emitting metal and is detected in the patent using positron emission-tomography. In yet another embodiment the molecule is labeled with a paramagnetic label and is detected in a patient using magnetic resonance imaging (MRI).

Kits

The present invention provides kits that can be used in the above methods. In one embodiment a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit Preferably, the kits of the present invention further comprise a control antibody which does not react with the polypeptide of interest. In another specific embodiment the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the fist antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody isattached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, SL Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Fusion Proteins

Any VEGF-2 polypeptide can be used to generate fusion proteins. For example, the VEGF-2 polypeptide, when fused to a second protein, can be used as an antigenic tag. Antibodies raised against the VEGF-2 polypeptide can be used to indirectly detect the second protein by binding to the VEGF-2. Moreover, because secreted proteins target cellular locations based on trafficking signals, the VEGF-2 polypeptides can be used as a targeting molecule once fused to other proteins.

Examples of domains that can be fused to VEGF-2 polypeptides include not only heterologous signal sequences, but also other heterologous functional regions. The fusion does not necessarily need to be direct, but may occur through linker sequences.

Moreover, fusion proteins may also be engineered to improve characteristics of the VEGF-2 polypeptide. For instance, a region of additional amino acids, particularly charged amino acids, may be added to the N-terminus of the VEGF-2 polypeptide to improve stability and persistence during purification from the host cell or subsequent handling and storage. Also, peptide moieties may be added to the VEGF-2 polypeptide to facilitate purification. Such regions may be removed prior to final preparation of the VEGF-2 polypeptide. The addition of peptide moieties to facilitate handling of polypeptides are familiar and routine techniques in the art.

Moreover, VEGF-2 polypeptides, including fragments, and specifically epitopes, can be combined with parts of the constant domain of immunoglobulins (IgG), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., *Nature* 331:84-86 (1988).) Fusion proteins having disulfide-linked dimeric structures (due to the IgG) can also be more efficient in binding and neutralizing other molecules, than the monomeric secreted protein or protein fragment alone. (Fountoulakis et al., *J. Biochem.* 270:3958-3964 (1995).)

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharnacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., *J. Molecular Recognition* 8:52-58 (1995); K. Johanson et al., *J. Biol. Chem.* 270:9459-9471 (1995).) :

Moreover, the VEGF-2 polypeptides can be fused to marker sequences, such as a peptide which facilitates purification of VEGF-2. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad Sci. USA 86:821-824 (1989), for instance, hexa-histidine provides for convenient purification of the fusion protein. Another peptide tag useful for purification, the "HA" tag, corresponds to an epitope derived from the influenza hemagglutinin protein. (Wilson et al., *Cell* 37:767 (1984).)

Thus, any of these above fusions can be engineered using the VEGF-2 polynucleotides or the polypeptides.

Vectors and Host Cells

The present invention also relates to recombinant vectors, which include the isolated nucleic acid molecules of the present invention, and to host cells containing the recombinant vectors, as well as to methods of making such vectors and host cells and for using them for production of VEGF-2 polypeptides or peptides by recombinant techniques.

Host cells are genetically engineered (transduced, transformed, or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants, or amplifying the VEGF-2 genes of the invention. The culture conditions, such as temperature, pH and the like, are those previously used with the host cell selected for expression, and will be apparent to the skilled artisan.

The polynucleotides of the present invention may be employed for producing polypeptides by recombinant techniques. Thus, for example, the polynucleotide sequence may be included in any one of a variety of expression vectors for expressing a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus, and pseudorabies. However, any other plasmid or vector may be used so long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain at least one selectable marker gene to provide a phenotypic trait for selection of transformed host cells. Such markers include dihydrofolate reductase (DHFR) or neomycin resistance for eukaryotic cell culture, and tetracycline or ampicillin resistance for culturing in *E. coli* and other bacteria.

The vector containing the appropriate DNA sequence as herein above described, as well as an appropriate promoter or control sequence, may be employed to transform an appropriate host to permit the host to express the protein. Representative examples of appropriate hosts, include but are not limited to: bacterial cells, such as *E. coli, Salmonella typhimurium,* and *Streptomyces;* fungal cells, such as yeast; insect cells, such as *Drosophila* S2 and *Spodoptera* 539; animal cells such as CHO, COS, and Bowes melanoma; and plant cells. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example—bacterial: pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

In addition to the use of expression vectors in the practice of the present invention, the present invention further includes novel expression vectors comprising operator and promoter elements operatively linked to nucleotide sequences encoding a protein of interest One example of such a vector is pHE4a which is described in detail below.

As summarized in FIGS. 16 and 17, components of the pHE4a vector (SEQ ID NO:9) include: 1) a neomycinphosphotransferase gene as a selection marker, 2) an E. coli origin of replication, 3) a T5 phage promoter sequence, 4) two lac operator sequences, 5) a Shine-Delgarno sequence, 6) the lactose operon repressor gene (lacIq) and 7) a multiple cloning site linker region. The origin of replication (oriC) is derived from pUC19 (LTI, Gaithersburg, Md.). The promoter sequence and operator sequences were made synthetically. Synthetic production of nucleic acid sequences is well known in the art. CLONTECH 95/96 Catalog, pages 215-216, CLONTECH, 1020 East Meadow Circle, Palo Alto, Calif. 94303. The pHE4a vector was deposited with the ATCC™ on Feb. 25, 1998, and given accession number 209645.

A nucleotide sequence encoding VEGF-2 (SEQ ID NO:1), is operatively linked to the promoter and operator of pHE4a by restricting the vector with NdeI and either XbaI, BamHI, XhoI, or Asp718, and isolating the larger fragment (the multiple cloning site region is about 310 nucleotides) on a gel. The nucleotide sequence encoding VEGF-2 (SEQ ID NO:1) having the appropriate restriction sites is generated, for example, according to the PCR protocol described in Example 1, using PCR primers having restriction sites for NdeI (as the 5' primer) and either XbaI, BamHI, XhoI, or Asp718 (as the 3' primer). The PCR insert is gel purified and restricted with compatible enzymes. The insert and vector are ligated according to standard protocols.

As noted above, the pHE4a vector contains a lacIq gene. LacIq is an allele of the lacIq gene which confers tight regulation of the lac operator. Amann, E. et al., Gene 69:301-315 (1988); Stark, M., Gene 51:255-267 (1987). The lacIq gene encodes a repressor protein which binds to lac operator sequences and blocks transcription of down-stream (i.e., 3') sequences. However, the lacIq gene product dissociates from the lac operator in the presence of either lactose or certain lactose analogs, e.g., isopropyl B-D-thiogalactopyranoside (IPTG). VEGF-2 thus is not produced in appreciable quantities in uninduced host cells containing the pHE4a vector. Induction of these host cells by the addition of an agent such as IPTG, however, results in the expression of the VEGF-2 coding sequence.

The promoter/operator sequences of the pHE4a vector (SEQ ID NO:10) comprise a T5 phage promoter and two lac operator sequences. One operator is located 5' to the transcriptional start site and the other is located 3' to the same site. These operators, when present in combination with the lacIq gene product, confer tight repression of down-stream sequences in the absence of a lac operon inducer, e.g., IPTG, Expression of operatively linked sequences located down-stream from the lac operators may be induced by the addition of a lac operon inducer, such as IPTG. Binding of a lac inducer to the lacIq proteins results in their release from the lac operator sequences and the initiation of transcription of operatively linked sequences. Lac operon regulation of gene expression is reviewed in Devlin, T., TEXTBOOK OF BIOCHEMISTRY WITH CLINICAL CORRELATIONS, 4th Edition (1997), pages 802-807.

The pHE4 series of vectors contain all of the components of the pHE4a vector except for the VEGF-2 coding sequence. Features of the pHE4a vectors include optimized synthetic T5 phage promoter, lac operator, and Shine-Delgarno sequences. Further, these sequences are also optimally spaced so that expression of an inserted gene may be tightly regulated and high level of expression occurs upon induction.

Among known bacterial promoters suitable for use in the production of proteins of the present invention include the E. coli lac1 and lacZ promoters, the T3 and T7 promoters, the gpt promoter, the lambda PR and PL promoters and the trp promoter. Suitable eukaryotic promoters include the CMV immediate early promoter, the HSV thymidine linase promoter, the early and late SV40 promoters, the promoters of retroviral LTRs, such as those of the Rous Sarcoma Virus (RSV), and metallothionein promoters, such as the mouse metallothionein-I promoter.

The pHE4a vector also contains a Shine-Delgarno sequence 5' to the AUG initiation codon. Shine-Delgarno sequences are short sequences generally located about 10 nucleotides up-stream (i.e., 5') from the AUG initiation codon. These sequences essentially direct prokaryotic ribosomes to the AUG initiation codon. Thus, the present invention is also directed to expression vector useful for the production of the proteins of the present invention. This aspect of the invention is exemplified by the pHE4a vector (SEQ ID NO:9).

Promoter regions can be selected from any desired gene using CAT (chloramphenicol transferase) vectors or other vectors with selectable markers. Two appropriate vectors are pKK232-8 and pCM7. Particular named bacterial promoters include lac1, lacZ, T3, T7, gpt, lambda PR, PL and trp. Eukaryotic promoters include CMV immediate early, HSV thymidine kinase, early and late SV40, LTRs from retrovirus, and mouse metallothionein-1. Selection of the appropriate vector and promoter is well within the level of ordinary skill in the art. In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, electroporation, transduction, infection, or other methods (Davis, L., et al., Basic Methods in Molecular Biology (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook. et al., Molecular Cloning: A Laboratory Manual, Second Edition, Cold Spring Harbor Laboratory, Cold Spring Harbor, N.Y. (1989), the disclosure of which is hereby incorporated by reference.

Transcription of a DNA encoding the polypeptides of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces,* and *Staphylococcus,* although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC™ 37017). Such commercial vectors include, for example, pKK223-3 (Pharmacia Fine Chemicals, Uppsala, Sweden) and GEM1 (Promega Biotec, Madison. Wis., USA). These pBR322 "backbone" sections are combined with an appropriate promoter and the structural sequence to be expressed.

Following transformation of a suitable host strain and growth of the host strain to an appropriate cell density, the selected promoter is derepressed by appropriate means (e.g., temperature shift or chemical induction) and cells are cultured for an additional period.

Cells are typically harvested by centrifugation, disrupted by physical or chemical means, and the resulting crude extract retained for further purification. Microbial cells employed in expression of proteins can be disrupted by any convenient method, well known to those skilled in the art, including freeze-thaw cycling, sonication, mechanical disruption, or use of cell lysing agents.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., VEGF-2 sequence), and/or to include genetic material (e.g., heterologous promoters) that is operably associated with VEGF-2 sequence of the invention, and which activates, alters, and/or amplifies endogenous VEGF-2 polynucleotides. For example, techniques known in the art may be used to operably associate heterologous control regions and endogenous polynucleotide sequences (e.g. encoding VEGF-2) via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., *Proc. Natl. Acad. Sci. USA* 86:8932-8935 (1989); and Zijlstra et al., *Nature* 342:435438 (1989), the disclosures of each of which are incorporated by reference in their entireties).

The host cell can be a higher eukaryotic cell, such as a mammalian cell (e.g., a human derived cell), or a lower eukaryotic cell, such as a yeast cell, or the host cell can be a prokaryotic cell, such as a bacterial cell. The host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., glycosylation, phosphorylation, cleavage) of proteins. Appropriate cell lines can be chosen to ensure the desired modifications and processing of the protein expressed.

The polypeptides can be recovered and purified from recombinant cell cultures by methods used heretofore, including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. It is preferred to have low concentrations (approximately 0.1-5 mM) of calcium ion present during purification (Price et al., *J. Biol. Chem.* 244: 917 (1969)). Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian. or other eukaryotic carbohydrates or may be non-glycosylated. Polypeptides of the invention may also include an initial methionine amino acid residue.

VEGF-2 Agonist and Antagonists

This invention is also related to a method of screening compounds to identify those which are VEGF-2 agonists or antagonists. An example of such a method takes advantage of the ability of VEGF-2 to significantly stimulate the proliferation of human endothelial cells in the presence of the comitogen Con A. Endothelial cells are obtained and cultured in 96-well flat-bottomed culture plates (Costar, Cambridge, Mass.) in a reaction mixture supplemented with Con-A (Calbiochem, La Jolla, Calif.). Con-A, polypeptides of the present invention and the compound to be screened are added. After incubation at 37EC, cultures are pulsed with 1 FCi of $^3$[H]thymidine (5 Ci/mmol; 1 Ci=37 BGq; NEN) for a sufficient time to incorporate the $^3$[M1] and harvested onto glass fiber filters (Cambridge Technology, Watertown, Mass.). Mean $^3$[H]-thymidine incorporation (cpm) of triplicate cultures is determined using a liquid scintillation counter (Beckman Instruments, Irvine, Calif.). Significant $^3$[H]thymidine incorporation, as compared to a control assay where the compound is excluded, indicates stimulation of endothelial cell proliferation.

To assay for antagonists, the assay described above is performed and the ability of the compound to inhibit $^3$[H]thymidine incorporation in the presence of VEGF-2 indicates that the compound is an antagonist to VEGF-2. Alternatively, VEGF-2 antagonists may be detected by combining VEGF-2 and a potential antagonist with membrane-bound VEGF-2 receptors or recombinant receptors under appropriate conditions for a competitive inhibition assay. VEGF-2 can be labeled, such as by radioactivity, such that the number of VEGF-2 molecules bound to the receptor can determine the effectiveness of the potential antagonist.

Alternatively, the response of a known second messenger system following interaction of VEGF-2 and receptor would be measured and compared in the presence or absence of the compound. Such second messenger systems include but are not limited to, cAMP guanylate cyclase, ion channels or phosphoinositide hydrolysis. In another method, a mammalian cell or membrane preparation expressing the VEGF-2 receptor is incubated with labeled VEGF-2 in the presence of the compound. The ability of the compound to enhance or block this interaction could then be measured.

Potential VEGF-2 antagonists include an antibody, or in some cases, an oligonucleotide, which bind to the polypeptide and effectively eliminate VEGF-2 function. Alternatively, a potential antagonist may be a closely related protein which binds to VEGF-2 receptors, however, they are inactive forms of the polypeptide and thereby prevent the action of VEGF-2. Examples of these antagonists include a negative dominant mutant of the VEGF-2 polypeptide, for example, one chain of the hetero-dimeric form of VEGF-2 may be dominant and may be mutated such that biological activity is not retained. An example of a negative dominant mutant includes truncated versions of a dimeric VEGF-2 which is capable of interacting with another dimer to form wild type VEGF-2, however, the resulting homo-dimer is inactive and fails to exhibit characteristic VEGF activity.

Another potential VEGF-2 antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res.6:3073 (1979); Cooney et al., Science 241:456 (1988); and Dervan et al., Science 251:1360 (1991)), thereby preventing transcription and the production of VEGF-2. The antisense RNA oligonucleotide hybridizes to the mRNA in vivo and blocks translation of the mRNA molecule into the VEGF-2 polypeptide (Antisense—Okano, J. Neurochem.56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of VEGF-2. Potential VEGF-2 antagonists also include small molecules which bind to and occupy the active site of the polypeptide thereby making the catalytic site inaccessible to substrate such that normal biological activity is prevented. Examples of small molecules include but are not limited to small peptides or peptide-like molecules.

Antisense oligonucleotide technology provides a novel approach to the inhibition of gene expression (see generally, Agrawal (1992) Trends in Biotech. 10:152; Wagner (1994) Nature 372:333-335; and Stein et al. (1993) Science 261: 1004-1012). By binding to the complementary nucleic acid sequence (the sense strand), antisense oligonucleotide are able to inhibit splicing and translation of RNA. In this way, antisense oligonucleotides are able to inhibit protein expression. Antisense oligonucleotides have also been shown to bind to genomic DNA, forming a triplex, and inhibit transcription. Furthermore, a 17 mer base sequence statistically occurs only once in the human genome, and thus extremely precise targeting of specific sequences is possible with such antisense oligonucleotides.

The antagonists may be employed to limit angiogenesis necessary for solid tumor metastasis. The identification of VEGF-2 can be used for the generation of certain inhibitors of vascular endothelial growth factor. Since angiogenesis and neovascularization are essential steps in solid tumor growth, inhibition of angiogenic activity of the vascular endothelial growth factor is very useful to prevent the further growth, retard, or even regress solid tumors. Although the level of expression of VEGF-2 is extremely low in normal tissues including breast, it can be found expressed at moderate levels in at least two breast tumor cell lines that are derived from malignant tumors. It is, therefore, possible that VEGF-2 is involved in tumor angiogenesis and growth.

Gliomas are also a type of neoplasia which may be treated with the antagonists of the present invention.

The antagonists may also be used to treat chronic inflammation caused by increased vascular permeability. In addition to these disorders, the antagonists may also be employed to treat retinopathy associated with diabetes, rheumatoid arthritis and psoriasis.

The antagonists may be employed in a composition with a pharmaceutically acceptable carrier, e.g., as hereinafter described.

Truncated versions of VEGF2 can also be produced that are capable of interacting with wild type VEGF2 to form dimers that fail to activate endothelial cell growth, therefore inactivating the endogenous VEGF2. Or, mutant forms of VEGF2 form dimers themselves and occupy the ligand binding domain of the proper tyrosine kinase receptors on the target cell surface, but fail to activate cell growth.

Alternatively, antagonists to the polypeptides of the present invention may be employed which bind to the receptors to which a polypeptide of the present invention normally binds. The antagonists may be closely related proteins such that they recognize and bind to the receptor sites of the natural protein, however, they are inactive forms of the natural protein and thereby prevent the action of VEGF2 since receptor sites are occupied. In these ways, the action of the VEGF2 is prevented and the antagonist/inhibitors may be used therapeutically as an anti-tumor drug by occupying the receptor sites of tumors which are recognized by VEGF2 or by inactivating VEGF2 itself. The antagonist/inhibitors may also be used to prevent inflammation due to the increased vascular permeability action of VEGF2. The antagonist/inhibitors may also be used to treat solid tumor growth, diabetic retinopathy, psoriasis and rheumatoid arthritis.

The antagonist/inhibitors may be employed in a composition with a pharmaceutically acceptable carrier, e.g., as hereinabove described. Moreover, as shown in Example 9, antibodies specific for VEGF-2 may be combined with VEGF-2 polypeptides to increase endothelial cell response. Endothelial cells responding to a combination of VEGF-2 polypeptide and VEGF-2 specific antibodies include vascular or lymphatic vessels. The combination of VEGF-2 specific antibodies and VEGF-2 polypeptide may be used to treat individuals in need of an increase in proliferation of endothelial cells, such as angiogenesis and/or lymphangiogenesis, as described throughout the specification.

Therapeutic Applications of VEGF-2

As used in the section below, "VEGF-2" is intended to refer to the full-length and mature forms of VEGF-2 polynucleotides and polypeptides described herein and to the VEGF-2 analogs, derivatives, and mutant polynucleotides and polypeptides described herein.

The VEGF-2 polypeptide of the present invention is a mitogen for photoreceptor cells. As shown in FIGS. 12-15, VEGF-2 increases cell number, cell survival, rhodopsin expression, and the number of rhodopsin cells in retinal cultures.

Accordingly, VEGF-2 may be employed to treat disorders of the eye, including injuries and diseases. These disorders include angioid streaks, retinitis pigmentosa, Kearn's Syndrome, pigment pattern dystrophies, retinal perforations, retinitis, chorioretinitis, cytomegalovirus retinitis, acute retinal necrosis syndrome, central alveolar choroidal dystrophy, dominant drusen, hereditary hemorrhagic macular dystrophy, North Carolina macular dystrophy, pericentral choroidal dystrophy, adult foveomacular dystrophy, benign concentric annular macular dystrophy, central aureolar pigment epithelial dystrophy, congenital macular coloboma, dominantly inherited cystoid macular edema, familial foveal retinoschisis, fenestrated sheen macular dystrophy, progressive foveal dystrophy, slowly progressive macular dystrophy, Sorsby's pseudoinflammatory dystrophy, cone-rod dystrophy, progressive cone dystrophy, Leber's congenital amaurosis, Goldman-Favre syndrome, Bardet-Biedl syndrome, Bassen-Kornzweig syndrome (abetalipoproteinemia), Best disease (vitelliform dystrophy), choroidemia, gyrate atrophy, congenital amaurosis, Refsum syndrome, Stargardt disease and Usher syndrome. Other retinopathies that may benefit from VEGF-2 admninistration include age-related macular degeneration (dry and wet forms), diabetic retinopathy, peripheral vitreoretinopathies, photic retinopathies, surgery-induced retinopathies, viral retinopathies (such as HIV retinopathy related to AIDS), ischemic retinopathies, retinal detachment and traumatic retinopathy.

VEGF-2 may be administered along with other proteins which are therapeutic for eye cells, including, but not limited to: retinoic acid, mitogens such as insulin, insulin-like growth factors, epidermal growth factor, vasoactive growth factor, pituitary adenylate cyclase activating polypeptide and somatostatin; neurotrophic factors such as glial cell line-derived neurotrophic factor, brain derived neurotrophic factor, neurotrophin-3, neurotrophin-4/5, neurotrophin-6, insulin-like growth factor, ciliary neurotrophic factor, acidic and basic fibroblast growth factors, fibroblast growth factor-5, transforming growth factor-beta, and cocaine-amphetamine regulated transcript (CART); and other growth factors such as epidermal growth factor, leukemia inhibitory factor, interleukins, interferons, and colony stimulating factors; as well as molecules and materials which are the functional equivalents to these factors.

Additionally, antibodies may further be used in an immunoassay to detect the presence of tumors in certain individuals. Enzyme immunoassay can be performed from the blood sample of an individual. Elevated levels of VEGF2 can be considered diagnostic of cancer.

Pharmaceutical Compositions

The VEGF-2 polypeptides and polynucleotides of the present invention may be employed in combination with a suitable pharmaceutical carrier to comprise a pharmaceutical composition. Such compositions comprise a therapeutically effective amount of the polypeptide, polynucleotide, agonist or antagonist and a pharmaceutically acceptable carrier or excipient. Such a carrier includes, but is not limited to, antioxidants, preservatives, coloring, flavoring and diluting agents, emulsifying agents, suspending agents, solvents, fillers, bulking agents, buffers, delivery vehicles, diluents, excipients and/or pharmaceutical adjuvants. The formulation should suit the mode of administration. For example, suitable vehicles include saline, buffered saline, dextrose, water, glycerol, ethanol, and combinations thereof.

The primary solvent in a vehicle may be either aqueous or non-aqueous in nature. In addition, the vehicle may contain other pharmaceutically-acceptable excipients for modifying or maintaining the pH, osmolarity, viscosity, clarity, color, sterility, stability, rate of dissolution, or odor of the formulation. Similarly, the vehicle may contain still other pharmaceutically-acceptable excipients for modifying or maintaining the rate of release of VEGF-2, or for promoting the absorption or penetration of VEGF-2 across the membranes of the eye. Such excipients are those substances usually and customarily employed to formulate dosages for parenteral administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or in a form, e.g., lyophilized, requiring reconstitution prior to administration.

The invention also provides a pharmaceutical pack or kit comprising one or more containers filled with one or more of the ingredients of the pharmaceutical compositions of the invention. Associated with such containers can be a notice in the form prescribed by a governmental agency regulating the manufacture, use or sale of pharmaceuticals or biological products, which notice reflects approval by the agency of manufacture, use or sale for human administration. In addition, the polypeptides, agonists and antagonists of the present invention may be employed in conjunction with other therapeutic compounds.

The VEGF-2 polypeptide or polynucleotide may be administered in pharmaceutical compositions in combination with one or more pharmaceutically acceptable excipients. It will be understood that, when administered to a human patient, the total daily usage of the pharmaceutical compositions of the present invention will be decided by the attending physician within the scope of sound medical judgment. The specific therapeutically effective dose level for any particular patient will depend upon a variety of factors including the type and degree of the response to be achieved; the specific composition an other agent, if any, employed; the age, body weight, general health, sex and diet of the patient; the time of administration, route of administration, and rate of excretion of the composition; the duration of the treatment; drugs (such as a chemotherapeutic agent) used in combination or coincidental with the specific composition; and like factors well known in the medical arts. Suitable formulations, known in the art, can be found in *Remington's Pharmaceutical Sciences* (latest edition), Mack Publishing Company, Easton, Pa.

The VEGF-2 composition to be used in the therapy will be formulated and dosed in a fashion consistent with good medical practice, taking into account the clinical condition of the individual patient (especially the side effects of treatment with VEGF-2 alone), the site of delivery of the VEGF-2 composition, the method of administration, the scheduling of administration, and other factors known to practitioners. The "effective amount" of VEGF-2 for purposes herein is thus determined by such considerations.

The pharmaceutical compositions may be administered in a convenient manner such as by the oral, topical, intravenous, intraperitoneal, intramuscular, intraarticular, subcutaneous, intranasal, intratracheal, intraocular or intradermal routes. The pharmaceutical compositions are administered in an amount which is effective for treating and/or prophylaxis of the specific indication. In most cases, the VEGF-2 dosage is from about 1 μg/kg to about 30 mg/kg body weight daily, taking into account the routes of administration, symptoms, etc. However, the dosage can be as low as 0.001 μg/kg. For example, in the specific case of topical administration dosages are preferably administered from about 0.01 μg to 9 mg per $cm^2$. In the case of intraocular administration, dosages are preferably administered from about 0.001 μg/ml to about 10 mg/ml, and more preferably from about 0.05 mg/ml to about 4 mg/ml.

As a general proposition, the total pharmaceutically effective amount of the VEGF-2 administered parenterally per more preferably dose will be in the range of about 1 μg/kg/day to 100 mg/kg/day of patient body weight, although, as noted above, this will be subject to therapeutic discretion. If given continuously, the VEGF-2 is typically administered at a dose rate of about 1 μg/kg/hour to about 50 μg/kg/hour, either by 1-4 injections per day or by continuous subcutaneous infusions, for example, using a mini-pump. An intravenous bag solution or bottle solution may also be employed.

VEGF-2 is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat No. 3,773,919, EP 58,481), copolymers of L-glutamic acid and gamma-ethyl-L-glutamate (U. Sidman et al., *Biopolymers* 22:547-556 (1983)), poly (2-hydroxyethyl methacrylate) (R. Langer et al., *J. Biomed Mater. Res.* 15:167-277 (1981), and R. Langer, *Chem. Tech.* 12:98-105 (1982)), ethylene vinyl acetate (R. Langer et al., Id.) or poly-D-(−)-3-hydroxybutyric acid (EP 133,988). Sustained-release VEGF-2 compositions also include liposomally entrapped VEGF-2. Liposomes containing VEGF-2 are prepared by methods known per se: DE 3,218,121; Epstein, et al., *Proc. Natl. Acad. Sci. USA* 82:3688-3692 (1985); Hwang et al., *Proc. Natl. Acad. Sci. USA* 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal VEGF-2 therapy.

For parenteral administration, in one embodiment, the VEGF-2 is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

In certain embodiments, VEGF-2 is administered orally. VEGF-2 which is administered in this fashion may be encapsulated and may be formulated with or without those carriers customarily used in the compounding of solid dosage forms. The capsule may be designed to release the active portion of the formulation at the point in the gastrointestinal tract when bioavailability is maximized and pre-systemic degradation is minimized. Additional excipients may be included to facilitate absorption of VEGF-2. Diluents, flavorings, low melting point waxes, vegetable oils, lubricants, suspending agents, tablet disintegrating agents, and binders may also be employed.

VEGF-2 may also be administered to the eye to treat photoreceptor injuries, disorders and pathologies in animals and humans as a drop, or within ointments, gels, liposomes, microparticulates, or biocompatible polymer discs, pellets or carried within contact lenses. The intraocular composition may also contain a physiologically compatible ophthalmic vehicle as those skilled in the art can select using conventional criteria. The vehicles may be selected from the known ophthalmic vehicles which include but are not limited to water, polyethers such as polyethylene glycol 400, polyvinyls such as polyvinyl alcohol, povidone, cellulose derivatives such as carboxymethylcellulose, methylcellulose and hydroxypropyl methylcellulose, petroleum derivatives such as mineral oil and white petrolatum, animal fats such as lanolin, vegetable fats such as peanut oil, polymers of acrylic acid such as carboxylpolymethylene gel, polysaccharides such as dextans and glycosaminoglycans such as sodium chloride and potassium, chloride, zinc chloride and buffer such as sodium bicarbonate or sodium lactate. High molecular weight molecules can also be used. Physiologically compatible preservatives which do not inactivate the VIEGF-2 present in the composition include alcohols such as chlorobutanol, benzalknonium chloride and EDTA, or any other appropriate preservative known to those skilled in the art.

For example, VEGF-2 may be administered directly intraocularly from about 1 μg/eye to about 1 mg/eye in a single injection or in multiple injections. The formulation of topical ophthalmic preparations, including ophthalmic solutions, suspensions and ointments is well known to those skilled in the art (see Remington's Pharmaceutical Sciences, 18th Edition, Chapter 86, pages 1581-1592, Mack Publishing Company, 1990). Other modes of administration are available, including intracameral injections (which may be made directly into the anterior chamber or directly into the vitreous chamber), subconjunctival injections and retrobulbar injections, and methods and means for producing ophthalmic preparations suitable for such modes of administration are also well known. VEGF-2 may also be administered in the subretinal space between the photoreceptor layer and retinal pigmentosa epithelial layers.

As used herein, "extraocular" refers to the ocular surface and the (external) space between the eyeball and the eyelid. Examples of extraocular regions include the eyelid fornix or cul-de-sac, the conjunctival surface and the corneal surface. This location is external to all ocular tissue and an invasive procedure is not required to access this region. Examples of extraocular systems include inserts and "topically" applied drops, gels or ointments which may be used to deliver therapeutic material to these regions. Extraocular devices are generally easily removable, even by the patient.

The following patents disclose extraocular systems which are used to administer drugs to the extraocular regions. Higuchi et al. disclose in U.S. Pat. Nos. 3,981,303, 3,986,510 and 3,995,635 a biodegradable ocular insert which contains a drug. The insert can be made in different shapes for retention in the cul-de-sac of the eyeball, the extraocular space between the eyeball and the eyelid. Several common biocompatible polymers are disclosed as suitable for use in fabricating this device. These polymers include zinc alginate, poly (lactic acid), poly (vinyl alcohol), poly (anhydrides) and poly (glycolic acid). The patents also describe membrane coated devices with reduced permeation to the drug and hollow chambers holding the drug formulation.

U.S. Pat. No. 4,217,898, discloses microporous reservoirs which are used for controlled drug delivery. These devices are placed extraocularly in the ocular cul-de-sac. Among the polymer systems of interest are poly (vinylchloride)-co-poly (vinyl acetate) copolymers. Kaufman discloses in U.S. Pat. Nos. 4,865,846 and 4,882,150 an ophthalmic drug delivery system which contains at least one bio-erodible material or ointment carrier for the conjunctival sac. The patent discloses polymer systems, such as poly (lactide), poly (glycolide), poly (vinyl alcohol) and cross linked collagen as suitable delivery systems.

In the presently described use of VEGF-2 of the treatment of retinal disease or injury it is also advantageous that a topically applied ophthalmic formulation include an agent to promote the penetration or transport of the therapeutic agent into the eye. Such agents are known in the art. For example, Ke et al., U.S. Pat. No. 5,221,696 disclose the use of materials to enhance the penetration of ophthalmic preparations through the cornea.

Intraocular systems are those systems which are suitable for use in any tissue compartment within, between or around the tissue layers of the eye itself. These locations include subconjunctival (under the ocular mucous membrane adjacent to the eyeball), orbital (behind the eyeball), and intracameral (within the chambers of the eyeball itself). In contrast to extraocular systems, an invasive procedure consisting of injection or implantation is required to access these regions.

The following patents disclose intraocular devices. Wong, U.S. Pat. No. 4,853,224, discloses microencapsulated drugs for introduction into the chamber of the eye. Polymers which are used in this system include polyesters and polyethers. Lee, U.S. Pat. No. 4,863,457, discloses a biodegradable device which is surgically implanted intraocularly for the sustained release of therapeutic agents. The device is designed for surgical implantation under the conjunctiva (mucous membrane of the eyeball). Krezancaki, U.S. Pat. No. 4,188,373, discloses a pharmaceutical vehicle which gels at human body temperature. This vehicle is an aqueous suspension of the drug and gums or cellulose derived synthetic derivatives. Haslam et al. disclose in U.S. Pat. Nos. 4,474,751 and 4,474,752 a polymer-drug system which is liquid at room temperature and gels at body temperature. Suitable polymers used in this system include polyoxyethylene and polyoxypropylene. Davis et al. disclose in U.S. Pat. No. 5,384,333 a biodegradable injectable drug delivery polymer which provides long term drug release. The drug composition is made up of a pharmaceutically active agent in a biodegradable polymer matrix, where the polymer matrix is a solid at temperatures in the range 20EC to 37EC, and is flowable at temperatures in the range 38EC to 52EC. The drug delivery polymer is not limited to the delivery of soluble or liquid drug formulations. For example, the polymer can be used as a matrix for stabilizing and retaining at the site of injection drug-containing microspheres, liposomes or other particulate-bound drugs.

A particularly suitable vehicle for intraocular injection is sterile distilled water in which VEGF-2 is formulated as a sterile, isotonic solution, properly preserved. Yet another ophthalmic preparation may involve the formulation of VEGF-2 with an agent such as injectable microspheres or liposomes, that provides for the slow or sustained release of the protein which may then be delivered as a depot injection. Other suitable means for the intraocular introduction of VEGF-2 includes implantable drug delivery devices which contain VEGF-2.

The ophthalmic preparations of the present invention, particularly topical preparations, may include other components, for example ophthalmically acceptable preservatives, tonicity agents, cosolvents, wetting agents, complexing agents, buffering agents, antimicrobials, antioxidants and surfactants, as are well known in the art. For example, suitable tonicity enhancing agents include alkali metal halides (preferably sodium or potassium chloride), mannitol, sorbitol and the like. Sufficient tonicity enhancing agent is advantageously added so that the formulation to be instilled into the eye is hypotonic or substantially isotonic. Suitable preservatives include, but are not limited to, benzalkonium chloride, thimerosal, phenethyl alcohol, methylparaben, propylparaben, chlorhexidine, sorbic acid and the like. Hydrogen peroxide may also be used as preservative. Suitable cosolvents include, but are not limited to, glycerin, propylene glycol and polyethylene glycol. Suitable complexing agents include caffeine, polyvinylpyrrolidone, beta-cyclodextrin or hydroxypropyl-beta-cyclodextrin. Suitable surfactants or wetting agents include, but are not limited to, sorbitan esters, polysorbates such as polysorbate 80, tromethamine, lecithin, cholesterol, tyloxapol and the like. The buffers can be conventional buffers such as borate, citrate, phosphate, bicarbonate, or Tris-HCl.

The formulation components are present in concentration that are acceptable to the extraocular or intraocular site of administration. For example, buffers are used to maintain the composition at physiological pH or at slightly lower pH, typically within a pH range of from about 5 to about 8.

Additional formulation components may include materials which provide for the prolonged ocular residence of the extraocularly aduinistered therapeutic agent so as to maximize the topical contact and promote absorbtion. Suitable materials include polymers or gel forming materials which provide for increased viscosity of the ophthalmic preparation. Chitosan is a particularly suitable material as an ocular release-rate controlling agent in sustained release liquid ophthalmic drug formulations (see U.S. Pat. No. 5,422,116, Yen, et. al.) The suitability of the formulations of the instant invention for controlled release (e.g., sustained and prolonged delivery) of an ophthalmic treating agent in the eye can be determined by various procedures known in the art e.g., as described in *Journal of Controlled Release* 6:367-373, 1987, as well as variations thereof.

Yet another ophthalmic preparation may involve an effective quantity of VEGF-2 in a mixture with non-toxic ophthalmically acceptable excipients which are suitable for the manufacture of tablets. By dissolving the tablets in sterile water, or other appropriate vehicle, ophthalmic solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Generally, the formulations are prepared by contacting the VEGF-2 uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes. Suitable formulations, known in the art, can be found in *Remington's Pharmaceutical Sciences* (latest edition), Mack Publishing Company, Easton, Pa.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

VEGF-2 is typically formulated in such vehicles at a concentration of about 0.01 μg/ml to 100 mg/ml, preferably 0.01 μg/ml to 10 mg/ml, at a pH of about 3 to 8. It will be understood that the use of certain of the foregoing excipients, carriers, or stabilizers will result in the formation of VEGF-2 salts.

VEGF-2 to be used for therapeutic administration must be sterile. Sterility is readily accomplished by filtration through sterile filtration membranes (e.g., 0.2 micron membranes). Therapeutic VEGF-2 compositions generally are placed into a container having a sterile access port, for example, an intravenous solution bag or vial having a stopper pierceable by a hypodermic injection needle.

VEGF-2 ordinarily will be stored in unit or multi-dose containers, for example, sealed ampules or vials, as an aqueous solution or as a lyophilized formulation for reconstitution. As an example of a lyophilized formulation, 10 ml vials are filled with 5 ml of sterile-filtered 1% (w/v) aqueous VEGF-2 solution, and the resulting mixture is lyophilized. The infusion solution is prepared by reconstituting the lyophilized VEGF-2 using bacteriostatic Water-for-Injection.

Gene Therapy Methods

Another aspect of the present invention is to gene therapy methods for treating disorders, diseases and conditions. The gene therapy methods relate to the introduction of nucleic acid (DNA, RNA and antisense DNA or RNA) sequences into an animal to achieve expression of the VEGF-2 polypeptide of the present invention. This method requires a polynucleotide which codes for a VEGF-2 polypeptide operatively linked to a promoter and any other genetic elements necessary for the expression of the polypeptide by the target tissue. Such gene therapy and delivery techniques are known in the art, see, for example, WO90/11092, WO98/11779; U.S. Pat. Nos. 5,693,622, 5,705,151, 5,580,859; Tabata H. et al. (1997) *Cardiovasc. Res.* 35(3):470-479, Chao, J. et al. (1997) *Pharmacol. Res.* 35(6):517-522, Wolff, J. A. (1997) *Neuromuscul. Disord.* 7(5):314-318, Schwartz, B. et al. (1996) *Gene Ther.* 3(5):405-411, Tsurumi, Y. et al. (1996) *Circulation* 94(12): 3281-3290 (incorporated herein by reference).

As discussed more fully below, the VEGF-2 polynucleotide sequences preferably have a therapeutic effect after being taken up by a cell. Examples of polynucleotides that are themselves therapeutic are anti-sense DNA and RNA; DNA coding for an anti-sense RNA; or DNA coding for tRNA or rRNA to replace defective or deficient endogenous molecules. For example, a promoter may be operably linked to a DNA sequence encoding for an antisense RNA. The antisense RNA oligonucleotide hybridizes to the mRNA in vivo and blocks translation of an mRNA molecule into a polypeptide (Okano, *J. Neurochem* 56:560 (1991)). The antisense RNA must be of sufficient length and complementarity to prevent translation of its target mRNA.

Thus, for example, cells from a patient may be engineered with a polynucleotide (DNA or RNA) comprising a promoter operably linked to a VEGF-2 polynucleotide ex vivo, with the engineered cells then being provided to a patient to be treated with the polypeptide. Such methods are well-known in the art. For example, see Belldegrun, A., et al., *J. Natl. Cancer Inst.* 85: 207-216 (1993); Ferrantini, M. et al., *Cancer Research* 53: 1107-1112 (1993); Ferrantini, M. et al., *J. Immunology* 153: 4604-4615 (1994); Kaido, T,, et al., *Int. J. Cancer* 60: 221-229 (1995); Ogura, H., et al., *Cancer Research* 50: 5102-5106 (1990); Santodonato, L., et al., *Human Gene Therapy* 7:1-10 (1996); Santodonato, L., et al., *Gene Therapy* 4:1246-1255 (1997); and Zhang, J. -F, et al., *Cancer Gene Therapy* 3: 31-38 (1996)), which are herein incorporated by reference. In one embodiment, the cells which are engineered are photoreceptor cells. These engineered cells may be reintroduced into the patient through direct injection to the tissue of origin, the tissues surrounding the tissue of origin, veins or arteries, or through catheter injection. In one embodiment, the engineered cells are attached to the sclera to produce and release VEGF-2 protein directly into the vitreous humor.

Photoreceptor cell transplantation studies designed to replace defective or lost cells due to retinal disease or damage have been performed successfully in animal models of retinal degeneration (Silverman and Hughes, *Invest. Ophthalmol. Vis. Sci.* 30:1684-1690(1989); Gouras et al., *Neuro-Ophthalmol.* 10:165-176 (1990)). It is contemplated that photoreceptor cells may be obtained from donor eyes and maintained in culture as described herein. The cells would then be used as a source of purified photoreceptors to be transplanted via the subretinal space into the retina of patients suffering from retinal disease or damage. These patients will be treated with immunosuppressive therapies to eliminate immunological responses and rejection of the grafted cells. The ex vivo donor retinas will be cultured in the presence of VEGF-2, in order to enhance their growth and survival. The patients that will receive photoreceptor cell transplants will be treated with intravitreal VEGF-2 needed to promote the survival and the maturation of the grafted photoreceptors.

As discussed in more detail below, the VEGF-2 polynucleotide constructs can be delivered by any method that delivers injectable materials to the cells of an animal, such as, injection into the interstitial space of tissues (heart, muscle, skin, lung, liver, and the like). The VEGF-2 polynucleotide constructs may be delivered in a pharmaceutically acceptable liquid or aqueous carrier.

In one embodiment, the VEGF-2 polynucleotide is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin™ or precipitating agents and the like. However, the VEGF-2 polynucleotides can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference. U.S. Pat. No. 5,770,580 describes gene therapy methods for delivery into the eye.

The VEGF-2 polynucleotide vector constructs used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of VEGF-2 DNA. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for VEGF-2.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The VEGF-2 polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Especially preferred is the eye. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues, especially the eye. However, other parenteral routes may also be used, such as, inhalation of an aerosol formulation particularly for delivery to lungs or bronchial tissues, throat or mucous membranes of the nose. In addition, naked VEGF-2 DNA constructs can be delivered to arteries during angioplasty by the catheter used in the procedure. The naked polynucleotides are delivered by also be delivered by topical administration and so-called "gene guns". These delivery methods are known in the art.

The constructs may also be delivered with delivery vehicles such as viral sequences, viral particles, liposome formulations, lipofectin™, precipitating agents, etc. Such methods of delivery are known in the art.

In certain embodiments, the VEGF-2 polynucleotide constructs are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., *Proc. Natl. Acad. Sci. USA* (1987) 84:7413-7416, which is herein incorporated by reference); mRNA (Malone et al., *Proc. Natl. Acad. Sci. USA* (1989) 86:6077-6081, which is herein incorporated by reference); and purified transcription factors (Debs et al., *J. Biol. Chem.* (1990) 265:10189-10192, which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin™, from GIBCO BRL, Grand Island, N.Y. (See, also, Felgner et al., *Proc. Natl. Acad. Sci. USA* (1987) 84:7413-7416, which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication No. WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., P. Felgner et al., *Proc. Natl. Acad. Sci. USA* 84:7413-7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others.

These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art. The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., *Methods of Immunology* (1983), 101:512-527, which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated.

When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., *Biochim. Biophys. Acta* (1975) 394:483; Wilson et al., *Cell* (1979) 17:77); ether injection (Deamer, D. and Bangham, A., *Biochim. Biophys. Acta* (1976) 443:629; Ostro et al., *Biochem. Biophys. Res. Commun.* (1977) 76:836; Fraley et al., *Proc. Natl. Acad. Sci. USA* (1979) 76:3348); detergent dialysis (Enoch, H. and Strittmatter, P., *Proc. Natl. Acad. Sci. USA* (1979) 76:145); and reverse-phase evaporation (REV) (Fraley et al., *J. Biol. Chem.* (1980) 255:10431; Szoka, F. and Papahadjopoulos, D., *Proc. Natl. Acad. Sci. USA* (1978) 75:145; Schaefer-Ridder et al., *Science* (1982) 215:166), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication no. WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication no. WO 94/9469 (which are herein incorporated by reference) provide methods for delivering DNA-cationic lipid complexes to mammals.

In certain embodiments, cells are be engineered, ex vivo or in vivo, using a retroviral particle containing RNA which comprises a sequence encoding VEGF-2. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, φ-2, φ-AM, PA12, T19-14X, VT-19-17-H2, φCRE, φCRIP, GP+E-86, GP+envAm12, and DAN cell lines as described in Miller, *Human Gene Therapy* 1:5-14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include polynucleotide encoding VEGF-2. Such retroviral vector particles then may be employed, to transduce eukaryotic cells, either in vitro or in vivo. The transduced eukaryotic cells will express VEGF-2.

In certain other embodiments, cells are engineered, ex vivo or in vivo, with VEGF-2 polynucleotide contained in an adenovirus vector. Adenovirus can be manipulated such that it encodes and expresses VEGF-2, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz, A. R., et al. (1974) *Am. Rev. Respir. Dis.* 109:233-238). Finally, adenovirus mediated gene transfer has been demonstrated in a number of instances including transfer of alpha-1-antitrypsin and CFRR to the lungs of cotton rats (Rosenfeld, M. A. et al. (1991) *Science* 252:431-434; Rosenfeld et al., (1992) *Cell* 68:143-155). Furthermore, extensive studies to attempt to establish adenovirus as a causative agent in human cancer were uniformly negative (Green, M. et al. (1979) *Proc. Natl. Acad. Sci. USA* 76:6606).

Suitable adenoviral vectors useful in the present invention are described, for example, in Kozarsky and Wilson, *Curr. Opin. Genet. Devel.* 3:499-503 (1993); Rosenfeld et al., *Cell* 68:143-155 (1992); Engelhardt et al., *Human Genet. Ther.* 4:759-769 (1993); Yang et al., *Nature Genet.* 7:362-369 (1994); Wilson etal., Nature 365:691-692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express the VEGF-2 polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, N., *Curr. Topics in Microbiol. Immunol.* 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The VEGF-2 polynucleotide construct is inserted into the AAV vector using standard cloning methods, such as those found in Sambrook et al., *Molecular Cloning: A Laboratory Manual*, Cold Spring Harbor Press (1989). The recombinant AAV vector is then transfected into packaging cells which are infected with a helper virus, using any standard technique, including lipofection, electroporation, calcium phosphate. precipitation, etc. Appropriate helper viruses include adenoviruses, cytomegaloviruses, vaccinia viruses, or herpes viruses. Once the packaging cells are transfected and infected, they will produce infectious AAV viral particles which contain the VEGF-2 polynucleotide construct. These viral particles are then used to transduce eukaryotic cells, either ex vivo or in vivo. The transduced cells will contain the VEGF-2 polynucleotide construct integrated into its genome, and will express VEGF-2.

Another method of gene therapy involves operably associating heterologous control regions and endogenous polynucleotide sequences (e.g. encoding VEGF-2) via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., *Proc. Natl. Acad. Sci. USA* 86:8932-8935 (1989); and Zijlstra et al., *Nature* 342:435-438 (1989). This method involves the activation of a gene which is present in the target cells, but which is not normally expressed in the cells, or is expressed at a lower level than desired.

Polynucleotide constructs are made, using standard techniques known in the ark which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the VEGF-2 desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous VEGF-2 sequence is placed under the control of the promoter. The promoter then drives the expression of the endogenous VEGF-2 sequence.

Preferably, the polynucleotide encoding VEGF-2 contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers (Kaneda et al., *Science* 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., *Proc. Natl. Acad. Sci. USA* 189: 11277-11281, 1992, which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject The precise amount, number of doses, and timing of doses will be determined by the attending physician or veterinarian.

Therapeutic compositions of the present invention can be administered to any animal, preferably to mammals and birds. Preferred mammals include humans, dogs, cats, mice, rats, rabbits sheep, cattle, horses and pigs, with humans being particularly preferred.

Nucleic Acid Utilities

VEGF-2 nucleic acid sequences and VEGF-2 polypeptides may also be employed for in vitro purposes related to scientific research, synthesis of DNA and manufacture of DNA vectors, and for the production of diagnostics and therapeutics to treat human disease. For example, VEGF-2 may be employed for in vitro culturing of photoreceptor cells, where it is added to the conditional medium in a concentration from 10 µg/ml to 10 ng/ml.

Fragments of the full length VEGF-2 gene may be used as a hybridization probe for a cDNA library to isolate other genes which have a high sequence similarity to the gene or similar biological activity. Probes of this type generally have at least 50 base pairs, although they may have a greater number of bases. The probe may also be used to identify a cDNA clone corresponding to a full length transcript and a genomic clone or clones that contain the complete VEGF-2 gene including regulatory and promoter regions, exons, and introns. An example of a screen comprises isolating the coding region of the VEGF-2 gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

This invention provides methods for identification of VEGF-2 receptors. The gene encoding the receptor can be identified by numerous methods known to those of skill in the art, for example, ligand panning and FACS sorting (Coligan et al.,*Current Protocols in Immun.*, 1(2), Chapter 5, (1991)). Preferably, expression cloning is employed wherein polyadenylated RNA is prepared from a cell responsive to VEGF-2, and a cDNA library created from this RNA is divided into pools and used to transfect COS cells or other cells that are not responsive to VEGF-2. Transfected cells which are grown on glass slides are exposed to labeled VEGF-2. VEGF-2 can be labeled by a variety of means including iodination or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clone that encodes the putative receptor.

As an alternative approach for receptor identification, labeled VEGF-2 can be photoaffinity linked with cell membrane or extract preparations that express the receptor molecule. Cross-linked material is resolved by PAGE and exposed to X-ray film. The labeled complex containing VEGF-2 is then excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

EXAMPLES

The present invention will be further described with reference to the following examples; however, it is to be understood that the present invention is not limited to such examples. All parts or amounts, unless otherwise specified, are by weight.

In order to facilitate understanding of the following examples, certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 mg of plasmid or DNA fragment is used with about 2 units of enzyme in about 20 Fl of buffer solution. For the purpose of isolating DNA fragments for plasmid construction, typically 5 to 50 mg of DNA are digested with 20 to 250 units of enzyme in a larger volume. Appropriate buffers and substrate amounts for particular restriction enzymes are specified by the manufacturer. Incubation times of about 1 hour at 37EC are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., *Nucleic Acids Res.* 8:4057 (1980).

"Oligonucleotides" refer to either a single stranded polydeoxynucleotide or two complementary polydeoxynucleotide strands, which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Sambrook et al., *Molecular Cloning: A Laboratory Manual*, Second Edition, Cold Spring Harbor Laboratory, Cold Spring Harbor, N.Y. (1989), p. 146). Unless otherwise provided, ligation may be accomplished using known buffers and conditions with 10 units of T4 DNA ligase ("ligase") per 0.5 mg of approximately equimolar amounts of the DNA fragments to be ligated.

Unless otherwise stated, transformation was performed as described by the method of Graham, F, and Van der Eb, A., *Virology* 52:456-457 (1973).

Example 1

Expression Pattern of VEGF-2 in Human Tissues and Breast Cancer Cell Lines

Northern blot analysis was carried out to examine the levels of expression of VEGF-2 in human tissues and breast cancer cell lines in human tissues. Total cellular RNA samples were isolated with RNAzol™ B system (Biotecx Laboratories, Inc.). About 10 mg of total RNA isolated from each breast tissue and cell line specified was separated on 1% agarose gel and blotted onto a nylon filter, (Sambrook et al., *Molecular Cloning: A Laboratory Manual*, Second Edition, Cold Spring Harbor Laboratory, Cold Spring Harbor, N.Y. (1989)). The labeling reaction was done according to the Stratagene Prime-It kit with 50 ng DNA fragment. The labeled DNA was purified with a Select-G-50 column from 5 Prime+3 Prime, Inc (Boulder, Colo.). The filter was then hybridized with a radioactive labeled full length VEGF-2 gene at 1,000,000 cpm/ml in 0.5 M $NaPO_4$ and 7% SDS overnight at 65° C. After washing twice at room temperature and twice at 60° C. with 0.5×SSC, 0.1% SDS, the filters were then exposed at −70° C. overnight with an intensifying screen. A message of 1.6 Kd was observed in 2 breast cancer cell lines. FIG. 5, lane #4 represents a very tumorigenic cell line that is estrogen independent for growth.

Also, 10 mg of total RNA from 10 human adult tissues were separated on an agarose gel and blotted onto a nylon filter. The filter was then hybridized with radioactively labeled VEGF-2 probe in 7% SDS, 0.5 M NaPO4, pH 7.2; 1% BSA overnight at 65° C. Following washing in 0.2×SSC at 65° C., the filter was exposed to film for 24 days at −70° C. with intensifying screen. See FIG. 6.

Example 2

Expression of the Truncated Form of VEGF-2 (SEQ ID NO:4) by In Vitro Transcription and Translation The VEGF-2 cDNA was transcribed and translated in vitro to determine the size of the translatable polypeptide encoded by the truncated form of VEGF-2 and a partial VEGF-2 cDNA. The two inserts of VEGF-2 in the pbluescript SK vector were amplified by PCR with three pairs of primers, 1) M13-reverse and forward primers; 2) M13-reverse primer and VEGF,primer F4; and 3) M13-reverse primer and VEGF primer F5. The sequence of these primers are as follows.

M13-2 reverse primer: 5'-ATGCTTCCGGCTCGTATG-3' (SEQ ID NO:11)

This sequence is located upstream of the 5' end of the VEGF-2 cDNA insert in the pBluescript vector and is in an anti-sense orientation as the cDNA.

A T3 promoter sequence is located between this primer and the VEGF-2 cDNA.

```
M13-2 forward primer:
5'GGGTTTTCCCAGTCACGAC-3'    (SEQ ID NO:12)
```

This sequence is located downstream of the 3' end of the VEGF-2 cDNA insert in the pbluescript vector and is in an anti-sense orientation as the cDNA insert.

```
VEGF primer F4:
5'-CCACATGGTTCAGGAAAGACA-3'    (SEQ ID NO:13)
```

This sequence is located within the VEGF-2 cDNA in an anti-sense orientation from bp 1259-1239, which is about 169 bp away from the 3' end of the stop codon and about 266 bp before the last nucleotide of the cDNA.

PCR reaction with all three pairs of primers produce amplified products with T3 promoter sequence in front of the cDNA insert. The first and third pairs of primers produce PCR products that encode the polypeptide of VEGF-2 shown in SEQ ID NO:4. The second pair of primers produce PCR product that misses 36 amino acids coding sequence at the C-terminus of the VEGF-2 polypeptide.

Approximately 0.5 mg of PCR product from first pair of primers, 1 mg from second pair of primers, 1 mg from third pair of primers were used for in vitro transcription/translation. The in vitro transcription/translation reaction was performed in a 25 Fl of volume, using the $T_NTJ$ Coupled Reticulocyte Lysate Systems (Promega, CAT# L4950). Specifically, the reaction contains 12.5 Fl of TNT rabbit reticulocyte lysate 2 Fl of TNT reaction buffer, 1 Fl of T3 polymerase, 1 Fl of 1 mM amino acid mixture (minus methionine), 4 Fl of $^{35}S$-methionine (>1000 Ci/mmol, 10 mCi/ml), 1 Fl of 40 U/µl; RNasin ribonuclease inhibitor, 0.5 or 1 mg of PCR products. Nuclease-free $H_2O$ was added to bring the volume to 25 Fl. The reaction was incubated at 30° C. for 2 hours. Five microliters of the reaction product was analyzed on a 4-20% gradient SDS-PAGE gel. After fixing in 25% isopropanol and 10% acetic acid, the gel was dried and exposed to an X-ray film overnight at 70° C.

Figure 7:
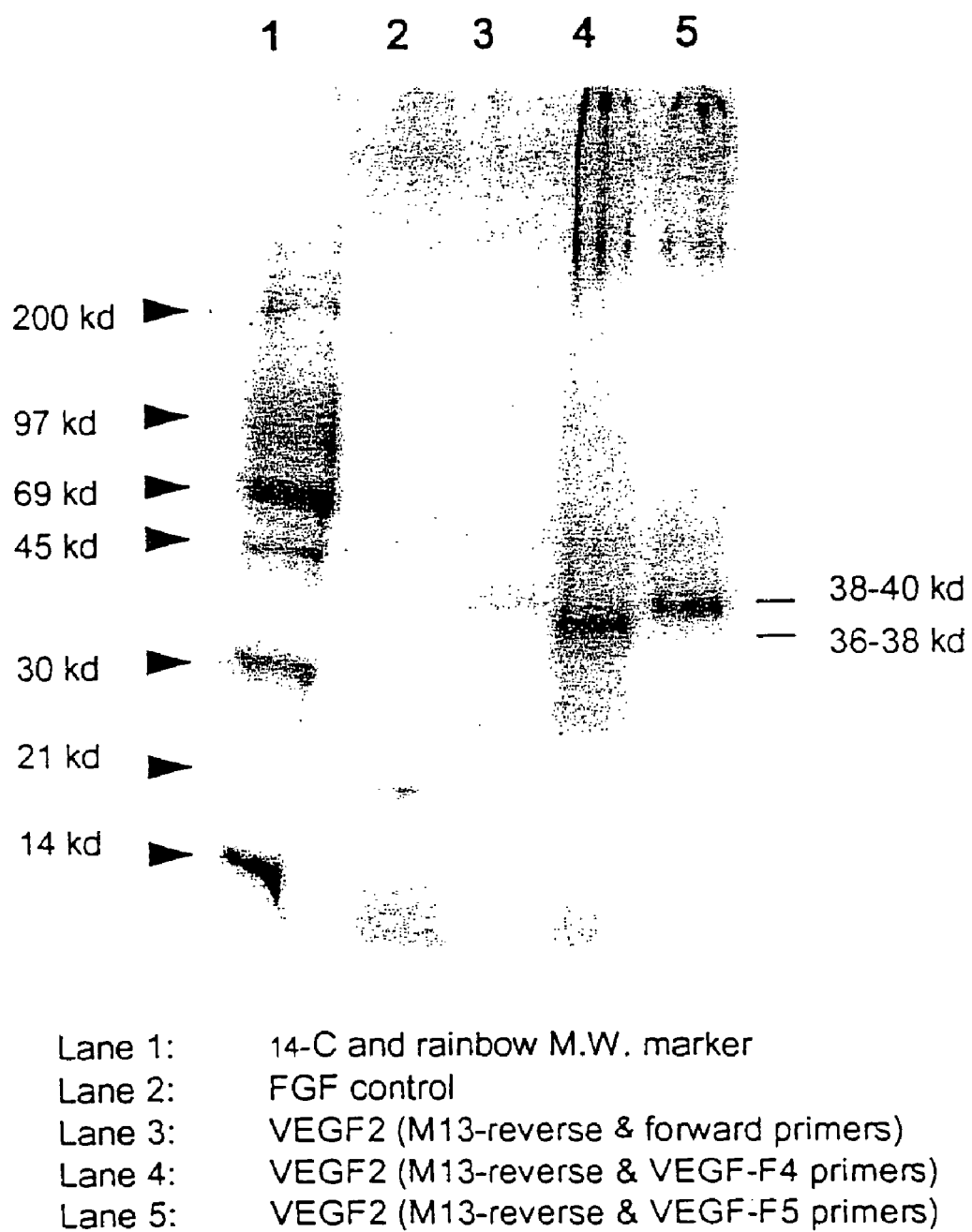
FIG. 7 shows a photograph of an SDS-PAGE gel after in vitro transcription, translation and electrophoresis of the polypeptide of the present invention. Lane 1: $^{14}C$ and rainbow M.W. marker; Lane 2: FGF control; Lane 3: VEGF-2 produced by M13-reverse and forward primers; Lane 4: VEGF-2 produced by M13 reverse and VEGF-F4 primers; Lane 5: VEGF-2 produced by M13 reverse and VEGF-F5 primers.
Figures 9, 10:
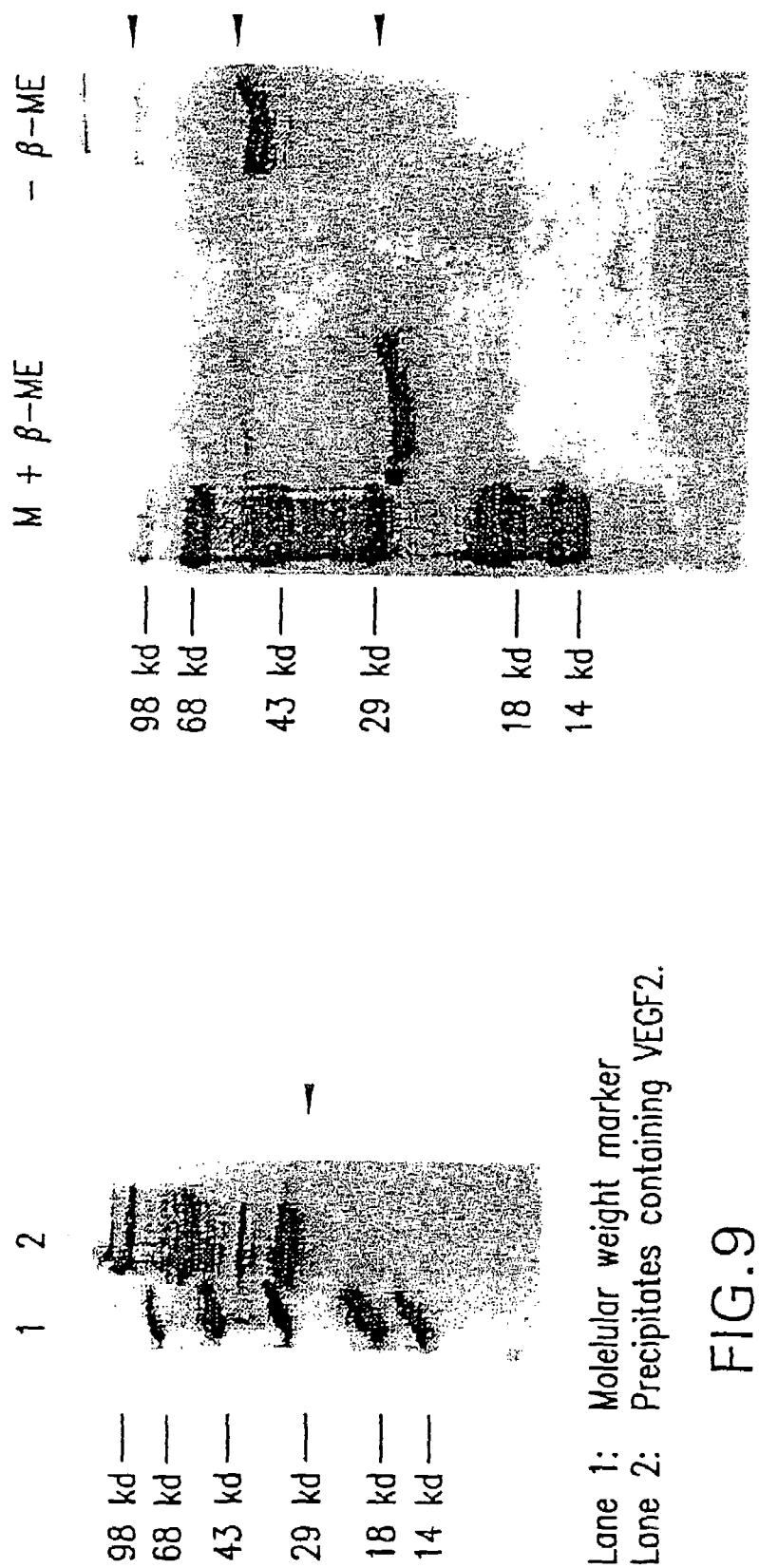
FIG. 9 depicts a photograph of an SDS-PAGE gel. The medium from Sf9 cells infected with a nucleic acid sequence of the present invention was precipitated. The resuspended precipitate was analyzed by SDS-PAGE and stained with Coomassie brilliant blue.
FIG. 10 depicts a photograph of an SDS-PAGE gel. VEGF-2 was purified from the medium supernatant and analyzed by SDS-PAGE in the presence or absence of the reducing agent b-mercaptoethanol and stained by Coomassie brilliant blue.
Figure 11:
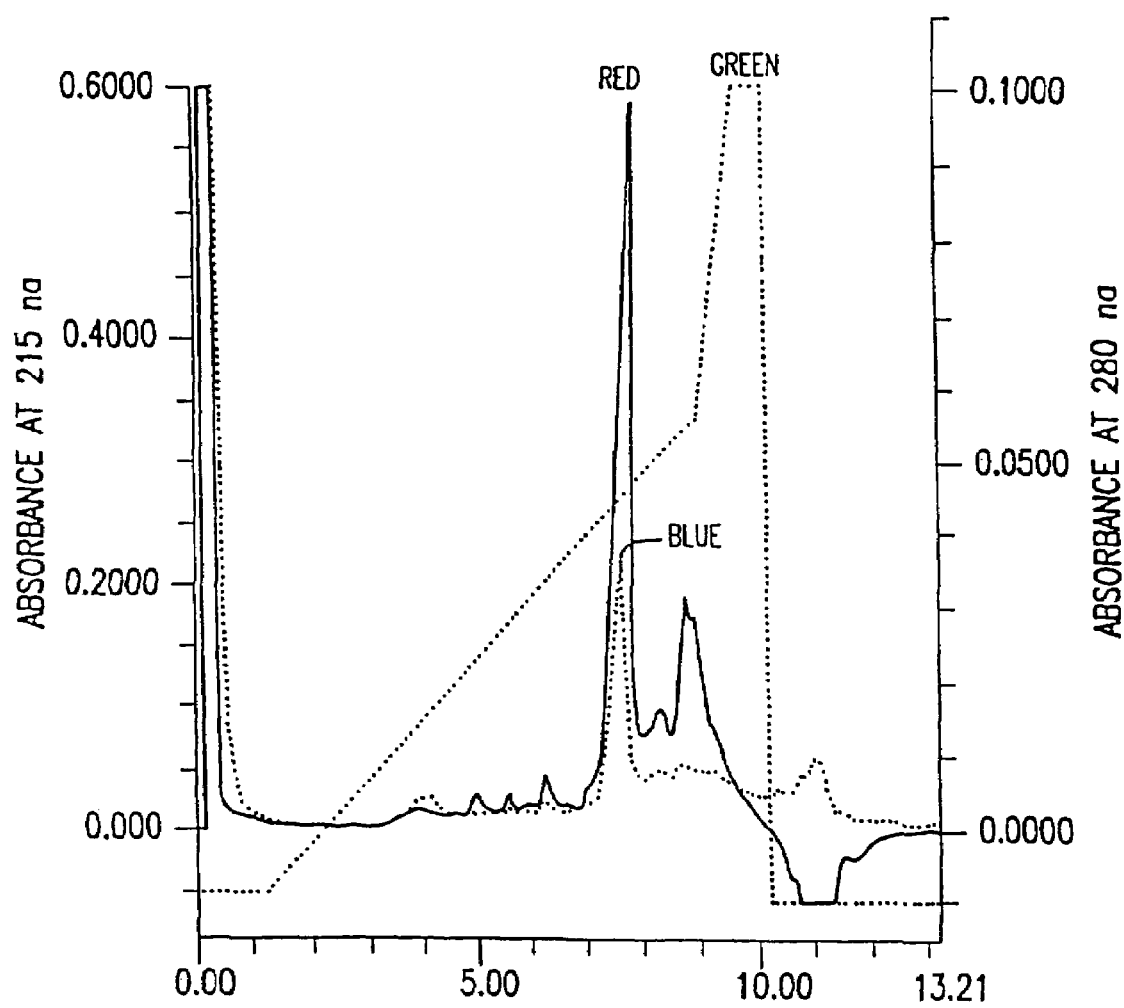
FIG. 11 depicts reverse phase HPLC analysis of purified VEGF-2 using a RP-300 column (0.21×3 cm, Applied Biosystems, Inc.). The column was equilibrated with 0.1% trifluoroacetic acid (Solvent A) and the proteins eluted with a 7.5 min gradient from 0 to 60% Solvent B, composed of acetonitrile containing 0.07% TFA. The protein elution was monitored by absorbance at 215 nm ("red" line) and 280 nm ("blue" line). The percentage of Solvent B is shown by the "green" line.
Figure 12:
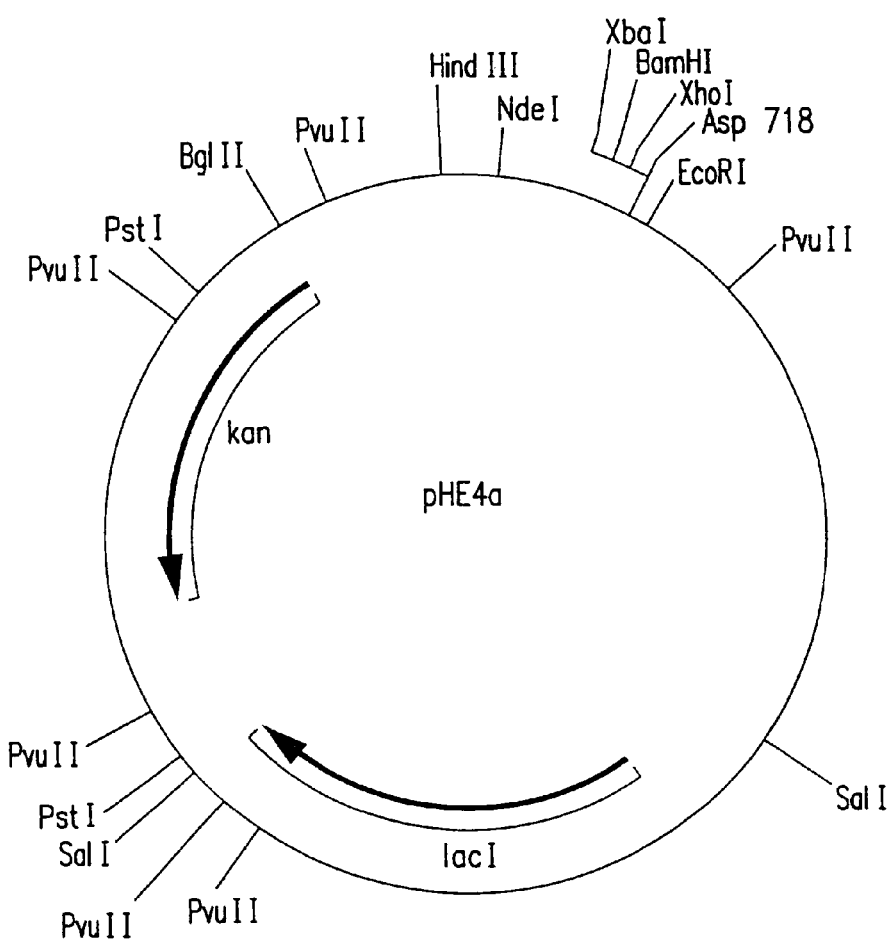
FIG. 12 shows a schematic representation of the pHE4-5 expression vector (SEQ ID NO:9) and the subcloned VEGF-2 cDNA coding sequence. The locations of the kanamycin resistance marker gene, the VEGF-2 coding sequence, the oriC sequence, and the lacIq coding sequence are indicated.

As shown in FIG. 7, PCR products containing the truncated VEGF-2 cDNA (ie., as depicted in SEQ ID NO:3) and the cDNA missing 266 bp in the 3' un-translated region (3'-UTR) produced the same length of translated products, whose molecular weights are estimated to be 38-40 kd (lanes 1 and 3). The cDNA missing all the 3'UTR and missing sequence encoding the C-terminal 36 amino acids was translated into a polypeptide with an estimated molecular weight of 36-38 kd (lane 2).

Example 3

Cloning and Expression of VEGF-2 Using the Baculovirus Expression System

The DNA sequence encoding the VEGF-2 protein without 46 amino acids at the N-terminus, see ATCC™ No. 97149, was amplified using PCR oligonucleotide primers corresponding to the 5' and 3' sequences of the gene:

The 5' primer has the sequence TGT AAT ACG ACT CAC TAT AGG GAT CCC GCC ATG GAG GCC ACG GCT TAT GC (SEQ ID NO:14) and contains a BamHI restriction enzyme site (in bold) and 17 nucleotide sequence complementary to the 5' sequence of VEGF-2 (nt. 150-166).

The 3' primer has the sequence GATC TCT AGA TTA GCT CAT TTG TGG TCT (SEQ ID NO:15) and contains the cleavage site for the restriction enzyme XbaI and 18 nucleotides complementary to the 3' sequence of VEGF-2, including the stop codon and 15 nt sequence before stop codon.

The amplified sequences were isolated from a 1% agarose gel using a commercially available kit ("Geneclean™," BIO 101, Inc., La Jolla, Calif.). The fragment was then digested with the endonuclease BamHI and XbaI and then purified again on a 1% agarose gel. This fragment was ligated to pAcGP67A baculovirus transfer vector (Pharmingen) at the BamHI and XbaI sites. Through this ligation, VEGF-2 cDNA was cloned in frame with the signal sequence of baculovirus gp67 gene and was located at the 3' end of the signal sequence in the vector. This is designated pAcGP67A-VEGF-2.

To clone VEGF-2 with the signal sequence of gp67 gene to the pRGI vector for expression, VEGF-2 with the signal sequence and some upstream sequence were excised from the pAcGP67A-VEGF-2 plasmid at the Xho restriction endonuclease site located upstream of the VEGF-2 cDNA and at the XbaI restriction endonuclease site by XhoI and XbaI restriction enzyme. This fragment was separated from the rest of vector on a 1% agarose gel and was purified using "Geneclean™" kit. It was designated F2.

The PRG1 vector (modification of pVL941 vector) is used for the expression of the VEGF-2 protein using the baculovirus expression system (for review see: Summers, M. D. and Smith, G. E., "*A Manual of Methods for Baculovirus Vectors and Insect Cell Culture Procedures,*" Texas Agricultural Experimental Station Bulletin No. 1555, (1987)). This expression vector contains the strong polyhedrin promoter of the *Autographa californica* nuclear polyhedrosis virus (AcMNPV) followed by the recognition sites for the restriction endonucleases BamHI, SmaI, XbaI, BglII and Asp718. A site for restriction endonuclease XhoI is located upstream of BamHI site. The sequence between XhoI and BamHI is the same as that in PAcGp67A (static on tape) vector. The polyadenylation site of the simian virus (SV)40 is used for efficient polyadenylation. For an easy selection of recombinant virus the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRGI such as pAc373, pVL941 and pAcIM1 (Luckow, V. A. and Summers, M. D., *Virology* 170: 31-39 (1989)).

The plasmid was digested with the restriction enzymes XboI and XbaI and then dephosphorylated using calf intestinal phosphatase by procedures known in the art. The DNA was then isolated from a 1% agarose gel using the commercially available kit ("Geneclean™" BIO 101 Inc., La Jolla, Calif.). This vector DNA is designated V2.

Fragment F2 and the dephosphorylated plasmid V2 were ligated with T4 DNA ligase. *E. coli* HB101 cells were then transformed and bacteria identified that contained the plasmid (pBac gp67-VEGF-2) with the VEGF-2 gene using the enzymes BamHI and XbaI. The sequence of the cloned fragment was confirmed by DNA sequencing.

5 mg of the plasmid pBac gp67-VEGF-2 was cotransfected with 1.0 mg of a commercially available linearized baculovirus ("BaculoGold™J baculovirus DNA", Pharmingen, San Diego, Calif.) using the lipofectin™ method (Feigner et al., *Proc. Natl. Acad. Sci. USA* 84:7413-7417 (1987)).

1 mg of BaculoGold™J virus DNA and 5 mg of the plasmid pBac gp67-VEGF-2 were mixed in a sterile well of a microtiter plate containing 50 ml of serum free Grace's medium (Life Technologies Inc., Gaithersburg, Md.). Afterwards 10 ml Lipofectin™ plus 90 ml Grace's medium were added, mixed and incubated for 15 minutes at room temperature. Then the transfection mixture was added dropwise to the Sf9 insect cells (ATCCT CRL 1711) seeded in a 35 mM tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith, supra. As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9-10). Four days after the serial dilution, the virus was added to the cells, blue stained plaques were picked with the tip of an Eppendorf pipette. The agar containing the recombinant viruses was then resuspended in an Eppendorf tube containing 200 ml of Grace's medium. The agar was removed by a brief centrifugation and the supernatant containing the recombinant baculovirus was used to infect Sf9 cells seeded in 35 mM dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-gp67-VEGF-2 at a multiplicity of infection (MOf) of 1. Six hours later the medium was removed and replaced with SF900 II medium minus methionine and cysteine (Life Technologies Inc., Gaithersburg). 42 hours later 5 mCi of $^{35}S$-methionine and 5 mCi $^{35}S$ cysteine (Amersham) were added. The cells were further incubated for 16 hours before they were harvested by centrifugation and the labeled proteins visualized by SDS-PAGE and autoradiography.

Protein from the medium and cytoplasm of the Sf9 cells was analyzed by SDS-PAGE under non-reducing and reducing conditions. See FIGS. 8A and 8B, respectively. The medium was dialyzed against 50 mM MES, pH 5.8. Precipitates were obtained after dialysis and resuspended in 100 mM Na Citrate, pH 5.0. The resuspended precipitate was analyzed again by SDS-PAGE and was stained with Coomassie Brilliant Blue. See FIG. 9.

The medium supematant was also diluted 1:10 in 50 mM MES, pH 5.8 and applied to an SP-650M column (1.0×6.6 cm, Toyopearl) at a flow rate of 1 ml/min. Protein was eluted with step gradients at 200, 300 and 500 mM NaCl. The VEGF-2 was obtained using the elution at 500 mM. The eluate was analyzed by SDS-PAGE in the presence or absence of reducing agent, b-mercaptoethanol and stained by Coomassie Brilliant Blue. See FIG. 10.

Example 4

Expression of Recombinant VEGF-2 in COS Cells

The expression of plasmid, VEGF-2-HA is derived from a vector pcDNA1/Amp (Invitrogen) containing: 1) SV40 origin of replication, 2) ampicillin resistance gene, 3) *E. coli* replication origin, 4) CMV promoter followed by a polylinker region, an SV40 intron and polyadenylation site. A DNA fragment encoding the entire VEGF-2 precursor and a HA tag fused in frame to its 3' end was cloned into the polylinker region of the vector, therefore, the recombinant protein expression is directed under the CMV promoter. The HA tag corresponds to an epitope derived from the influenza hemagglutinin protein as previously described (Wilson et al., *Cell* 37:767 (1984)). The infusion of HA tag to the target protein allows easy detection of the recombinant protein with an antibody that recognizes the HA epitope.

The plasmid construction strategy is described as follows:

The DNA sequence encoding VEGF-2, ATCC™ No. 97149, was constructed by PCR using two primers: the 5' primer (CGC GGA TCC ATG ACT GTA CTC TAC CCA) (SEQ ID NO:16) contains a BamHI site followed by 18 nucleotides of VEGF-2 coding sequence starting from the initiation codon; the 3' sequence (CCC TCT AGA TCA AGC GTA GTC TGG GAC GTC GTA TGG GTA CTC GAG GCT CAT TTG TGG TCT 3') (SEQ ID NO:17) contains complementary sequences to an XbaI site, HA tag, XhoI site, and the last 15 nucleotides of the VEGF-2 coding sequence (not including the stop codon). Therefore, the PCR product contains a BamHI site, coding sequence followed by an XhoI restriction endonuclease site and HA tag fused in frame, a translation termination stop codon next to the HA tag, and an XbaI site. The PCR amplified DNA fragment and the vector, pcDNAU1/Amp, were digested with BamHI and XbaI restriction enzyme and ligated. The ligation mixture was transformed into E. coli strain SURE (Stratagene Cloning Systems, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant VEGF-2, COS cells were transfected with the expression vector by DEAE-DEXTRAN method (J. Sambrook, E. Fritsch, T, Maniatis, *Molecular Cloning: A Laboratory Manual,* Cold Spring Laboratory Press, (1989)). The expression of the VEGF-2-HA protein was detected by radiolabelling and immunoprecipitation method (E. Harlow and D. Lane, *Antibodies: A Laboratory Manual,* Cold Spring Harbor Laboratory Press, (1988)). Cells were labeled for 8 hours with $^{35}$S-cysteine two days post transfection. Culture media was then collected and cells were lysed with detergent (RIPA buffer (150 mM NaCl, 1% NP-40, 0.1% SDS, 1% NP-40, 0.5% DOC, 50 mM Tris, pH 7.5) (Wilson et al., *Cell* 37:767 (1984)). Both cell lysate and culture media were precipitated with an HA specific monoclonal antibody. Proteins precipitated were analyzed on 15% SDS-PAGE gels.

Example 5

Construction of Amino Terminal and Carboxy Terminal Deletion Mutants

In order to identify and analyze biologically active VEGF-2 polypeptides, a panel of deletion mutants of VEGF-2 was constructed using the expression vector pBE4a.

1. Construction of VEGF-2 T103-L215 in pHE4

To permit Polymerase Chain Reaction directed amplification and sub-cloning of VEGF-2 T103-L215 (amino acids 103 to 215 in FIG. 1 or SEQ ID NO:2) into the E. coli protein expression vector, pHE4, two oligonucleotide primers complementary to the desired region of VEGF-2 were synthesized with the following base sequence:

Primer (Nde I/START and 18 nt of coding sequence):

(SEQ ID NO: 18)
5'-GCA GCA CAT ATG ACA GAA GAG ACT ATA AAA-3'

Primer (Asp718, STOP, and 15 nt of coding sequence):

(SEQ ID NO:19)
5'-GCA GCA GGT ACC TCA CAG TTT AGA CAT GCA-3'

The above described 5' primer (SEQ ID NO:18), incorporates an NdeI restriction site and the above described 3' Primer (SEQ ID NO:19), incorporates an Asp718 restriction site. The 5' primer (SEQ ID NO:18) also contains an ATG sequence adjacent and in frame with the VEGF-2 coding region to allow translation of the cloned fragment in E. coli while the 3' primer (SEQ ID NO: 19) contains one stop codon (preferentially utilized in E. coli) adjacent and in frame with the VEGF-2 coding region which ensures correct translational termination in E. coli.

The Polymerase Chain Reaction was performed using standard conditions well known to those skilled in the art and the nucleotide sequence for the mature VEGF-2 (aa 24-419 in SEQ ID NO:2) as, for example, constructed in Example 3 as template. The resulting amplicon was restriction digested with NdeI and Asp718 and subcloned into NdeI/Asp718 digested pHE4a expression vector.

2. Construction of VEGF-2 T103-R227 in pHE4

To permit Polymerase Chain Reaction directed amplification and sub-cloning of VEGF-2 T103-R227 (amino acids 103 to 227 in FIG. 1 or SEQ ID NO:2) into the E. coli protein expression vector, pHE4, two oligonucleotide primers complementary to the desired region of VEGF-2 were synthesized with the following base sequence:

5' Primer (Nde I/START and 18 nt of coding sequence):

(SEQ ID NO:20)
5'-GCA GCA CAT ATG ACA GAA GAG ACT ATA AAA-3'

3' Primer (Asp 718, STOP, and 15 nt of coding sequence):

(SEQ ID NO:21)
5'-GCA GCA GGT ACC TCA ACG TCT AAT AAT GGA-3'

In the case of the above described primers, an NdeI or Asp718 restriction site was incorporated he 5' primer and 3' primer, respectively. The 5' primer (SEQ ID NO:20) also contains an ATG sequence adjacent and in frame with the VEGF-2 coding region to allow translation of the cloned fragment in E. coli, while the 3' Primer (SEQ ID NO:21) contains one stop codon (preferentially utilized in E. coli) adjacent and in frame with the VEGF-2 coding region which ensures correct translational termination in E. coli.

The Polymerase Chain Reaction was performed using standard conditions well known to those skilled in the art and the nucleotide sequence for the mature VEGF-2 (aa 24-419 in SEQ ID NO:2) as, for example, constructed in Example 3, as template. The resulting amplicon was restriction digested with NdeI and Asp718 and subcloned into NdeI/Asp7l8 digested pHE4a protein expression vector.

3. Construction of VEGF-2 T103-L215 in pA2GP

In this illustrative example, the plasmid shuttle vector pA2 GP is used to insert the cloned DNA encoding the N-terminal and C-terminal deleted VEGF-2 protein (amino acids 103-215 in FIG. 1 or SEQ ID NO:2), into a baculovirus to express the N-terminal and C-terminal deleted VEGF-2 protein, using a baculovirus leader and standard methods as described in Summers et al., *A Manual of Methods for Baculovirus Vectors and Insect Cell Culture Procedures,* Texas Agricultural Experimental Station Bulletin No. 1555 (1987). This expression vector contains the strong polyhedrin promoter of the *Autographa californica* nuclear polyhedrosis virus (AcM-NPV) followed by the secretory signal peptide (leader) of the baculovirus gp67 protein and convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate viable virus that expresses the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31-39 (1989).

The cDNA sequence encoding the VEGF-2 protein without 102 amino acids at the N-terminus and without 204 amino acids at the C-terminus in FIG. 1, was amplified using PCR oligonucleotide primers corresponding to the 5' and 3' sequences of the gene.

The 5' primer has the sequence 5'-GCA GCA GGA TCC CAC AGA AGA GAC TAT AAA-3' (SEQ ID NO:22) containing the BamHI restriction enzyme site (in bold) followed by 1 spacer nt to stay in-frame with the vector-supplied signal peptide, and 17 nt of coding sequence bases of VEGF-2 protein. The 3' primer has the sequence 5'-GCA GCA TCT AGA TCA CAG TTT AGA CAT GCA-3' (SEQ ID NO:23) containing the XbaI restriction site (in bold) followed by a stop codon and 17 nucleotides complementary to the 3' coding sequence of VEGF-2.

The amplified sequences were isolated from a 1% agarose gel using a commercially available kit ("Geneclean™," BIO 101, Inc., La Jolla, Calif.). The fragment was then digested with the endonuclease BamHI and XbaI and then purified again on a 1% agarose gel. This fragment was ligated to pA2 GP baculovirus transfer vector (Supplier) at the BamHI and XbaI sites. Through this ligation, VEGF-2 cDNA representing the N-terminal and C-terminal deleted VEGF-2 protein (amino acids 103-215 in FIG. 1 or SEQ ID NO:2) was cloned in frame with the signal sequence of baculovirus GP gene and was located at the 3' end of the signal sequence in the vector. This is designated pA2GPVEGF-2.T103-L215.

4. Construction of VEGF-2 T103-R227 in pA2GP

The cDNA sequence encoding the VEGF-2 protein without 102 amino acids at the N-terminus and without 192 amino acids at the C-terminus in FIG. 1 (i.e., amino acids 103-227 of SEQ ID NO:2) was amplified using PCR oligonucleotide primers corresponding to the 5' and 3' sequences of the gene.

The 5'-GCA GCA GGA TCC CAC AGA AGA GAC TAT AAA ATT TGC TGC-3' primer has the sequence (SEQ ID NO:24) containing the BamHI restriction enzyme site (in bold) followed by 1 spacer nt to stay in-frame with the vector-supplied signal peptide, and 26 nt of coding sequence bases of VEGF-2 protein. The 3' primer has the sequence 5'-GCA GCA TCT AGA TCA ACG TCT AAT AAT GGA ATG AAC-3' (SEQ ID NO:25) containing the XbaI restriction site (in bold) followed by a stop codon and 21 nucleotides complementary to the 3' coding sequence of VEGF-2.

The amplified sequences were isolated from a 1% agarose gel using a commercially available kit ("Geneclean™," BIO 101, Inc., La Jolla, Calif.). The fragment was then digested with the endonuclease BamHI and XbaI and then purified again on a 1% agarose gel. This fragment was ligated to pA2 GP baculovirus transfer vector (Supplier) at the BamHI and XbaI sites. Through this ligation, VEGF-2 cDNA representing the N-terminal and C-terminal deleted VEGF-2 protein (amino acids 103-227 in FIG. 1 or SEQ ID NO:2) was cloned in frame with the signal sequence of baculovirus GP gene and was located at the 3' end of the signal sequence in the vector. This construct is designated pA2GPVEGF-2.T103-R227.

5. Construction of VEGF-2 in pC1

The expression vectors pC1 and pC4 contain the strong promoter (LTR) of the Rous Sarcoma Virus (Cullen et al., *Molecular and Cellular Biology*, 438-447 (March, 1985)) plus a fragment of the CMV-enhancer (Boshart et al., *Cell* 41:521-530 (1985)). Multiple cloning sites, e.g., with the restriction enzyme cleavage sites BamHI, XbaI and Asp718, facilitate the cloning of the gene of interest. The vectors contain in addition the 3N intron, the polyadenylation and termination signal of the rat preproinsulin gene.

The vector pC1 is used for the expression of VEGF-2 protein. Plasmid pC1 is a derivative of the plasmid pSV2-dhfr [ATCC™ Accession No. 37146]. Both plasmids contain the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357-1370, Hamlin, J. L. and Ma, C. 1990, *Biochem. et Biophys. Acta.* 1097:107-143, Page, M. J. and Sydenham, M. A. 1991, *Biotechnology* 9:64-68). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC1 contains for the expression of the gene of interest a strong promoter of the long terminal repeat (LTR) of the Rouse Sarcoma Virus (Cullen, et al., *Molecular and Cellular Biology*, March 1985:438-4470) plus a fragment isolated from the enhancer of the immediate early gene of human cytomegalovirus (CMV) (Boshart et al., *Cell* 41:521-530, 1985). Downstream of the promoter are the following single restriction enzyme cleavage sites that allow the integration of the genes: BamHI, Pvull, and Nrul. Behind these cloning sites the plasmid contains translational stop codons in all three reading frames followed by the 3N intron and the polyadenylation site of the rat preproinsulin gene. Other high efficient promoters can also be used for the expression, e.g., the human b-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC1 is digested with the restriction enzyme BamHI and then dephosphorylated using calf intestinal phosphates by procedures known in the art. The vector is then isolated from a 1% agarose gel.

The DNA sequence encoding VEGF-2, ATCC™ Accession No. 97149, was constructed by PCR using two primers corresponding to the 5' and 3'ends of the VEGF-2 gene: the 5' Primer (5'-GAT CGA TCC ATC ATG CAC TCG CTG GGC TTC TTC TCT GTG GCG TGT TCT CTG CTC G-3' (SEQ ID NO:26)) contains a Klenow-filled BamHI site and 40 nt of VEGF-2 coding sequence starting from the initiation codon; the 3' primer (5'-GCA GGG TAC GGA TCC TAG ATT AGC TCA TTT GTG GTC TTT-3' (SEQ ID NO:27)) contains a BamHI site and 16 nt of VEGF-2 coding sequence not including the stop codon.

The PCR amplified DNA fragment is isolated from a 1% agarose gel as described above and then digested with the endonuclease BamHI and then purified again on a 1% agarose gel. The isolated fragment and the dephosphorylated vector are then ligated with T4 DNA ligase. *E. coli* HB101 cells are then transformed and bacteria identified that contained the plasmid pC1. The sequence and orientation of the inserted gene is confirmed by DNA sequencing. This construct is designated pC1VEGF-2.

6. Construction of pC4SigVEGF-2 T103-L215

Plasmid pC4Sig is plasmid pC4 (Accession No. 209646) containing a human IgG Fc portion as well as a protein signal sequence.

To permit Polymerase Chain Reaction directed amplification and sub-cloning of VEGF-2 T103-L215 (amino acids 103 to 215 in FIG. 1 or SEQ ID NO:2) into pC4Sig, two oligonucleotide primers complementary to the desired region of VEGF-2 were synthesized with the following base sequence:

5' Primer (Bam HI and 26 nt of coding sequence):

```
                                      (SEQ ID NO:28)
5'-GCA GCA GGA TCC ACA GAA GAG ACT ATA AAA TTT GCT
                                               GC-3'
```

3' Primer (XbaI, STOP, and 15 nt of coding sequence):

```
                                      (SEQ ID NO:29)
5'-CGT CGT TCT AGA TCA CAG TTT AGA CAT GCA TCG GCA
                                                G-3'
```

The Polymerase Chain Reaction was performed using standard conditions well known to those skilled in the art and the nucleotide sequence for the mature VEGF-2 (aa 24-419) as, for example, constructed in Example 3, as template. The resulting amplicon was restriction digested with BamHI and XbaI and subcloned into BamHI /XbaI digested pC4Sig vector.

7. Construction of pC4SigVEGF-2 T103-R227

To permit Polymerase Chain Reaction directed amplification and sub-cloning of VEGF-2 T103-L215 (amino acids 103 to 227 in FIG. 1 or SEQ ID NO:2) into pC4Sig, two oligonucleotide primers complementary to the desired region of VEGF-2 were synthesized with the following base sequence:

5' Primer (Bam HI and 26 nt of coding sequence):

```
                                      (SEQ ID NO:30)
5'-GCA GCA GGA TCC ACA GAA GAG ACT ATA AAA TTT GCT
                                               GC-3'
```

3' Primer (Xba I, STOP, and 21 nt of coding sequence):

```
                                      (SEQ ID NO:31)
5'-GCA GCA TCT AGA TCA ACG TCT AAT AAT GGA ATG
                                              AAC-3'
```

The Polymerase Chain Reaction was performed using standard conditions well known to those skilled in the art and the nucleotide sequence for the mature VEGF-2 (aa 24419) as, for example, constructed in Example 3, as template. The resulting amplicon was restriction digested with BamHI and XbaI and subcloned into BamHI/XbaI digested pC4Sig vector.

8. Construction of pC4VEGF-2 M1-M263

The expression vector pC4 contains the strong promoter (LTR) of the Rous Sarcoma Virus (Cullen et al., *Molecular and Cellular Biology,* 438-447 (March, 1985)) plus a fragment of the CMV-enhancer (Boshart et al., *Cell* 41:521-530 (1985)). Multiple cloning sites, e.g., with the restriction enzyme cleavage sites BamHI, XbaI and Asp718, facilitate the cloning of the gene of interest. The vector contains in addition the 3N intron, the polyadenylation and termination signal of the rat preproinsulin gene.

In this illustrative example, the cloned DNA encoding the C-terminal deleted VEGF-2 M1-M263 protein (amino acids 1-263 in FIG. 1 or SEQ ID NO:2) is inserted into the plasmid vector pC4 to express the C-terminal deleted VEGF-2 protein.

To permit Polymerase Chain Reaction directed amplification and sub-cloning of VEGF-2 M1-M263 into the expression vector, pC4, two oligonucleotide primers complementary to the desired region of VEGF-2 were synthesized with the following base sequence:

```
5' Primer                             (SEQ ID NO:32)
5'-GAC TGG ATC CGC CAC CAT GCA CTC GCT GGG CTT CTT
CTC-3'

3' Primer                             (SEQ ID NO:33)
5'-GAC TGG TAC CTT ATC ACA TAA AAT CTT CCT GAG
CC-3'
```

In the case of the above described 5' primer, an BamHI restriction site was incorporated, while in the case of the 3' primer, an Asp718 restriction site was incorporated. The 5' primer also contains 6 nt, 20 nt of VEGF-2 coding sequence, and an ATG sequence adjacent and in frame with the VEGF-2 coding region to allow translation of the cloned fragment in *E. coli,* while the 3' primer contains 2 nt, 20 nt of VEGF-2 coding sequence, and one stop codon (preferentially utilized in *E. coli*) adjacent and in frame with the VEGF-2 coding region which ensures correct translational termination in *E. coli.*

The Polymerase Chain Reaction was performed using standard conditions well known to those skilled in the art and the nucleotide sequence for the mature VEGF-2 (aa 24-419) as constructed, for example, in Example 3 as template. The resulting amplicon was restriction digested with BamHI and Asp718 and subcloned into BamHI/Asp718 digested pC4 protein expression vector. This construct is designated pC4VEGF-2 M1-M263.

9. Construction of pC4VEGF-2 M1-D311

In this illustrative example, the cloned DNA encoding the C-terminal deleted VEGF-2 M1-D311 protein (amino acids 1-311 in FIG. 1 or SEQ ID NO:2) is inserted into the plasmid vector pC4 to express the C-terminal deleted VEGF-2 protein.

To permit Polymerase Chain Reaction directed amplification and sub-cloning of VEGF-2 M1-D311 into the expression vector, pC4, two oligonucleotide primers complementary to the desired region of VEGF-2 were synthesized with the following base sequence:

```
5' Primer                                    (SEQ ID NO:34)
5'-GAC TGG ATC CGC CAC CAT GCA CTC GCT GGG CTT CTT
CTC-3'

3' Primer                                    (SEQ ID NO:35)
5'-GAC TGG TAC CTT ATC AGT CTA GTT CTT TGT GGG
G-3'
```

In the case of the above described 5' primer, an BamHI restriction site was incorporated, while in the case of the 3' primer, an Asp718 restriction site was incorporated. The 5' primer also contains 6 nt, 20 nt of VEGF-2 coding sequence, and an ATG sequence adjacent and in flame with the VEGF-2 coding region to allow translation of the cloned fragment in *E. coli,* while the 3' primer contains 2 nt, 20 nt of VEGF-2 coding sequence, and one stop codon (preferentially utilized in *E. coli*) adjacent and in frame with the VEGF-2 coding region which ensures correct translational termination in *E. coli.*

The Polymerase Chain Reaction was performed using standard conditions well known to those skilled in the art and the nucleotide sequence for the mature VEGF-2 (aa 24-419) as constructed, for example, in Example 3 as template. The resulting amplicon was restriction digested with BamHI and Asp718 and subcloned into BamHI/Asp718 digested pC4 protein expression vector.

10. Construction of pC4VEGF-2 M1-Q367

In this illustrative example, the cloned DNA encoding the C-terminal deleted VEGF-2 M1-D311 protein (amino acids 1-311 in SEQ ID NO:2) is inserted into the plasmid vector pC4 to express the C-terminal deleted VEGF-2 protein.

To permit Polymerase Chain Reaction directed amplification and sub-cloning of VEGF-2 M1-D311 into the expression vector, pC4, two oligonucleotide primers complementary to the desired region of VEGF-2 were synthesized with the following base sequence:

```
5' Primer                              (SEQ ID NO:36)
5'-GAC TGG ATC CGC CAC CAT GCA CTC GCT GGG CTT CTT
CTC-3'

3' Primer                              (SEQ ID NO:37)
5'-GAC TGG TAC CTC ATT ACT GTG GAC TTT CTG TAC ATT
C-3'
```

In the case of the above described 5' primer, an BamH1restriction site was incorporated, while in the case of the 3' primer, an Asp718 restriction site was incorporated. The 5' primer also contains 6 nt, 20 nt of VEGF-2 coding sequence, and an ATG sequence adjacent and in frame with the VEGF-2 coding region to allow translation of the cloned fragment in *E. coli,* while the 3' primer contains 2 nt, 20 nt of VEGF-2 coding sequence, and one stop codon (preferentially utilized in *E. coli*) adjacent and in frame with the VEGF-2 coding region which ensures correct translational termination in *E. coli.*

The Polymerase Chain Reaction was performed using standard conditions well known to those skilled in the art and the nucleotide sequence for the mature VEGF-2 (aa 24-419) as constructed, for example, in Example 3 as template. The resulting amplicon was restriction digested with BamHI and Asp718 and subcloned into BamHI/Asp718 digested pC4 protein expression vector. This construct is designated pC4VEGF-2 M1-Q367.

Example 6

Method of Treatment Using Gene Therapy for Production of VEGF-2 Polypeptide—In Vivo Suitable template DNA for production of mRNA coding for VEGF-2 is prepared in accordance with a standard recombinant DNA methodology. Sterile and endotoxin-free oligonucleotides are diluted in Sterile and endotoxin-free oligonucleotides are diluted in Balanced Salt Solution (BSS, Alcon, Fort Worth, Tex.) so as to have the same pH and electrolyte concentration as the aqueous or vitreous of the eye. Emalphor EC620 (2.5%, GAF Corp.) (Bursell et al. (1993) *J. Clin. Invest.* 92:2872-2876), a petroleum product, is added to change viscosity and aid in delivery properties. Doses to achieve intravitreal concentrations ranging from 0.1 μM-100 μM are administered. The volume delivered is between 1 μl and 1 ml depending on the volume of the eye.

The intubated patient is Anesthetized with fluorane. The face and eyes are prepared with a betadine scrub and draped in the usual sterile fashion. The sterile polynucleotide with vehicle is injected with a 33 gauge needle on a sterile syringe at the posterior limbus (pars plana) through full thickness sclera into the vitreous. No closing suture is required unless there is leakage. Antibiotic drops containing gentanlicin or erythromycin ointment is applied to the surface of the globe in the palpebral fissure several times per day until there is complete wound closure. The frequency of injection ranges from every other day to once every 6 months or less, depending on the severity of the disease process, the degree of intraocular inflammation, the character of the vehicle (i.e., slow release characteristics), and the tolerance of the eye to injections. Short and long term follow-up check-ups for possible retinal detachment from the injections are necessary.

The eye upon dilation is monitored for signs of inflammation, infection, and photoreceptor growth by both an direct and a indirect ophthalmoscope to view the retina and fundus. Monitoring can be as frequent as every day in cases where premature infants are threatened with retinal detachment The frequency of monitoring will diminish with resolution of disease.

The patient is treated weekly with intraocular injections of polynucleotide resuspended in the appropriate vehicle (BSS, Emanfour) at concentrations within the range of 0.1 to 100 μM. This treatment may be supplemented with systemic delivery of polynucleotide (i.e., intravenous, subcutaneous, or intramuscular) from 2 to 5 times per day to once a month.

Example 7

Method of Treatment Using Gene Therapy—Ex Vivo Homologous Recombination

Photoreceptor cells are obtained from a subject by biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM $Na_2 HPO_4$, 6 mM dextrose). The cells are recentrifuged, the supernatant aspirated, and the cells resuspended in electroporation buffer containing 1 mg/ml acetylated bovine serum albumin. The final cell suspension contains approximately $3\times10^6$ cells/ml. Electroporation should be performed immediately following resuspension.

Plasmid DNA is prepared according to standard techniques. To construct a plasmid for targeting to the VEGF-2 locus, plasmid pUC18 (MBI Fermentas, Amherst, N.Y.) is digested with HindIII. The CMV promoter is amplified by PCR with an XbaI site on the 5' end and a BamHI site on the 3'end. Two VEGF-2 non-coding sequences are amplified via PCR: one VEGF-2 non-coding sequence (VEGF-2 fragment 1) is amplified with a HindIII site at the 5' end and an Xba site at the 3'end; the other VEGF-2 non-coding sequence (VEGF-2 fragment 2) is amplified with a BamHI site at the 5'end and a HindIII site at the 3'end. The CMV promoter and VEGF-2 fragments are digested with the appropriate enzymes (CMV promoter—XbaI and BamHI; VEGF-2 fragment 1—XbaI; VEGF-2 fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 µg/ml. 0.5 ml of the cell suspension (containing approximately $1.5\times10^6$ cells) is then added to the cuvette, and the cell suspension and DNA solutions are gently mixed. Electroporation is performed with a Gene-Pulser apparatus (Bio-Rad). Capacitance and voltage are set at 960 µF and 250-300 V, respectively. As voltage increases, cell survival decreases, but the percentage of surviving cells that stably incorporate the introduced DNA into their genome increases dramatically. Given these parameters, a pulse time of approximately 14-20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37EC. The following day, the media is aspirated and replaced with 10 ml of fresh media and incubated for a further 16-24 hours.

The engineered photoreceptor cells are then injected into the host. The photoreceptor cells now produce the protein product.

Example 8

VEGF-2 Activity on Retinal Cells

The retina has proven to be an advantageous experimental model for studying the role of intrinsic and extrinsic factors in the regulation of the development of neuronal and non-neuronal cell types from a more primitive neuroepithelial cell. The differentiated retina is composed of seven cell types: sensory (rod and cone photoreceptors), glia (Miiller cells), and two types of neurons, intemeurons (horizontal, bipolar, and amacrine), and projection neurons (ganglion cells) (for review see Dowling, 1987). The development of the various cell types in the retina does not occur synchronously with the majority of the cones, and ganglion and horizontal cells developing before birth (for review see Altshuler et al., 1991; Harris, 1991; Reh, 1991). In contrast, differentiation of a majority of the rods, the main cell type in the rat retina, occurs postnatally. Clonal analysis of the progeny of retinal precursor cells has demonstrated that the progenitor cells can produce various combinations of retinal cell types indicating that the progenitors are either totipotent or multipotent depending on the developmental age examined (Turner and Cepko, 1987; Turner et al., 1990; Wetts and Fraser, 1998). Furthermore, findings from both in vivo and in vitro studies demonstrate that the final phenotype of the retinal cells is largely lineage independent which suggest that the changing microenvironment within the retina has a role in determining the cellular potential of the progenitor cells as well as the differentiated phenotype of the progeny (Watanabe and Raff, 1990, 1992; Harris, 1991; Reh, 1991; Ezzeddine et al. 1997).

In vitro, retinal cell proliferation and differentiation is regulated by a variety of factors; for example, FGF-2 (Hicks and Courtois, 1992), CNTF (Ezzeddine et al., 1997; Fuhrmann et al., 1995), LIF (Ezzeddine et al., 1997), TGF_ (Lilleen and Cepko, 1992), retinoic acid (Kelly et al., 1994), and EGF (Lillien, 1995). Recently, Yang and Cepko (1996) have identified and characterized the expression pattern of VEGFR-2/FLK-1 in developing and adult retina. VEGFR transcripts are first detected at E11.5 in association with the developing retinal vasculature and with the central region of the neural retina. By developmental day E15, VEGFR-2 expression extends to the periphery of the retina consistent with the outward gradient of retinal development (Young, 1985; LaVail et al., 1991). VEGFR-2 expression was largely localized to the ventricular zone during the perinatal period when neurogenesis is at its peak and a large number of postmitotic neurons are being formed.

As shown below, the major in vitro effect of VEGF is during early development and involves the proliferation of multipotent progenitor cells since the level of BrdU and the number of photoreceptor and amacrine cells are increased. VEGF-2 enhanced the proliferation of retinal cells derived from E15 embryos and the magnitude of the response increased with age. The early proliferative response to VEGF-2 administration was not effected by CNTF. However, CNTF did inhibit the VEGF-2 induced increase in the level of rhodopsin protein.

Experimental Procedures

Animals. Timed pregnant animals are obtained from Harlan. Sprague-Dawley (Indianapolis, Ind.). All animal related procedures are conducted in strict compliance with approved institutional protocols and in accordance with provisions for animal care and use described in the Guide for the Care and Use of Laboratory Animals (NIH publication No. 86-23, 1985).

Retinal Cultures The retinal tissue are obtained from either late embryonic or neonatal rats. The dissociated primary cells are prepared by incubating the tissue in 0.25% trypsin for 6 min at 37° C. Following the inactivation of the trypsin by a 5 min incubation in growth medium (F12:Dulbecco's modified Eagle's medium (DMEM) containing 1% fetal bovine serum, 1% hormonal supplements (N2, Bottenstein, 1983), 1% glutamine and 0.5% penicillin-streptomycin (10,000 units/ml and 10 mg/ml, respectively, Gibco, Grand Island, N.Y.) containing 50 µg/ml deoxyribonuclease type I (Sigma, St. Louis, Mo.), the tissue fragments are passed repeatedly through a Pasteur pipette with a constricted tip of a diameter of approximately 1 mm. The dissociated cells are collected by centrifugation (800 xg, 5 min) and resuspended in growth medium. The cells are seeded in 96 well plates precoated with poly-L-lysine (50 µg/ml, Sigma) and laminin (10 µg/ml, Gibco), at a density of 425 cells/$mm^2$ unless stated otherwise. The cultures are gradually shifted to growth medium without serum by changing one-half of the medium every other day. The trophic factors are replenished with each medium change.

Hippocampal Astrocytes Purified cultures of astrocytes are prepared from rat hippocampi using a method previously described (Greene et al., 1998).

Rhodopsin Immunohistochemistry and Cell Counting Procedures For the immunohistochemical staining, the cultures are fixed overnight in 4% paraformaldehyde containing 4% sucrose. For rhodopsin and syntaxin staining, the cultures are permeabilized with 0.05% saponin in PBS for 30 min. The non-specific IgG binding is inhibited by incubating the cells in PBS containing 5% horse serum and 2% BSA for 3 h at room temperature. The cultures are then incubated overnight at 4° C. with anti-rhodopsin (1:10,000, Rho 4D2, Dr. Molday, University of British Columbia) or anti-syntaxin (1:10,000, Sigma) diluted in PBS containing 5% horse serum and 2% BSA (Molday, 1989). Following the removal of the primary antibody, the cultures are incubated with a biotinylated anti-mouse antibody (1:2,500) for 90 min. The avidin-biotin-peroxidase complex, diluted 1:50 in PBS containing 5% horse serum and 2% BSA, is then added for 60 minutes. To visualize the bound peroxidase, diaminobenzidine is used at a final concentration of 0.4 mg/ml in a 0.1M acetate buffer containing 2.5% nickel sulfate. The number of immunopositive cells per well is determined by counting the labeled cells in an area representing 11% of the total surface area of the well and then corrected for the total surface area.

BrdU Immunohistochemistry The retinal cells are incubated with BrdU for 4 h and subsequently, washed twice with PBS. Growth medium is then added back to the cultures, which are then maintained in vitro for various time intervals. At the end of the incubation period, the cultures are fixed and immunohistochemically stained for the incorporated BrdU as per manufacturer's (Boehringer Mannheim, Indianapolis, Ind.) instructions.

Rhodopsin and GFAP ELISAs For the rhodopsin ELISA, the cultures are rinsed with PBS and fixed overnight with 4% paraformaldehyde containing 4% sucrose. The cultures are then rinsed with PBS and permeabilized with 0.05% saponin in PBS for 30 min at room temperature. The non-specific protein binding sites are suppressed by incubating the cells in PBS containing 5% horse serum and 2% BSA (blocking buffer) for at least 3 h. The cultures are incubated overnight with the mouse anti-rhodopsin antibody (diluted 1:500 in blocking buffer) and then subsequently, with goat anti-mouse IgG conjugated to horseradish peroxidase (diluted 1:2,500) in blocking solution. The cultures are washed extensively with PBS and then the substrate (3, 3', 5, 5'-tetramethylbenzidine) is added to the wells and the plates were incubated in the dark for 60 min. The reaction is stopped by adding 2 M $H_2SO_4$ and the amount of product formed is quantitated by measuring the absorbance at 450 nm. The absorption of the reagent blank ranged from 0.1 to 0.15 and is not subtracted from the indicated values. The GFAP ELISA is conducted essentially as previously described (Greene et al., 1998).

Cell survival assay based on Calcein AM measurements. At the end of the incubation period the cultures were rinsed once with Ham's F-12. The calcein AM was added to a final concentration of 2 µM in 100 µl of Ham's F-12 and the cultures were incubated for 60 min at 37 degree C. At the end of the incubation period the cultures were rinsed. The absorbance at 530 nm was determined on an ELISA plate reader.

High-affinity GABA uptake The level of high-affinity GABA uptake is determined as previously described (Greene et al., 1998).

[$^3$H]Thymidine Incorporation The cultures are treated with trophic factors for 24 h and during the last 4 h, the cells are labeled with [$^3$H]thymidine, at a final concentration of 0.33 µM (25 Ci/mmol, Amersham, Arlington Heights, Ill.). The incorporated [$^3$H]thymidine is precipitated with ice-cold 10% trichloroacetic acid for 24 h. Subsequently, the cells are rinsed with ice-cold water. Following lysis in 0.5 M NaOH, the lysates and PBS rinses (500 µl) are pooled, and counted.

RESULTS

Figure 14A:
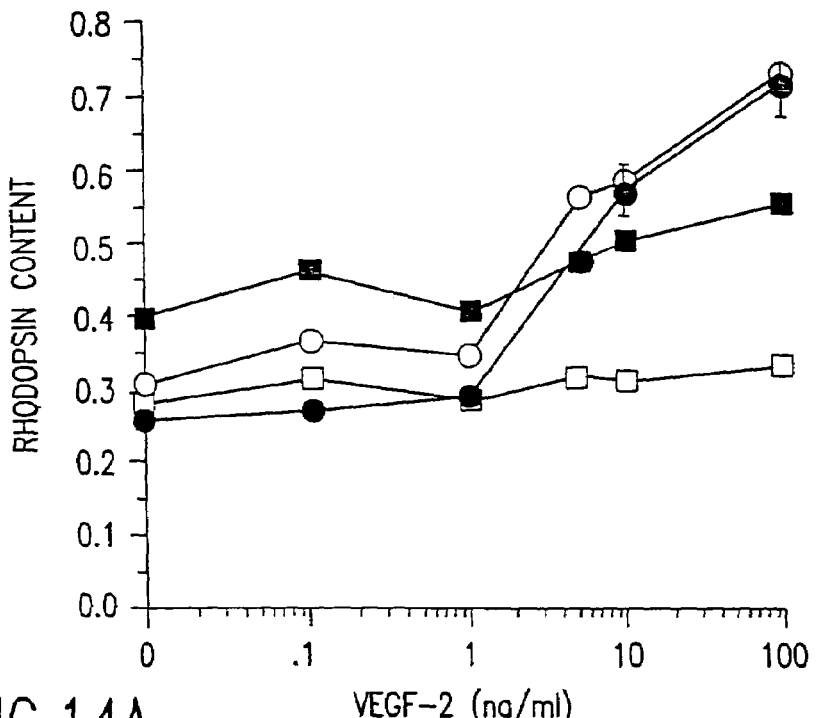
FIG. 14A-D shows that VEGF-2 treatment increases the level of rhodopsin protein and the number of photoreceptor cells. Dissociated retinal cells were prepared from P1 animals, plated at a density of 425 cells/mm$^2$ and treated with VEGF-2 (A and B) or VEGF-2 (C and D). After 2 (open squares), 5 (solid squares), 7 (open circles), or 9 (solid squares) days, the total number of cells in the cultures was estimated by measuring the calcein emission. The cultures were then fixed and the levels of rhodopsin protein quantitated by ELISA.
Figure 14B:
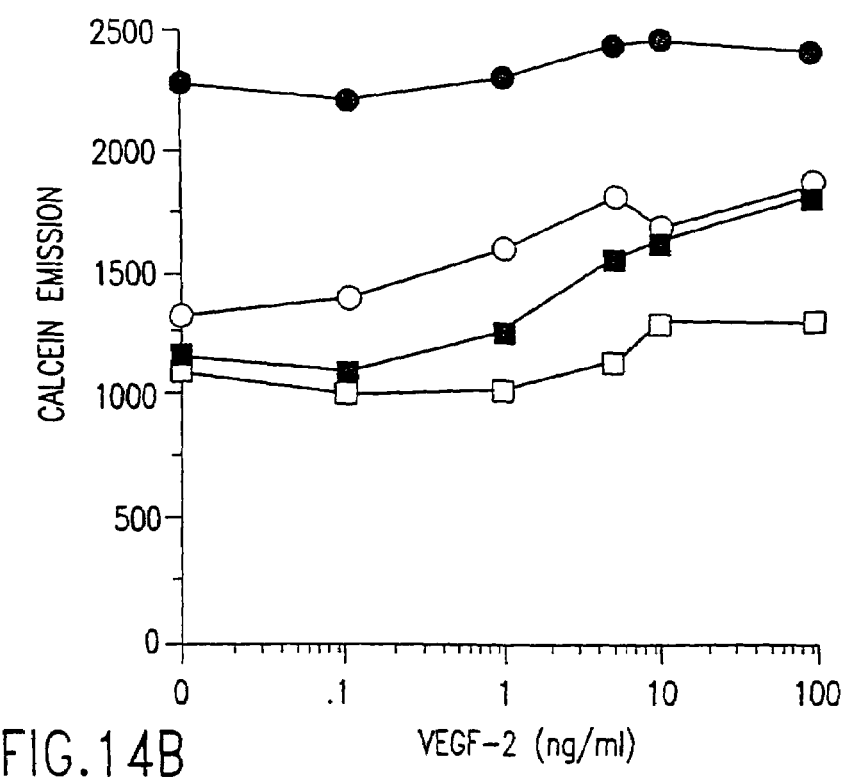
Figure 14C:
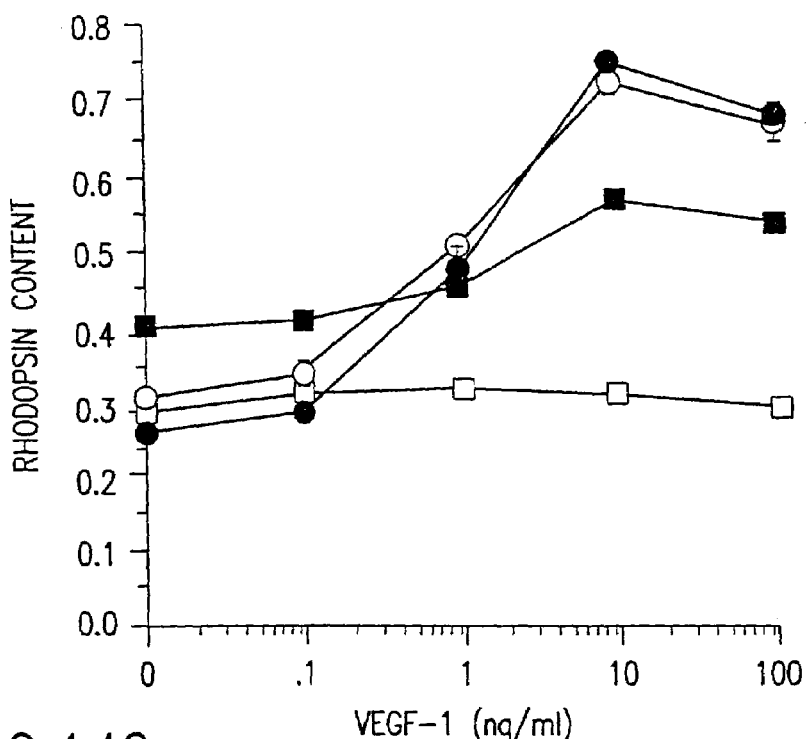
Figure 14D:
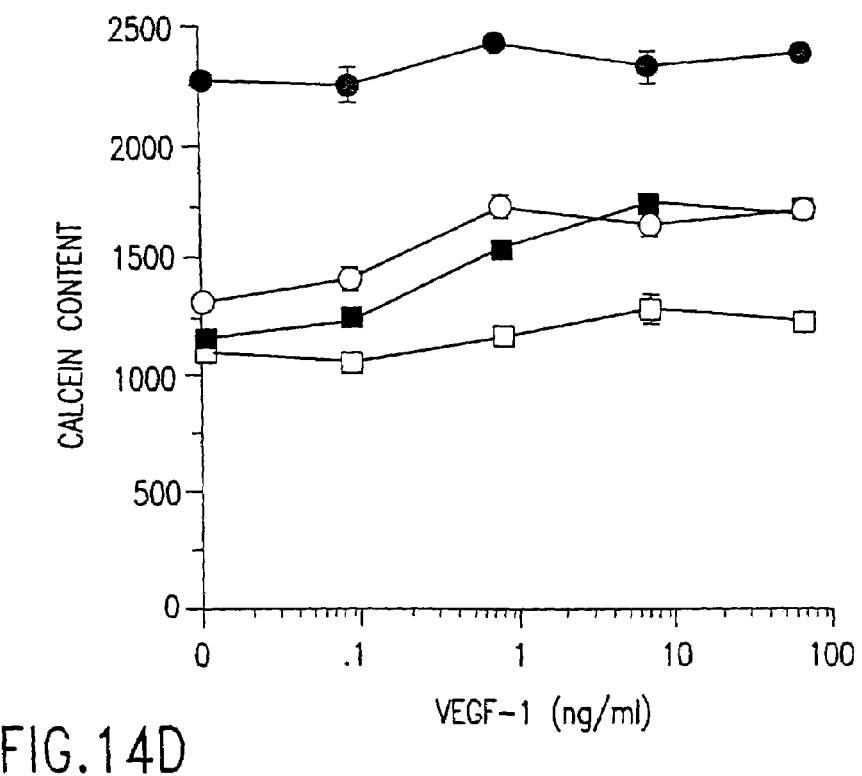

The regulatory role of VEGFs on photoreceptor cell development is initially investigated using cultures derived from postnatal day 1 (PN1) animals. Previous reports have demonstrated that multipotent progenitors are present during this developmental period and retain their capacity to differentiate into photoreceptor cells as well as other retinal cell types in vitro (Marrow et al., 1998). Treatment with VEGF-2 or VEGF-1. (R and D Systems, Minneapolis, Minn.) induces a dose- and time-dependent increase in the level of rhodopsin protein in the retinal cultures (FIG. 14A). The time course of the VEGF-induced increase in rhodopsin is relatively slow, consistent with the known developmental profile of photoreceptor cells. After 5 days of treatment, a 25-40% increase in rhodopsin protein is noted with 10 to 100 ng/ml of VEGF-2. However, by 7 to 9 days of treatment, these same concentrations of VEGF-2 produced a 200-250% increase in rhodopsin protein. Furthermore, at these later time points, concentrations of VEGF as low as 1 ng/ml significantly increased rhodopsin levels. Changes in the amount of rhodopsin may reflect changes in the level of expression of the protein or changes in the number of photoreceptor cells or both. To ascertain if VEGF treatment effected the total number of retinal cells, the level of emission of calcein AM is monitored. An approximate 25-50% increase in calcein emission is observed after a 5-7 day treatment with at least 10 ng/ml of VEGF-2 (FIG. 14B). A pronounced increase in the basal level of calcein emission is noted in the retinal cultures between 7 and 9 days indicating that retinal cell proliferation that is independent of exogenous VEGF had increased by this later time point The presence of VEGF-2, even at concentrations as high as 100 ng/ml, for 9 days did not further increase the number of retinal cells. However, there is not a concomitant increase in the basal level of rhodopsin protein after 9 days in culture suggesting that the proliferation of other cell types accounts for the increase in the level of calcein emission (FIG. 14A). Treatment with VEGF-1 induced similar changes in the level of rhodopsin and calcein emission to those described for VEGF-2 (FIGS. 14C and 14D, respectively).

Figure 15:
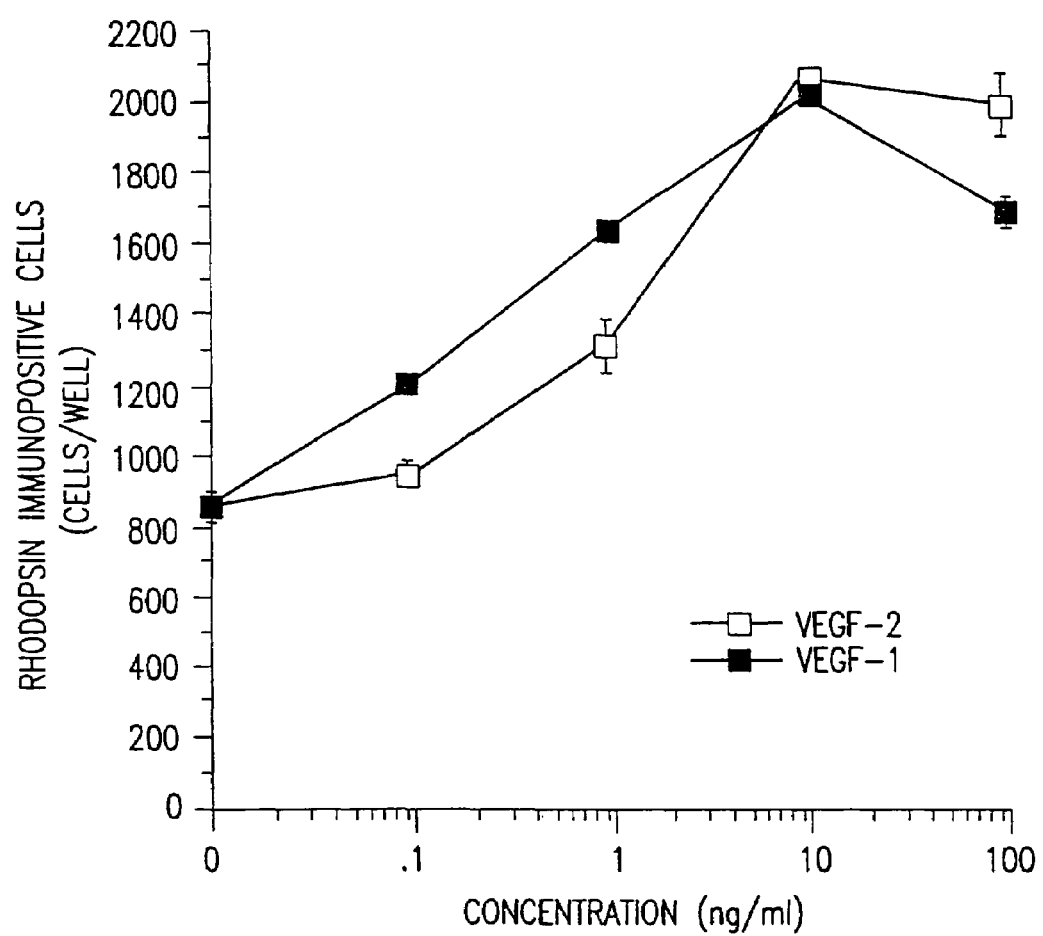
FIG. 15 shows that the number of rhodopsin immunopositive cells increased as a function of VEGF-2 concentration. The retinal cells were maintained in vitro for 8 days in the presence of either VEGF-1 or VEGF-2. The cultures were then fixed and immunohistochemically stained for rhodopsin.

To determine if the increase in rhodopsin content and calcein emission reflected an increase in the number of photoreceptor cells, cultures are treated with VEGF-1 or VEGF-2 for 9 days and then immunohistochemically stained for rhodopsin. To quantitate the effects of VEGF treatment, cell counts are made. The number of rhodopsin immunopositive cells increased as a function of concentration with the response having an EC50 value of 0.25 and 1.5 ng/ml for VEGF-1 and VEGF-2, respectively (FIG. 15). At a saturating concentration of VEGF-2, a 2.4-fold increase in the number of rods is observed. Furthermore, the response is stable in the presence of concentrations of VEGF-2 as high as 100 ng/ml suggesting that VEGF-2 does not readily induce a desensitization of the biological response. The dose response observed with VEGF-1 is similar to that obtained with VEGF-2 which is consistent with the results from the rhodopsin ELISAs.

Figure 16A:
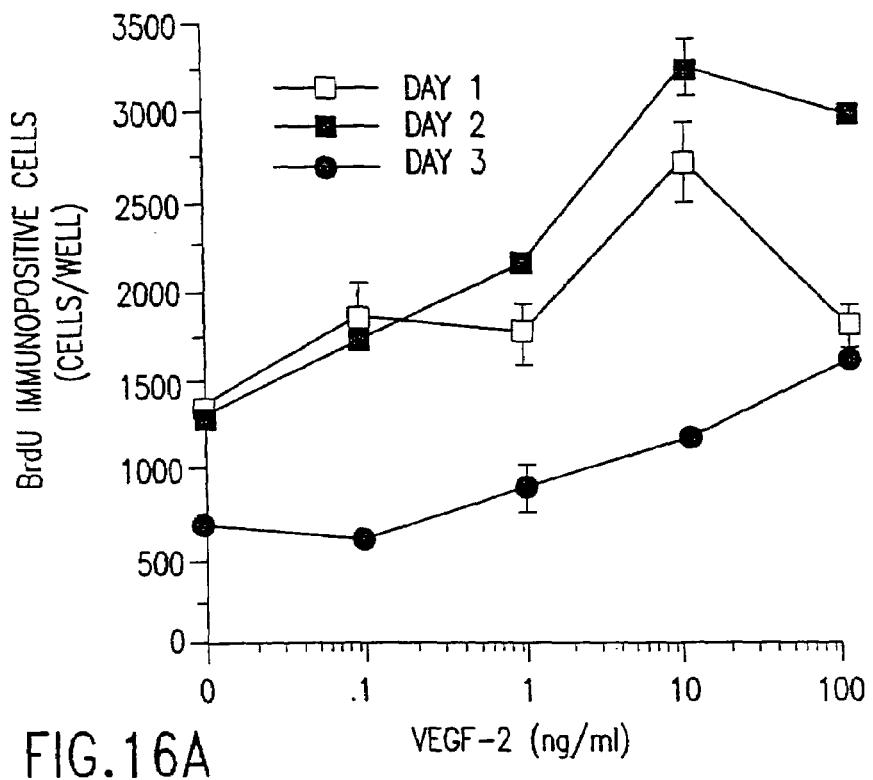
FIG. 16A-C shows that VEGF-2 increases BrdU and [3H] thymidine incorporation in retinal cultures in a developmentally restricted manner. The cells were isolated from P1 animals and plated at a density of 425 cells/mm$^2$. The cultures were initially treated 4 hours after plating with either VEGF or VEGF-2. After 1, 2, or 3 days, the cultures were labeled for 4 hours with BrdU. The cells were then fixed and processed for BrdU immunohistochemistry.
Figure 16B:
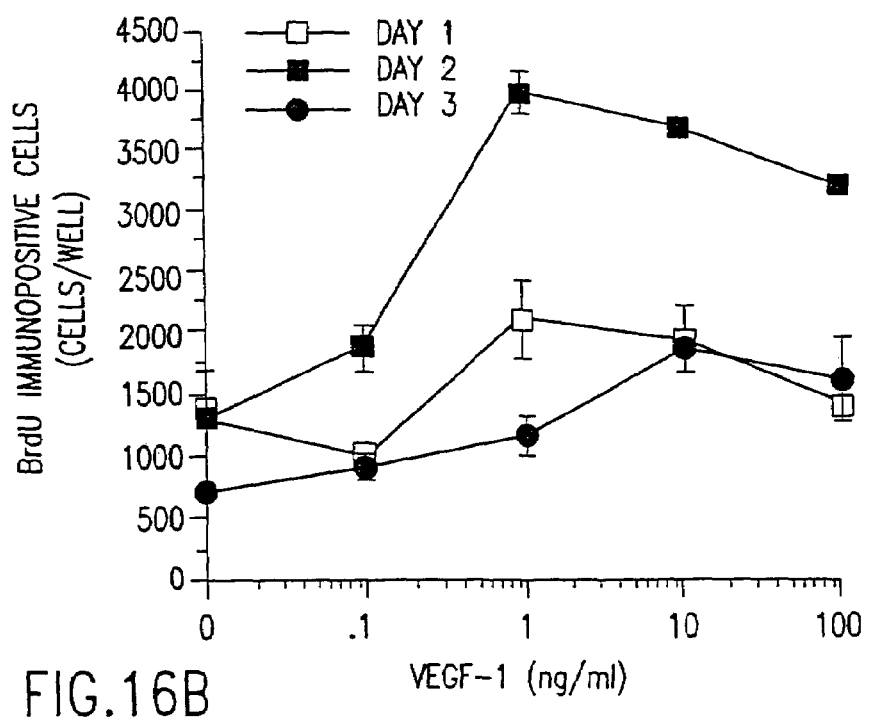
Figure 16C:
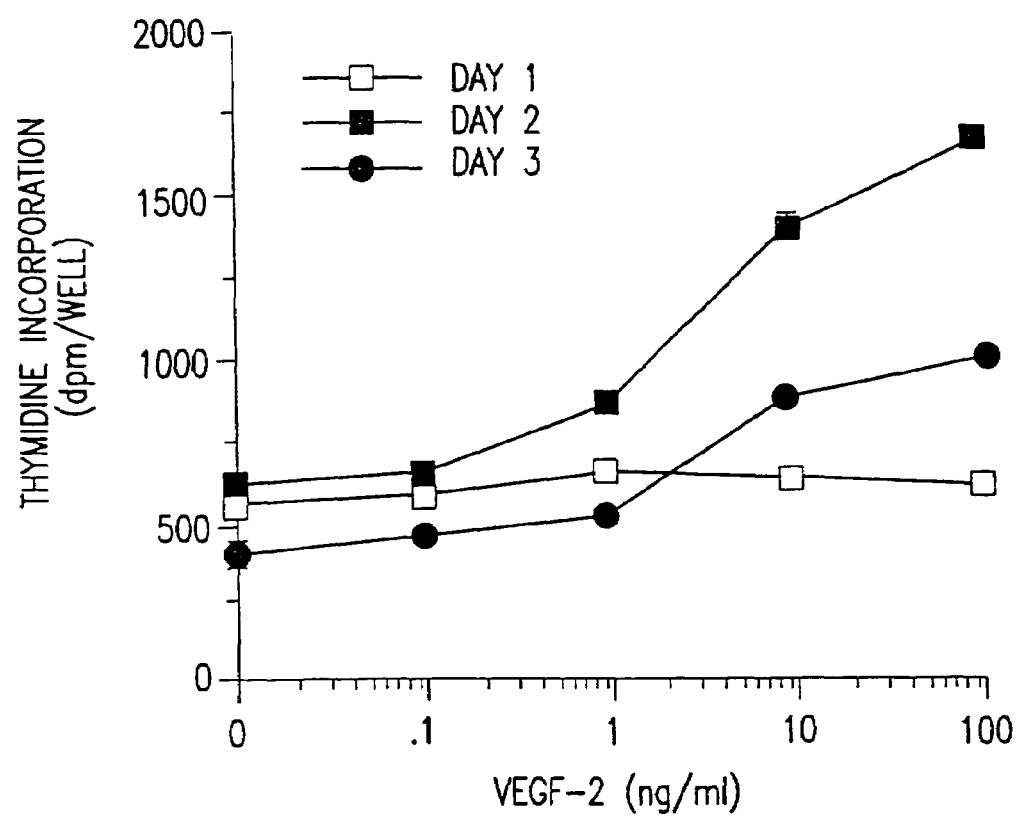

The mechanism by which VEGF-2 induces an increase in photoreceptor cell number may involve an increase in the proliferation of precursor cells, enhanced survival of differentiated photoreceptor cells, and/or the redirection of the rod lineage pathway. To investigate if VEGF-2 is mitogenic for retinal cells, the cultures are treated with factors 4 h after plating and then subsequently labeled with BrdU after 24, 48 or 72 h. At the end of the final labeling period (72 h), the cultures are fixed and the incorporated BrdU is immunohistochemically detected. A significant increase in the number of BrdU labeled cells is not observe until after 48 h of treatment, when 10 ng/ml of VEGF-2 or VEGF-1 induced a 2- to 3-fold increase (FIGS. 16A and 16B, respectively). The EC50 value for the response is calculated as 1 ng/ml. The 48 h time point appeared near maximal since after an incubation of 72 h, the level of BrdU incorporation had declined in the VEGF treated cultures regardless of concentration. However, this decline in the number of immunopositive cells is not specifically related to VEGF administration. The basal level of BrdU incorporation decreased from 1300 to 700 immunopositive cells per well suggesting that a general loss in the proliferative activity of the retinal progenitor cells is occurring during this time period. In spite of the lower over-all proliferative activity in the cultures at the later time points, VEGF administration still resulted in a 2-fold increase in the number of BrdU labeled cells. Similar results are obtained using [$^3$H] thymidine incorporation (FIG. 16C).

Figure 17A:
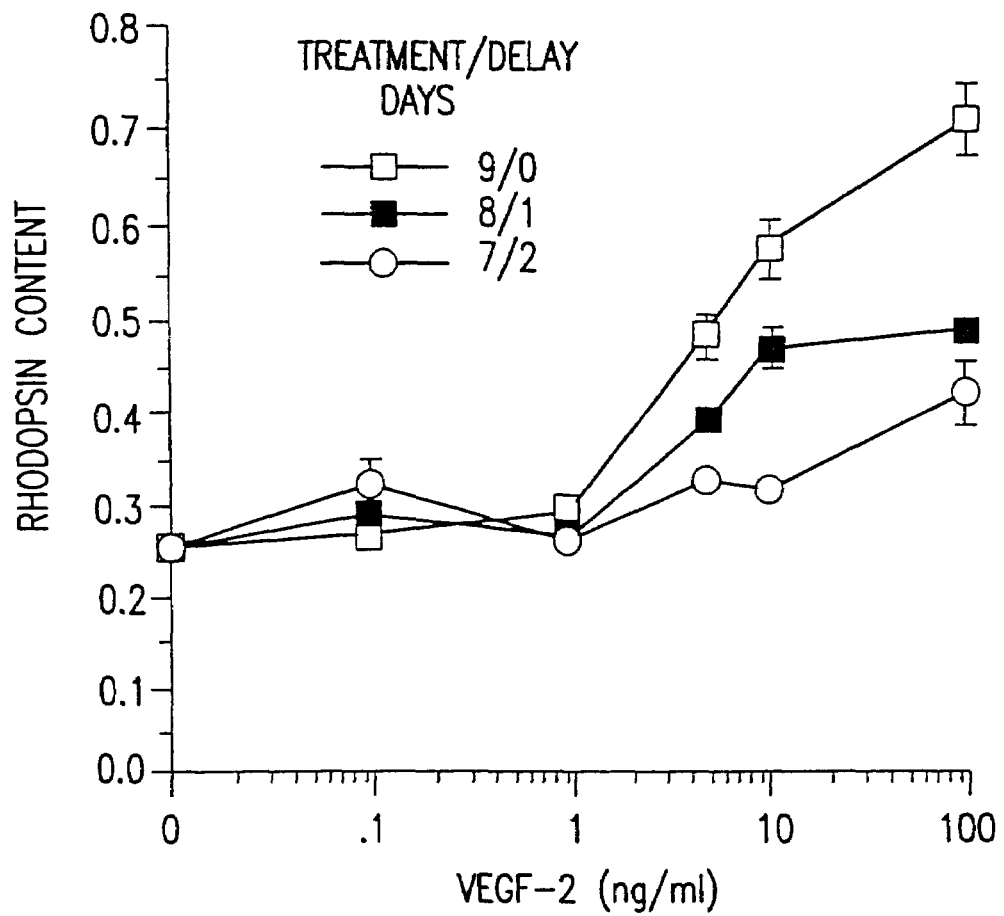
FIG. 17A-B shows the loss of the response to VEGF-2 or VEGF-1 as a function of the time lapsed between the isolation of the cells and the initial addition of the factors. One set of cultures was initially treated with factors 4 hours after plating (9/0) and subsequently, additional sets were treated after 24 or 48 hours (8/1 or 7/2, respectively). After 9 days in culture, the cells were fixed and the level of rhodopsin protein was quantitated by ELISA assay.
Figure 17B:
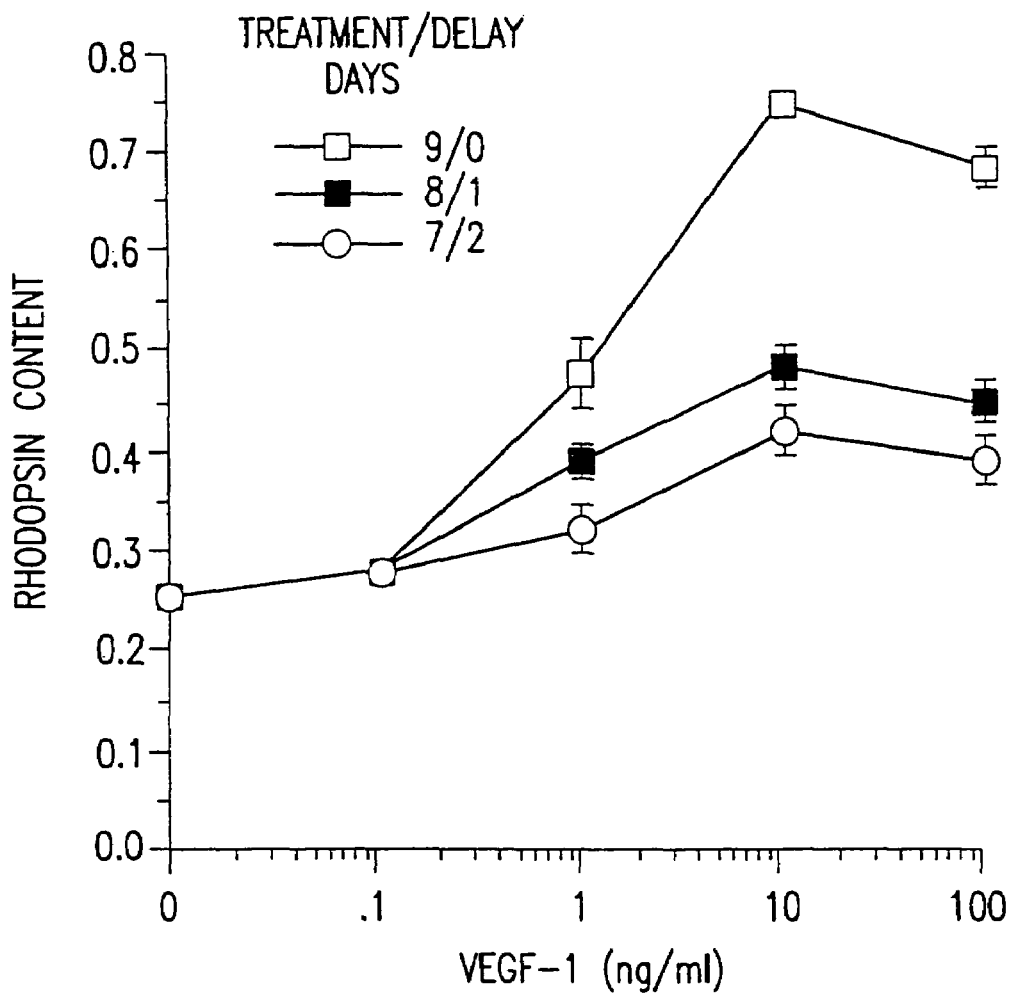

To further characterize a role for VEGF during the early in vitro culture period, the effect that delaying the addition of the factor to the cultures had on the level of rhodopsin protein is examined. The initial addition of VEGF is made 4, 24, or 48 h after plating and the cultures are subsequently maintained for 9 days and then prepared for the rhodopsin ELISA. The loss of the response to VEGF-2 or VEGF-1 as a function of the time lapsed between the isolation of the cells and the initial addition of the factors is depicted in FIGS. 17A and 17B, respectively. The addition of factors within 4 h of the plating of the cells resulted in a 3-fold increase in the level of rhodopsin. However, delaying the initial treatment with VEGF by 24 or 48 h resulted in the reduction of the maximal response by 28 and 43%, respectively. Furthermore, after a delay of 48 h, only treatment with 100 ng/ml of VEGF-2 induced a significant increase in rhodopsin content. Thus suggesting that the proliferative effect that the VEGFs are having on retinal cells is developmentally restricted and involves the proliferation of photoreceptor progenitors.

Figure 18A:
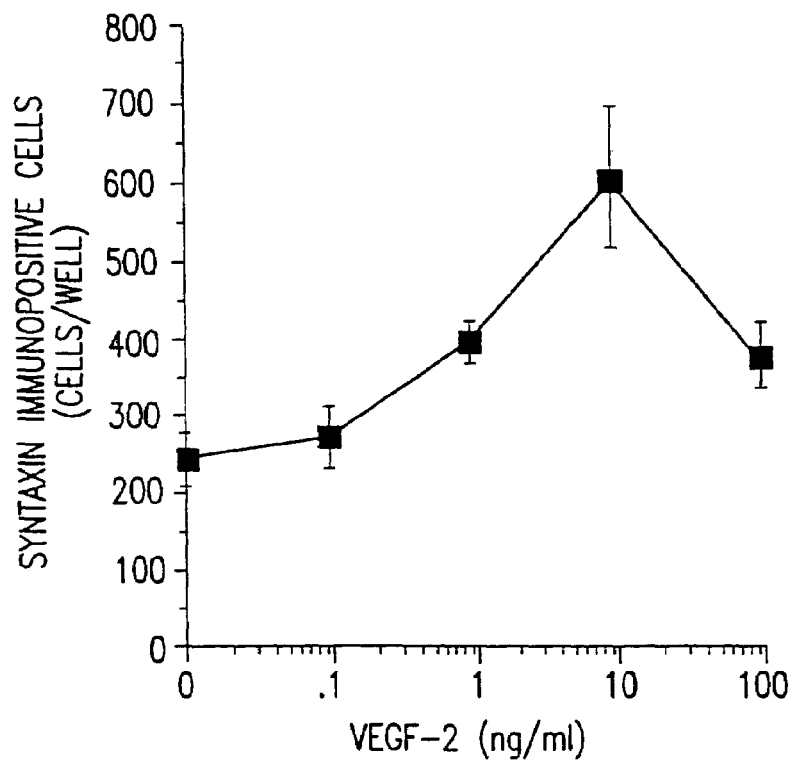
FIG. 18A-C shows VEGF increases the number of Amacrine but not Muller or Endothelial cells. Retinal cells were treated for 8 days with the indicated concentrations of VEGF-2. The cells were then fixed and immunohistochemically stained for syntaxin (A), analyzed for the level of high-affinity GABA uptake (B), or GFAP (C).
Figure 18B:
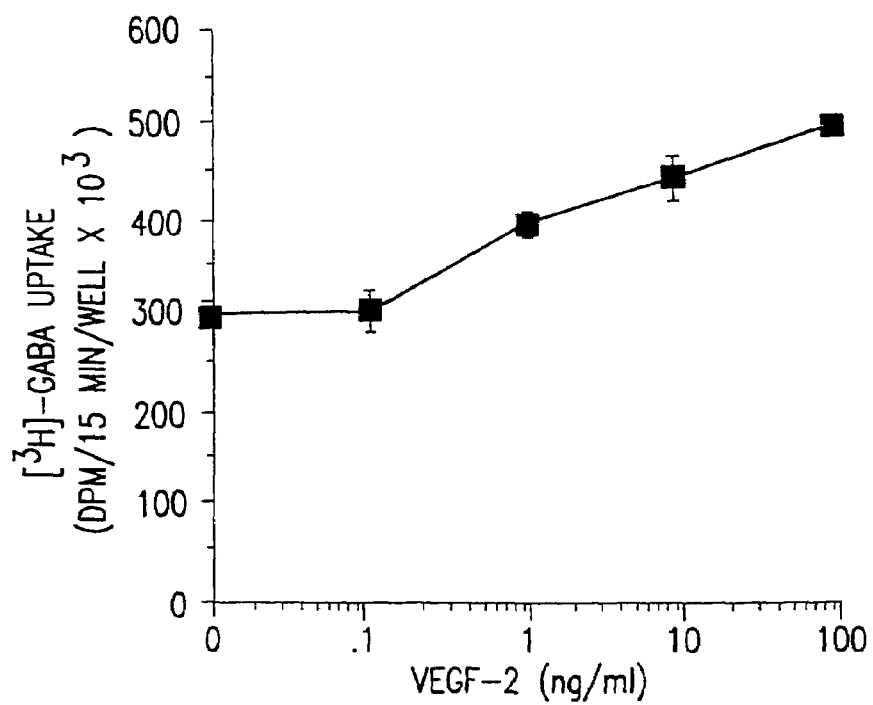

The possibility that VEGF effects other retinal cell types that are born postnatally e.g. amacrine and Moller cells, is also investigated. The morphology of amacrine cells, identified on the basis of their expression of syntaxin, is examined. (Data not shown). Treatment with either VEGF induced a dose-dependent increase in the number of syntaxin immunopositive cells with 10 ng/ml inducing a maximal increase of approximately 2.4-fold as compared to the vehicle treated controls (FIG. 18A). In contrast to the results with the rhodopsin ELISA and cell counts, 100 ng/ml of VEGF-1 or -2 induced a smaller increase in the number of syntaxin immunopositive cells than is observed with 10 ng/ml. To further characterize the effect VEGF-2 treatment on the phenotype of amacrine cells, the level of high-affinity GABA uptake is measured. FIG. 18B depicts the dose-dependent increase in GABA uptake induced by VEGF. The dose response curve is similar to that observed when using the number of immunopositive syntaxin cells as the endpoint with a significant increase and saturation in GABA uptake occurring with 1 and 10 ng/ml of VEGF-2, respectively.

Figure 18C:
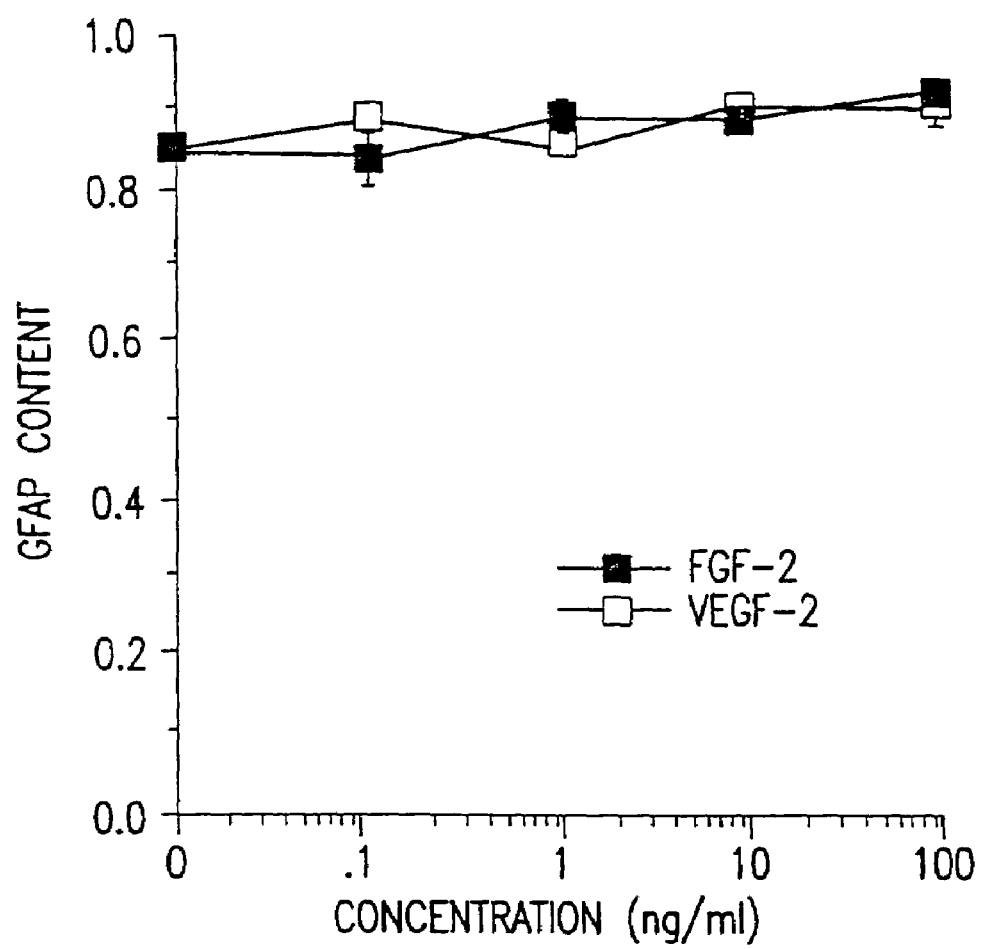

Müller glial cells are identified on the basis of their expression of glial fibillary acidic protein (Björklund et al., 1985). To determine if VEGF-2 has an effect on the number of Müller cells or on the level of differentiation, the amount of GFAP protein is measured by ELISA. After 7 days in culture, there is no significance difference in the level of GFAP, when comparing treatment with factors versus the vehicle control (FIG. 18C). Furthermore, treatment with VEGF-2 did not increase the number of endothelial cells, immunopositive cells, in the retinal cultures (data not shown).

To further characterize the developmental pattern of the VEGF response, retinal cells are isolated at different developmental stages, and the mitogenic response to VEGF-2 is quantitated after 48 h by labeling the cultures with [$^3$H]thymidine. In addition, as it has been noted previously that the differentiation of photoreceptor cells in vitro is density dependent, the effect that plating density has on the response to VEGF is also investigated.

Figure 19A:
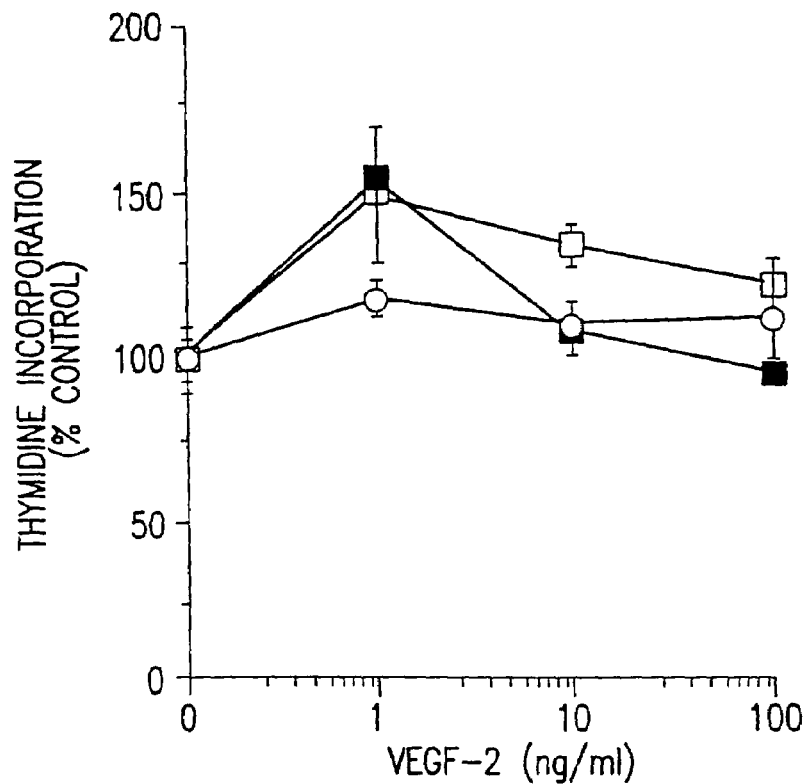
FIG. 19A-C shows the effect of developmental age on the response to VEGF-2. Retinal cells derived from E15 (A), E20 (B) or P1 (C) animals were plated at a density of 212 (open squares), 318 (solid squares), or 425 cells/nun$^2$. Four hours after plating, the cultures were treated with the indicated concentrations of VEGF-2. After 24 hours, the cultures were switched to serum-free medium and the factors were added again. The cultures were then labeled with [3H] thymidine after 48 hours.

When the cultures are derived from E15 animals and plated at a density of 212 cells/mm$^2$, the basal level of [$^3$H]thymidine incorporation is 1589±94 dpm/well and treatment with VEGF-2 induced a maximal increase of 50% (FIG. 19A). In contrast to the dose response observed with P1 cultures where saturation occurs at 10 ng/ml, the proliferative response in the E15 cultures saturates at a concentration of 1 ng/ml. Furthermore, there is an inverse relationship between the plating density and the mitogenic response to VEGF-2. At a density of 318 cells/mm$^2$, a leftward shift in the dose response curve is noted with concentrations higher than 1 ng/ml causing a desensitization of the response. At the highest density tested (425 cells/mM$^2$), the retinal cells are unresponsive to VEGF-2. It is interesting to note that FGF-2 (10 ng/ml), which has a similar biological activity as VEGF-2 in the P1 cultures (see below), inhibited the proliferation in the E15 cultures by as much as 62% in the higher density cultures (data not shown).

Figure 19B:
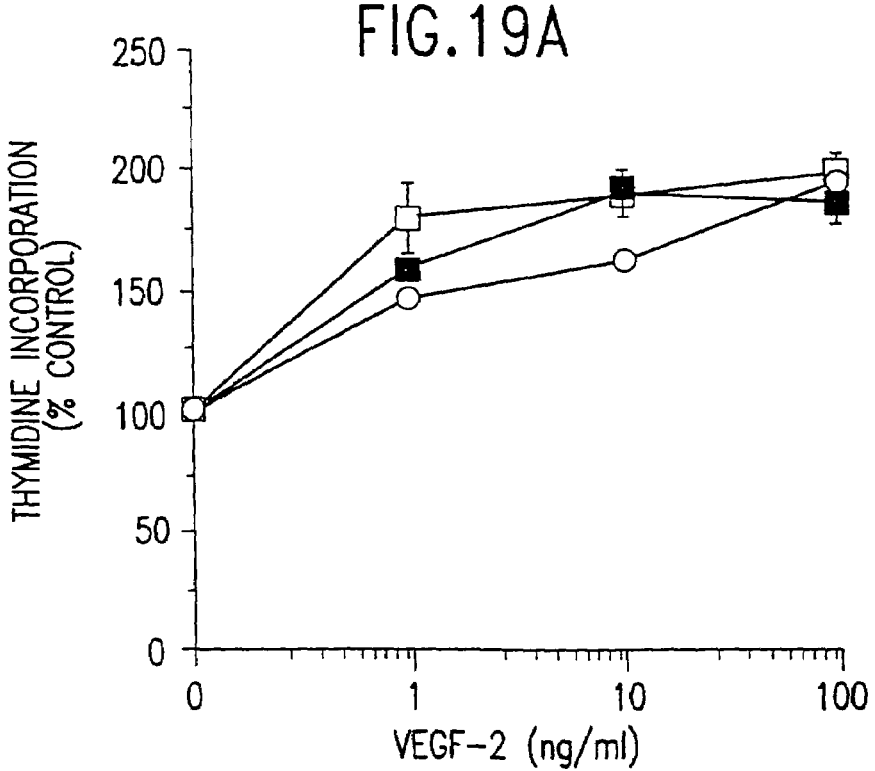
Figure 19C:
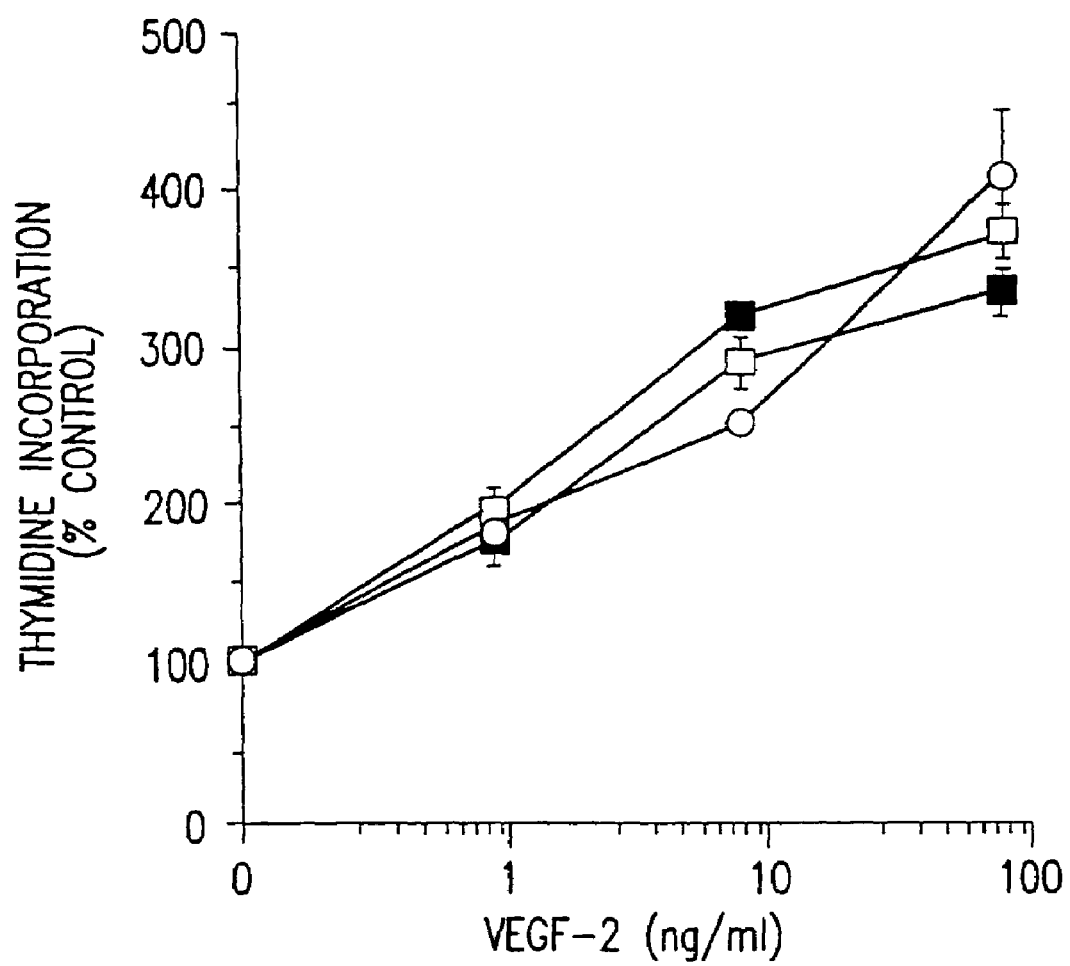

In cultures derived from E20 animals the basal level of [$^3$H]thymidine incorporation at a plating density of 212 cells/mm$^2$ is 3361±192 and the level of stimulation of [$^3$H]thymidine incorporation with VEGF-2 treatment is generally greater, ranging up to 80-100%, at the lower plating densities (FIG. 19B). There is still a trend toward VEGF-2 having less of an effect in cultures plated at the highest density. However, the inhibitory effect is much less pronounced. By P1, where the basal level of [$^3$H]thymidine incorporation is 478±33, there is a leftward shift in the dose response with saturation occurring at 10 ng/ml and the extent of the maximal increase is greater, in the range of 300% (FIG. 19C). Furthermore, there is no discernible effect of plating density on the response to VEGF-2.

Figure 20A:
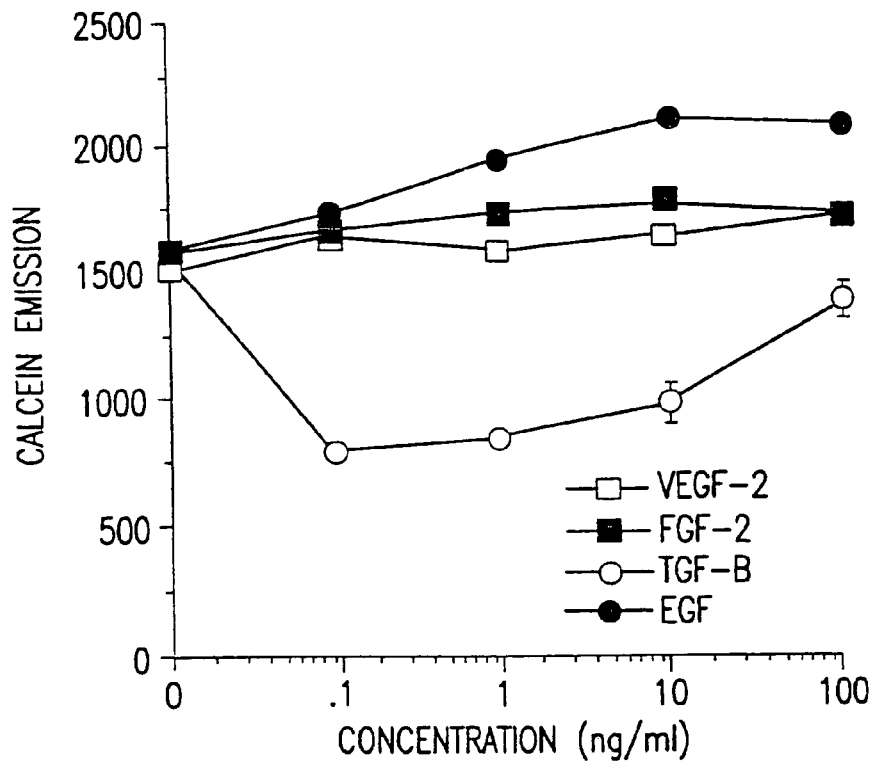
FIG. 20A-B compares the response of retinal cells to VEGF-2 and other factors. The cultures were seeded at a density of 425 cells/mm$^2$ and treated for 9 days. Panel A shows the total number of cells in the cultures was estimated using calcein, while panel B shows the level of rhodopsin protein determined by ELISA assay.
Figure 20B:
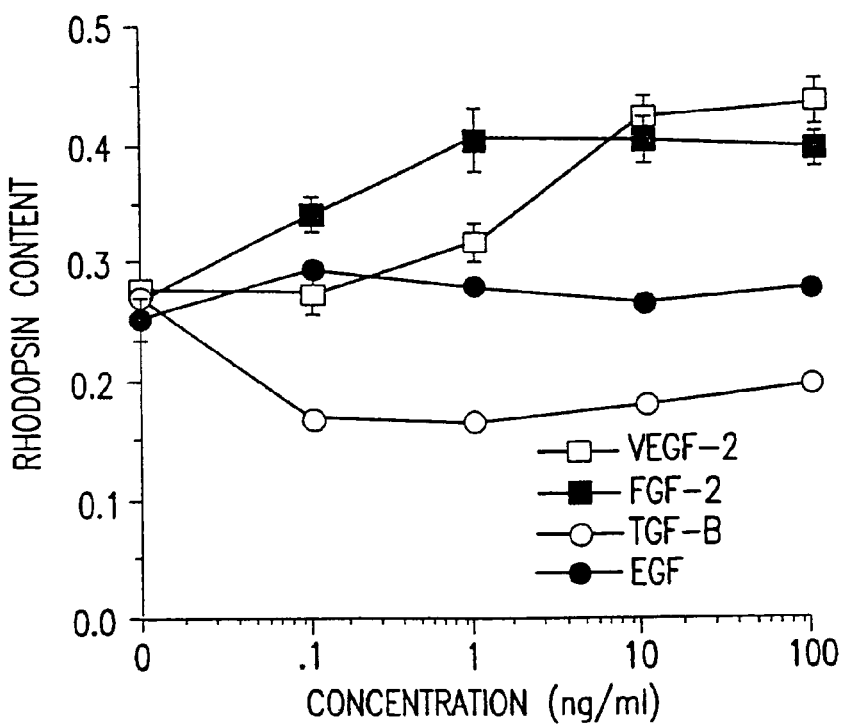

To characterize more fully the responsiveness of the rod or rod progenitor cells, the effect that EGF, FGF-2 or TGFβ-1 has on the number of retinal cells and on the level of rhodopsin protein is compared to that achieved with VEGF-2. EGF, a mitogen for various cell types, induces a 31% increase in the number of retinal cells with the response saturating at 1 ng/ml and remaining stable up to 100 ng/ml (FIG. 20A). However, there is no concomitant increase in the level of rhodopsin protein in the EGF treated cultures (FIG. 20B). FGF-2 in a concentration range of 1-100 ng/ml induces a small increase (13%) in the number of retinal cells. Furthermore, FGF-2, which activates a number of the FGF receptors, induces an increase in the level of rhodopsin protein. A 45% increase in the level of rhodopsin is observed with concentrations of FGF-2 as low as 1 ng/ml resulting in an EC50 value for the response in the range of 0.5 ng/ml. Treatment with TGFβ-1 results in a decrease in both the number of retinal cells and the level of rhodopsin protein. At a concentration of 0.1 ng/ml, TGFβ-1 maximally decreased calcein expression and the level of rhodopsin protein by 40 and 90%, respectively.

Figure 21A:
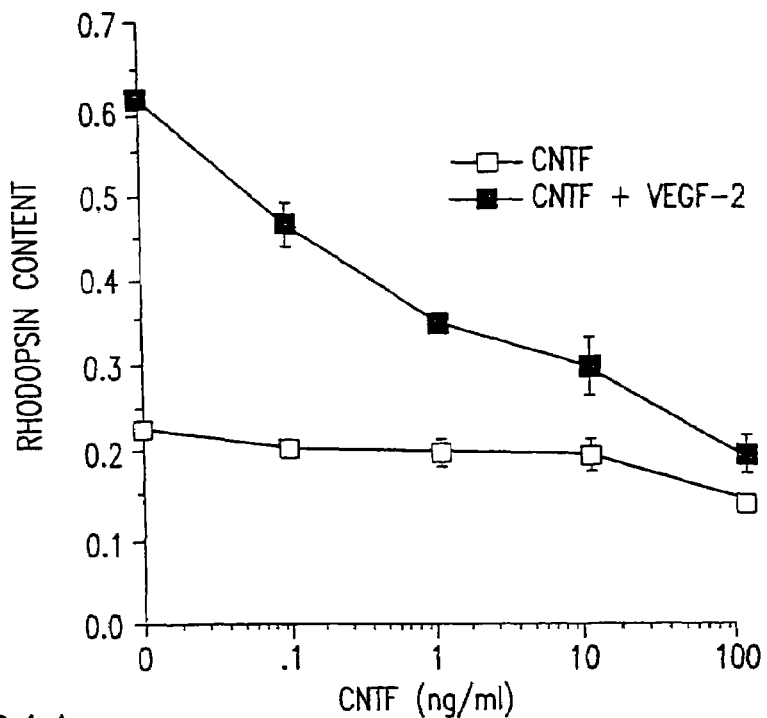
FIG. 21A-C shows that CNTF inhibits the response of the photoreceptor cell progenitors to VEGF-2. Retinal cultures were treated 24 hours after plating with the indicated concentrations of CNTF in the presence or absence of 150 ng/ml of VEGF-2. After 8 days in vitro, the amount of rhodopsin protein was quantitated (A) and the total number of cells in the cultures was determined (B). (C) To determine the effect of CNTF treatment on the early proliferative response induced by VEGF-1, the cultures were treated with the indicated concentrations of VEGF-2 in the presence or absence of 100 ng/ml CNTF. After 48 hours, the cultures were labeled for 4 hours with [3H] thymidine.
Figure 21B:
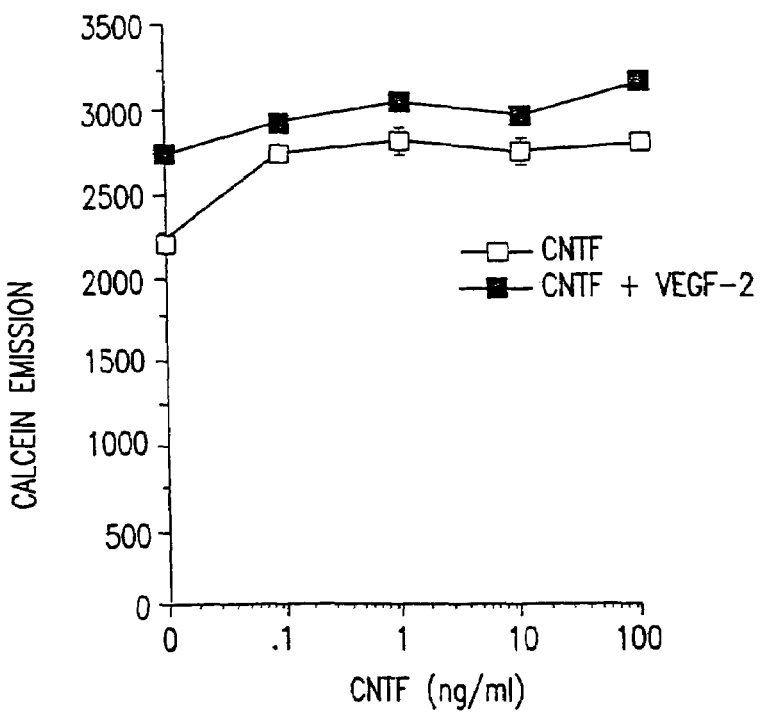
Figure 21C:
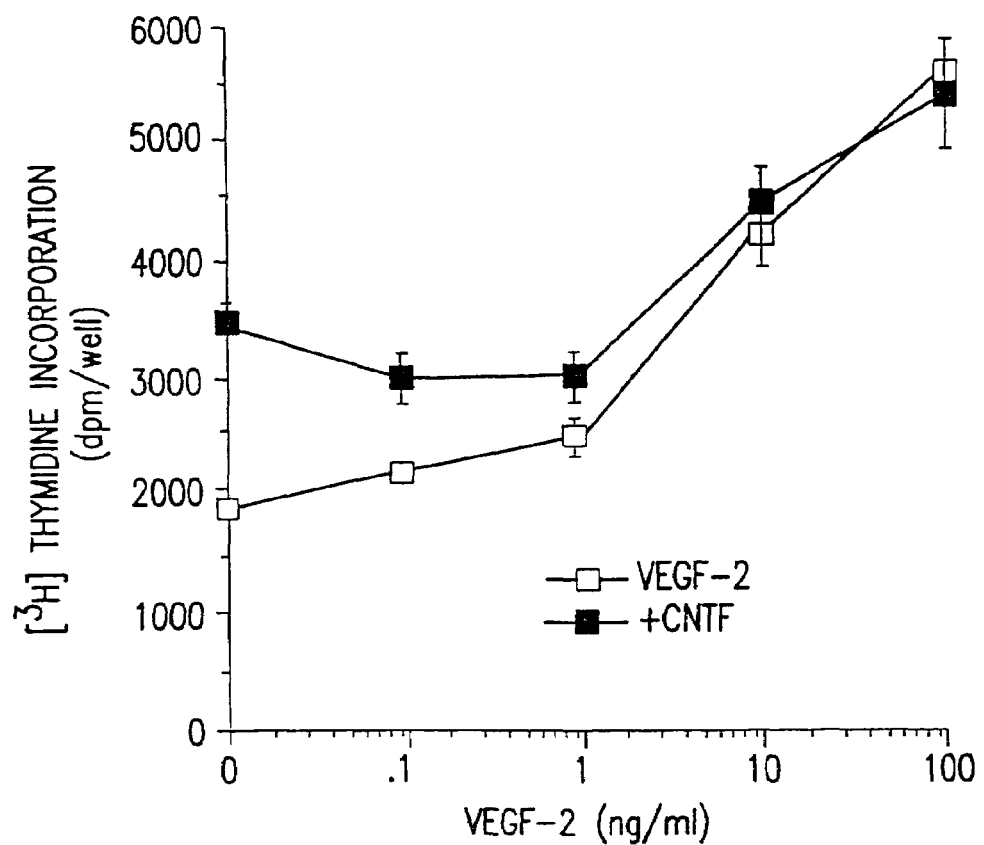

The results from the BrdU labeling experiments demonstrate that VEGF-2 enhances the rate of proliferation of retinal progenitor cells. Since the developmental pathway of photoreceptor cells is thought to be lineage independent and thus under the regulation of environmental factors (Ezzeddine Z D et al., 1997), VEGF may also modulate photoreceptor cell development at additional downstream sites. It has been determined previously that CNTF inhibits the differentiation of photoreceptor cells relatively late in their developmental pathway by redirecting their phenotype toward the bipolar cell lineage. To investigate the potential interaction of the two factors by co-treating retinal cultures with VEGF-2 at a concentration that is saturating for the induction of photoreceptor cells and various concentrations of CNTF. The increase in rhodopsin protein induced by VEGF-2 is inhibited by CNTF in a dose-dependent manner (FIG. 21A). The inhibitory response had an IC50 value of 0.4 ng/ml and treatment with 100 ng/ml of CNTF resulted in the complete inhibition of the VEGF-2 response. However, treatment with CNTF did not alter the total number of retinal cells in the cultures (FIG. 21B). To determine if the inhibitory effect of CNTF is an early or late event, the effect that co-administration of CNTF had on the increased level of [$^3$H]thymidine incorporation induced by VEGF-2 is tested. In contrast to the previous results, the addition of CNTF did not inhibit the VEGF induced proliferative response (FIG. 21C). These findings further substantiate that these two factors regulate photoreceptor cell development at different points in the lineage pathway.

DISCUSSION

The above experiments identify and characterize the effect of VEGF-1 and VEGF-2 on retinal cells in vitro. Treatment with VEGF in the sub-nanomolar range induces an increase in the number of photoreceptor and amacrine cells as well as increases the level of rhodopsin protein and high-affinity GABA uptake. Time course studies demonstrate that VEGF induces a maximal increase in [$^3$H]thymidine incorporation within 48 h of its addition and delaying the treatment of the cultures by 24-48 h results in the loss of the proliferative and differentiation responses. The mitogenic response was developmentally regulated with VEGF-2 inducing an increase in [$^3$H]thymidine incorporation with cells derived from E15, E20 and P1 animals. In comparison with members of other trophic factor families, the response to treatment with VEGF-2 and FGF-2 were similar in that both factors increased the level of rhodopsin protein without inducing an increase in the total number of cells after 9 days in culture. The co-administration of CNTF with VEGF-2 resulted in the inhibition of the VEGF induced increase in the level of rhodopsin but not in the proliferative response.

The VEGF receptor family is currently composed of four members (for review see Klagsbrun and D'Amore, 1996; Wen et al., 1998). The receptors demonstrate distinct yet overlapping ligand specificity. VEGFR-1 (Flt-1) and VEGFR-2 (Flk-1) bind the various forms of VEGF-1; while, VEGFR-2 and VEGFR-3 (Flt-4) bind VEGF-2. Thus both VEGF-1 and VEGF-2 activate VEGFR-2 (Joukov et al., 1998) and both ligands have similar biological activities in the retinal cultures. Recently, Yang and Cepko (1996) described the developmental expression pattern of VEGFR-2 in the retina. Extent from the expected expression of the receptor on the newly forming vasculature, receptors were also present on components of the neural retina. This expression pattern is maintained during development as the retina grows in a centripetal manner.

The effect of developmental age on the response of the retinal progenitor cells to VEGF is consistent with the developmental expression pattern of the receptor (Yang and Cepko, 1996). Mitogenic effects of VEGF, based on [$^3$H]thymidine incorporation studies, were noted at the earliest developmental time point examined, E15, as well as at E20 and P1. The magnitude of the proliferative effect increased with age reaching a peak by P1. VEGF-2 is more efficacious on E15 and E20 cultures than at P1 since that response saturated at 1 as opposed to 10 ng/ml, respectively. Furthermore, the basal level of proliferation in vitro also changed with developmental age with the highest levels observed at E17. The finding that the basal level of proliferation was relatively low at E15 but increased 4-fold with a 2-fold increase in cell density, a greater proportional increase than was observed at the other developmental ages, suggests that endogenous mitogens may underlie the desensitization that occurs with VEGF-2 treatment in the E15 cultures. Moreover, these data indicate that increased levels of VEGF during early development may have a negative impact on the differentiation of photoreceptor cells. The influence of developmental age on the response of retinal progenitor cells to other growth factors has also been observed (Altshuler and Cepko, 1992). Lillien and Cepko (1992) reported that the proliferative response of retinal cells in monolayer cultures to FGF-1 and FGF-2 was greater at earlier gestational ages (e.g. E15 and E18) and by E21 or P0 a rightward shift in the dose response curve was apparent.

Previous studies in goldfish and frog have suggested that amacrine cell development is regulated by cell-cell contact (Negishi et al., 1982; Reh and Tully, 1986). More recently, the importance of cell-cell contact for the in vitro development of photoreceptor cells was also described by Wantabe and Raff (1990, 1992) in reaggregated cultures and then later by Altshuler and Cepko (1992) with dissociated retinal cells plated in collagen gels. In the former study, when E15 retinal cells were reaggregated with a 50-fold excess of neonatal retinal cells, there was no change in the developmental time when the rhodopsin immunopositive cells were observed. However, there was a significant increase in the proportion of the E15 cells that eventually differentiated into photoreceptor cells. In the case of the monolayer cultures used in this study, there is a dissociation between the VEGF-2 induced early proliferative response and the later differentiation of photoreceptor cells. For example, VEGF-2 increases [$^3$H]thymidine incorporation by 3-4-fold in cultures seeded at densities as low as 212 cells/mm$^2$ and treatment for 7 days resulted in cell densities equivalent to those achieved at the higher plating densities (e.g. 425 cells/mm$^2$). However, there was no detectable rhodopsin protein or immunopositive cells in these cultures. These results suggest that there is not only a critical cell-cell interaction necessary for the development of photoreceptor cells but also a time frame during which the stimulus produced via cell contact is probable necessary.

Comparing the time course of the VEGF-induced proliferation to the developmental time course of the appearance of rhodopsin protein indicates that there is an approximate 5 day lag between the two events. The appearance of rhodopsin protein likely reflects the induction of gene transcription since the two events have been shown to be closely correlated (Treisman et al., 1988). This time interval is similar to that observed by Morrow et al. (1998) in vivo and in vitro studies when considering progenitor cells derived from animals within an age range of E20 to P3. Furthermore between 5 and 9 days in vitro, we observed the greatest increase in the level of rhodopsin protein and this time period is within the postnatal developmental period (day 6-10) in vivo during which there is a pronounced appearance of rhodopsin immunopositive cells (Morrow et al., 1998). The correlation in these developmental time windows suggests that although VEGF-2 induces the proliferation of photoreceptor progenitor cells, it does not induce a significant delay in the differentiation of photoreceptor cells. As might be expected if the progenitor cells were prevented from leaving the cell cycle.

In comparison to members of other trophic factor families, the response to VEGF-2 resembled that of FGF-2 in that both factors increased the level of rhodopsin protein while inducing relatively small increases in the total number of retinal cells after 9 days in vitro. In addition, a proliferative response, based on [$^3$H]thymidine incorporation and cell counts, to FGF-2 was noted by Lillien and Cepko (1992) as late as P3 suggesting that FGF-2 retains some mitogenic activity in postnatal cultures. In contrast to our findings with VEGF-2, Fontaine et al. (1998) demonstrated that FGF-2 also has a survival effect on photoreceptor cells derived from P5 animals (data not shown). TGFβ-1 treatment resulted in a decrease in both the number of retinal cells and the level of rhodopsin protein. Kimichi et al. (1988) reported similar observations using human fetal retinal cultures with the exception that maximal inhibition with the human cells required 0.5 ng/ml of TGFB-1 as compared to the less than 0.1 ng/ml required in the rodent cultures.

CNTF, a member of the neuropoietic family of cytokines, is known to effect the development of photoreceptor cells in vitro and in vivo and to enhance the survival of photoreceptor cells following light-induced damage (Unoki and LaVail, 1994; Fuhrman et al., 1995; Ezzeddine et al., 1997; Cayouette et al., 1998). In contrast to CNTF, VEGF-2 did not rescue photoreceptor cells in the constant light-induced damage model (LaVail et al., 1992; Wen et al., 1995; R. Wen and R. Alderson, unpublished data). Treatment of postnatal rat retinal explant cultures with CNTF,results in an increase in the number of cells expressing bipolar cell markers with a loss in the population of cells expressing rhodopsin. Analysis of the effect of CNTF on the fate of [$^3$H]thymidine labeled P0 retinal cells suggests that the cytokine does not induce the proliferation or increase the survival of this cell population (Ezzeddine et al., 1997). Furthermore, the initiation of the effect of CNTF occurred at about the time that the cells became post-mitotic and begin to express rhodopsin. These data are consistent with the findings reported here demonstrating that CNTF inhibits the VEGF-2 induced increase in rhodopsin protein observed between 5 and 7 days in culture, but not its mitogenic activity observed between 1 and 2 days.

During the course of development in the retina, oxygen levels control the microarchitecture of retinal vessels that in turn match the pattern of differentiation of retinal neurons (Chan-Ling et al., 1990; Phelps, 1990). Stone et al. (1995) have demonstrated that in the retina, astrocytes and microglia respond to hypoxia by synthesizing and secreting VEGF which in turn induces vessel formation. The studies reported here suggest that the early differentiation events regulated by VEGF involve not only vessel formation but also photoreceptor progenitor cell proliferation. This ultimately may result in the coordinated development of numerous cell types in the retina.

Example 9

Enhanced Response of Endothelial Cells to VEGF-2 and Antibody Co-treatment

Antibodies generated by HGS have been shown to bind to VEGF-2 by ELISA assays, but are not thought to bind to the sites involved in receptor interactions. Monoclonal 13D was mapped to an epitope on the N-terminal side of the molecule and monoclonal 13A2 was mapped to an epitope on the C-terminal end. (See FIG. 24). The polyclonal antibody recognizes a number of different sites but it is not believed to bind to the segment of the active protein which interacts with the receptor. These antibodies were used to quantitatively determine stimulation or inhibition of the proliferation of bovine lymphatic endothelial cells (LEC) by co-treating with VEGF-2 and the above antibodies.

An alamar blue™ LEC proliferation assay was used, which incorporates a fluorometric growth indicator based on detection of metabolic activity. The Alamar blue™ is an oxidation-reduction indicator that both fluoresces and changes color in response to chemical reduction of growth medium resulting from cell growth. As cells grow in culture, innate metabolic activity results in a chemical reduction of the immediate surrounding environment. Reduction related to growth causes the indicator to change from oxidized (non-fluorescent blue) form to reduced (fluorescent red) form. i.e. stimulated proliferation will produce a stronger signal and inhibited proliferation will produce a weaker signal and the total signal is proportional to the total number of cells.

The materials used for the alamar blue™ LEC proliferation assay include: Alamar Blue™ (Biosource Cat# DAL1100); DMEM 10% FBS+PennStrep+Glutamine+75 mg BBE+45 mg Heparin (Growth media); DMEM 10% FBS+PennStrep+Glutamine (Starvation Media); DMEM 0.5% FBS+PennStrep+Glutamine (sample dilution media); CytoFluor™ Fluorescence reader; 96 well plate(s); and LEC cells.

The alamar blue™ assay was performed as follows. For timing purposes it is best to seed the cells onto the 96 well plate(s) on a Wednesday, change to starvation media on Thursday, inoculate samples on Friday, incubate over the weekend then add alamar blue™ incubate and read on Monday.

LEC cells were seeded in growth media at a density of 5000 cells/well of a 96 well plate and placed at 37° C. overnight. After the overnight incubation of the LEC cells, the growth media was removed and replaced with starvation medium and incubated for another 24 hours at 37° C. After the second 24 hour incubation, the cells were inoculated with the appropriate dilutions of protein sample(s) (prepared in DMEM+0.5% FBS) in triplicate wells. Once the cells have been inoculated with the samples the plate was placed back in the 37° C. incubator for three days.

After three days, 10 μl of stock alamar blue™ was added to each well and the plate was placed back in the 37° C. incubator for four hours. The plate was then read at 530 nm excitation and 590 nm emission using the CytoFluor™ fluorescence reader. Direct output is recorded in relative fluorescence units.

The background level of activity was observed with the starvation medium alone. This is compared to the output observed from the positive control samples (VEGF-1 and/or bFGF) and the HGS protein dilutions.

Three different antibody preparations made by HGS (2 mouse monoclonals, 13A2, 13D6 and a rabbit polyclonal antibody) were evaluated for their ability to modulate the response of LECs to VEGF-2 mediated activation. It was previously determined that a proliferative response of LECs could be observed at a concentration of 1000 ng/ml of VEGF-2. Therefore, VEGF-2 samples at a concentration 1000 ng/ml in DMEM were premixed with one of the three different anti-VEGF-2 antibodies (10 μg/ml) and used in the alamar blue™ assay system to determine the influence on LEC proliferation. Controls in the first experiment included VEGF-2 alone (1000 ng/ml), bFGF,(10 ng/ml, positive control), IL-2 (irrelevant protein negative control) and starvation medium (assay negative control). The repeat experiment also included antibody alone (10 μg/ml) as a negative control.

Figure 22:
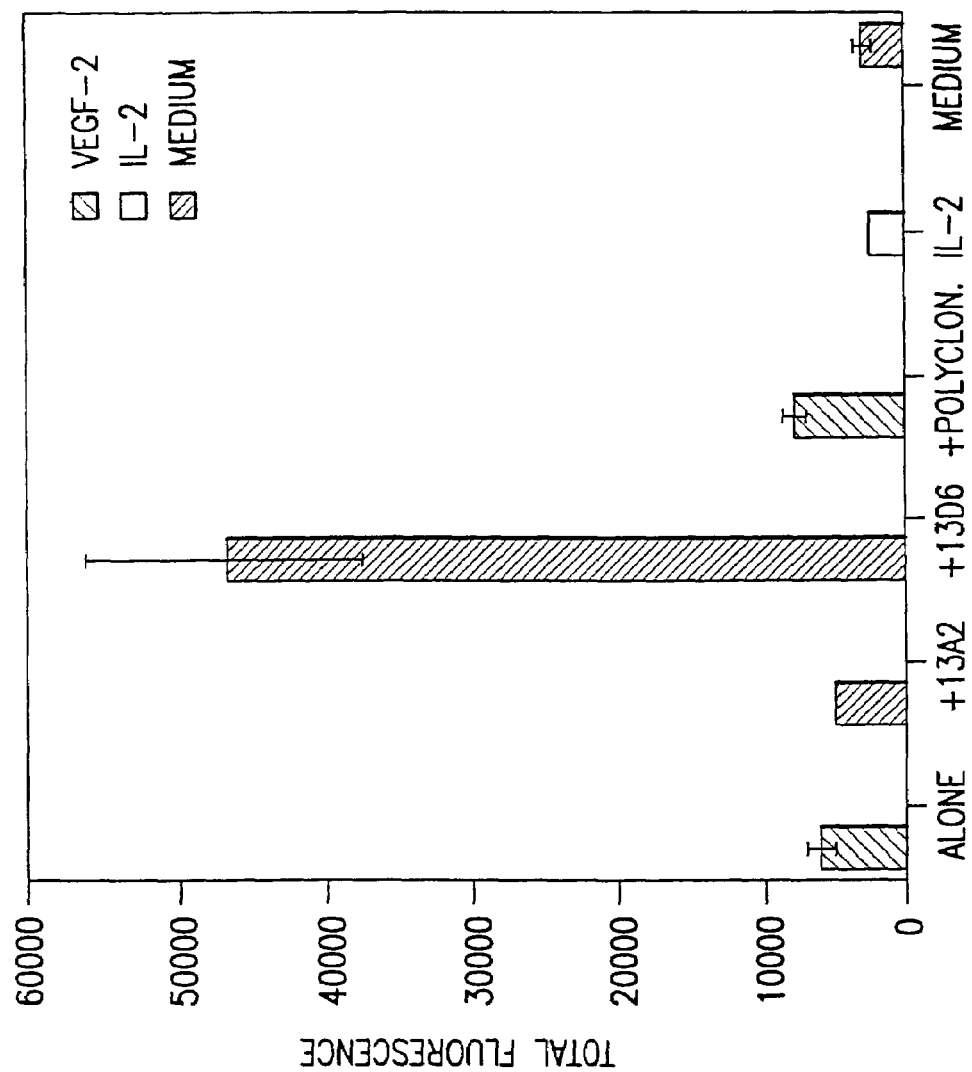
FIG. 22 shows the enhanced LEC proliferation in response to VEGF-2 and antibody treatment.

As shown in FIG. 22, VEGF-2 treatment of LECs at a concentration of 1000 ng/ml resulted in a proliferative response relative to the negative controls, which was consistent with previous proliferative assays conducted with these cells. Simultaneous treatment of LECs with VEGF-2 and monoclonal 13A2 did not augment the proliferative response above the level achieved with VEGF-2 alone. However, an enhanced proliferative response was observed with the 13D6 monoclonal and to a lesser degree, with the rabbit polyclonal antibody.

Figure 23:
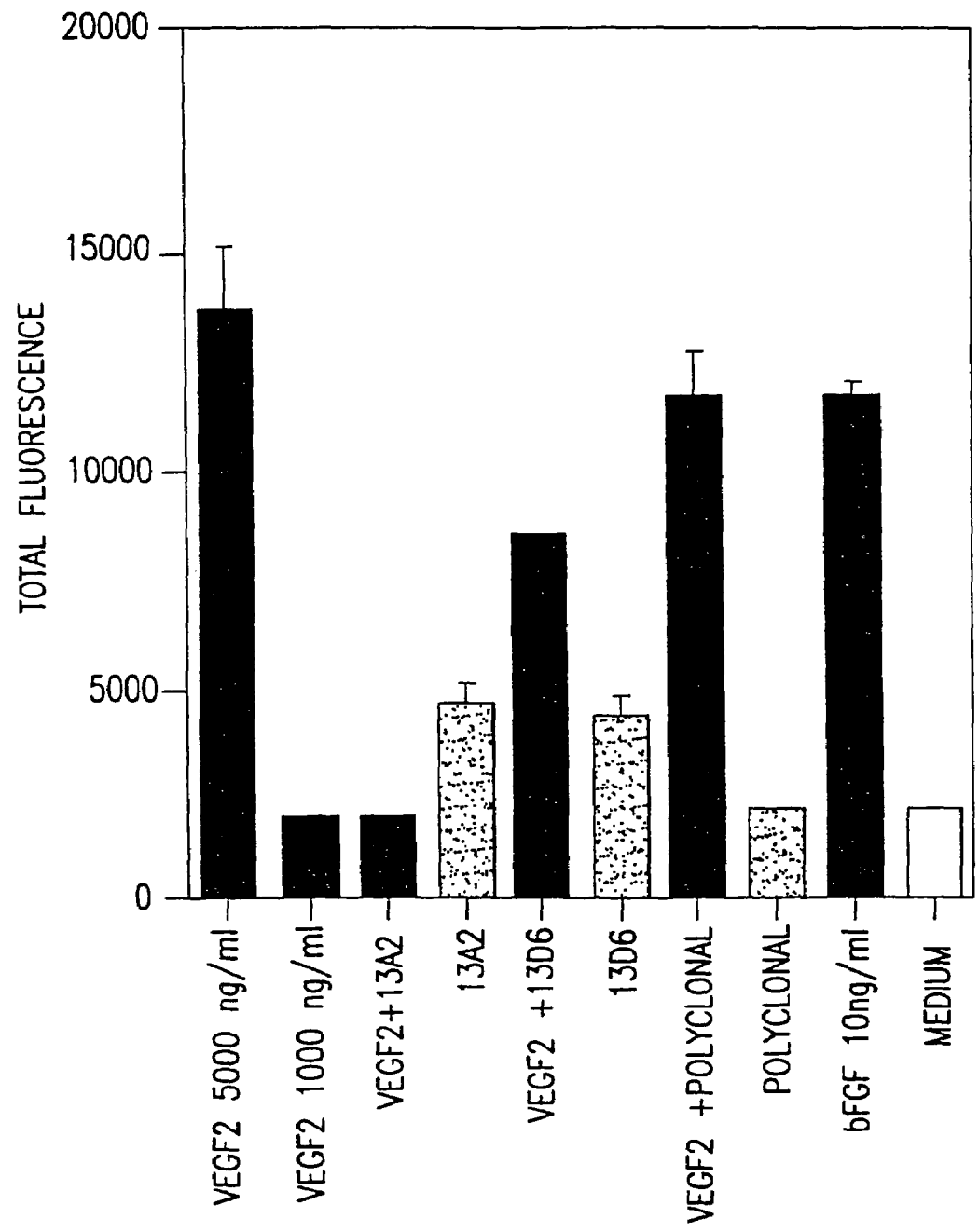
FIG. 23 shows LEC proliferation in response to VEGF-2 and VEGF-2:antibody combination.

As shown in FIG. 23, the experiment was repeated under more stringent conditions, using 1000 cells/well as an initial cell concentration and included stimulation with the antibody alone in order to control for possible direct effects of the antibodies on the LECs. This experiment demonstrated augmentation of VEGF-2 mediated proliferation by the 13D6 and polyclonal antibodies above the proliferative response observed with VEGF-2 or the antibodies alone. As observed in the previous experiment, the 13A2 antibody did not induce an augmented proliferative response.

These observations suggest that antibody mediated crosslinking of VEGF-2 molecules bound to receptors (VEGFR2 or VEGFR3) may induce receptor dimerization. Such a process may be used to intensify the signaling resulting from the VEGF-2 binding to its receptors.

Example 10

Mouse Immunization for Monoclonal Antibody Production

Animals are individually housed and received food and water ad libitum. All manipulations are performed using aseptic techniques. The experiments are conducted according to the rules and guidelines of Human Genome Sciences, Inc. Institutional Animal Care and Use Committee and the Guidelines for the Care and Use of Laboratory Animals.

Dilute concentration of protein in 350 μls of phosphate buffered solution (PBS), or other neutral buffer, to a final protein concentration of 0.43 mg/ml. With 0.35 mls. Freund's Complete Adjuvant, emulsify the adjuvant and protein solution for a period of ten minutes using two glass 3 cc syringes and a three way disposable stopcock (Baxter Cat. No. 2C6240). To test emulsion for quality, place 50 μls of the emulsion onto the surface of cold water in a beaker. If the emulsion does not remain as an intact white droplet, then further mixing is required.

Draw all of the emulsion into one syringe, and using a 27 gauge needle, inject mouse subcutaneously with a total of 200 μls of emulsion distributed among 4-8 sites including axillary and inguinal areas, the back of the neck, and along the back.

Following two to three weeks, repeat the above injection substituting Freund's Incomplete Adjuvant (as opposed to Freund's Complete Adjuvant).

Following an additional two to three weeks, a third injection is given as outlined above, making sure to use Freund's Incomplete Adjuvant.

Ten to Fourteen days following the third injection, obtain 100-200 μls of blood from the mouse by tail vein bleed. Incubate the blood at 37° C. for 60 minutes, and then allow to cool overnight at 4° C. Following incubation at 4oC, centrifuge the blood for ten minutes. Transfer the serum to a new tube, and test for mouse serum titer. If titer is found to be low, intraperitoneal (ip) injections can be given at biweekly intervals. For ip injections, prepare 10-20 μgs protein per mouse in a volume of 200-400 μls of PBS per mouse. Using a 1 cc syringe and a 26 gauge needle, inject the solution into the mouse. Do a second tail bleed 10-14 days following injection, and retest the mouse serum titer.

Example 11

Mouse Serum Titer ELISA

Coat the ELISA plate with 50 μl/well of purified antigen at 2 μgs/ml PBS. Cover the ELISA plate with parafilm and incubate at 4° C. overnight in a humid chamber. Following incubation, wash the plate four times with 200 μl/well of PBS per wash. Block with 3% BSA, 200 μls/well for 60 minutes at room temperature. Shake out blocking solution.

Add serum samples in duplicate, 50 μls/well, at dilutions of $10^{-2}$, $10^{-3}$, $10^{-4}$, $10^{-5}$, $10^{-6}$, and $10^{-7}$, diluted in PBS containing 0.1% BSA. Include blanks of buffer as well as positive and negative control serum at the above dilutions. Incubate at room temp for 1-2 hours. Wash with PBST (PBS with 0.05% tween), 250 μls/well, four times.

Add 50 μls/well of Biotinylated Anti-Mouse IgG at a concentration of 0.5 μg/ml in PBST containing 0.1% BSA and 2% Horse Serum. Incubate at room temperature for 30 to 60 minutes. Wash plate four times with PBST.

Add 50 μls/well of ABC reagent (Vector Cat. No. PK-6100) to the plate and incubate at room temperature for 30 minutes. Wash plate six times with PBST.

Prepare substrate for ELISA detection by dissolving 1 tetramethylbenzidine Dihydrochloride (TMB) tablet (Sigma Cat No. T-3405) in 5 mls. of ddH$_2$O. Add 5 mls. of 0.1M Phosphate Citrate Buffer (25.7 mls of 0.2M dibasic sodium phosphate, 24.3 mls of 0.1M citric acid monohydrate, pH 5.0). Add 2 μls of fresh 30% hydrogen peroxide, vortex and use immediately.

Following incubation and washing of the plate, add 100 μls of substrate solution and incubate at room temperature for approximately 15-30 minutes. Stop the reaction by adding 25 μls/well of 2M H$_2$SO$_4$, and read the plate at 450 nm within 30 minutes versus the controls.

Example 12

Fusion Protocol for Hybridoma Production

One week prior to the fusion step, make P3x growth medium (1×DMEM 0% (Gibco Cat No. 11965-019), 5-10% Fetal Bovine Serum, 1×L-Glutamine (Biofluids Cat. No. 300), and 1× Sodium Pyruvate (Biofluids Cat No. 333). Thaw a new vial of P3X mouse myeloma cells into 1 well of a 6-well dish (see thawing protocol, infra) and start expanding them in P3X growth medium. If viability is good the next day transfer to a 100 mm dish. Cell density must not exceed $10^6$ cells/ml or greater. Furthermore, membranes of these cells should not look granular. By the day of the fusion procedure there should 6-8 plates at 5-8×$10^5$ cells/ml. It is a good idea to test some P3X cells in HAT medium. All cells should be dead within around 4 days. If not then P3X cells should be grown in P3X medium containing 15 μg/ml 8-azaguanine to eliminate revertants.

Four days prior to the fusion procedure, the mouse should be immunized with an ip injection of approximately 10 gg of high purity protein.

One day before the fusion, split the P3X cells and feed them with fresh medium as needed so that cells will be healthy and growing in log phase by the next day.

On the day of the fusion procedure, place 50 mls of P3X media, PEG solution and HAT media (1×DMEM 0%, 20% Fetal Bovine Serum, 4% Hybridoma Supplement-BM Condimed HI (Boehringer-Mannheim), 1× L-Glutamine, 1×NEAA, 1× Sodium Pyruvate, 1×HAT (Sigma Cat No. H0262), 1×0.05M 2ME, and 1× Penicillin-Streptomycin) in a 37° C. water bath. Have available approximately 100 ml cold DMEM 0%.

Check all P3X plates for possible contamination and to assess health of cells. Resuspend cells from 4 plates or flasks and combine in 50 ml tubes. Centrifuge at 200×G for 10 min. Aspirate the supernatant. Resuspend each tube with 10 mls DMEM 0% and pool. Count live cells using trypan blue viability stain (viability should be greater than 90%). The total number of cells should be 2-4×10$^7$ cells. If there are not enough cells then repeat the process with some more plates. Let cells sit at ambient room temperature (ART) until needed in future step.

Prepare hood where spleen will be removed with: 70% EtOH, sterile instruments including sieve and plunger, 2 petri dishes containing 10 ml DMEM 0% and 15 ml centrifuge tubes (2).

The mouse is sacrificed, and the spleen is then harvested from the carcass. Place the spleen in the petri dish containing DMEM 0%. Place the sieve in the other dish containing 10 ml DMEM 0% and cover with plate lid. Transfer the spleen to the sieve using a sterile pair of foreceps, and using the syringes with needles, tease the spleen apart so that cells spill out into the media. Then, using the other plunger, gently squish the spleen through the sieve. Avoid grinding the spleen organ tissue through the sieve as this will result in heavy fibroblast growth.

Remove the sieve and transfer the spleen cell suspension to a 15 ml centrifuge tube. Wash remaining cells from the dish with 5 mls DMEM 0%, and add to the tube. Allow the tube to sit for 5 minutes to allow large debris to settle to the bottom. Then transfer the cell suspension, minus debris, to the second 15 ml tube. Centrifuge the cells for 10 min. at 200×G, Aspirate s/n and resuspend the spleen cells in 5 mls DMEM 0%. Add 5 more mls of DMEM 0%, and transfer the entire volume to a 50 ml tube.

Remove 10 μls of the spleen cell suspension, and add to 500 μls of Trypan blue in order to count lymphocytes. (Note: normally a spleen will consistently yield 10$^8$ lymphocytes).

Fusion

To the 50 ml centrifuge tube containing the spleen cells add sufficient P3X cells to make a lymphocyte to P3X cells ratio of 5:1. (e.g. for 10$^8$ lymphocytes you will need 2×10$^7$ P3X cells). Bring the total volume up to 45-50 mls with DMEM 0%, and centrifuge at 200×G for 10 minutes. Prepare a transfer hood with a timer, warm PEG, warm P3X media, and a beaker of water approximately 38-40° C. Aspirate all of the supernatant from the P3X-lymphocyte pellet and attempt to loosen the pellet by flicking the tube. Place the tube in the small water bath. Keep the fusion tube in the warm water, and while gently shaking, add 1 ml of PEG dropwise over 1 minute. Then, let sit with occasional shaking for 1-2 minutes, following which add 1 ml of P3X media dropwise over 1 minute. Next, add 3 mls. of P3X media dropwise over 1 minute, followed by the addition of 10 mls. of P3X media dropwise over 1 minute.

Gently add P3X media to make the total volume 45 mls. Allow the tube to sit for 10 minutes, then centrifuge at 200×G for 10 minutes. Aspirate the supernatant and gently resuspend the pellet in 5 mls or less of HAT medium. Transfer the cell suspension to the bottle containing 400 mls of HAT medium and swirl to mix. Pour some of the cell suspension into a sterile reservoir.

Plant cells in 96 well plates, 200 μls/well, using a 12 channel pipettor with filtered tips. Place plates in the incubator. Monitor plates every day for hybridoma growth or contamination. Allow plates to incubate for three days. The first feeding (medium change) is done by around day 7 by aspirating off approximately half the media in each well using the 8-position manifold and replacing it with 100-150 μls/well HT medium. Feeding a week or so before the first screening helps to dilute out any antibody produced by the unfused lymphocyte cells which have been found to continue producing antibody after 2 weeks in culture. Many or all of the wells will be ready to be sampled for screening within 2 weeks after the fusion when the colony or colonies fill more than half the well and the supernatant has changed color to a orange/yellow.

Example 13

ELISA Screening of Mouse Hybridomas

To screen the mouse hybridomas, coat the ELISA plate (Immulon 2 "U" bottom microtiter plate (Dynatech Cat No. 011-010-3555)) with 50 μls/well of the antigen at 2 μgs/ml PBS. Cover the ELISA plate with plastic seal and incubate at 4° C. overnight. Following incubation, wash the plate four times with 200 μls/well of PBS per wash. Block with 3% BSA, 200 μls/well for 60 minutes at room temperature. Shake out blocking solution.

Add hybridoma supernatants, 150 μls/well, into a Corning 96 well assay plate, then transfer 50 μls of each supernatant from the Corning assay plate into the ELISA plate. Include blanks of culture medium as well as positive and negative mouse serum controls. Incubate at room temp for 1-2 hours, or overnight at 4° C. Wash with PBST (PBS with 0.05% tween), 250 μls/well, four times.

Add 50 μls/well of Biotinylated Anti-Mouse IgG H+L, at a concentration of 0.5 μg/ml in PBST containing 0.1-0.3% BSA and 1% Horse Serum. Incubate at room temperature for 30 to 60 minutes. Wash plate four times with PBST.

Add 50 μls/well of ABC reagent (Vector Cat. No. PK-6100) to the plate and incubate at room temperature for 30 minutes. Wash plate six times with PBST.

Prepare substrate for ELISA detection by dissolving 1 tetramethylbenzidine Dihydrochloride (TMB) tablet (Sigma Cat No. T-3405) in 5 mls. of ddH$_2$O. Add 5 mls. of 0.1M Phosphate Citrate Buffer (25.7 mls of 0.2M dibasic sodium phosphate, 24.3 mls of 0.1M citric acid monohydrate, pH 5.0). Add 2 μls of fresh 30% hydrogen peroxide, vortex and use immediately.

Following incubation and washing of the plate, add 100 μls of substrate solution and incubate at room temperature for approximately 15-30 minutes. Stop the reaction by adding 25 μls/well of 2M H$_2$SO$_4$, and read the plate at 450 nm within 30 minutes versus the controls.

Example 14

Testing Relative Affinity of Monoclonals Derived from Culture Supernatants

A. Determining Antigen Coating Concentration

Make approximately 1 ml of the antigen at a concentration of 4 μgs/ml in PBS. Transfer to a microdilution tube. Place 0.5 ml PBS in each of 9 microdilution tubes, then do serial dilutions of ½ by transferring 0.5 ml from tube to tube starting from the 4 μgs/ml tube. You will now have tubes containing 4, 2, 1, 0.5, 0.25, 0.125, 0.06, 0.03, 0.015 and 0.0075 μgs/ml. Coat a plate with the above concentrations, 6 wells each, 50 μl/well.

Cover and incubate over night at 4° C. Following incubation, wash the plate four times with 200 µls/well of PBS per wash. Block with 3% BSA, 200 µls/well for 60 minutes at room temperature. Shake out blocking solution.

Look at the titer curve of mouse serum which is positive to the antigen. Determine the serum dilution which is just at the top of the titration curve. Add the positive mouse serum at this dilution in PBS containing 0.1% BSA, 50 µls/well, rows B-D, columns 2-11. Include negative control serum at the above dilution in rows E-G, columns 2-11. Incubate overnight at 4° C. Following incubation, subtract Negative Control Serum values from Positive Control Serum values. Plot mean value (O.D. 450) against antigen concentration on linear scale. Determine antigen coating concentration which will give a submaximal O.D. This is the coating concentration to use for the relative affinity assay.

B. Determining the Mouse IgG Concentration of the Hybridoma Supernatant Sample Using the Boehringer Mannheim Biochemica Kit "Mouse-IgG ELISA" (Cat. No. 1333 151)

Dilute the coating buffer concentrate 1/10 with ddH$_2$O. Ten to twenty mls. will be necessary. Obtain an aliquot of capture antibody. Thaw 3 tubes of Post Coating Buffer Concentrate (blocking solution). Twelve wells will be necessary for the standards and 4-6 wells for each supernatant to be tested. Calculate the number of mls of diluted Capture Antibody necessary assuming 50 µls/well of coating volume. Dilute Capture Antibody in the following proportion:

$$\frac{25 \text{ ul Capture } Ab}{1 \text{ ml Coating Buff}} = \frac{X \text{ µl Capture } Ab}{\# \text{ ml Coating Buff}}$$

Coat Nunc plate with the solution and incubate 30 mins at room temperature on a shaker. Dilute the concentrated Post Coating Buffer 1/10 in ddH$_2$O. Wash the plate with ELISA wash buffer (0.9% NaCl, 0.1% Tweeen 20), and block with 200 µls/well of Post Coating Buffer (Block solution) for 15 minutes at room temperature.

Dilute the IgG standard into Post Coating Buffer (blocking solution) to the following concentrations: 0.2, 0.1, 0.05, 0.025, 0.0125 and 0.00625 µgs/ml in Post Coating Buffer.

Dilute supernatants into blocking buffer to make final concentrations of 1/100 and 1/1000. Following the blocking step, wash the plate and add 50 µls/well of diluted IgG standards and diluted supernatants in duplicate. Incubate for 30 minutes at room temperature on a shaker.

Dilute the conjugate solution into Post Coating Buffer (block solution) according to the proportion below:

$$\frac{50 \text{ µl Conjugate}}{1 \text{ ml Block sol}} = \frac{X \text{ µl Conjugate}}{\# \text{ ml Block sol}}$$

Wash the plate and add 50 µl/well of conjugate. Incubate the plate for 30 minutes at room temperature on shaker.

Dissolve 1 substrate tablet in 5 mls substrate buffer. Wash the plate and add 50 µls/well of substrate. Incubate 30 minutes at room temperature on a shaker and read at 405 nm.

C. Relative Affinity Assay

Coat appropriate ELISA plate(s) overnight at 4° C. with the antigen concentration previously determined. Block plate as above. Make ⅓ serial dilutions into PBS+0.1 % BSA of test supernatant.

Add 50 µls/well of the dilutions of the supernatant sample, including the undiluted sample, to the ELISA plate(s) in duplicates or triplicates. The positive control consists of a few wells of the positive control mouse serum at the same concentration as used for determining the antigen coating concentration. The negative control consists of a few wells of the dilution buffer. Cover and incubate overnight at 4° C.

Plot the IgG concentration of each supernatant against the mean-value (O.D. 450) on a 4 parameter curve fit Supernatant curves that are more to the left are the supernatants with the highest affinities.

Example 15

Ascites Production in Mice

Hybridoma cells should be healthy and in log phase of growth for ascites production. Transfer cells to a 15 ml. tube and count. Determine the volume which contains 4×10$^6$ cells, transfer that volume to a second tube and centrifuge the cells. Resuspend the pellet in 0.9 mls of HBSS (Hank's Balanced Salt Solution) and transfer to an eppendorf tube.

Fill a 1 cc syringe with the cell suspension and inject mice ip as follows: 0.2 cc per mouse if the original cell number was 4×10$^6$ and 0.3 cc if the original cell number was 3×10$^6$. When the abdomen is very distended and slightly taught to the touch, like a balloon, (usually by day 9 or 10 but sometimes as late as day 14) then it is time to "tap the mouse".

A. Tapping:

Hold the mouse in your left hand and use an alcohol pad to wipe off the area of the abdomen just above the mouse's left hind leg. While holding the mouse above an open 15 ml centrifuge tube, insert a 19 gauge needle into the abdomen. Ascites fluid should immediately begin to drip out of the end of the needle into the centrifuge tube. An average mouse should yield 3-6 mls. of ascites fluid.

B. Processing and Storage of Ascites:

Pool ascitic fluid collected from each mouse in the group (all injected with the same hybridoma) and leave at room temperature for 1-2 hours or place at 37° C. for 15-30 minutes. Then place ascites at 4° C. overnight to allow for clot formation. Centrifuge clotted ascites for 10 minutes. Transfer the liquid ascites to a 50 ml centrifuge tube, and store the tube at −20° C. Subsequent taps may be added to this 50 ml tube. When all mice are sacrificed, the pooled ascites can be thawed, respun, and aliquotted for long term storage at −20° C. or −70° C. Ascites should be titered by ELISA.

Example 16

Protocol for Freezing and Thawing Mouse Hybridoma and Myeloma Cells

A. Freezing

Cells to be frozen down should be healthy, in log phase of growth and at a concentration of roughly 5-8×10$^5$ cells/ml. Resuspend cells from a 6 well plate or flask, transfer to a 15 ml tube and count. Calculate the number of total cells and divide by 1-3×10$^6$ cells per vial to determine the number of vials to be frozen down.

Pellet the cells at 200-300×G for 5-10 minutes. Aspirate the supernatant from the pellet and resuspend in sufficient cold freeze medium (50% FBS, 10% DMSO in DMEM; or Origen DMSO Freeze Medium (IGEN), Fisher Cat No. IG-50-0715) to achieve the desired number of cells/vial per ml (cell densities should be in a range from 5×10$^5$ to 1×10$^7$ cells/vial). Immediately transfer the cell suspension to the cryovials, 1 ml per vial, and place on ice. Transfer the vials to a controlled rate freezer and place the freezer at −70° c. for overnight.

After 24 hours transfer the vials to a liquid nitrogen tank or −130° C. freezer for long term storage.

B. Thawing

Add 10 ml cold media (e.g. P3X media) to 15 ml tube. Retrieve cryovial of frozen cells and keep on dry ice until ready to thaw. Thaw cells quickly in 37° C. water bath. Hold vial during thawing and keep shaking gently until there is just a small bit of ice left in vial. Don't allow the contents to warm above 4° C. Alcohol off the outside of the cryovial.

Using a sterile pasteur pipette and without touching the edges of the cryovial, transfer the cell suspension in the vial to the 10 mls. of cold media. Spin at 200-300×G for 5-10 minutes. Aspirate the supernatant and resuspend the pellet in 6 mls. of HT Cloning Media (supra). Transfer to 1 well of a 6 well dish. Assess the viability after 24 hours. Viability should not be less than 50%.

Example 17 In Vitro Assay for Angiogenic Protein Activity

The following assay is designed to detect angiogenic protein activity, preferably VEGF-2 activity. For example, a chimeric receptor is generated by fusing the nucleotides encoding for the extracellular domain of the Flt-4 receptor (SEQ ID NO:38) (Galland et al., *Genomics* 13 (2):475-478 (1992), which is herein incorporated by reference in its entirety), to the nucleotides encoding for the transmembrane domain and intracellular domain of Flk-1 (SEQ ID NO:39) (Davis-Smyth et al., *EMBO J.* 15(18):4919-4927 (1996), which is herein incorporated by reference in its entirety). Thus, the chimeric receptor would include amino acids 1 to 775 of SEQ ID NO:38, fused to amino acids 765 to 1356 of SEQ ID NO:39, respectively.

Alternatively, the chimeric receptor may be designed as outlined above, but would substitute the transmembrane and intracellular domains of the erythropoietin receptor (EPOR) for the transmembrane and intracellular domains of the Flk-1 receptor, as discussed in Pacifici et al., *JBC* 269(3): 1571-1574 (1994), which is herein incorporated by reference in its entirety (see specifically FIG. 1).

The resulting DNA encoding for the chimeric receptor is cloned into an appropriate mammalian, baculoviral, or bacterial expression vector, such as, for example, pC4, pCDNA3, or pA2, as discussed supra. Mammalian host cells that could be used for expression of the chimeric receptor include NIH3T3 (supra), or the pre-B cell line BaF3 (Achen et al., *PNAS* 95(2): 548-553 (1998), which is herein incorporated by reference in its entirety).

To test for activity, the angiogenic protein can be brought into contact with a cell line expressing the chimeric receptor, or extracts thereof. Then, angiogenic protein binding to the chimeric receptor can be detected by measuring any resulting signal transduced by the chimeric receptor.

Numerous modifications and variations of the present invention are possible in light of the above teachings and, therefore, within the scope of the appended claims, the invention may be practiced otherwise than as particularly described.

The entire disclosure of all publications (including patents, patent applications, journal articles, laboratory manuals, books, or other documents) cited herein are hereby incorporated by reference.

Additionally, the entire specification, including the Sequence Listing of U.S. application Ser. No. 09/107,997, filed Jun. 30, 1998, and PCT Application Number US 99/05021 filed Mar. 10, 1999, are hereby incorporated by reference in their entirety.

What is claimed is:

1. A method of treating an injury to or disorder of an eye, said injury or disorder comprising proliferation of a photoreceptor cell, comprising administering to a subject in need thereof an antibody or fragment thereof that specifically binds VEGF-2 in an amount sufficient to inhibit proliferation of photoreceptor cells.

2. The method of claim 1, wherein the antibody or framgent thereof is a polyclonal antibody.

3. The method of claim 1, wherein the antibody or fragment thereof is a monoclonal antibody.

4. The method of claim 1, wherein the antibody or framgent thereof is a humanized antibody.

5. The method of claim 1, wherein the subject is a mammal.

6. The method of claim 5, wherein the subject is a human.

7. The method of claim 1, wherein the antibody or fragment thereof is administered as a pharmaceutical composition with a pharmaceutically acceptable carrier.

8. The method of claim 1, wherein the antibody or framgent thereof is administered to the subject at a dose from 0.1 mg/kg to 100 mg/kg body weight.

9. The method of claim 8, wherein the antibody or framgent thereof is administered to the subject at a dose from 0.1 mg/kg to 20 mg/kg body weight.

10. The method of claim 9, wherein the antibody or fragment thereof is administered to the subject at a dose from 1 mg/kg to 10 mg/kg body weight.

11. The method of claim 1, wherein the injury or disorder is neoplasia.

* * * * *

UNITED STATES PATENT AND TRADEMARK OFFICE
CERTIFICATE OF CORRECTION

| | |
|---|---|
| PATENT NO. | : 7,524,501 B2 |
| APPLICATION NO. | : 11/078507 |
| DATED | : April 28, 2009 |
| INVENTOR(S) | : Alderson et al. |

Page 1 of 1

It is certified that error appears in the above-identified patent and that said Letters Patent is hereby corrected as shown below:

In column 165, line 8, claim 2, delete "framgent" and insert therein --fragment--

In column 165, line 12, claim 4, delete "framgent" and insert therein --fragment--

In column 166, line 4, claim 8, delete "framgent" and insert therein --fragment--

In column 166, line 7, claim 9, delete "framgent" and insert therein --fragment--

Signed and Sealed this

Sixteenth Day of June, 2009

JOHN DOLL
*Acting Director of the United States Patent and Trademark Office*

SEQUENCE LISTING

```
<160> NUMBER OF SEQ ID NOS: 39

<210> SEQ ID NO 1
<211> LENGTH: 1674
<212> TYPE: DNA
<213> ORGANISM: homo sapiens
<220> FEATURE:
<221> NAME/KEY: CDS
<222> LOCATION: (12)..(1268)
<220> FEATURE:
<221> NAME/KEY: mat_peptide
<222> LOCATION: (81)..()
<220> FEATURE:
<221> NAME/KEY: sig_peptide
<222> LOCATION: (12)..(80)

<400> SEQUENCE: 1
gtccttccac c atg cac tcg ctg ggc ttc ttc tct gtg gcg tgt tct ctg      50
            Met His Ser Leu Gly Phe Phe Ser Val Ala Cys Ser Leu
                -20                         -15 ctc gcc gct gcg ctg ctc ccg ggt cct cgc gag gcg ccc gcc gcc gcc      98
Leu Ala Ala Ala Leu Leu Pro Gly Pro Arg Glu Ala Pro Ala Ala Ala
-10                 -5              -1  1                   5 gcc gcc ttc gag tcc gga ctc gac ctc tcg gac gcg gag ccc gac gcg     146
Ala Ala Phe Glu Ser Gly Leu Asp Leu Ser Asp Ala Glu Pro Asp Ala
             10                  15                  20 ggc gag gcc acg gct tat gca agc aaa gat ctg gag gag cag tta cgg     194
Gly Glu Ala Thr Ala Tyr Ala Ser Lys Asp Leu Glu Glu Gln Leu Arg
```

-continued

```
                25                  30                  35
tct gtg tcc agt gta gat gaa ctc atg act gta ctc tac cca gaa tat     242
Ser Val Ser Ser Val Asp Glu Leu Met Thr Val Leu Tyr Pro Glu Tyr
    40                  45                  50 tgg aaa atg tac aag tgt cag cta agg aaa gga ggc tgg caa cat aac     290
Trp Lys Met Tyr Lys Cys Gln Leu Arg Lys Gly Gly Trp Gln His Asn
 55                  60                  65                  70 aga gaa cag gcc aac ctc aac tca agg aca gaa gag act ata aaa ttt     338
Arg Glu Gln Ala Asn Leu Asn Ser Arg Thr Glu Glu Thr Ile Lys Phe
                 75                  80                  85 gct gca gca cat tat aat aca gag atc ttg aaa agt att gat aat gag     386
Ala Ala Ala His Tyr Asn Thr Glu Ile Leu Lys Ser Ile Asp Asn Glu
         90                  95                 100 tgg aga aag act caa tgc atg cca cgg gag gtg tgt ata gat gtg ggg     434
Trp Arg Lys Thr Gln Cys Met Pro Arg Glu Val Cys Ile Asp Val Gly
    105                 110                 115 aag gag ttt gga gtc gcg aca aac acc ttc ttt aaa cct cca tgt gtg     482
Lys Glu Phe Gly Val Ala Thr Asn Thr Phe Phe Lys Pro Pro Cys Val
120                 125                 130 tcc gtc tac aga tgt ggg ggt tgc tgc aat agt gag ggg ctg cag tgc     530
Ser Val Tyr Arg Cys Gly Gly Cys Cys Asn Ser Glu Gly Leu Gln Cys
135                 140                 145                 150 atg aac acc agc acg agc tac ctc agc aag acg tta ttt gaa att aca     578
Met Asn Thr Ser Thr Ser Tyr Leu Ser Lys Thr Leu Phe Glu Ile Thr
                155                 160                 165 gtg cct ctc tct caa ggc ccc aaa cca gta aca atc agt ttt gcc aat     626
Val Pro Leu Ser Gln Gly Pro Lys Pro Val Thr Ile Ser Phe Ala Asn
        170                 175                 180 cac act tcc tgc cga tgc atg tct aaa ctg gat gtt tac aga caa gtt     674
His Thr Ser Cys Arg Cys Met Ser Lys Leu Asp Val Tyr Arg Gln Val
            185                 190                 195 cat tcc att att aga cgt tcc ctg cca gca aca cta cca cag tgt cag     722
His Ser Ile Ile Arg Arg Ser Leu Pro Ala Thr Leu Pro Gln Cys Gln
200                 205                 210 gca gcg aac aag acc tgc ccc acc aat tac atg tgg aat aat cac atc     770
Ala Ala Asn Lys Thr Cys Pro Thr Asn Tyr Met Trp Asn Asn His Ile
215                 220                 225                 230 tgc aga tgc ctg gct cag gaa gat ttt atg ttt tcc tcg gat gct gga     818
Cys Arg Cys Leu Ala Gln Glu Asp Phe Met Phe Ser Ser Asp Ala Gly
                235                 240                 245 gat gac tca aca gat gga ttc cat gac atc tgt gga cca aac aag gag     866
Asp Asp Ser Thr Asp Gly Phe His Asp Ile Cys Gly Pro Asn Lys Glu
        250                 255                 260 ctg gat gaa gag acc tgt cag tgt gtc tgc aga gcg ggg ctt cgg cct     914
Leu Asp Glu Glu Thr Cys Gln Cys Val Cys Arg Ala Gly Leu Arg Pro
            265                 270                 275 gcc agc tgt gga ccc cac aaa gaa cta gac aga aac tca tgc cag tgt     962
Ala Ser Cys Gly Pro His Lys Glu Leu Asp Arg Asn Ser Cys Gln Cys
280                 285                 290 gtc tgt aaa aac aaa ctc ttc ccc agc caa tgt ggg gcc aac cga gaa    1010
Val Cys Lys Asn Lys Leu Phe Pro Ser Gln Cys Gly Ala Asn Arg Glu
295                 300                 305                 310 ttt gat gaa aac aca tgc cag tgt gta tgt aaa aga acc tgc ccc aga    1058
Phe Asp Glu Asn Thr Cys Gln Cys Val Cys Lys Arg Thr Cys Pro Arg
                315                 320                 325 aat caa ccc cta aat cct gga aaa tgt gcc tgt gaa tgt aca gaa agt    1106
Asn Gln Pro Leu Asn Pro Gly Lys Cys Ala Cys Glu Cys Thr Glu Ser
        330                 335                 340 cca cag aaa tgc ttg tta aaa gga aag aag ttc cac cac caa aca tgc    1154
Pro Gln Lys Cys Leu Leu Lys Gly Lys Lys Phe His His Gln Thr Cys
```

-continued

```
Pro Gln Lys Cys Leu Leu Lys Gly Lys Phe His His Gln Thr Cys
        345                 350                 355
agc tgt tac aga cgg cca tgt acg aac cgc cag aag gct tgt gag cca    1202
Ser Cys Tyr Arg Arg Pro Cys Thr Asn Arg Gln Lys Ala Cys Glu Pro
    360                 365                 370
gga ttt tca tat agt gaa gaa gtg tgt cgt tgt gtc cct tca tat tgg    1250
Gly Phe Ser Tyr Ser Glu Glu Val Cys Arg Cys Val Pro Ser Tyr Trp
375                 380                 385                 390
caa aga cca caa atg agc taagattgta ctgttttcca gttcatcgat           1298
Gln Arg Pro Gln Met Ser
                395 tttctattat ggaaaactgt gttgccacag tagaactgtc tgtgaacaga gagacccttg    1358
tgggtccatg ctaacaaaga caaaagtctg tctttcctga accatgtgga taactttaca    1418
gaaatggact ggagctcatc tgcaaaaggc ctcttgtaaa gactggtttt ctgccaatga    1478
ccaaacagcc aagatttttcc tcttgtgatt tctttaaaag aatgactata taatttattt    1538
ccactaaaaa tattgtttct gcattcattt ttatagcaac aacaattggt aaaactcact    1598
gtgatcaata tttttatatc atgcaaaata tgtttaaaat aaaatgaaaa ttgtatttat    1658
aaaaaaaaaa aaaaaa                                                    1674
```

<210> SEQ ID NO 2
<211> LENGTH: 419
<212> TYPE: PRT
<213> ORGANISM: homo sapiens

<400> SEQUENCE: 2

```
Met His Ser Leu Gly Phe Phe Ser Val Ala Cys Ser Leu Leu Ala Ala
            -20                 -15                 -10
Ala Leu Leu Pro Gly Pro Arg Glu Ala Pro Ala Ala Ala Ala Phe
         -5                  -1   1               5
Glu Ser Gly Leu Asp Leu Ser Asp Ala Glu Pro Asp Ala Gly Glu Ala
10                  15                  20                  25
Thr Ala Tyr Ala Ser Lys Asp Leu Glu Glu Gln Leu Arg Ser Val Ser
                30                  35                  40
Ser Val Asp Glu Leu Met Thr Val Leu Tyr Pro Glu Tyr Trp Lys Met
            45                  50                  55
Tyr Lys Cys Gln Leu Arg Lys Gly Gly Trp Gln His Asn Arg Glu Gln
        60                  65                  70
Ala Asn Leu Asn Ser Arg Thr Glu Glu Thr Ile Lys Phe Ala Ala Ala
    75                  80                  85
His Tyr Asn Thr Glu Ile Leu Lys Ser Ile Asp Asn Glu Trp Arg Lys
90                  95                  100                 105
Thr Gln Cys Met Pro Arg Glu Val Cys Ile Asp Val Gly Lys Glu Phe
                110                 115                 120
Gly Val Ala Thr Asn Thr Phe Phe Lys Pro Pro Cys Val Ser Val Tyr
            125                 130                 135
Arg Cys Gly Gly Cys Cys Asn Ser Glu Gly Leu Gln Cys Met Asn Thr
        140                 145                 150
Ser Thr Ser Tyr Leu Ser Lys Thr Leu Phe Glu Ile Thr Val Pro Leu
    155                 160                 165
Ser Gln Gly Pro Lys Pro Val Thr Ile Ser Phe Ala Asn His Thr Ser
170                 175                 180                 185
Cys Arg Cys Met Ser Lys Leu Asp Val Tyr Arg Gln Val His Ser Ile
                190                 195                 200
```

```
Ile Arg Arg Ser Leu Pro Ala Thr Leu Pro Gln Cys Gln Ala Ala Asn
            205                 210                 215
Lys Thr Cys Pro Thr Asn Tyr Met Trp Asn Asn His Ile Cys Arg Cys
            220                 225                 230
Leu Ala Gln Glu Asp Phe Met Phe Ser Ser Asp Ala Gly Asp Asp Ser
            235                 240                 245
Thr Asp Gly Phe His Asp Ile Cys Gly Pro Asn Lys Glu Leu Asp Glu
250                 255                 260                 265
Glu Thr Cys Gln Cys Val Cys Arg Ala Gly Leu Arg Pro Ala Ser Cys
            270                 275                 280
Gly Pro His Lys Glu Leu Asp Arg Asn Ser Cys Gln Cys Val Cys Lys
            285                 290                 295
Asn Lys Leu Phe Pro Ser Gln Cys Gly Ala Asn Arg Glu Phe Asp Glu
            300                 305                 310
Asn Thr Cys Gln Cys Val Cys Lys Arg Thr Cys Pro Arg Asn Gln Pro
            315                 320                 325
Leu Asn Pro Gly Lys Cys Ala Cys Glu Cys Thr Glu Ser Pro Gln Lys
330                 335                 340                 345
Cys Leu Leu Lys Gly Lys Lys Phe His His Gln Thr Cys Ser Cys Tyr
                350                 355                 360
Arg Arg Pro Cys Thr Asn Arg Gln Lys Ala Cys Glu Pro Gly Phe Ser
            365                 370                 375
Tyr Ser Glu Glu Val Cys Arg Cys Val Pro Ser Tyr Trp Gln Arg Pro
            380                 385                 390
Gln Met Ser
    395

<210> SEQ ID NO 3
<211> LENGTH: 1526
<212> TYPE: DNA
<213> ORGANISM: homo sapiens

<400> SEQUENCE: 3
cgaggccacg gcttatgcaa gcaaagatct ggaggagcag ttacggtctg tgtccagtgt      60
agatgaactc atgactgtac tctacccaga atattggaaa atgtacaagt gtcagctaag     120
gaaaggaggc tggcaacata acagagaaca ggccaacctc aactcaagga cagaagagac     180
tataaaattt gctgcagcac attataatac agagatcttg aaaagtattg ataatgagtg     240
gagaaagact caatgcatgc cacgggaggt gtgtatagat gtggggaagg agtttggagt     300
cgcgacaaac accttcttta aacctccatg tgtgtccgtc tacagatgtg ggggttgctg     360
caatagtgag gggctgcagt gcatgaacac cagcacgagc tacctcagca agacgttatt     420
tgaaattaca gtgcctctct ctcaaggccc caaaccagta caatcagtt ttgccaatca      480 cacttcctgc cgatgcatgt ctaaactgga tgtttacaga caagttcatt ccattattag     540
acgttccctg ccagcaacac taccacagtg tcaggcagcg aacaagacct gccccaccaa     600
ttacatgtgg aataatcaca tctgcagatg cctggctcag aagatttta tgttttcctc      660 ggatgctgga gatgactcaa cagatggatt ccatgacatc tgtggaccaa acaaggagct     720
ggatgaagag acctgtcagt gtgtctgcag agcggggctt cggcctgcca gctgtggacc     780
ccacaaagaa ctagacagaa actcatgcca gtgtgtctgt aaaacaaac tcttccccag      840 ccaatgtggg gccaaccgag aatttgatga aacacatgc cagtgtgtat gtaaaagaac      900
ctgccccaga aatcaacccc taaatcctgg aaaatgtgcc tgtgaatgta cagaaagtcc     960
```

-continued

```
acagaaatgc ttgttaaaag gaaagaagtt ccaccaccaa acatgcagct gttacagacg    1020
gccatgtacg aaccgccaga aggcttgtga gccaggattt tcatatagtg aagaagtgtg    1080
tcgttgtgtc ccttcatatt ggcaaagacc acaaatgagc taagattgta ctgttttcca    1140
gttcatcgat tttctattat ggaaaactgt gttgccacag tagaactgtc tgtgaacaga    1200
gagacccttg tgggtccatg ctaacaaaga caaaagtctg tctttcctga accatgtgga    1260
taactttaca gaaatggact ggagctcatc tgcaaaaggc ctcttgtaaa gactggtttt    1320
ctgccaatga ccaaacagcc aagatttttcc tcttgtgatt tctttaaaag aatgactata    1380
taatttattt ccactaaaaa tattgtttct gcattcattt ttatagcaac aacaattggt    1440
aaaactcact gtgatcaata tttttatatc atgcaaaata tgtttaaaat aaaatgaaaa    1500
ttgtatttat aaaaaaaaaa aaaaaa                                          1526
```

<210> SEQ ID NO 4
<211> LENGTH: 350
<212> TYPE: PRT
<213> ORGANISM: homo sapiens

<400> SEQUENCE: 4

```
Met Thr Val Leu Tyr Pro Glu Tyr Trp Lys Met Tyr Lys Cys Gln Leu
1               5                   10                  15

Arg Lys Gly Gly Trp Gln His Asn Arg Glu Gln Ala Asn Leu Asn Ser
            20                  25                  30

Arg Thr Glu Glu Thr Ile Lys Phe Ala Ala Ala His Tyr Asn Thr Glu
        35                  40                  45

Ile Leu Lys Ser Ile Asp Asn Glu Trp Arg Lys Thr Gln Cys Met Pro
    50                  55                  60

Arg Glu Val Cys Ile Asp Val Gly Lys Glu Phe Gly Val Ala Thr Asn
65                  70                  75                  80

Thr Phe Phe Lys Pro Pro Cys Val Ser Val Tyr Arg Cys Gly Gly Cys
                85                  90                  95

Cys Asn Ser Glu Gly Leu Gln Cys Met Asn Thr Ser Thr Ser Tyr Leu
            100                 105                 110

Ser Lys Thr Leu Phe Glu Ile Thr Val Pro Leu Ser Gln Gly Pro Lys
        115                 120                 125

Pro Val Thr Ile Ser Phe Ala Asn His Thr Ser Cys Arg Cys Met Ser
    130                 135                 140

Lys Leu Asp Val Tyr Arg Gln Val His Ser Ile Ile Arg Arg Ser Leu
145                 150                 155                 160

Pro Ala Thr Leu Pro Gln Cys Gln Ala Ala Asn Lys Thr Cys Pro Thr
                165                 170                 175

Asn Tyr Met Trp Asn Asn His Ile Cys Arg Cys Leu Ala Gln Glu Asp
            180                 185                 190

Phe Met Phe Ser Ser Asp Ala Gly Asp Asp Ser Thr Asp Gly Phe His
        195                 200                 205

Asp Ile Cys Gly Pro Asn Lys Glu Leu Asp Glu Glu Thr Cys Gln Cys
    210                 215                 220

Val Cys Arg Ala Gly Leu Arg Pro Ala Ser Cys Gly Pro His Lys Glu
225                 230                 235                 240

Leu Asp Arg Asn Ser Cys Gln Cys Val Cys Lys Asn Lys Leu Phe Pro
                245                 250                 255

Ser Gln Cys Gly Ala Asn Arg Glu Phe Asp Glu Asn Thr Cys Gln Cys
            260                 265                 270
```

```
Val Cys Lys Arg Thr Cys Pro Arg Asn Gln Pro Leu Asn Pro Gly Lys
        275                 280                 285

Cys Ala Cys Glu Cys Thr Glu Ser Pro Gln Lys Cys Leu Leu Lys Gly
        290                 295                 300

Lys Lys Phe His His Gln Thr Cys Ser Cys Tyr Arg Arg Pro Cys Thr
305                 310                 315                 320

Asn Arg Gln Lys Ala Cys Glu Pro Gly Phe Ser Tyr Ser Glu Val
                325                 330                 335

Cys Arg Cys Val Pro Ser Tyr Trp Gln Arg Pro Gln Met Ser
            340                 345                 350

<210> SEQ ID NO 5
<211> LENGTH: 196
<212> TYPE: PRT
<213> ORGANISM: homo sapiens

<400> SEQUENCE: 5

Met Arg Thr Leu Ala Cys Leu Leu Leu Gly Cys Gly Tyr Leu Ala
1               5                   10                  15

His Val Leu Ala Glu Glu Ala Glu Ile Pro Arg Glu Val Ile Glu Arg
            20                  25                  30

Leu Ala Arg Ser Gln Ile His Ser Ile Arg Asp Leu Gln Arg Leu Leu
        35                  40                  45

Glu Ile Asp Ser Val Gly Ser Glu Asp Ser Leu Asp Thr Ser Leu Arg
    50                  55                  60

Ala His Gly Val His Ala Thr Lys His Val Pro Glu Lys Arg Pro Leu
65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
            100                 105                 110

Thr Ser Ala Asn Phe Leu Ile Trp Pro Pro Cys Val Glu Val Lys Arg
        115                 120                 125

Cys Thr Gly Cys Cys Asn Thr Ser Ser Val Lys Cys Gln Pro Ser Arg
    130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Asp Val Arg
        195

<210> SEQ ID NO 6
<211> LENGTH: 241
<212> TYPE: PRT
<213> ORGANISM: homo sapiens

<400> SEQUENCE: 6

Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
        35                  40                  45
```

His Gly Asp Pro Gly Glu Glu Asp Gly Ala Glu Leu Asp Leu Asn Met
50                      55                      60

Thr Arg Ser His Ser Gly Glu Leu Glu Ser Leu Ala Arg Gly Arg
65                      70                      75                      80

Arg Ser Leu Gly Ser Leu Thr Ile Ala Glu Pro Ala Met Ile Ala Glu
                    85                      90                      95

Cys Lys Thr Arg Thr Glu Val Phe Glu Ile Ser Arg Arg Leu Ile Asp
                100                     105                     110

Arg Thr Asn Ala Asn Phe Leu Val Trp Pro Pro Cys Val Glu Val Gln
                115                     120                     125

Arg Cys Ser Gly Cys Cys Asn Asn Arg Asn Val Gln Cys Arg Pro Thr
130                     135                     140

Gln Val Gln Leu Arg Pro Val Gln Val Arg Lys Ile Glu Ile Val Arg
145                     150                     155                     160

Lys Lys Pro Ile Phe Lys Lys Ala Thr Val Thr Leu Glu Asp His Leu
                165                     170                     175

Ala Cys Lys Cys Glu Thr Val Ala Ala Ala Arg Pro Val Thr Arg Ser
                180                     185                     190

Pro Gly Gly Ser Gln Glu Gln Arg Ala Lys Thr Pro Gln Thr Arg Val
                195                     200                     205

Thr Ile Arg Thr Val Arg Val Arg Arg Pro Pro Lys Gly Lys His Arg
210                     215                     220

Lys Phe Lys His Thr His Asp Lys Thr Ala Leu Lys Glu Thr Leu Gly
225                     230                     235                     240

Ala

<210> SEQ ID NO 7
<211> LENGTH: 232
<212> TYPE: PRT
<213> ORGANISM: homo sapiens

<400> SEQUENCE: 7

Met Asn Phe Leu Leu Ser Trp Val His Trp Ser Leu Ala Leu Leu Leu
1               5                       10                      15

Tyr Leu His His Ala Lys Trp Ser Gln Ala Ala Pro Met Ala Glu Gly
                20                      25                      30

Gly Gly Gln Asn His His Glu Val Val Lys Phe Met Asp Val Tyr Gln
                35                      40                      45

Arg Ser Tyr Cys His Pro Ile Glu Thr Leu Val Asp Ile Phe Gln Glu
50                      55                      60

Tyr Pro Asp Glu Ile Glu Tyr Ile Phe Lys Pro Ser Cys Val Pro Leu
65                      70                      75                      80

Met Arg Cys Gly Gly Cys Cys Asn Asp Glu Gly Leu Glu Cys Val Pro
                85                      90                      95

Thr Glu Glu Ser Asn Ile Thr Met Gln Ile Met Arg Ile Lys Pro His
                100                     105                     110

Gln Gly Gln His Ile Gly Glu Met Ser Phe Leu Gln His Asn Lys Cys
                115                     120                     125

Glu Cys Arg Pro Lys Lys Asp Arg Ala Arg Gln Glu Lys Lys Ser Val
130                     135                     140

Arg Gly Lys Gly Lys Gly Gln Lys Arg Lys Arg Lys Lys Ser Arg Tyr
145                     150                     155                     160

Lys Ser Trp Ser Val Tyr Val Gly Ala Arg Cys Cys Leu Met Pro Trp
                165                     170                     175

-continued

```
Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230

<210> SEQ ID NO 8
<211> LENGTH: 14
<212> TYPE: PRT
<213> ORGANISM: homo sapiens
<220> FEATURE:
<221> NAME/KEY: SITE
<222> LOCATION: (2)..(2)
<223> OTHER INFORMATION: Xaa is equal to any amino acid found in a
      naturally occuring protein.
<220> FEATURE:
<221> NAME/KEY: SITE
<222> LOCATION: (5)..(5)
<223> OTHER INFORMATION: Xaa is equal to any amino acid found in a
      naturally occuring protein.
<220> FEATURE:
<221> NAME/KEY: SITE
<222> LOCATION: (6)..(6)
<223> OTHER INFORMATION: Xaa is equal to any amino acid found in a
      naturally occuring protein.
<220> FEATURE:
<221> NAME/KEY: SITE
<222> LOCATION: (7)..(7)
<223> OTHER INFORMATION: Xaa is equal to any amino acid found in a
      naturally occuring protein.
<220> FEATURE:
<221> NAME/KEY: SITE
<222> LOCATION: (10)..(10)
<223> OTHER INFORMATION: Xaa is equal to any amino acid found in a
      naturally occuring protein.

<400> SEQUENCE: 8

Pro Xaa Cys Val Xaa Xaa Xaa Arg Cys Xaa Gly Cys Cys Asn
1               5                   10

<210> SEQ ID NO 9
<211> LENGTH: 3974
<212> TYPE: DNA
<213> ORGANISM: Expression vector pHEA4-5
<220> FEATURE:
<221> NAME/KEY: misc_feature
<222> LOCATION: (1)..(3974)
<223> OTHER INFORMATION: Expression vector pHE4-5

<400> SEQUENCE: 9
ggtacctaag tgagtagggc gtccgatcga cggacgcctt ttttttgaat tcgtaatcat      60
ggtcatagct gtttcctgtg tgaaattgtt atccgctcac aattccacac aacatacgag     120
ccggaagcat aaagtgtaaa gcctggggtg cctaatgagt gagctaactc acattaattg     180
cgttgcgctc actgcccgct ttccagtcgg gaaacctgtc gtgccagctg cattaatgaa     240
tcggccaacg cgcggggaga ggcggtttgc gtattgggcg ctcttccgct tcctcgctca     300
ctgactcgct gcgctcggtc gttcggctgc ggcgagcggt atcagctcac tcaaaggcgg     360
taatacggtt atccacagaa tcaggggata acgcaggaaa gaacatgtga gcaaaaggcc     420
agcaaaaggc caggaaccgt aaaaaggccg cgttgctggc gtttttccat aggctccgcc     480 ccccctgacga gcatcacaaa aatcgacgct caagtcagag gtggcgaaac ccgacaggac     540
tataaagata ccaggcgttt ccccctggaa gctccctcgt gcgctctcct gttccgaccc     600
```

```
tgccgcttac cggatacctg tccgcctttc tccttcggg  aagcgtggcg ctttctcata   660
gctcacgctg taggtatctc agttcggtgt aggtcgttcg ctccaagctg gctgtgtgc   720
acgaaccccc cgttcagccc gaccgctgcg ccttatccgg taactatcgt cttgagtcca   780
acccggtaag acacgactta tcgccactgg cagcagccac tggtaacagg attagcagag   840
cgaggtatgt aggcggtgct acagagttct tgaagtggtg cctaactac  ggctacacta   900
gaagaacagt atttggtatc tgcgctctgc tgaagccagt taccttcgga aaagagttg    960
gtagctcttg atccgcaaa  caaaccaccg ctggtagcgg tggttttttt gtttgcaagc  1020
agcagattac gcgcagaaaa aaaggatctc aagaagatcc tttgatcttt tctacggggt  1080
ctgacgctca gtggaacgaa aactcacgtt aagggatttt ggtcatgaga ttatcgtcga  1140
caattcgcgc gcgaaggcga agcggcatgc atttacgttg acaccatcga atggtgcaaa  1200
acctttcgcg gtatggcatg atagcgcccg gaagagagtc aattcagggt ggtgaatgtg  1260
aaaccagtaa cgttatacga tgtcgcagag tatgccggtg tctcttatca gaccgtttcc  1320
cgcgtggtga accaggccag ccacgtttct gcgaaaacgc gggaaaaagt ggaagcggcg  1380
atggcggagc tgaattacat tcccaaccgc gtggcacaac aactggcggg caaacagtcg  1440
ttgctgattg gcgttgccac ctccagtctg gccctcacg  cgccgtcgca aattgtcgcg  1500
gcgattaaat ctcgcgccga tcaactgggt gccagcgtgg tggtgtcgat ggtagaacga  1560
agcggcgtcg aagcctgtaa agcggcggtg cacaatcttc tcgcgcaacg cgtcagtggg  1620
ctgatcatta actatccgct ggatgaccag gatgccattg ctgtgaagc  tgcctgcact  1680
aatgttccgg cgttatttct tgatgtctct gaccagacac ccatcaacag tattattttc  1740
tcccatgaag acggtacgcg actgggcgtg gagcatctgg tcgcattggg tcaccagcaa  1800
atcgcgctgt tagcgggccc attaagttct gtctcggcgc gtctgcgtct ggctggctgg  1860
cataaatatc tcactcgcaa tcaaattcag ccgatagcgg aacgggaagg cgactggagt  1920
gccatgtccg gttttcaaca aaccatgcaa atgctgaatg agggcatcgt tcccactgcg  1980
atgctggttg ccaacgatca gatggcgctg ggcgcaatgc gcgccattac cgagtccggg  2040
ctgcgcgttg gtgcggatat ctcggtagtg ggatacgacg ataccgaaga cagctcatgt  2100
tatatcccgc cgttaaccac catcaaacag gattttcgcc tgctggggca aaccagcgtg  2160
gaccgcttgc tgcaactctc tcagggccag gcggtgaagg gcaatcagct gttgccgtc   2220
tcactggtga aaagaaaaac caccctggcg cccaatacgc aaaccgcctc tccccgcgcg  2280
ttggccgatt cattaatgca gctggcacga caggtttccc gactggaaag cgggcagtga  2340
gcgcaacgca attaatgtaa gttagcgcga attgtcgacc aaagcggcca tcgtgcctcc  2400
ccactcctgc agttcggggg catggatgcg cggatagccg ctgctggttt cctggatgcc  2460
gacggatttg cactgccggt agaactccgc gaggtcgtcc agcctcaggc agcagctgaa  2520
ccaactcgcg aggggatcga gcccggggtg ggcgaagaac tccagcatga gatcccccgcg  2580
ctggaggatc atccagccgg cgtcccggaa aacgattccg aagcccaacc tttcatagaa  2640
ggcggcggtg gaatcgaaat ctcgtgatgg caggttgggc gtcgcttggt cggtcatttc  2700
gaaccccaga gtcccgctca aagaactcg  tcaagaaggc gatagaaggc gatgcgctgc  2760
gaatcgggag cggcgatacc gtaaagcacg aggaagcggt cagcccattc gccgccaagc  2820
tcttcagcaa tatcacgggt agccaacgct atgtcctgat agcggtccgc cacacccagc  2880
cggccacagt cgatgaatcc agaaaagcgg ccattttcca ccatgatatt cggcaagcag  2940
```

-continued

```
gcatcgccat gggtcacgac gagatcctcg ccgtcgggca tgcgcgcctt gagcctggcg    3000
aacagttcgg ctggcgcgag cccctgatgc tcttcgtcca gatcatcctg atcgacaaga    3060
ccggcttcca tccgagtacg tgctcgctcg atgcgatgtt tcgcttggtg gtcgaatggg    3120
caggtagccg gatcaagcgt atgcagccgc cgcattgcat cagccatgat ggatactttc    3180
tcggcaggag caaggtgaga tgacaggaga tcctgccccg gcacttcgcc caatagcagc    3240
cagtcccttc ccgcttcagt gacaacgtcg agcacagctg cgcaaggaac gcccgtcgtg    3300
gccagccacg atagccgcgc tgcctcgtcc tgcagttcat tcagggcacc ggacaggtcg    3360
gtcttgacaa aaagaaccgg gcgcccctgc gctgacagcc ggaacacggc ggcatcagag    3420
cagccgattg tctgttgtgc ccagtcatag ccgaatagcc tctccaccca gcggccgga     3480 gaacctgcgt gcaatccatc ttgttcaatc atgcgaaacg atcctcatcc tgtctcttga    3540
tcagatcttg atccctgcg ccatcagatc cttggcggca agaaagccat ccagtttact     3600
ttgcagggct tccaaccctt accagagggc gccccagctg gcaattccgg ttcgcttgct    3660
gtccataaaa ccgcccagtc tagctatcgc catgtaagcc cactgcaagc tacctgcttt    3720
ctctttgcgc ttgcgttttc ccttgtccag atagcccagt agctgacatt catccggggt    3780
cagcaccgtt tctgcggact ggctttctac gtgttccgct tcctttagca gcccttgcgc    3840
cctgagtgct tgcggcagcg tgaagcttaa aaaactgcaa aaatagtttt gacttgtgag    3900
cggataacaa ttaagatgta cccaattgtg agcggataac aatttcacac attaaagagg    3960
agaaattaca tatg                                                      3974
```

<210> SEQ ID NO 10
<211> LENGTH: 112
<212> TYPE: DNA
<213> ORGANISM: promoter consensus sequence
<220> FEATURE:
<221> NAME/KEY: promoter
<222> LOCATION: (1)..(112)
<223> OTHER INFORMATION: regulatory elements of the pHE promotor: two
      lac operator sequences, Shine-Delgarno sequence, and terminal Hind
      III and Nde I restriction sites

<400> SEQUENCE: 10

```
aagcttaaaa aactgcaaaa aatagtttga cttgtgagcg gataacaatt aagatgtacc    60
caattgtgag cggataacaa tttcacacat taaagaggag aaattacata tg            112
```

<210> SEQ ID NO 11
<211> LENGTH: 18
<212> TYPE: DNA
<213> ORGANISM: oligonucleotide
<220> FEATURE:
<221> NAME/KEY: primer_bind
<222> LOCATION: (1)..(18)
<223> OTHER INFORMATION: M13-2 reverse primer

<400> SEQUENCE: 11

```
atgcttccgg ctcgtatg                                                  18
```

<210> SEQ ID NO 12
<211> LENGTH: 19
<212> TYPE: DNA
<213> ORGANISM: oligonucleotide
<220> FEATURE:
<221> NAME/KEY: primer_bind
<222> LOCATION: (1)..(19)
<223> OTHER INFORMATION: M13-2 forward primer

<400> SEQUENCE: 12

```
gggttttccc agtcacgac                                              19

<210> SEQ ID NO 13
<211> LENGTH: 21
<212> TYPE: DNA
<213> ORGANISM: oligonucleotide
<220> FEATURE:
<221> NAME/KEY: primer_bind
<222> LOCATION: (1)..(21)
<223> OTHER INFORMATION: VEGF-2 5' primer F4

<400> SEQUENCE: 13
ccacatggtt caggaaagac a                                           21

<210> SEQ ID NO 14
<211> LENGTH: 50
<212> TYPE: DNA
<213> ORGANISM: oligonucleotide
<220> FEATURE:
<221> NAME/KEY: primer_bind
<222> LOCATION: (1)..(50)
<223> OTHER INFORMATION: VEGF-2 5' primer containing a BamH1 site

<400> SEQUENCE: 14
tgtaatacga ctcactatag ggatcccgcc atggaggcca cggcttatgc            50

<210> SEQ ID NO 15
<211> LENGTH: 28
<212> TYPE: DNA
<213> ORGANISM: oligonucleotide
<220> FEATURE:
<221> NAME/KEY: primer_bind
<222> LOCATION: (1)..(28)
<223> OTHER INFORMATION: VEGF-2 3' primer containing an XbaI cleavage
      site

<400> SEQUENCE: 15
gatctctaga ttagctcatt tgtggtct                                    28

<210> SEQ ID NO 16
<211> LENGTH: 27
<212> TYPE: DNA
<213> ORGANISM: oligonucleotide
<220> FEATURE:
<221> NAME/KEY: primer_bind
<222> LOCATION: (1)..(27)
<223> OTHER INFORMATION: VEGF-2 5' primer containing a BamH1 site

<400> SEQUENCE: 16
cgcggatcca tgactgtact ctaccca                                     27

<210> SEQ ID NO 17
<211> LENGTH: 60
<212> TYPE: DNA
<213> ORGANISM: oligonucleotide
<220> FEATURE:
<221> NAME/KEY: primer_bind
<222> LOCATION: (1)..(60)
<223> OTHER INFORMATION: VEGF-2 3' primer containing complementary
      sequences to XbaI, HA tag, and XhoI sites

<400> SEQUENCE: 17
cgctctagat caagcgtagt ctgggacgtc gtatgggtac tcgaggctca tttgtggtct 60

<210> SEQ ID NO 18
<211> LENGTH: 30
<212> TYPE: DNA
```

<213> ORGANISM: oligonucleotide
<220> FEATURE:
<221> NAME/KEY: primer_bind
<222> LOCATION: (1)..(30)
<223> OTHER INFORMATION: VEGF-2 5' primer containing an NdeI site and
      start codon

<400> SEQUENCE: 18
gcagcacata tgacagaaga gactataaaa                                      30

<210> SEQ ID NO 19
<211> LENGTH: 30
<212> TYPE: DNA
<213> ORGANISM: oligonucleotide
<220> FEATURE:
<221> NAME/KEY: primer_bind
<222> LOCATION: (1)..(30)
<223> OTHER INFORMATION: VEGF-2 3' primer containing an Asp718 site and
      a stop codon

<400> SEQUENCE: 19
gcagcaggta cctcacagtt tagacatgca                                      30

<210> SEQ ID NO 20
<211> LENGTH: 30
<212> TYPE: DNA
<213> ORGANISM: oligonucleotide
<220> FEATURE:
<221> NAME/KEY: primer_bind
<222> LOCATION: (1)..(30)
<223> OTHER INFORMATION: VEGF-2 5' primer containing an NdeI site and a
      start codon

<400> SEQUENCE: 20
gcagcacata tgacagaaga gactataaaa                                      30

<210> SEQ ID NO 21
<211> LENGTH: 30
<212> TYPE: DNA
<213> ORGANISM: oligonucleotide
<220> FEATURE:
<221> NAME/KEY: primer_bind
<222> LOCATION: (1)..(30)
<223> OTHER INFORMATION: VEGF-2 3' primer containing an Asp718 site and
      a stop codon

<400> SEQUENCE: 21
gcagcaggta cctcaacgtc taataatgga                                      30

<210> SEQ ID NO 22
<211> LENGTH: 30
<212> TYPE: DNA
<213> ORGANISM: oligonucleotide
<220> FEATURE:
<221> NAME/KEY: primer_bind
<222> LOCATION: (1)..(30)
<223> OTHER INFORMATION: VEGF-2 5' primer containing a BamHI site and
      one nucleotide spacer

<400> SEQUENCE: 22
gcagcaggat cccacagaag agactataaa                                      30

<210> SEQ ID NO 23
<211> LENGTH: 30
<212> TYPE: DNA
<213> ORGANISM: oligonucleotide
<220> FEATURE:
<221> NAME/KEY: primer_bind
<222> LOCATION: (1)..(30)

-continued

<223> OTHER INFORMATION: VEGF-2 3' primer containing an XbaI site and a
      stop codon

<400> SEQUENCE: 23
gcagcatcta gatcacagtt tagacatgca                                        30

<210> SEQ ID NO 24
<211> LENGTH: 39
<212> TYPE: DNA
<213> ORGANISM: oligonucleotide
<220> FEATURE:
<221> NAME/KEY: primer_bind
<222> LOCATION: (1)..(39)
<223> OTHER INFORMATION: VEGF-2 5' primer containing a Bam HIsite and a
      one nucleotide spacer

<400> SEQUENCE: 24
gcagcaggat cccacagaag agactataaa atttgctgc                              39

<210> SEQ ID NO 25
<211> LENGTH: 36
<212> TYPE: DNA
<213> ORGANISM: oligonucleotide
<220> FEATURE:
<221> NAME/KEY: primer_bind
<222> LOCATION: (1)..(36)
<223> OTHER INFORMATION: VEGF-2 3' primer containing an XbaI site and a
      stop codon

<400> SEQUENCE: 25
gcagcatcta gatcaacgtc taataatgga atgaac                                 36

<210> SEQ ID NO 26
<211> LENGTH: 55
<212> TYPE: DNA
<213> ORGANISM: oligonucleotide
<220> FEATURE:
<221> NAME/KEY: primer_bind
<222> LOCATION: (1)..(55)
<223> OTHER INFORMATION: VEGF-2 5' primer containing a Klenow-filled
      BamHI site

<400> SEQUENCE: 26
gatcgatcca tcatgcactc gctgggcttc ttctctgtgg cgtgttctct gctcg            55

<210> SEQ ID NO 27
<211> LENGTH: 39
<212> TYPE: DNA
<213> ORGANISM: oligonucleotide
<220> FEATURE:
<221> NAME/KEY: primer_bind
<222> LOCATION: (1)..(39)
<223> OTHER INFORMATION: VEGF-2 3' primer containing a BamHI site with
      no stop codon

<400> SEQUENCE: 27
gcagggtacg gatcctagat tagctcattt gtggtcttt                              39

<210> SEQ ID NO 28
<211> LENGTH: 38
<212> TYPE: DNA
<213> ORGANISM: oligonucleotide
<220> FEATURE:
<221> NAME/KEY: primer_bind
<222> LOCATION: (1)..(38)
<223> OTHER INFORMATION: VEGF-2 5' primer containing a BamHI site

<400> SEQUENCE: 28

-continued

```
gcagcaggat ccacagaaga gactataaaa tttgctgc                              38
```

<210> SEQ ID NO 29
<211> LENGTH: 37
<212> TYPE: DNA
<213> ORGANISM: oligonucleotide
<220> FEATURE:
<221> NAME/KEY: primer_bind
<222> LOCATION: (1)..(37)
<223> OTHER INFORMATION: VEGF-2 3' primer containing an XbaI site and a
      stop codon

<400> SEQUENCE: 29

```
cgtcgttcta gatcacagtt tagacatgca tcggcag                               37
```

<210> SEQ ID NO 30
<211> LENGTH: 38
<212> TYPE: DNA
<213> ORGANISM: oligonucleotide
<220> FEATURE:
<221> NAME/KEY: primer_bind
<222> LOCATION: (1)..(38)
<223> OTHER INFORMATION: VEGF-2 5' primer containing a BamHI site

<400> SEQUENCE: 30

```
gcagcaggat ccacagaaga gactataaaa tttgctgc                              38
```

<210> SEQ ID NO 31
<211> LENGTH: 36
<212> TYPE: DNA
<213> ORGANISM: oligonucleotide
<220> FEATURE:
<221> NAME/KEY: primer_bind
<222> LOCATION: (1)..(36)
<223> OTHER INFORMATION: VEGF-2 3' primer containing an XbaI site and a
      stop codon

<400> SEQUENCE: 31

```
gcagcatcta gatcaacgtc taataatgga atgaac                                36
```

<210> SEQ ID NO 32
<211> LENGTH: 39
<212> TYPE: DNA
<213> ORGANISM: oligonucleotide
<220> FEATURE:
<221> NAME/KEY: primer_bind
<222> LOCATION: (1)..(39)
<223> OTHER INFORMATION: VEGF-2 5' primer containing a BamHI site and a
      start codon

<400> SEQUENCE: 32

```
gactggatcc gccaccatgc actcgctggg cttcttctc                             39
```

<210> SEQ ID NO 33
<211> LENGTH: 35
<212> TYPE: DNA
<213> ORGANISM: oligonucleotide
<220> FEATURE:
<221> NAME/KEY: primer_bind
<222> LOCATION: (1)..(35)
<223> OTHER INFORMATION: VEGF-2 3' primer containing an Asp718 site

<400> SEQUENCE: 33

```
gactggtacc ttatcacata aaatcttcct gagcc                                 35
```

<210> SEQ ID NO 34
<211> LENGTH: 39
<212> TYPE: DNA

```
<213> ORGANISM: oligonucleotide
<220> FEATURE:
<221> NAME/KEY: primer_bind
<222> LOCATION: (1)..(39)
<223> OTHER INFORMATION: VEGF-2 5' primer containing a BamHI site and a
      start codon

<400> SEQUENCE: 34
gactggatcc gccaccatgc actcgctggg cttcttctc                         39

<210> SEQ ID NO 35
<211> LENGTH: 34
<212> TYPE: DNA
<213> ORGANISM: oligonucleotide
<220> FEATURE:
<221> NAME/KEY: primer_bind
<222> LOCATION: (1)..(34)
<223> OTHER INFORMATION: VEGF-2 3' primer containing an Asp718 site and
      a stop codon

<400> SEQUENCE: 35
gactggtacc ttatcagtct agttctttgt gggg                              34

<210> SEQ ID NO 36
<211> LENGTH: 39
<212> TYPE: DNA
<213> ORGANISM: oligonucleotide
<220> FEATURE:
<221> NAME/KEY: primer_bind
<222> LOCATION: (1)..(39)
<223> OTHER INFORMATION: VEGF-2 5' primer containing a BamHI site and a
      start codon

<400> SEQUENCE: 36
gactggatcc gccaccatgc actcgctggg cttcttctc                         39

<210> SEQ ID NO 37
<211> LENGTH: 37
<212> TYPE: DNA
<213> ORGANISM: oligonucleotide
<220> FEATURE:
<221> NAME/KEY: primer_bind
<222> LOCATION: (1)..(37)
<223> OTHER INFORMATION: VEGF-2 3' primer containing an Asp718 site and
      a stop codon

<400> SEQUENCE: 37
gactggtacc tcattactgt ggactttctg tacattc                           37

<210> SEQ ID NO 38
<211> LENGTH: 1298
<212> TYPE: PRT
<213> ORGANISM: homo sapiens

<400> SEQUENCE: 38

Met Gln Arg Gly Ala Ala Leu Cys Leu Arg Leu Trp Leu Cys Leu Gly
1               5                   10                  15

Leu Leu Asp Gly Leu Val Ser Asp Tyr Ser Met Thr Pro Pro Thr Leu
            20                  25                  30

Asn Ile Thr Glu Glu Ser His Val Ile Asp Thr Gly Asp Ser Leu Ser
        35                  40                  45

Ile Ser Cys Arg Gly Gln His Pro Leu Glu Trp Ala Trp Pro Gly Ala
    50                  55                  60

Gln Glu Ala Pro Ala Thr Gly Asp Lys Asp Ser Glu Asp Thr Gly Val
65                  70                  75                  80
```

```
Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
            115                 120                 125

Tyr Val Phe Val Arg Asp Phe Glu Gln Pro Phe Ile Asn Lys Pro Asp
        130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
        195                 200                 205

Thr Trp Gly Asp Gln Asp Phe Leu Ser Asn Pro Phe Leu Val His Ile
210                 215                 220

Thr Gly Asn Glu Leu Tyr Asp Ile Gln Leu Leu Pro Arg Lys Ser Leu
225                 230                 235                 240

Glu Leu Leu Val Gly Glu Lys Leu Val Leu Asn Cys Thr Val Trp Ala
                245                 250                 255

Glu Phe Asn Ser Gly Val Thr Phe Asp Trp Asp Tyr Pro Gly Lys Gln
            260                 265                 270

Ala Glu Arg Gly Lys Trp Val Pro Glu Arg Arg Ser Gln Gln Thr His
        275                 280                 285

Thr Glu Leu Ser Ser Ile Leu Thr Ile His Asn Val Ser Gln His Asp
290                 295                 300

Leu Gly Ser Tyr Val Cys Lys Ala Asn Asn Gly Ile Gln Arg Phe Arg
305                 310                 315                 320

Glu Ser Thr Glu Val Ile Val His Glu Asn Pro Phe Ile Ser Val Glu
                325                 330                 335

Trp Leu Lys Gly Pro Ile Leu Glu Ala Thr Ala Gly Asp Glu Leu Val
            340                 345                 350

Lys Leu Pro Val Lys Leu Ala Ala Tyr Pro Pro Pro Glu Phe Gln Trp
        355                 360                 365

Tyr Lys Asp Gly Lys Ala Leu Ser Gly Arg His Ser Pro His Ala Leu
        370                 375                 380

Val Leu Lys Glu Val Thr Glu Ala Ser Thr Gly Thr Tyr Thr Leu Ala
385                 390                 395                 400

Leu Trp Asn Ser Ala Ala Gly Leu Arg Arg Asn Ile Ser Leu Glu Leu
                405                 410                 415

Val Val Asn Val Pro Pro Gln Ile His Glu Lys Glu Ala Ser Ser Pro
            420                 425                 430

Ser Ile Tyr Ser Arg His Ser Arg Gln Ala Leu Thr Cys Thr Ala Tyr
        435                 440                 445

Gly Val Pro Leu Pro Leu Ser Ile Gln Trp His Trp Arg Pro Trp Thr
        450                 455                 460

Pro Cys Lys Met Phe Ala Gln Arg Ser Leu Arg Arg Arg Gln Gln Gln
465                 470                 475                 480

Asp Leu Met Pro Gln Cys Arg Asp Trp Arg Ala Val Thr Thr Gln Asp
                485                 490                 495

Ala Val Asn Pro Ile Glu Ser Leu Asp Thr Trp Thr Glu Phe Val Glu
```

-continued

```
                500             505             510
Gly Lys Asn Lys Thr Val Ser Lys Leu Val Ile Gln Asn Ala Asn Val
        515                 520                 525

Ser Ala Met Tyr Lys Cys Val Val Ser Asn Lys Val Gly Gln Asp Glu
        530                 535                 540

Arg Leu Ile Tyr Phe Tyr Val Thr Thr Ile Pro Asp Gly Phe Thr Ile
545                 550                 555                 560

Glu Ser Lys Pro Ser Glu Glu Leu Leu Glu Gly Gln Pro Val Leu Leu
                565                 570                 575

Ser Cys Gln Ala Asp Ser Tyr Lys Tyr Glu His Leu Arg Trp Tyr Arg
        580                 585                 590

Leu Asn Leu Ser Thr Leu His Asp Ala His Gly Asn Pro Leu Leu Leu
        595                 600                 605

Asp Cys Lys Asn Val His Leu Phe Ala Thr Pro Leu Ala Ala Ser Leu
        610                 615                 620

Glu Glu Val Ala Pro Gly Ala Arg His Ala Thr Leu Ser Leu Ser Ile
625                 630                 635                 640

Pro Arg Val Ala Pro Glu His Glu Gly His Tyr Val Cys Glu Val Gln
                645                 650                 655

Asp Arg Arg Ser His Asp Lys His Cys His Lys Lys Tyr Leu Ser Val
                660                 665                 670

Gln Ala Leu Glu Ala Pro Arg Leu Thr Gln Asn Leu Thr Asp Leu Leu
        675                 680                 685

Val Asn Val Ser Asp Ser Leu Glu Met Gln Cys Leu Val Ala Gly Ala
        690                 695                 700

His Ala Pro Ser Ile Val Trp Tyr Lys Asp Glu Arg Leu Leu Glu Glu
705                 710                 715                 720

Lys Ser Gly Val Asp Leu Ala Asp Ser Asn Gln Lys Leu Ser Ile Gln
                725                 730                 735

Arg Val Arg Glu Glu Asp Ala Gly Pro Tyr Leu Cys Ser Val Cys Arg
                740                 745                 750

Pro Lys Gly Cys Val Asn Ser Ser Ala Ser Val Ala Val Glu Gly Ser
        755                 760                 765

Glu Asp Lys Gly Ser Met Glu Ile Val Ile Leu Val Gly Thr Gly Val
        770                 775                 780

Ile Ala Val Phe Phe Trp Val Leu Leu Leu Leu Ile Phe Cys Asn Met
785                 790                 795                 800

Arg Arg Pro Ala His Ala Asp Ile Lys Thr Gly Tyr Leu Ser Ile Ile
                805                 810                 815

Met Asp Pro Gly Glu Val Pro Leu Glu Glu Gln Cys Glu Tyr Leu Ser
                820                 825                 830

Tyr Asp Ala Ser Gln Trp Glu Phe Pro Arg Glu Arg Leu His Leu Gly
        835                 840                 845

Arg Val Leu Gly Tyr Gly Ala Phe Gly Lys Val Val Glu Ala Ser Ala
        850                 855                 860

Phe Gly Ile His Lys Gly Ser Ser Cys Asp Thr Val Ala Val Lys Met
865                 870                 875                 880

Leu Lys Glu Gly Ala Thr Ala Ser Glu Gln Arg Ala Leu Met Ser Glu
                885                 890                 895

Leu Lys Ile Leu Ile His Ile Gly Asn His Leu Asn Val Val Asn Leu
                900                 905                 910

Leu Gly Ala Cys Thr Lys Pro Gln Gly Pro Leu Met Val Ile Val Glu
        915                 920                 925
```

```
Phe Cys Lys Tyr Gly Asn Leu Ser Asn Phe Leu Arg Ala Lys Arg Asp
    930                 935                 940
Ala Phe Ser Pro Cys Ala Glu Lys Ser Pro Glu Gln Arg Gly Arg Phe
945                 950                 955                 960
Arg Ala Met Val Glu Leu Ala Arg Leu Asp Arg Arg Pro Gly Ser
                965                 970                 975
Ser Asp Arg Val Leu Phe Ala Arg Phe Ser Lys Thr Glu Gly Gly Ala
            980                 985                 990
Arg Arg Ala Ser Pro Asp Gln Glu Ala Glu Asp Leu Trp Leu Ser Pro
        995                 1000                1005
Leu Thr Met Glu Asp Leu Val Cys Tyr Ser Phe Gln Val Ala Arg
    1010                1015                1020
Gly Met Glu Phe Leu Ala Ser Arg Lys Cys Ile His Arg Asp Leu
    1025                1030                1035
Ala Ala Arg Asn Ile Leu Leu Ser Glu Ser Asp Val Val Lys Ile
    1040                1045                1050
Cys Asp Phe Gly Leu Ala Arg Asp Ile Tyr Lys Asp Pro Asp Tyr
    1055                1060                1065
Val Arg Lys Gly Ser Ala Arg Leu Pro Leu Lys Trp Met Ala Pro
    1070                1075                1080
Glu Ser Ile Phe Asp Lys Val Tyr Thr Thr Gln Ser Asp Val Trp
    1085                1090                1095
Ser Phe Gly Val Leu Leu Trp Glu Ile Phe Ser Leu Gly Ala Ser
    1100                1105                1110
Pro Tyr Pro Gly Val Gln Ile Asn Glu Glu Phe Cys Gln Arg Val
    1115                1120                1125
Arg Asp Gly Thr Arg Met Arg Ala Pro Glu Leu Ala Thr Pro Ala
    1130                1135                1140
Ile Arg His Ile Met Leu Asn Cys Trp Ser Gly Asp Pro Lys Ala
    1145                1150                1155
Arg Pro Ala Phe Ser Asp Leu Val Glu Ile Leu Gly Asp Leu Leu
    1160                1165                1170
Gln Gly Arg Gly Leu Gln Glu Glu Glu Val Cys Met Ala Pro
    1175                1180                1185
Arg Ser Ser Gln Ser Ser Glu Glu Gly Ser Phe Ser Gln Val Ser
    1190                1195                1200
Thr Met Ala Leu His Ile Ala Gln Ala Asp Ala Glu Asp Ser Pro
    1205                1210                1215
Pro Ser Leu Gln Arg His Ser Leu Ala Ala Arg Tyr Tyr Asn Trp
    1220                1225                1230
Val Ser Phe Pro Gly Cys Leu Ala Arg Gly Ala Glu Thr Arg Gly
    1235                1240                1245
Ser Ser Arg Met Lys Thr Phe Glu Glu Phe Pro Met Thr Pro Thr
    1250                1255                1260
Thr Tyr Lys Gly Ser Val Asp Asn Gln Thr Asp Ser Gly Met Val
    1265                1270                1275
Leu Ala Ser Glu Glu Phe Glu Gln Ile Glu Ser Arg His Arg Gln
    1280                1285                1290
Glu Ser Gly Phe Arg
    1295

<210> SEQ ID NO 39
<211> LENGTH: 758
```

```
<212> TYPE: PRT
<213> ORGANISM: homo sapiens

<400> SEQUENCE: 39

Met Val Ser Tyr Trp Asp Thr Gly Val Leu Leu Cys Ala Leu Leu Ser
1               5                   10                  15

Cys Leu Leu Leu Thr Gly Ser Ser Gly Ser Lys Leu Lys Asp Pro
            20                  25                  30

Glu Leu Ser Leu Lys Gly Thr Gln His Ile Met Gln Ala Gly Gln Thr
            35                  40                  45

Leu His Leu Gln Cys Arg Gly Glu Ala Ala His Lys Trp Ser Leu Pro
50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
            115                 120                 125

Ser Asp Thr Gly Arg Pro Phe Val Glu Met Tyr Ser Glu Ile Pro Glu
130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
            195                 200                 205

Ala Thr Val Asn Gly His Leu Tyr Lys Thr Asn Tyr Leu Thr His Arg
210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
            275                 280                 285

Ala Asn Ile Phe Tyr Ser Val Leu Thr Ile Asp Lys Met Gln Asn Lys
290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
            355                 360                 365

Trp Leu Lys Asp Gly Leu Pro Ala Thr Glu Lys Ser Ala Arg Tyr Leu
370                 375                 380

Thr Arg Gly Tyr Ser Leu Ile Ile Lys Asp Val Thr Glu Glu Asp Ala
385                 390                 395                 400
```

```
Gly Asn Tyr Thr Ile Leu Leu Ser Ile Lys Gln Ser Asn Val Phe Lys
            405                 410                 415

Asn Leu Thr Ala Thr Leu Ile Val Asn Val Lys Pro Gln Ile Tyr Glu
        420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
        450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
            485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
            515                 520                 525

Ile Ser Gly Ile Tyr Ile Cys Ile Ala Ser Asn Lys Val Gly Thr Val
            530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
            565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
            595                 600                 605

Met Ala Ile Thr Lys Glu His Ser Ile Thr Leu Asn Leu Thr Ile Met
            610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
            645                 650                 655

Asp Gln Glu Ala Pro Tyr Leu Leu Arg Asn Leu Ser Asp His Thr Val
            660                 665                 670

Ala Ile Ser Ser Ser Thr Thr Leu Asp Cys His Ala Asn Gly Val Pro
            675                 680                 685

Glu Pro Gln Ile Thr Trp Phe Lys Asn Asn His Lys Ile Gln Gln Glu
            690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
            725                 730                 735

Lys Gly Ser Val Glu Ser Ser Ala Tyr Leu Thr Val Gln Gly Thr Ser
            740                 745                 750

Asp Lys Ser Asn Phe Glu
            755
```